US011957713B2

(12) United States Patent
Biffi et al.

(10) Patent No.: US 11,957,713 B2
(45) Date of Patent: Apr. 16, 2024

(54) COMPOSITIONS AND METHODS FOR TREATING DISEASES AND DISORDERS OF THE CENTRAL NERVOUS SYSTEM

(71) Applicants: CHILDREN'S MEDICAL CENTER CORPORATION, Boston, MA (US); OSPEDALE SAN RAFFAELE S.R.L., Milan (IT); POLITECNICO DI MILANO, Milan (IT); FONDAZIONE TELETHON ETS, Rome (IT); DANA-FARBER CANCER INSTITUTE, INC., Boston, MA (US)

(72) Inventors: Alessandra Biffi, Boston, MA (US); Marco Peviani, Boston, MA (US); Davide Moscatelli, Milan (IT); Alessia Capotondo, Milan (IT); Rita Milazzo, Milan (IT); Umberto Capasso Palmiero, Milan (IT)

(73) Assignees: CHILDREN'S MEDICAL CENTER CORPORATION, Boston, MA (US); OSPEDALE SAN RAFFAELE S.R.L., Milan (IT); POLITECNICO DI MILANO, Milan (IT); FONDAZIONE TELETHON ETS, Rome (IT); DANA-FARBER CANCER INSTITUTE, INC, Boston, MA (US)

( * ) Notice: Subject to any disclaimer, the term of this patent is extended or adjusted under 35 U.S.C. 154(b) by 268 days.

(21) Appl. No.: 16/341,704

(22) PCT Filed: Oct. 16, 2017

(86) PCT No.: PCT/US2017/056774
§ 371 (c)(1),
(2) Date: Apr. 12, 2019

(87) PCT Pub. No.: WO2018/071898
PCT Pub. Date: Apr. 19, 2018

(65) Prior Publication Data
US 2020/0038439 A1 Feb. 6, 2020

Related U.S. Application Data

(60) Provisional application No. 62/408,664, filed on Oct. 14, 2016.

(51) Int. Cl.
| | | |
|---|---|---|
| C12N 5/071 | (2010.01) | |
| A61K 35/12 | (2015.01) | |
| A61P 25/28 | (2006.01) | |
| C12N 15/86 | (2006.01) | |
| A01K 67/0271 | (2024.01) | |
| A61K 9/00 | (2006.01) | |
| A61K 45/06 | (2006.01) | |

(52) U.S. Cl.
CPC .............. *A61K 35/12* (2013.01); *A61P 25/28* (2018.01); *C12N 15/86* (2013.01); *A01K 67/0271* (2013.01); *A01K 2227/10* (2013.01); *A61K 9/0019* (2013.01); *A61K 2035/124* (2013.01); *A61K 45/06* (2013.01); *C12N 2740/15043* (2013.01)

(58) Field of Classification Search
CPC ...... C12N 5/06; C12N 5/0634; C12N 5/0647; A61P 25/28
See application file for complete search history.

(56) References Cited

U.S. PATENT DOCUMENTS

| | | |
|---|---|---|
| 6,537,785 B1 | 3/2003 | Canfield |
| 8,093,209 B2 | 1/2012 | Laskowitz et al. |
| 9,339,512 B2 | 5/2016 | Widdowson et al. |
| 2001/0038836 A1 | 11/2001 | During et al. |
| 2004/0067500 A1 | 4/2004 | Gould-Rothberg et al. |
| 2007/0009500 A1 | 1/2007 | Blazar et al. |
| 2007/0081992 A1 | 4/2007 | Pardridge et al. |
| 2008/0254017 A1 | 10/2008 | Kane et al. |
| 2009/0318333 A1 | 12/2009 | Vallee |
| 2010/0166759 A1 | 7/2010 | Berezin et al. |
| 2010/0221225 A1 | 9/2010 | Byrne et al. |
| 2010/0233084 A1 | 9/2010 | Narasimhaswamy et al. |
| 2012/0003202 A1 | 1/2012 | Calias et al. |
| 2014/0017212 A1 | 1/2014 | Rebar |

(Continued)

FOREIGN PATENT DOCUMENTS

| | | |
|---|---|---|
| JP | 2007051980 A | 3/2007 |
| JP | 2015527083 A | 9/2015 |

(Continued)

OTHER PUBLICATIONS

King et al., 2010, US 20100151573 A1.*
During et al., 2001, US 20010038836 A1.*
Purschke et al., 2011, US 20110223127 A1.*
Rossi et al., 2018, US 20180187156 A1, effective filing date, Jun. 25, 2015.*
Paes et al., 2017, Cell Biology and Toxicology, vol. 33, No. 3, pp. 233-250.*
Ikehara et al., 2013, Frontier in Cell and Developmental Biology, vol. 1, Article 2, p. 1-2.*
Cooper et al., 2015, International Journal of Surgery, vol. 23, p. 211-216.*
Liu et al., 2017, Frontiers in Immunology, vol. 8, article 645, p. 1-6.*

(Continued)

*Primary Examiner* — Shin Lin Chen
(74) *Attorney, Agent, or Firm* — Melissa Hunter-Ensor; Nathan Hsu; Greenberg Traurig, LLP

(57) ABSTRACT

The present invention provides compositions and methods for the treatment or prevention of a neurological disease or disorder of the central nervous system (e.g., a storage disorder, lysosomal storage disorder, neurodegenerative disease, etc.) by reconstitution of brain myeloid cell and microglia upon transplantation of hematopoietic cells enriched in microglia reconstitution potential. The invention also provides compositions and methods for ablating and reconstituting microglia.

8 Claims, 63 Drawing Sheets

Specification includes a Sequence Listing.

(56) References Cited

U.S. PATENT DOCUMENTS

| | | | |
|---|---|---|---|
| 2014/0235697 A1 | 8/2014 | Weiner et al. | |
| 2015/0223436 A1 | 8/2015 | Rossi et al. | |
| 2016/0256492 A1 | 9/2016 | Naldini et al. | |
| 2017/0333527 A1 | 11/2017 | Fukuta et al. | |
| 2018/0161357 A1 | 6/2018 | Jackson et al. | |
| 2019/0367584 A1 | 12/2019 | Biffi et al. | |
| 2020/0278356 A1 | 9/2020 | Biffi et al. | |

FOREIGN PATENT DOCUMENTS

| | | |
|---|---|---|
| WO | 1996002670 A1 | 2/1996 |
| WO | 2000029846 A2 | 5/2000 |
| WO | 2000073482 A1 | 12/2000 |
| WO | 2002096439 A1 | 12/2002 |
| WO | 2004015089 A2 | 2/2004 |
| WO | 2006102933 A1 | 10/2006 |
| WO | 2010012667 A1 | 2/2010 |
| WO | 2013030785 A1 | 3/2013 |
| WO | 2014039745 A1 | 3/2014 |
| WO | 2015164750 A2 | 10/2015 |
| WO | 2016039163 A1 | 3/2016 |
| WO | 2016094880 A1 | 6/2016 |

OTHER PUBLICATIONS

Hu et al., "Hematopoietic Stem Cell Transplantation and Lentiviral Vector-Based Gene Therapy for Krabbe's Disease: Present Convictions and Future Prospects," Journal of Neuroscience Research, Sep. 17, 2016, vol. 94, pp. 1152-1168.

International Search Report and Written Opinion for corresponding PCT Patent Application No. PCT/US2017/056774, dated Feb. 13, 2018 (18 pages).

Cartier et al., "Hematopoietic stem cell transplantation and hematopoietic stem cell gene therapy in X-linked adrenoleukodystrophy," Brain Pathology, Jul. 1, 2010, vol. 20, No. 4, pp. 857-862.

Kuo et al., "Theoretical and practical applications of the intracerebroventricular route for CSF sampling and drug administration in CNS drug discovery research: A mini review," Journal of Neuroscience Methods, Jun. 14, 2014, vol. 233, pp. 166-171.

Sessa et al., "Lentiviral haemopoietic stem-cell gene therapy in early-onset metachromatic leukodystrophy: an ad-hoc analysis of a non-randomised, open-label, phase 1/2 trial," The Lancet, Jun. 8, 2016, vol. 388, No. 10043, pp. 476-487.

Partial European Search Report in corresponding European Patent Application No. 17860210.8, dated Mar. 19, 2020 (16 pages).

Ambjorn et al., "Metallothionein and a peptide modeled after metallothionein, EmtinB, induce neuronal differentiation and survival through binding to receptors of the low-density lipoprotein receptor family," Journal of Neurochemistry, 2008, vol. 104, No. 1, pp. 21-37.

Andrews, Glen K., "Regulation of Metallothionein Gene Expression by Oxidative Stress and Metal Ions," Biochemical Pharmacology, Jan. 1, 2000, vol. 59, No. 1, pp. 95-104.

Arnal et al., "Clinical utility of copper, ceruloplasmin, and metallothionein plasma determinations in human neurodegenerative patients and their first-degree relatives," Brain Research, Mar. 10, 2010, vol. 1319, pp. 118-130.

Aronovich et al., "Lysosomal storage disease: Gene therapy on both sides of the blood-brain barrier," Molecular Genetics and Metabolism, Feb. 2015, vol. 114, No. 2, pp. 83-93.

Atagi et al., "Apolipoprotein E Is a Ligand for Triggering Receptor Expressed on Myeloid Cells 2 (TREM2)," The Journal of Biological Chemistry, Oct. 23, 2015, vol. 290, No. 43, pp. 26043-26050.

Baird et al., "Metallothionein protects against oxidative stress-induced lysosomal destabilization," Biochemical Journal, Feb. 2006, vol. 394, No. 1, pp. 275-283.

Biffi, Alessandra, "Gene therapy for lysosomal storage disorders: a good start," Human Molecular Genetics, 2016, vol. 25, No. R1, pp. R65-R75.

Biffi et al., "Lentiviral Hematopoietic Stem Cell Gene Therapy Benefits Metachromatic Leukodystrophy," Science, American Association for the Advancement of Science, Jul. 11, 2013, pp. 1-16.

Cai et al., "Zinc- or cadmium-pre-induced metallothionein protects human central nervous system cells and astrocytes from radiation-induced apoptosis," Toxicology Letters, 2004, vol. 146, No. 3, pp. 217-226.

Cesani et al., "Metallothioneins as Dynamic Markers for Brain Disease in Lysosomal Disorders," Annals of Neurology, 2014, vol. 75, No. 1, pp. 127-137.

Chimienti et al., "Zinc Resistance Impairs Sensitivity to Oxidative Stress in Hela Cells: Protection Through Metallothioneins Expression," Free Radical Biology and Medicine, 2001, vol. 31, No. 10, pp. 1179-1190.

Chung et al., "New insight into the molecular pathways of metallothionein-mediated neuroprotection and regeneration," Journal of Neurochemistry, Jan. 2008, vol. 104, No. 1, pp. 14-20.

Chung et al., "Redefining the Role of Metallothionein within the Injured Brain: Extracellular Metallothioneins Play an Important Role in the Astrocyte-Neuron Response to Injury," The Journal of Biological Chemistry, May 30, 2008, vol. 283, No. 22, pp. 15349-15358.

ClinicalTrials.gov Identifier: NCT01560182.
ClinicalTrials.gov Identifier: NCT01801709.
ClinicalTrials.gov Identifier: NCT02055118.
ClinicalTrials.gov Identifier: NCT02725580.

Comes et al., "Influence of Transgenic Metallothionein-1 on Gliosis, CA1 Neuronal Loss, and Brain Metal Levels of the Tg2576 Mouse Model of Alzheimer's Disease," International Journal of Molecular Sciences, 2017, vol. 18, Article No. 251, pp. 1-12.

Deverman et al., "Cre-dependent selection yields AAV variants for widespread gene transfer to the adult brain," Nature Biotechnology, Feb. 2016, vol. 34, No. 2, pp. 204-209.

Di Foggia et al., "Bmi1 enhances skeletal muscle regeneration through MT1-mediated oxidative stress protection in a mouse model of dystrophinopathy," Journal of Experimental Medicine, Dec. 1, 2014, vol. 211, No. 13, pp. 2617-2633.

Ebadi et al., "Metallothionein-mediated neuroprotection in genetically engineered mouse models of Parkinson's disease," Brain Research: Molecular Brain Research, Mar. 24, 2005, vol. 134, No. 1, pp. 67-75.

Eichler et al., "Hematopoietic Stem-Cell Gene Therapy for Cerebral Adrenoleukodystrophy," The New England Journal of Medicine, Oct. 26, 2017, vol. 377, No. 17, pp. 1630-1638.

Engelen et al., "X-linked adrenoleukodystrophy (X-ALD): clinical presentation and guidelines for diagnosis, follow-up and management," Orphanet Journal of Rare Diseases, 2012, vol. 7, Article No. 51, pp. 1-14.

Escolar et al., "Transplantation of Umbilical-Cord Blood in Babies with Infantile Krabbe's Disease," The New England Journal of Medicine, May 19, 2005, vol. 352, No. 20, pp. 2069-2081.

Filippon et al., "Oxidative stress in patients with mucopolysaccharidosis type II before and during enzyme replacement therapy," Molecular Genetics and Metabolism, 2011, vol. 103, No. 2, pp. 121-127.

Futerman et al., "The Cell Biology of Lysosomal Storage Disorders," Nature Reviews: Molecular Cell Biology, Jul. 2004, vol. 5, No. 7, pp. 554-565.

Hennecke et al., "RNA biomarkers of Parkinson's disease: developing tools for novel therapies," Biomarkers in Medicine, 2008, vol. 2, No. 1, pp. 41-53.

Hidalgo et al., "Expression of Metallothionein-I, -II, and -III in Alzheimer Disease and Animal Models of Neuroinflammation," Experimental Biology and Medicine (Maywood, NJ), Oct. 2006, vol. 231, No. 9, pp. 1450-1458.

Ito et al., "The Potential Roles of Metallothionein as a Therapeutic Target for Cerebral Ischemia and Retinal Diseases," Current Pharmaceutical Biotechnology, 2013, vol. 14, No. 4, pp. 400-407.

Kemp et al., "ABCD1 Mutations and the X-linked Adrenoleukodystrophy Mutation Database: Role in Diagnosis and Clinical Correlations," Human Mutation, 2001, vol. 18, No. 6, pp. 499-515.

(56) References Cited

OTHER PUBLICATIONS

Kemper et al., "Newborn screening for X-linked adrenoleukodystrophy: evidence summary and advisory committee recommendation," Genetics in Medicine, Jan. 2017, vol. 19, No. 1, pp. 121-126.
Kimura et al., "Function of Metallothionein in Gene Expression and Signal Transduction: Newly Found Protective Role of Metallothionein," Journal of Health Science, 2008, vol. 54, No. 3, pp. 251-260.
Lin et al., "Mitigation of cerebellar neuropathy in globoid cell leukodystrophy mice by AAV-mediated gene therapy," Gene, 2015, vol. 571, No. 1, pp. 81-90.
Macauley et al., "Cerebellar Pathology and Motor Deficits in the Palmitoyl Protein Thioesterase 1-Deficient Mouse," Experimental Neurology, May 2009, vol. 217, No. 1, pp. 124-135.
Manso et al., "Overexpression of Metallothionein-1 Modulates the Phenotype of the Tg2576 Mouse Model of Alzheimer's Disease," Journal of Alzheimer's Disease, 2016, vol. 51, No. 1, pp. 81-95.
Miller et al., "Outcomes after allogeneic hematopoietic cell transplantation for childhood cerebral adrenoleukodystrophy: the largest single-institution cohort report," Blood, Aug. 18, 2011, vol. 118, No. 7, pp. 1971-1978.
Moser, Hugo W., "Adrenoleukodystrophy: phenotype, genetics, pathogenesis and therapy," Brain, Aug. 1997, vol. 120, No. 8, pp. 1485-1508.
Musolino et al., "Hematopoietic Stem Cell Transplantation in the Leukodystrophies: A Systematic Review of the Literature," Neuropediatrics, Jun. 2014, vol. 45, No. 3, pp. 169-174.
Nakao et al., "Atypical expression of circadian clock genes in denervated mouse skeletal muscle," Chronobiology International, 2015, vol. 32, No. 4, pp. 486-496.
Nicaise et al., "A Microglial Hypothesis of Globoid Cell Leukodystrophy Pathology," Journal of Neuroscience Research, Nov. 2016, vol. 94, No. 11, pp. 1049-1061.
Pachiappan et al., "Glial inflammation and neurodegeneration induced by candoxin, a novel neurotoxin from Bungarus candidus venom: global gene expression analysis using microarray," Toxicon, Dec. 15, 2005, vol. 46, No. 8, pp. 883-899.
Palmiter et al., "Distal Regulatory Elements from the Mouse Metallothionein Locus Stimulate Gene Expression in Transgenic Mice," Molecular and Cellular Biology, Sep. 1993, vol. 13, No. 9, pp. 5266-5275.
Perego et al., "Temporal pattern of expression and colocalization of microglia/macrophage phenotype markers following brain ischemic injury in mice," Journal of Neuroinflammation, 2011, vol. 8, Article No. 174, pp. 1-19.
Platt, Frances M., "Sphingolipid lysosomal storage disorders," Nature, Jun. 5, 2014, vol. 510, pp. 68-75.
Qi et al., "Myricitrin Modulates NADPH Oxidase-Dependent ROS Production to Inhibit Endotoxin-Mediated Inflammation by Blocking the JAK/STAT1 and NOX2/p47phox Pathways," Oxidative Medicine and Cellular Longevity, Jun. 20, 2017, vol. 2017, Article ID 9738745, pp. 1-20.
Rojo et al., "Redox Control of Microglial Function: Molecular Mechanisms and Functional Significance," Antioxidants & Redox Signaling, 2014, vol. 21, No. 12, pp. 1766-1801.
Settembre et al., "Signals for the lysosome: a control center for cellular clearance and energy metabolism," Nature Reviews: Molecular Cell Biology, May 2013, vol. 14, No. 5, pp. 283-296.
Sharma et al., "Biomarkers in Parkinson's disease (recent update)," Neurochemistry International, 2013, vol. 63, No. 3, pp. 201-229.
Tokuda et al., "Overexpression of metallothionein-I, a copper-regulating protein, attenuates intracellular copper dyshomeostasis and extends lifespan in a mouse model of amyotrophic lateral sclerosis caused by mutant superoxide dismutase-1," Human Molecular Genetics, 2014, vol. 23, No. 5, pp. 1271-1285.
Vela et al., "Induction of metallothionein in astrocytes and microglia in the spinal cord from the myelin-deficient jimpy mouse," Brain Research, 1997, vol. 767, No. 2, pp. 345-355.
Villani et al., "Cytokines, Neurotrophins, and Oxidative Stress in Brain Disease From Mucopolysaccharidosis IIIB," Journal of Neuroscience Research, 2007, vol. 85, No. 3, pp. 612-622.
Wang et al., "Metalliothionein Inhibits Doxorubicin-Induced Mitochondrial Cytochrome c Release and Caspase-3 Activation in Cardiomyocytes," The Journal of Pharmacology and Experimental Therapeutics, 2001, vol. 298, No. 2, pp. 461-468.
West et al., "Metallothionein in the central nervous system: roles in protection, regeneration and cognition," Neurotoxicology, May 2008, vol. 29, No. 3, pp. 488-502.
Wiesinger et al., "The genetic landscape of X-linked adrenoleukodystrophy: inheritance, mutations, modifier genes, and diagnosis," The Application of Clinical Genetics, 2015, vol. 8, pp. 109-121.
Yu et al., "Metallothionein III is reduced in Alzheimer's disease," Brain Research, Mar. 9, 2001, vol. 894, No. 1, pp. 37-45.
Extended European Search Report issued in European Patent Application No. 18741761.3, dated Jun. 19, 2020 (9 pages).
Extended European Search Report issued in European Patent Application No. 18741510.4, dated Nov. 18, 2020 (10 pages).
International Search Report and Written Opinion issued in International Patent Application No. PCT/US2018/013908, dated Jun. 14, 2018 (10 pages).
International Search Report and Written Opinion issued in International Patent Application No. PCT/US2018/013909, dated May 8, 2018 (11 pages).
International Search Report and Written Opinion issued in International Patent Application No. PCT/US20/53824, dated Mar. 22, 2021 (21 pages).
International Search Report and Written Opinion issued in International Patent Application No. PCT/US20/53826, dated Feb. 9, 2021 (18 pages).
Extended European Search Report issued in corresponding European Patent Applicaiton No. 17860210.8, dated Jun. 30, 2020 (13 pages).
Ajami et al., "Infiltrating monocytes trigger EAE progression, but do not contribute to the resident microglia pool," Nature Neuroscience, Sep. 2011, vol. 14, No. 9, pp. 1142-1149.
Ajami et al., "Local self-renewal can sustain CNS microglia maintenance and function throughout adult life," Nature Neuroscience, Dec. 2007, vol. 10, No. 12, pp. 1538-1543.
Aubourg et al., "Reversal of Early Neurologic and Neuroradiologic Manifestations of X-linked Adrenoleukodystrophy by Bone Marrow Transplantation," The New England Journal of Medicine, Jun. 28, 1990, vol. 322, No. 26, pp. 1860-1866.
Banati et al., "Positron emission tomography and functional characterization of a complete PBR/TSPO knockout," Nature Communications, 2014, vol. 5, Article No. 5452, pp. 1-12.
Bennett et al., "New tools for studying microglia in the mouse and human CNS," Proceedings of the National Academy of Sciences of the United States of America, Feb. 16, 2016, vol. 113, pp. E1738-E1746.
Biffi et al., "Correction of metachromatic leukodystrophy in the mouse model by transplantation of genetically modified hematopoietic stem cells," The Journal of Clinical Investigation, Apr. 2004, vol. 113, No. 8, pp. 1118-1129.
Biffi et al., "Gene therapy of metachromatic leukodystrophy reverses neurological damage and deficits in mice," The Journal of Clinical Investigation, Nov. 2006, vol. 116, No. 11, pp. 3070-3082.
Butovsky et al., "Identification of a Unique TGF-β Dependent Molecular and Functional Signature in Microglia," Nature Neuroscience, Jan. 2014, vol. 17, No. 1, pp. 131-143.
Capotondo et al., "Brain conditioning is instrumental for successful microglia reconstitution following hematopoietic stem cell transplantation," Proceedings of the National Academy of Sciences of the United States of America, Sep. 11, 2012, vol. 109, No. 37, pp. 15018-15023.
Cartier et al., "Hematopoietic Stem Cell Gene Therapy with a Lentiviral Vector in X-Linked Adrenoleukodystrophy," Science, Nov. 6, 2009, vol. 326, pp. 818-823.

(56) References Cited

OTHER PUBLICATIONS

Cesani et al., "Characterization of New Arylsulfatase A Gene Mutations Reinforces Genotype-Phenotype Correlation in Metachromatic Leukodystrophy," Human Mutation, 2009, vol. 30, pp. E936-E945.
Chiu et al., "A Neurodegeneration-Specific Gene-Expression Signature of Acutely Isolated Microglia from an Amyotrophic Lateral Sclerosis Mouse Model," Cell Reports, Jul. 25, 2013, vol. 4, pp. 385-401.
Colonna et al., "Microglia Function in the Central Nervous System During Health and Neurodegeneration," Annual Review of Immunology, 2017, vol. 35, pp. 441-468.
Dar et al., "Mutual, reciprocal SDF-1/CXCR4 interactions between hematopoietic and bone marrow stromal cells regulate human stem cell migration and development in NOD/SCID chimeric mice," Experimental Hematology, 2006, vol. 34, pp. 967-975.
Eichler et al., "Is Microglial Apoptosis an Early Pathogenic Change in Cerebral X-Linked Adrenoleukodystrophy?" Annals of Neurology, Jun. 2008, vol. 63, No. 6, pp. 729-742.
Elmore et al., "Colony-Stimulating Factor 1 Receptor Signaling Is Necessary for Microglia Viability, Unmasking a Microglia Progenitor Cell in the Adult Brain," Neuron, Apr. 16, 2014, vol. 82, pp. 380-397.
Gazit et al., "Fgd5 identifies hematopoietic stem cells in the murine bone marrow," The Journal of Experimental Medicine, 2014, vol. 211, No. 7, pp. 1315-1331.
Gentner et al., "Identification of Hematopoietic Stem Cell-Specific miRNAs Enables Gene Therapy of Globoid Cell Leukodystrophy," Science Translational Medicine, Nov. 17, 2010, vol. 2, Iss. 58, 58ra84, pp. 1-11, supplementary pp. 1-22.
Ginhoux et al., "Fate Mapping Analysis Reveals That Adult Microglia Derive from Primitive Macrophages," Science, Nov. 5, 2010, vol. 330, No. 6005, pp. 841-845.
Gosselin et al., "Environment Drives Selection and Function of Enhancers Controlling Tissue-Specific Macrophage Identities," Cell, Dec. 4, 2014, vol. 159, pp. 1327-1340.
Grommes et al., "Regulation of Microglial Phagocytosis and Inflammatory Gene Expression by Gas6 Acting on the Axl/Mer Family of Tyrosine Kinases," Journal of Neuroimmune Pharmacology, Jun. 2008, vol. 3, No. 2, pp. 130-140.
Hickman et al., "The Microglial Sensome Revealed by Direct RNA Sequencing," Nature Neuroscience, Dec. 2013, vol. 16, No. 12, pp. 1896-1905.
Jeyakumar et al., "Central nervous system inflammation is a hallmark of pathogenesis in mouse models of GM1 and GM2 gangliosidosis," Brain, 2003, vol. 126, pp. 974-987.
Matcovitch-Natan et al., "Microglia development follows a stepwise program to regulate brain homeostasis," Science, Aug. 19, 2016, vol. 353, Iss. 6301, p. 789, aad8670-1-aad8670-12.
Matzner et al., "Enzyme replacement improves nervous system pathology and function in a mouse model for metachromatic leukodystrophy," Human Molecular Genetics, 2005, vol. 14, No. 9, pp. 1139-1152.
Mildner et al., "Microglia in the adult brain arise from Ly-6ChiCCR2+ monocytes only under defined host conditions," Nature Neuroscience, Dec. 2007, vol. 10, No. 12, pp. 1544-1553.
Miyamoto et al., "Microglia and synapse interactions: fine tuning neural circuits and candidate molecules," Frontiers in Cellular Neuroscience, May 15, 2013, vol. 7, Article No. 70, pp. 1-6.
Ohmi et al., "Activated microglia in cortex of mouse models of mucopolysaccharidoses I and IIIB," Proceedings of the National Academy of Sciences of the United States of America, Feb. 18, 2003, vol. 100, No. 4, pp. 1902-1907.
Peviani et al., "Unraveling the Complexity of Amyotrophic Lateral Sclerosis: Recent Advances from the Transgenic Mutant SOD1 Mice," CNS & Neurological Disorders—Drug Targets, 2010, vol. 9, No. 4, pp. 491-503.
Rettig et al., "Mobilization of hematopoietic stem and progenitor cells using inhibitors of CXCR4 and VLA-4," Leukemia, 2012, vol. 26, pp. 34-53.
Simard et al., "Bone Marrow-Derived Microglia Play a Critical Role in Restricting Senile Plaque Formation in Alzheimer's Disease," Neuron, Feb. 16, 2006, vol. 49, pp. 489-502.
Subramanian et al., "Gene set enrichment analysis: A knowledge-based approach for interpreting genome-wide expression profiles," Proceedings of the National Academy of Sciences of the United States of America, Oct. 25, 2005, vol. 102, No. 43, pp. 15545-15550.
Sugiyama et al., "Maintenance of the Hematopoietic Stem Cell Pool by CXCL12-CXCR4 Chemokine Signaling in Bone Marrow Stromal Cell Niches," Immunity, Dec. 2006, vol. 25, pp. 977-988.
Tay et al., "Microglia across the lifespan: from origin to function in brain development, plasticity and cognition," The Journal of Physiology, 2017, vol. 595, No. 6, pp. 1929-1945.
Turner et al., "Evidence of widespread cerebral microglial activation in amyotrophic lateral sclerosis: an [11C](R)-PK11195 positron emission tomography study," Neurobiology of Disease, 2004, vol. 15, pp. 601-609.
Visigalli et al., "Gene therapy augments the efficacy of hematopoietic cell transplantation and fully corrects mucopolysaccharidosis type I phenotype in the mouse model," Blood, Dec. 9, 2010, vol. 116, No. 24, pp. 5130-5139.
Visigalli et al., "Monitoring disease evolution and treatment response in lysosomal disorders by the peripheral benzodiazepine receptor ligand PK11195," Neurobiology of Disease, 2009, vol. 34, pp. 51-62.
Wada et al., "Microglial activation precedes acute neurodegeneration in Sandhoff disease and is suppressed by bone marrow transplantation," Proceedings of the National Academy of Sciences of the United States of America, Sep. 26, 2000, vol. 97, No. 20, pp. 10954-10959.
Wang et al., "Translocator protein (Tspo) gene promoter-driven green fluorescent protein synthesis in transgenic mice: an in vivo model to study Tspo transcription," Cell and Tissue Research, Nov. 2012, vol. 350, No. 2, pp. 261-275.
Wilkinson et al., "Busulfan Conditioning Enhances Engraftment of Hematopoietic Donor-derived Cells in the Brain Compared With Irradiation," Molecular Therapy, Apr. 2013, vol. 21, No. 4, pp. 868-876.
Layre et al., "Novel composite core-shell nanoparticles as busulfan carriers," Journal of Controlled Release, 2006, vol. 111, No. 3, pp. 271-280.
Office Action dated Oct. 22, 2021 in corresponding Japanese Patent Application No. 2019-541686 (4 pages).
English translation of the Office Action dated Oct. 22, 2021 in corresponding Japanese Patent Application No. 2019-541686 (6 pages).
Biffi et al., "Gene therapy for leukodystrophies," Human Molecular Genetics, 2011, vol. 20, No. R1, pp. R42-R53.
Cavalca et al., "Metallothioneins are neuroprotective agents in lysosomal storage disorders," Annals of Neurology, Feb. 2018, vol. 83, No. 2, pp. 418-432.
"Lysosomal storage diseases," downloaded from Lysosomal storage disease—Wikipedia on Feb. 22, 2022, pp. 1-8.
Office Action dated Nov. 8, 2021 in corresponding European Patent Application No. 17860210.8 (7 pages).
Sasaki et al., "The level of c-kit expression predicts the activity of murine hematopoietic stem cells," Cytometry Research, 2014, vol. 24, No. 1, pp. 19-23. [English Abstract].
Wang et al., "A Case of Allogenic Hematopoietic Stem Cell transplantation for Treatment of Mucopolysaccharidosis Type I," Journal of Clinical Hematology, Jan. 2008, vol. 21, No. 1, pp. 41-43. [English Summary].
Zhang et al. Scientific and Technical Documentation Press, 2012, p. 10. [English Summary].
Office Action dated May 13, 2022 in corresponding Japanese Patent Application No. 2019-541686 (4 pages).
English translation of the Office Action dated May 13, 2022 in corresponding Japanese Patent Application No. 2019-541686 (9 pages).
Office Action dated Sep. 26, 2022 in corresponding Japanese Patent Application No. 2019-541686 (4 pages).

(56) References Cited

OTHER PUBLICATIONS

English translation of the Office Action dated Sep. 26, 2022 in corresponding Japanese Patent Application No. 2019-541686 (8 pages).
Office Action and Search Report dated Nov. 14, 2022 in corresponding Chinese Patent Application No. 201780077815.1 (20 pages).
English translation of the Office Action and Search Report dated Nov. 14, 2022 in corresponding Chinese Patent Application No. 201780077815.1 (21 pages).

* cited by examiner

H

I

A-2

GCTAGCAAGAAAACAACAGTTTTAAATATTAACTTTAGGGCCAGTAAGACGGCTCTGTG
GGTAAGGGTGCTGCTACTAAGCCAGAAACCCTGAATTTGGTCCTTGGAACCTACATGAT
GGGAGGAGAAACCACATCTGGCAAGCTCTCCACTGACCTCATGTACAAAATAAATGAAT
GTTACAAAAGGTAATTAAAGAATATCACTGATCTCTTCAGGAGGTAGGACAGTGGGGT
TCTGAGATAAAAATGGGCAGTGATTGACAGCAAACGGCTGGGCAGAATTGAAACCCTCAG
TGGAGTCCAGAGAAACCACTGGGGGAGGGGAGGACTAAAGAAGGGAAACAGAAGAAC
TAAGCAAGAACAGAGCGAGAAGAGCAACACGGGAAGTCCAGGGCCTTGAGTGACAGGC
ATTCCAGAAGAGAAGTGAGGAAACGAGAGAAACTGTTAAAAAAAAACTGTTAAAAAAAATT
CAGGTCTGAAAGTAACAATGAGGCCTTCCACACTGTCAGGATCATGGGAAGCCAGGCATG
ATGGTGCATGTCTGTATCCCCAGCACTTGAGAAGTCAGGATCATGGGTTCAAAGCCAGCC
TGGATTATACAGGAGACTCCAAAAATAAAGATTAACAAAAATGGGAGCTGGAGAAATGG

SEQUENCE LISTING

<160> NUMBER OF SEQ ID NOS: 3

<210> SEQ ID NO 1
<211> LENGTH: 1462
<212> TYPE: PRT
<213> ORGANISM: Homo sapiens

<400> SEQUENCE: 1

Met Phe Arg Gly Pro Lys Pro Pro Ile Ala Pro Lys Pro Arg Leu Thr
 1               5                  10                  15

Ala Pro Asn Glu Trp Arg Ala Ser Val Tyr Leu Asn Asp Ser Leu Asn
             20                  25                  30

Lys Cys Ser Asn Gly Arg Leu Pro Cys Val Asp Arg Gly Leu Asp Glu
         35                  40                  45

Gly Pro Arg Ser Ile Pro Lys Cys Ser Glu Ser Glu Thr Asp Glu Asp
     50                  55                  60

Tyr Ile Val Val Pro Arg Val Pro Leu Arg Glu Asp Glu Pro Lys Asp
 65                  70                  75                  80

Glu Gly Ser Val Gly Asn Lys Ala Leu Val Ser Pro Glu Ser Ser Ala
                 85                  90                  95

Glu Glu Glu Glu Glu Arg Glu Glu Gly Glu Ala Cys Gly Leu Glu
            100                 105                 110

Gly Thr Gly Ala Gly Glu Asp Ser Val Ala Pro Ala Ala Pro Gly Ala
        115                 120                 125

Gly Ala Leu Ser Arg Glu Gly Glu Glu Gly Thr Asp Leu Ala Leu Glu
    130                 135                 140

Asp Glu Gly Glu Gly Cys Ala Asp Glu Pro Gly Thr Leu Glu Gln Val
145                 150                 155                 160

Ser Arg Ser Glu Glu Glu Lys Leu Val Gln Pro His Arg Glu Cys
                165                 170                 175

Ser Leu Glu Asp Ser Gly Pro Trp Ala Gly Gly Val Phe Gln Ser
            180                 185                 190

Asp Leu Leu Leu Pro His Ile His Gly Glu Asp Gln Glu Pro Pro Asp
        195                 200                 205

Thr Pro Gly Glu Ala Glu Glu Asp Asp Glu Glu Gly Cys Ala Ser Thr
    210                 215                 220

```
Asp Pro Ala Gly Ala Asp Glu Gly Ser Gly Pro Asp Arg Pro Thr Glu
225                 230                 235                 240

Asp Met Gly Gln Asp Ala Glu Asp Thr Ser Glu Glu Pro Pro Glu Lys
            245                 250                 255

Glu Glu Leu Ala Gly Val Gln Glu Ala Glu Thr Ala Thr Asp Cys Pro
            260                 265                 270

Glu Val Leu Glu Glu Gly Cys Glu Glu Ala Thr Gly Val Thr Gly Gly
            275                 280                 285

Glu Gln Val Asp Leu Ser Glu Pro Pro Asp His Glu Lys Lys Thr Asn
        290                 295                 300

Gln Glu Val Ala Ala Ala Thr Leu Glu Asp His Ala Gln Asp Glu Ser
305                 310                 315                 320

Ala Glu Glu Ser Cys Gln Ile Val Pro Phe Glu Asn Asp Cys Met Glu
                325                 330                 335

Asp Phe Val Thr Ser Leu Thr Gly Ser Pro Tyr Glu Phe Phe Pro Thr
            340                 345                 350

Glu Ser Thr Ser Phe Cys Ser Glu Ser Cys Ser Pro Leu Ser Glu Ser
        355                 360                 365

Ala Lys Gly Leu Glu Ser Glu Gln Ala Pro Lys Leu Gly Leu Arg Ala
    370                 375                 380

Glu Glu Asn Pro Met Val Gly Ala Leu Cys Gly Gln Cys Gly Ser Leu
385                 390                 395                 400

Gln Gly Gly Ala Ala Glu Gly Pro Ala Ala Pro Asp Val Val Val Val
                405                 410                 415

Leu Glu Glu Glu Ala Leu Asp Asp Ala Leu Ala Asn Pro Tyr Val Met
            420                 425                 430

Gly Val Gly Leu Pro Gly Gln Ala Ala Pro Gly Glu Gly Gly Gln Ala
        435                 440                 445

Ala Ser Asp Ala Leu Gly Gly Tyr Gly Ser Lys Glu Glu Leu Asn Cys
450                 455                 460

Glu Ala Glu Gly Gly Leu Val Pro Ala Asp Arg Lys Asn Thr Ser Thr
465                 470                 475                 480

Arg Val Arg Pro His Ser Gly Lys Val Ala Gly Tyr Val Pro Glu Thr
            485                 490                 495

Val Pro Glu Glu Thr Gly Pro Glu Ala Gly Ser Ser Ala Pro Gly Ile
        500                 505                 510

Gly Gly Ala Ala Glu Glu Val Gly Lys Thr Leu Leu Ser Leu Glu Gly
    515                 520                 525

Lys Pro Leu Glu Ala Ser Arg Ala Leu Pro Ala Lys Pro Arg Ala Phe
    530                 535                 540

Thr Leu Tyr Pro Arg Ser Phe Ser Val Glu Gly Arg Glu Ile Pro Val
545                 550                 555                 560

Ser Val Tyr Gln Glu Pro Glu Gly Ser Gly Leu Asp Asp His Arg Ile
            565                 570                 575

Lys Arg Lys Glu Asp Asn Leu Ser Leu Ser Cys Val Ile Gly Ser Ser
        580                 585                 590

Gly Ser Phe Ser Gln Arg Asn His Leu Pro Ser Ser Gly Thr Ser Thr
    595                 600                 605

Pro Ser Ser Met Val Asp Ile Pro Pro Phe Asp Leu Ala Cys Ile
    610                 615                 620

Thr Lys Lys Pro Ile Thr Lys Ser Ser Pro Ser Leu Leu Ile Glu Ser
625                 630                 635                 640
```

-continued

```
Asp Ser Pro Asp Lys Tyr Lys Lys Lys Ser Ser Phe Lys Arg Phe
                645                 650                 655

Leu Ala Leu Thr Phe Lys Lys Thr Glu Asn Lys Leu His Val Asp
            660                 665                 670

Val Asn Val Ser Ser Ser Arg Ser Ser Ser Glu Ser Ser Tyr His Gly
                675                 680                 685

Pro Ser Arg Ile Leu Glu Val Asp Arg Arg Ser Leu Ser Asn Ser Pro
        690                 695                 700

Gln Leu Lys Ser Arg Thr Gly Lys Leu Arg Ala Ser Glu Ser Pro Ser
705                 710                 715                 720

Ser Leu Ile Phe Tyr Arg Asp Gly Lys Arg Lys Gly Val Pro Phe Ser
                725                 730                 735

Arg Thr Val Ser Arg Val Glu Ser Phe Glu Asp Arg Ser Arg Pro Pro
                740                 745                 750

Phe Leu Pro Leu Pro Leu Thr Lys Pro Arg Ser Ile Ser Phe Pro Ser
            755                 760                 765

Ala Asp Thr Ser Asp Tyr Glu Asn Ile Pro Ala Met Asn Ser Asp Tyr
        770                 775                 780

Glu Asn Ile Gln Ile Pro Pro Arg Arg Pro Ala Arg Ala Gly Ala Phe
785                 790                 795                 800

Thr Lys Leu Phe Glu Asp Gln Ser Arg Ala Leu Ser Thr Ala Asn Glu
                805                 810                 815

Asn Asp Gly Tyr Val Asp Met Ser Ser Phe Asn Ala Phe Glu Ser Lys
            820                 825                 830

Gln Gln Ser Ala Asp Gln Asp Ala Glu Ser Ala Tyr Thr Glu Pro Tyr
        835                 840                 845

Lys Val Cys Pro Ile Ser Ser Ala Ala Pro Lys Glu Asp Leu Thr Ser
    850                 855                 860

Asp Glu Glu Gln Arg Ser Ser Glu Glu Asp Ser Ala Ser Arg Asp
865                 870                 875                 880

Pro Ser Val Thr His Lys Val Glu Gly Gln Ser Arg Ala Leu Val Ile
                885                 890                 895

Ala Gln Glu Leu Leu Ser Ser Glu Lys Ala Tyr Val Glu Met Leu Gln
            900                 905                 910

His Leu Asn Leu Asp Phe His Gly Ala Val Met Arg Ala Leu Asp Asp
        915                 920                 925

Met Asp His Glu Gly Arg Asp Thr Leu Ala Arg Glu Glu Leu Arg Gln
    930                 935                 940

Gly Leu Ser Glu Leu Pro Ala Ile His Asp Leu His Gln Gly Ile Leu
945                 950                 955                 960

Glu Glu Leu Glu Glu Arg Leu Ser Asn Trp Glu Ser Gln Gln Lys Val
                965                 970                 975

Ala Asp Val Phe Leu Ala Arg Glu Gln Gly Phe Asp His His Ala Thr
            980                 985                 990

His Ile Leu Gln Phe Asp Arg Tyr Leu Gly Leu Leu Ser Glu Asn Cys
        995                 1000                1005

Leu His Ser Pro Arg Leu Ala Ala Val Arg Glu Phe Glu Gln
    1010                1015                1020

Ser Val Gln Gly Gly Ser Gln Thr Ala Lys His Arg Leu Leu Arg
    1025                1030                1035

Val Val Gln Arg Leu Phe Gln Tyr Gln Val Leu Leu Thr Asp Tyr
    1040                1045                1050

Leu Asn Asn Leu Cys Pro Asp Ser Ala Glu Tyr Asp Asn Thr Gln
```

```
                1055                1060                1065
Gly Ala Leu Ser Leu Ile Ser Lys Val Thr Asp Arg Ala Asn Asp
            1070                1075                1080
Ser Met Glu Gln Gly Glu Asn Leu Gln Lys Leu Val His Ile Glu
            1085                1090                1095
His Ser Val Arg Gly Gln Gly Asp Leu Leu Gln Pro Gly Arg Glu
            1100                1105                1110
Phe Leu Lys Glu Gly Thr Leu Met Lys Val Thr Gly Lys Asn Arg
            1115                1120                1125
Arg Pro Arg His Leu Phe Leu Met Asn Asp Val Leu Leu Tyr Thr
            1130                1135                1140
Tyr Pro Gln Lys Asp Gly Lys Tyr Arg Leu Lys Asn Thr Leu Ala
            1145                1150                1155
Val Ala Asn Met Lys Val Ser Arg Pro Val Met Glu Lys Val Pro
            1160                1165                1170
Tyr Ala Leu Lys Ile Glu Thr Ser Glu Ser Cys Leu Met Leu Ser
            1175                1180                1185
Ala Ser Ser Cys Ala Glu Arg Asp Glu Trp Tyr Gly Cys Leu Ser
            1190                1195                1200
Arg Ala Leu Pro Glu Asp Tyr Lys Ala Gln Ala Leu Ala Ala Phe
            1205                1210                1215
His His Ser Val Glu Ile Arg Glu Arg Leu Gly Val Ser Leu Gly
            1220                1225                1230
Glu Arg Pro Pro Thr Leu Val Pro Val Thr His Val Met Met Cys
            1235                1240                1245
Met Asn Cys Gly Cys Asp Phe Ser Leu Thr Leu Arg Arg His His
            1250                1255                1260
Cys His Ala Cys Gly Lys Ile Val Cys Arg Asn Cys Ser Arg Asn
            1265                1270                1275
Lys Tyr Pro Leu Lys Tyr Leu Lys Asp Arg Met Ala Lys Val Cys
            1280                1285                1290
Asp Gly Cys Phe Gly Glu Leu Lys Lys Arg Gly Arg Ala Val Pro
            1295                1300                1305
Gly Leu Met Arg Glu Arg Pro Val Ser Met Ser Phe Pro Leu Ser
            1310                1315                1320
Ser Pro Arg Phe Ser Gly Ser Ala Phe Ser Ser Val Phe Gln Ser
            1325                1330                1335
Ile Asn Pro Ser Thr Phe Lys Lys Gln Lys Lys Val Pro Ser Ala
            1340                1345                1350
Leu Thr Glu Val Ala Ala Ser Gly Glu Gly Ser Ala Ile Ser Gly
            1355                1360                1365
Tyr Leu Ser Arg Cys Lys Arg Gly Lys Arg His Trp Lys Lys Leu
            1370                1375                1380
Trp Phe Val Ile Lys Gly Lys Val Leu Tyr Thr Tyr Met Ala Ser
            1385                1390                1395
Glu Asp Lys Val Ala Leu Glu Ser Met Pro Leu Leu Gly Phe Thr
            1400                1405                1410
Ile Ala Pro Glu Lys Glu Gly Ser Ser Glu Val Gly Pro Ile
            1415                1420                1425
Phe His Leu Tyr His Lys Lys Thr Leu Phe Tyr Ser Phe Lys Ala
            1430                1435                1440
Glu Asp Thr Asn Ser Ala Gln Arg Trp Ile Glu Ala Met Glu Asp
            1445                1450                1455
```

```
Ala Ser Val Leu
        1460

<210> SEQ ID NO 2
<211> LENGTH: 1514
<212> TYPE: PRT
<213> ORGANISM: Mus sp.

<400> SEQUENCE: 2

Met His Arg Ala Asp Ser Pro Lys Pro Pro Leu Ala Pro Lys Pro Lys
1               5                   10                  15

Val Ala Thr Asn Pro Tyr Ala Pro Ala Ala Lys Phe Pro Pro Ser Gln
            20                  25                  30

Arg Pro Asp Ser Phe Pro Ser Pro Asn Ser Met Ser Arg Gly Pro Lys
        35                  40                  45

Pro Pro Ile Ala Pro Lys Pro Arg Leu Thr Gly Pro Ser Glu Tyr Leu
    50                  55                  60

Asn Asn Ser Leu Gly Lys Cys Ser Asn Gly Arg Leu Leu Cys Glu Asp
65                  70                  75                  80

Arg Gly Leu Tyr Asp Gly His His Ser Thr Leu Asn Cys Leu Glu Leu
                85                  90                  95

Glu Pro Asp Glu Gln Tyr Ile Met Val Pro Arg Ala Pro Gln Lys Glu
            100                 105                 110

Asp Thr Pro Val Asp Gly Ala Thr Glu Pro Gly Phe Glu Gly Glu
        115                 120                 125

Val Gln Glu His Gly Thr Glu Gln Thr Gly Thr Glu Gly Asp Leu Glu
    130                 135                 140

Ala Pro Asp Glu Glu Ala Pro Ser Arg Asp Ser Glu Glu Gly Met Val
145                 150                 155                 160

His Ala Leu Glu Asp Glu Asp Cys Asp His Asp Pro Glu Thr Asp Gly
                165                 170                 175

Thr Pro Thr Ser Pro Asp Glu Gly Ala Pro Ser Arg Asp Ser Glu Glu
            180                 185                 190

Gly Glu Glu Asp Cys Asp Gln Gly Pro Gly Met Glu Glu His Pro Met
        195                 200                 205

Ser Glu Glu Glu Gly Glu Glu Glu Val Lys Glu His Val Tyr Asn
    210                 215                 220

Ser Asp Asn Arg Ala Pro Trp Asp Gly Glu Glu Pro Phe Pro Asn Glu
225                 230                 235                 240

Val Ile Leu Thr His Val Arg Ser Gln Ser Pro Glu Val Pro Cys Trp
                245                 250                 255

Glu Pro Gly Pro Pro Glu Thr Pro Gly Glu Ala Glu Glu Asp Cys Glu
            260                 265                 270

Asp Ile Cys Asn Asn Thr Glu Pro Gly Lys Pro Asn Gln Asp Thr Gly
        275                 280                 285

Gln Asp Thr Glu Asp Ala Gly Met Gly Ser Pro Glu Ser Glu Val Ser
    290                 295                 300

Pro Asp Val Gln Glu Gln Glu Ala Ala Thr Asn Pro Glu Val Phe
305                 310                 315                 320

Glu Glu Asp Ser Ala Asp Ala Ala Glu Gly Asp Gln Ile Glu Gln
                325                 330                 335

Glu Glu Pro Pro Asn Cys Asp Glu Glu Ala Tyr Asn Arg Asp Ala Ala
            340                 345                 350

Ala Ala Thr Met Gln Val Gly Glu Asp Leu Gly Glu Glu Gly Asp His
```

```
            355                 360                 365
Val Gln Glu Asp Pro Ala Glu Glu Ser Cys Gln Ile Ile Pro Phe Glu
370                     375                 380

Ser Asp Ser Val Glu Glu Asp Phe Ser Pro Thr Leu Thr Glu Asn Pro
385                 390                 395                 400

Tyr Glu Ile Phe Pro Thr Glu Ser Thr Ser Phe Cys Asn Asn Thr Tyr
                405                 410                 415

Ser Leu Asp Glu Ser Ala Asn Gly His Glu Pro Val Cys Glu Ile Cys
            420                 425                 430

Val Glu Glu Val Pro Gly Val Gly Pro Pro Leu Asn Gln His Asp Ser
        435                 440                 445

Leu Pro Asp Gly Ser Gly Glu Asp Ser Pro Val Val Pro Asp Val Val
    450                 455                 460

Val Val Pro Glu Asn Glu Gly Pro Val Asp Asp Ala Leu Ser Ser Pro
465                 470                 475                 480

Tyr Val Met Gly Val Gly Leu Leu Ser Leu Gly Glu Gly Ala Gln Ser
                485                 490                 495

Asp Thr Gln Ala Ala Ser Gly Thr Leu Ser Gly Tyr Ser Thr Trp Glu
            500                 505                 510

Glu Gly Asp Ser Glu Gly Gly Gln Val Pro Val Asp Arg Lys Asn Ile
        515                 520                 525

Ala Thr Arg Ala Arg Pro His Ser Gly Lys Val Ala Gly His Val Pro
    530                 535                 540

Glu Thr Val Leu Glu Glu Thr Gly Pro Glu Thr Cys Ser Ser Gly Met
545                 550                 555                 560

Gly Ile Arg Asp Thr Ser Asp Glu Val Arg Lys Ile Gly Ile Leu Pro
                565                 570                 575

Glu Gly Lys Pro Pro Glu Cys Val Arg Ala Leu Pro Ala Lys Pro Arg
            580                 585                 590

Ala Phe Thr Leu Tyr Pro Arg Ser Phe Ser Val Glu Gly Arg Glu Ser
        595                 600                 605

Pro Leu Ser Met Phe Arg Glu Pro Glu Gly Ala Gly Leu Asp Ser His
    610                 615                 620

Arg Val Arg Arg Lys Glu Asp Asn Leu Ser Leu Pro Gly Ala Ile Gly
625                 630                 635                 640

Ser Ser Gly Ser Phe Ser Gln Arg Ser His Leu Pro Ser Ser Gly Thr
                645                 650                 655

Ser Thr Pro Ser Ser Val Val Asp Ile Pro Pro Pro Phe Asp Leu Ala
            660                 665                 670

Cys Ile Thr Lys Lys Pro Ile Thr Lys Ser Ser Pro Ser Leu Leu Ile
        675                 680                 685

Asp Gly Asp Thr Leu Glu Lys Ala Ser Lys Lys Lys Ser Ser Ser Phe
    690                 695                 700

Lys Arg Phe Leu Glu Leu Thr Phe Arg Lys Thr Glu Ser Lys Val
705                 710                 715                 720

His Val Asp Met Asn Leu Ser Ser Arg Ser Ser Glu Ser Ser
                725                 730                 735

Tyr His Gly Pro Ala Arg Val Leu Glu Leu Asp Arg Arg Ser Leu Ser
            740                 745                 750

Asn Ser Pro Gln Leu Lys Cys Arg Thr Gly Lys Leu Arg Ala Ser Asp
        755                 760                 765

Ser Pro Ala Ala Leu Ile Phe Tyr Arg Asp Ser Lys Arg Lys Gly Val
    770                 775                 780
```

-continued

```
Pro Phe Ser Arg Thr Val Ser Arg Val Glu Ser Phe Glu Asp Arg Ser
785                 790                 795                 800

Arg Pro Pro Phe Leu Pro Leu Pro Leu Thr Lys Pro Arg Ser Ile Ser
                805                 810                 815

Phe Pro Asn Ala Asp Thr Ser Asp Tyr Glu Asn Ile Pro Ala Met Asn
            820                 825                 830

Ser Asp Tyr Glu Asn Ile Gln Ile Pro Pro Arg Arg Pro Val Arg Thr
        835                 840                 845

Gly Thr Phe Thr Lys Leu Phe Glu Glu Gln Ser Arg Ala Leu Ser Thr
    850                 855                 860

Ala Asn Glu Asn Asp Gly Tyr Val Asp Met Ser Ser Phe Asn Ala Phe
865                 870                 875                 880

Glu Ser Lys Gln Gln Ser Ser Glu Gln Glu Ala Glu Ser Ala Tyr Thr
                885                 890                 895

Glu Pro Tyr Lys Val Cys Pro Ile Ser Ala Ala Pro Arg Glu Asp Leu
            900                 905                 910

Thr Ser Asp Glu Glu Gln Gly Ser Ser Glu Glu Glu Asp Ser Ala Ser
        915                 920                 925

Arg Asp Pro Ser Leu Ser His Lys Gly Glu Gly Gln Ser Arg Ala Leu
    930                 935                 940

Val Ile Ala Gln Glu Leu Leu Ser Ser Glu Lys Ala Tyr Val Gln Met
945                 950                 955                 960

Leu Gln His Leu Ser Leu Asp Phe His Gly Ala Val Leu Arg Ala Leu
                965                 970                 975

Glu Asn Val Glu Gln Glu Gly Arg Glu Pro Leu Ala Gln Glu Leu
            980                 985                 990

Arg Gln Gly Leu Arg Glu Leu Pro  Ala Ile Cys Asp Leu  His Gln Gly
        995                 1000                1005

Ile Leu  Glu Ser Leu Glu Gln  Arg Leu Gly Asp Cys  Gly Glu Gly
    1010                1015                1020

Gln Pro  Gln Val Ala Asp Ile  Phe Leu Ala Gln Glu   Gln Glu Phe
    1025                1030                1035

Glu His  His Ala Ala His Ile  Leu Gln Phe Asp Arg   Tyr Leu Gly
    1040                1045                1050

Leu Leu  Ala Glu Ser Cys Leu  Leu Ser Pro Arg Leu   Ala Thr Thr
    1055                1060                1065

Val Arg  Glu Phe Glu Gln Ser  Ser Gln Gly Gly Gly   Gln Ser Met
    1070                1075                1080

Lys His  Arg Met Leu Arg Val  Val Gln Arg Leu Phe   Gln Tyr Gln
    1085                1090                1095

Val Leu  Leu Thr Asp Tyr Leu  Asn Asn Leu Cys Pro   Asp Ser Ala
    1100                1105                1110

Glu Tyr  Asp Asn Thr Gln Ser  Ala Leu Thr Leu Ile   Ser Lys Val
    1115                1120                1125

Thr Asp  Arg Ala Asn Glu Ser  Met Glu Gln Gly Glu   Asn Leu Gln
    1130                1135                1140

Lys Leu  Val His Ile Glu Tyr  Ser Val Arg Gly Gln   Gly Asp Leu
    1145                1150                1155

Leu Gln  Pro Gly Arg Glu Phe  Leu Lys Glu Gly Thr   Leu Met Arg
    1160                1165                1170

Val Arg  Gly Lys Ser Arg His  Pro Arg His Leu Phe   Leu Met Asn
    1175                1180                1185
```

| | | | | | | | | | | |
|---|---|---|---|---|---|---|---|---|---|---|
| Asp | Thr | Leu | Leu | Tyr | Thr | His | Pro | Gln | Lys | Asp | Gly | Lys | Tyr | Arg |
| 1190 | | | | | 1195 | | | | | 1200 | | | | |

Leu Lys Ser Ser Leu Pro Val Ala Asn Met Lys Val Ser Arg Pro
1205             1210                1215

Val Met Asp Lys Val Pro Tyr Ala Leu Lys Ile Glu Thr Pro Glu
1220             1225                1230

Ser Cys Leu Thr Leu Ser Ala Ser Ser Cys Ala Glu Arg Asp Glu
1235             1240                1245

Trp His Tyr Cys Leu Ser Arg Ala Leu Pro Glu Asp Tyr Lys Thr
1250             1255                1260

Gln Ala Leu Ala Ala Phe His His Ser Val Glu Ile Arg Glu Arg
1265             1270                1275

Leu Gly Ile Ser Leu Gly Glu Arg Leu Pro Thr Leu Val Pro Val
1280             1285                1290

Thr His Ala Met Met Cys Met Asn Cys Gly Cys Asp Phe Ser Leu
1295             1300                1305

Thr Val Arg Arg His His Cys His Ala Cys Gly Lys Ile Val Cys
1310             1315                1320

Arg Asn Cys Ser Arg Asn Lys Tyr Pro Leu Lys Cys Leu Lys Asn
1325             1330                1335

Arg Met Ala Lys Val Cys Asp Gly Cys Phe Arg Glu Leu Lys Leu
1340             1345                1350

Arg Asn Gly Pro Val Pro Gly Ser Met Arg Glu Arg Pro Val Ser
1355             1360                1365

Met Ser Phe Pro Leu Ser Ser Arg Phe Ser Ser Gly Ser Ala
1370             1375                1380

Leu Ser Ser Val Phe Gln Ser Ile Ser Pro Ser Thr Phe Lys Lys
1385             1390                1395

Gln Lys Lys Val Pro Ser Ala Leu Ser Glu Val Ala Ala Ser Gly
1400             1405                1410

Glu Gly Ser Ala Ile Ser Gly Tyr Leu Ser Arg Cys Lys Ser Gly
1415             1420                1425

Lys Arg Arg Trp Lys Lys Leu Trp Leu Val Ile Lys Gly Lys Val
1430             1435                1440

Leu Tyr Thr Tyr Leu Ala Ser Glu Asp Lys Val Ala Met Glu Ser
1445             1450                1455

Ile Pro Leu Leu Gly Phe Thr Ile Ala Pro Glu Lys Glu Glu Gly
1460             1465                1470

Ser Ser Glu Val Gly Pro Val Phe His Leu Tyr His Lys Lys Thr
1475             1480                1485

Leu Phe Tyr Ser Phe Lys Ala Glu Asp Ser Asn Ser Ala Gln Arg
1490             1495                1500

Trp Met Glu Ala Met Glu Asp Ala Ser Val Leu
1505             1510

```
<210> SEQ ID NO 3
<211> LENGTH: 660
<212> TYPE: DNA
<213> ORGANISM: Mus sp.

<400> SEQUENCE: 3
gctagcaaga aaacaacagt ttttaaatat taactttagg gccagtaaga cggctctgtg      60
ggtaagggtg cttgctacta agccagaaac cctgaatttg gtccttggaa cctacatgat     120
gggaggagaa aaccacatct ggcaagctct ccactgacct catgtacaaa ataaatgaat     180
```

```
gttacaaaaa ggtaattaaa agaatatcac tgatctcttc aggaggtagg acagtggggt    240
tctgagataa aaatgggcag tgattgacag caaacggctg ggcagaattg aaaccctcag    300
tggagtccag aagaaaccac tgggggagg gggaggacta aagaagggaa acagaagaac     360
taagcaagaa cagagagcga gaagagcaac acgggaagtc cagggccttg agtgacaggc    420
attccagaaa gagaagtgag gaaacgaaag acgagaaact gttaaaaaaa aaaaaaaatt    480
caggtctgaa aagtaacaat gaggccttcc acactgtcag ggctgtggaa gccaggcatg    540
atggtgcatg tctgtatccc cagcacttga gaagtcagga tcatgggttc aaagccagcc    600
tggattatac aggagactcc aaaaataaag attaaacaaa aatgggagct ggagaaatgg    660
```

COMPOSITIONS AND METHODS FOR TREATING DISEASES AND DISORDERS OF THE CENTRAL NERVOUS SYSTEM

CROSS-REFERENCE TO RELATED APPLICATIONS

This application is the U.S. national phase application, pursuant to 35 U.S.C. § 371, of PCT International Application Ser. No.: PCT/US2017/056774, filed Oct. 16, 2017, designating the United States and published in English, which claims the benefit of the following U.S. Provisional Application No.: 62/408,664, filed Oct. 14, 2016. The entire contents of which are incorporated herein by reference.

STATEMENT OF RIGHTS TO INVENTIONS MADE UNDER FEDERALLY SPONSORED RESEARCH

The work leading to this invention has received funding from the European Union's Seventh Framework Programme (FP7/2007-2013) under grant agreement no and from the Italian Ministry of Health under grant no GR-2011-02347261.

BACKGROUND OF THE INVENTION

Most storage disorders (SDs) with central nervous system (CNS) involvement (neuroSDs) lack an effective and curative treatment and patients eventually succumb to their devastating disease. Frequently, disease onset occurs in very early infancy and is characterized by subtle manifestations, leading to diagnosis in clearly symptomatic if not advanced stage. NeuroSDs are also characterized by a rapid early disease progression, particularly in early onset variants. For these reasons therapeutic approaches that have been applied with some degree of success in pre-symptomatic neuroSD children, including for example, hematopoietic cell transplantation (HCT) in Krabbe disease and adrenoleukodystrophy, or hematopoietic stem cell (HSC) gene therapy (HSC GT) in Metachromatic Leukodystrophy (MLD), are not beneficial for the majority of neuroSD patients, with benefit being associated almost exclusively to procedures applied in pre- or early-symptomatic patients. One of the key reasons for the failure of these HSC-based approaches in ameliorating rapidly progressing SD brain diseases is the slow pace of replacement of resident CNS tissue macrophages/histiocytes and microglia by the transplanted hematopoietic cell progeny, compared to the rapid progression of the primary neurological disease. Indeed, while a rapid reconstitution of visceral organ macrophages by donor-derived cells has been clearly demonstrated following HCT, more limited and slower infiltration of the brain parenchyma by donor cells is supposed to occur. Thus, strategies aiming at enhancing and rendering faster this phenomenon are highly needed. Such strategies also have the potential to be therapeutically relevant for some acquired neurodegenerative conditions of adhulthood, which may benefit from therapeutic molecule delivery across the blood brain barrier through the progeny of the transplanted hematopoietic stem and progenitor cells (HSPCs) and/or modulation of the activated microglia phenotype that characterizes most of these conditions. These disorders, which include for example Amyotrophic Lateral Sclerosis (ALS), Alzheimer's diseases (AD) and Parkinson's Disease (PD) share several common disease/pathogenic mechanisms with neuroLSDs such as neuroinflammation and an active role of microglia. Accordingly, new compositions and methods of treatment are urgently required.

SUMMARY OF THE INVENTION

As described below, the present invention features compositions and methods for the treatment or prevention of a neurological disease or disorder of the central nervous system (e.g., a neurodegenerative storage disorder, acquired neurodegenerative disease, etc.) by means of establishing a CNS myeloid cell/microglia chimerism with either donor derived or engineered cells able to contribute to disease amelioration by different mechanisms, such as protein delivery or regulation of local inflammation or others. The invention provides compositions and methods for one or more of: (i) efficiently engrafting in the CNS cells with or that will acquire microglia features, including cells enriched in microglia reconstitution potential, microglial progenitor cells, for therapeutic purposes in the conditions listed above; (ii) engrafting selectively and exclusively in the CNS genetically modified cells with or that will acquire microglia features, including cells enriched in microglia reconstitution potential, microglial progenitor cells, for therapeutic purposes in the conditions listed above; and (iii) ablating resident myeloid populations, such as cells with proliferation ability, in the brain by CNS-selective methods (these methods may include nanoparticles that target microglia and or microglia progenitors). This methodology could be employed to achieve successful, timely and, in the case of exclusive CNS involvement, selective CNS engraftment of the transplanted cells in the brain and acquisition of myeloid/microglia features for delivery of therapeutic molecules and/or modulation of myeloid/microglia features upon partial renewal of the cell pool.

In one aspect, the invention provides a method of delivering a Hematopoietic Stem Cell (HSC to a subject involving administering the HSC by Intra-cerebral Ventricular Injection (ICV) in combination with ablative conditioning. In another aspect, the invention provides an isolated HSC transformed with a vector expressing a therapeutic polypeptide or polynucleotide, where the HSC is one or more of $CD34^+$, $CD38^-$, and $Fgd5^+$ (e.g., $CD34^+$, $CD38^-$; $CD34^+$, $CD38^-$, and $Fgd5^+$).

In another aspect, the invention provides an isolated Hematopoietic Stem Cell (HSC) transformed with a vector expressing a therapeutic polypeptide or polynucleotide, where the HSC is selected for one or more of $CD34^+$, $CD38^-$, and $Fgd5^+$ (e.g., $CD34^+$, $CD38^-$; $CD34^+$, $CD38^-$, and $Fgd5^+$).

In another aspect, the invention provides an isolated Hematopoietic Stem Cell (HSC) transformed with a vector expressing a therapeutic polypeptide or polynucleotide, where the HSC is one or more of $kit^+$, $Lin^-$, $Sca1^+$, $CD150^+$, $CD48^-$, $Fdg5^+$, $CX3CR1^-$, and $CD11b^-$ (e.g., $kit^+$, $Lin^-$, $Sca1^+$, $CD150$; $kit^+$, $Lin^-$, $Sca1^+$, $CD150^+$, $CD48^-$; $kit^+$, $Lin^-$, $Sca1^+$, $CD150^+$, $CD48^-$, $Fdg5^+$; $kit^+$, $Lin^-$, $Sca1^+$, $CD150^+$, $CD48^-$, $CX3CR1^-$; $kit^+$, $Lin^-$, $Sca1^+$, $CD150^+$, $CD48^-$, $Fdg5^+$, $CX3CR1^-$; and $kit^+$, $Lin^-$, $Sca1^+$, $CD150^+$, $CD48^-$, $Fdg5^+$, $CX3CR1^-$, and $CD11b^-$).

In another aspect, the invention provides a method of treating a subject having or being at increased risk of developing a lysosomal storage disorder or neurodegenerative disease, involving administering a Hematopoietic Stem Cell (HSC) that is one or more of $CD34^+$, $CD38^-$, and $Fgd5^+$ (e.g., $CD34^+$, $CD38^-$; $CD34^+$, $CD38^-$, and $Fgd5^+$), where the HSC is administered intravenously (IV) or by Intra-cerebral Ventricular Injection (ICV) in combination with ablative conditioning.

In another aspect, the invention provides a method of treating a subject having or being at increased risk of developing a lysosomal storage disorder or neurodegenerative disease, involving administering a Hematopoietic Stem Cell (HSC) that is one or more of kit$^+$, Lin$^-$, Sca1$^+$, CD150$^+$, CD48$^-$, Fdg5$^+$, CX3CR1$^-$, and CD11b$^-$ (e.g., kit$^+$, Lin$^-$, Sca1$^+$, CD150; kit$^+$, Lin$^-$, Sca1$^+$, CD150$^+$, CD48$^-$; kit$^+$, Lin$^-$, Sca1$^+$, CD150$^+$, CD48$^-$, Fdg5$^+$; kit$^+$, Lin$^-$, Sca1$^+$, CD150$^+$, CD48$^-$, CX3CR1$^-$; kit$^+$, Lin$^-$, Sca1$^+$, CD150$^+$, CD48$^-$, Fdg5$^+$, CX3CR1V; and kit$^+$, Lin$^-$, Sca1$^+$, CD150$^+$, CD48$^-$, Fdg5$^+$, CX3CR1$^-$, and CD11b$^-$), where the HSC is administered intravenously (IV) or by Intra-cerebral Ventricular Injection (ICV) in combination with ablative conditioning.

In another aspect, the invention provides a method of ablating endogenous microglia and reconstituting the microglia by HSC engraftment in a subject, the method involving administering to the subject a nanoparticle containing an cytotoxic agent The nanoparticles could be combined to one or more capture molecules by covalent binding to its surface, where the capture molecules specifically bind one or more markers expressed on a microglial cell, or progenitor thereof; and administering HSCs to the subject IV or ICV.

In another aspect, the invention provides a method of treating a lysosomal storage disorder in a subject, the method involving administering to the subject a nanoparticle containing an cytotoxic agent and one or more capture molecules covalently linked to the surface of the nanoparticle, where the capture molecules specifically bind one or more markers expressed on a microglial cell, or progenitor thereof; and administering a Hematopoietic Stem Cell (HSC) to the subject intravenously (IV) or by Intra-cerebral Ventricular Injection (ICV), where the HSC expresses a therapeutic polypeptide.

In another aspect, the invention provides a method of treating a neurodegenerative disease in a subject, the method involving administering to the subject a nanoparticle containing an cytotoxic agent and one or more capture molecules covalently linked to the surface of the nanoparticle, where the capture molecules specifically bind one or more markers expressed on a microglial cell, or progenitor thereof; and administering a Hematopoietic Stem Cell (HSC) to the subject intravenously (IV) or by Intra-cerebral Ventricular Injection (ICV), where the HSC expresses a therapeutic polypeptide or polynucleotide.

In another aspect, the invention provides a method for generating microglia chimerism in the brain of a subject independent from extra-CNS hematopoietic tissue chimerism involving transplanting HSPCs ICV and total bone marrow cells IV 0-5 days after busulfan myeloablation.

In another aspect, the invention provides a method for generating in a subject a sustained mixed hematopoietic chimerism in the brain and in the extra-CNS tissues in the short term with exogenous cells transplanted ICV and IV after busulfan myeloablation.

In another aspect, the invention provides a method for achieving regulated expression of exogenous genes within engineered microglia, the method comprising transduction of the hematopoietic equivalents of microglial progenitors by viral vectors encoding the gene of interest under the control of the TSPO promoter.

In another aspect, the invention provides a method for the functional identification of a brain-resident microglial progenitor cell by detecting γH2AX signal, where detecting γH2AX signal indicates the presence of brain-resident microglial progenitor cell.

In another aspect, the invention provides a kit comprising the isolated Hematopoietic Stem Cell (HSC) of claims the nanoparticle according to any aspect delineated herein.

In another aspect, the invention provides a nanoparticle able to target a microglial cell, or progenitor thereof.

In another aspect, the invention provides a method of delivering a nanoparticle to a subject, the method involving administering to the subject a nanoparticle by Intra-cerebral Ventricular Injection (ICV).

In another aspect, the invention provides a method of ablating a microglial cell or progenitor thereof in a subject involving administering to the subject a nanoparticle containing a cytotoxic agent and one or more capture molecules covalently linked to the surface of the nanoparticle, where the capture molecules specifically bind one or more markers expressed on a microglial cell, or progenitor thereof.

In various embodiments of any aspect delineated herein, the Hematopoietic Stem Cell (HSC) (e.g., human) is one or more of CD34$^+$, CD38$^-$, and Fdg5$^+$ (e.g., CD34$^+$, CD38$^-$; CD34$^+$, CD38$^-$, and Fdg5$^+$). In various embodiments of any aspect delineated herein, the Hematopoietic Stem Cell (HSC) (e.g., murine) is one or more of kite, Lin$^-$, Sca1$^+$, CD150$^+$, CD48$^-$, Fdg5$^+$, CX3CR1$^-$, and CD11b$^-$ (e.g., kit$^+$, Lin$^-$, Sca1$^+$, CD150; kit$^+$, Lin$^-$, Sca1$^+$, CD150$^+$, CD48$^-$; kit$^+$, Lin$^-$, Sca1$^+$, CD150$^+$, CD48$^-$, Fdg5$^+$; kit$^+$, Lin$^-$, Sca1$^+$, CD150$^+$, CD48$^-$, CX3CR1$^-$; kit$^+$, Lin$^-$, Sca1$^+$, CD150$^+$, CD48$^-$, Fdg5$^+$, CX3CR1$^-$; and kit$^+$, Lin$^-$, Sca1$^+$, CD150$^+$, CD48$^-$, Fdg5$^+$, CX3CR1V, and CD11b$^-$). In certain embodiments, the human Hematopoietic Stem Cell (HSC) is Fdg5$^+$. In various embodiments of any aspect delineated herein, the Hematopoietic Stem Cell (HSC) is functionally equivalent to a microglial progenitor cell upon transplantation In various embodiments of any aspect delineated herein, the HSC is capable of differentiating into a microglial cell. In various embodiments of any aspect delineated herein, the HSC is capable of reconstituting an ablated microglial cell.

In various embodiments of any aspect delineated herein, the subject has or is at increased risk of developing a lysosomal storage disorder. In various embodiments, the lysosomal storage disorder is selected from Adrenoleukodystrophy, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, globoid leukodystrophy, GM1 gangliosidosis, I-Cell disease/Mucolipidosis II, Infantile Free Sialic Acid Storage Disease/ISSD, Juvenile Hexosaminidase A Deficiency, Infantile neuronal ceroid lipofuscinosis, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease/Glycogen storage disease type II, Pycnodysostosis, Sandhoff disease, Schindler disease, Salla disease/Sialic Acid Storage Disease, Tay-Sachs/GM2 gangliosidosis and Wolman disease. In various embodiments of any aspect delineated herein, the lysosomal enzyme is one or more of α-glucosidase; glucocerebrosidase; β-galactosidase; β-Hexosaminidase A; β-Hexosaminidase B; Acid sphingomyelinase; Galactocerebrosidase; α-galactocerebrosidase; Acid ceramidase; Arylsulfatase A; α-L-lduronidase; lduronate-2-sulfatase; Heparan N-sulfatase; α-N-Acetylglucosaminidase; Acetyl-CoA: α-glucosaminide N-acetyltransferase; N-Acetylglucosamine-6- sulfate sulfatase; N-Acetylgalactosamine-6-sulfate sulfatase; Acid β-galactosidase; Arylsulfatase B; β-Glucuronidase; Acid α-mannosidase; Acid β-mannosidase; Acid α-L-fucosidase; Sialidase; α-N-acetylgalactosaminidase; and palmitoyl protein-thioesterase-1.

In various embodiments of any aspect delineated herein, the subject has or is at increased risk of developing a neurodegenerative disease. In various embodiments, the neurodegenerative disease is selected from amyotrophic lateral sclerosis (ALS), Alzheimer's disease and Parkinson's disease.

In various embodiments of any aspect delineated herein, the therapeutic polypeptide or polynucleotide is a lysosomal enzyme, ABCD protein, inhibitory nucleic acid or shRNA targeting one or more of miR155 and NOX2 (e.g. in ALS); TREM2; APOE2; and APPs alpha (e.g., in Alzheimer's Disease).

In various embodiments of any aspect delineated herein, the HSC is administered in combination with ablative conditioning. In various embodiments, the ablative conditioning comprises administering a cytotoxic agent to the subject. In various embodiments, the alkylating agent is one or more of busulfan, etoposide, and lomustine. In various embodiments, the ablative conditioning is performed prior to administering the HSC.

In various embodiments of any aspect delineated herein, the expression of the polypeptide or polynucleotide is by the TSPO promoter. In various embodiments of any aspect delineated herein, the polypeptide or polynucleotide is expressed from a polynucleotide inserted at the TSPO locus.

In various embodiments of any aspect delineated herein, the nanoparticle further contains a cytotoxic agent. In various embodiments, the cytotoxic agent is provided at a fixed dose for delivery of the cytotoxic agent to a microglial cell, or progenitor thereof. In certain embodiments, the alkylating agent is one or more of an alkylating agent, busulfan, etoposide, and lomustine. In various embodiments of any aspect delineated herein, the nanoparticle has one or more of optimized drug-loading efficiency, optimized drug release, and optimized stability. In various embodiments of any aspect delineated herein, the nanoparticle includes one or more capture molecules covalently linked to the surface of the nanoparticle, where the capture molecules specifically bind one or more markers expressed on a microglial cell, or progenitor thereof. In various embodiments of any aspect delineated herein, the nanoparticle is administered to the subject intravenously (IV) or by Intra-cerebral Ventricular Injection (ICV).

In various embodiments of any aspect delineated herein, the exogenous cells are HSCs transplanted ICV and IV at day 0. In various embodiments of any aspect delineated herein, the the chimerism is generated in a minor HLA mismatched transplant setting.

In various embodiments of any aspect delineated herein, the viral vector is a lentiviral vector. In various embodiments of any aspect delineated herein, the method involves targeted addition of the gene of interest at the TSPO locus in hematopoietic equivalents of microglial progenitors. In various embodiments of any aspect delineated herein, the method involves administering to a subject autologous engineered populations of microglial progenitors, where the subject has received brain ablation ICV for selective microglial reconstitution. In various embodiments of any aspect delineated herein, the method further involves administering unmanipulated autologous bone marrow cells. In various embodiments of any aspect delineated herein, the method further involves detecting Fdg5 expression to identify a brain-resident microglial progenitor cell.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

The term "antibody," as used herein, refers to an immunoglobulin molecule which specifically binds with an antigen. The term "antibody fragment" refers to a portion of an intact antibody and refers to the antigenic determining variable regions of an intact antibody.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "Fgd5 polypeptide" is meant a protein having about 85% or greater amino acid sequence identity to NCBI Accession No. NP_689749, NP_001307205, NP_766319, or a fragment thereof, and having chromatin binding or transcriptional regulatory activity. The sequence of an exemplary human Fgd5 protein is provided below:

```
   1 mfrgpkppia pkprltapne wrasvylnds lnkcsngrlp cvdrgldegp rsipkcsese
  61 tdedyivvpr vplredepkd egsvgnkalv spessaeeee ereeggeacg legtgageds
 121 vapaapgaga lsregeegtd laledegegc adepgtleqv srseeeeklv qphrecsled
 181 sgpwagegvf qsdlllphih gedqeppdtp geaeeddeeg castdpagad egsgpdrpte
 241 dmgqdaedts eeppekeela gvqeaetatd cpevleegce eatgvtggeq vdlseppdhe
 301 kktnqevaaa tledhaqdes aeescqivpf endcmedfvt sltgspyeff ptestsfcse
 361 scsplsesak gleseqapkl glraeenpmv galcgqcgsl qggaaegpaa pdvvvvleee
 421 alddalanpy vmgvglpgqa apgeggqaas dalggygske elnceaeggl vpadrkntst
 481 rvrphsgkva gyvpetvpee tgpeagssap giggaaeevg ktllslegkp leasralpak
 541 praftlyprs fsvegreipv svyqepegsg lddhrikrke dnlslscvig ssgsfsqrnh
 601 lpssgtstps smvdipppfd lacitkkpit ksspsllies dspdkykkkk ssfkrflalt
 661 fkkktenklh vdvnvsssrs ssessyhgps rilevdrrsl snspqlksrt gklrasesps
 721 slifyrdgkr kgvpfsrtvs rvesfedrsr ppflplpltk prsisfpsad tsdyenipam
 781 nsdyeniqip prrparagaf tklfedqsra lstanendgy vdmssfnafe skqqsadqda
 841 esaytepykv cpissaapke dltsdeeqrs seeedsasrd psvthkvegq sralviagel
 901 lssekayvem lqhlnldfhg avmralddmd hegrdtlare elrqglselp aihdlhqgil
 961 eeleerlsnw esqqkvadvf lareqgfdhh athilqfdry lgllsenclh sprlaaavre
1021 feqsvqggsq takhrllrvv qrlfqyqvll tdylnnlcpd saeydntqga lsliskvtdr
1081 andsmeqgen lqklvhiehs vrgqgdllqp greflkegtl mkvtgknrrp rhlflmndvl
1141 lytypqkdgk yrlkntlava nmkvsrpvme kvpyalkiet sesclmlsas scaerdewyg
1201 clsralpedy kagalaafhh sveirerlgv slgerpptlv pvthvmmcmn cgcdfsltlr
1261 rhhchacgki vcrncsrnky plkylkdrma kvcdgcfgel kkrgravpgl mrerpvsmsf
1321 plssprfsgs afssvfqsin pstfkkqkkv psaltevaas gegsaisgyl srckrgkrhw
1381 kklwfvikgk vlytymased kvalesmpll gftiapekee gssevgpifh lyhkktlfys
1441 fkaedtnsaq rwieamedas vl
```

The sequence of an exemplary murine Fgd5 protein is provided below:

```
   1 mhradspkpp lapkpkvatn pyapaakfpp sqrpdsfpsp nsmsrgpkpp iapkprltgp
  61 seylnnslgk csngrllced rglydghhst lnclelepde qyimvprapq kedtpvdgat
 121 eepgfegevq ehgteqtgte gdleapdeea psrdseegmv halededcdh dpetdgtpts
 181 pdegapsrds eegeedcdqg pgmeehpmse eegeeeevke hvynsdnrap wdgeepfpne
 241 vilthvrsqs pevpcwepgp petpgeaeed cedicnnntep gkpnqdtgqd tedagmgspe
 301 sevspdvqeq eaatdnpevf eedsadaaeg edqieqeepp ncdeeaynrd aaaatmqvge
 361 dlgeegdhvq edpaeescqi ipfesdsvee dfsptltenp yeifptests fcnntyslde
 421 sanghepvce icveevpgvg pplnqhdslp dgsgedspvv pdvvvvpene gpvddalssp
 481 yvmgvgllsl gegaqsdtqa asgtlsgyst weegdseggq vpvdrkniat rarphsgkva
```

-continued

```
 541 ghvpetvlee tgpetcssgm girdtsdevr kigilpegkp pecvralpak praftlyprs 601 fsvegrespl smfrepegag ldshrvrrke dnlslpgaig ssgsfsqrsh lpssgtstps 661 svvdipppfd lacitkkpit ksspsllidg dtlekaskkk kssfkrflel tfrkkteskv 721 hvdmnlsssr sssessyhgp arvleldrrs lsnspqlkcr tgklrasdsp aalifyrdsk 781 rkgvpfsrtv srvesfedrs rppflplplt kprsisfpna dtsdyenipa mnsdyeniqi 841 pprrpvrtgt ftklfeeqsr alstanendg yvdmssfnaf eskqqsseqe aesaytepyk 901 vcpisaapre dltsdeeqgs seeedsasrd pslshkgegq sralviagel lssekayvqm 961 lqhlsldfhg avlralenve qegreplaqe elrqglrelp aicdlhqgil esleqrlgdc 1021 gegqpqvadi flaqeqefeh haahilqfdr ylgllaescl lsprlattvr efeqssqggg 1081 qsmkhrmlry vqrlfqyqvl ltdylnnlcp dsaeydntqs altliskvtd ranesmeqge 1141 nlqklvhiey svrgqgdllq pgreflkegt lmrvrgksrh prhlflmndt llythpqkdg 1201 kyrlksslpv anmkvsrpvm dkvpyalkie tpescltlsa sscaerdewh yclsralped 1261 yktqalaafh hsveirerlg islgerlptl vpvthammcm ncgcdfsltv rrhhchacgk 1321 ivcrncsrnk yplkclknrm akvcdgcfre lklrngpvpg smrerpvsms fplsssrfss 1381 gsalssvfqs ispstfkkqk kvpsalseva asgegsaisg ylsrcksgkr rwkklwlvik 1441 gkvlytylas edkvamesip llgftiapek eegssevgpv fhlyhkktlf ysfkaedsns 1501 aqrwmeamed asvl
```

By "fragment" is meant a portion of a protein or nucleic acid that is substantially identical to a reference protein or nucleic acid. In some embodiments the portion retains at least 50%, 75%, or 80%, or more preferably 90%, 95%, or even 99% of the biological activity of the reference protein or nucleic acid described herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein "storage disorder (SD)" refers to any of a group of diseases resulting from abnormal metabolism leading to accumulation of a substrate (for example sulfatides, heparan sulphate, glycolipids, ceramide) in the lysosome or other cellular organelles. For example, lysosomal storage disorders (LSDs) are caused by lysosomal dysfunction usually as a consequence of deficiency of a single enzyme required for the metabolism of lipids, glycoproteins (sugar-containing proteins) or so-called mucopolysaccharides.

By "marker" is meant any clinical indicator, protein, metabolite, or polynucleotide having an alteration associated with a disease, disorder, or condition.

By "microglia" is meant an immune cell of the central nervous system.

By "nanoparticle" is meant a composite structure of nanoscale dimensions. In particular, nanoparticles are typically particles of a size in the range of from about 1 to about 1000 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in several therapeutic applications typically have a size of about 200 nm or below, and the ones used, in particular, for delivery associated with therapeutic agents typically have a diameter from about 1 to about 100 nm.

As used herein "neurodegenerative disease" refers to any of a group of diseases characterized by the progressive loss of structure and/or function of neurons, including death of neurons. Exemplary neurodegenerative diseases include, without limitation, amyotrophic lateral sclerosis, and Alzheimer's disease.

By "increasing proliferation" is meant increasing cell division of a cell in vivo or in vitro.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "reduces" is meant a negative alteration of at least 10%, 25%, 50%, 75%, or 100%.

By "reference" is meant a standard of comparison or control condition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "specifically binds" is meant a compound (e.g., peptide) that recognizes and binds a molecule (e.g., polypeptide), but which does not substantially recognize and bind other molecules in a sample, for example, a biological sample.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 1A depicts an experimental scheme for ICV transplantation of Lineage⁻ (Lin⁻) cells (that represent HSPCs in mice) in myeloablated mice (BU: myeloablation by busulfan treatment; IRR: lethally irradiation). Different time points of analysis are indicated. Lin⁻ cells were transduced with a Green Fluorescent Protein (GFP) encoding LV. FIG. 1B is a graph depicting frequency of GFP$^1$ cells identified within the total myeloid (CD45$^+$CD11b$^+$) brain compartment at different time points after ICV and IV HSPC transplantation in BU-treated (BU-TX) and irradiated (IRR) mice. N≥5 mice per time point and group; average and SD are shown. Two-way ANOVA showed a significant effect of the route of cell administration and time in BU and IRR mice (ICV vs IV and time p<0.005). These data show a rapid and robust myeloid cell engraftment in brain following intra-cerebral ventricular injection of HSPCs. The bars of the graph are shown in three sets of four bars. From left to right is IRR IV (gray), IRR ICV (white), BU IV (dark gray), BU ICV (darker gray) FIG. 1C depicts a reconstruction of a sagittal brain section of a representative ICV transplanted BU-TX mouse showing widespread distribution of GFP$^+$ cells at 90 days from GFP-transduced HSPC ICV injection. GFP (green/grey) and Topro III (TPIII, in light blue/light grey) for nuclei, are shown. Images were acquired at Delta Vision Olympus at magnification 20× and processed by the Soft Work 3.5.0; reconstruction was performed with Adobe Photoshop CS 8.0 software. FIG. 1D depicts immunofluorescence analysis for GFP (green/gray) and Iba-1 (red/light gray) on brain sections from BU_TX mice at 90 days after ICV transplantation of GFP-transduced HSPCs. M=merge. Magnifications 20× and 40× of the relative dotted box are shown. Images were acquired at confocal microscope Radiance 2100 (Bio-Rad) Ix70 and processed by the Soft Work 3.5.0. FIG. 1E is an experimental scheme for the transplantation of human CD34$^+$ cells (that represent HSPCs in humans and are considered the equivalent population to Lin⁻ cells from mice) transduced with GFP or Arylsulfatase A (ARSA) encoding LVs in NSG mice or Rag-/-γ-chain-/-As2-/- (RagMLD) mice pre-treated with BU 16 mg/kg×4 days (NSG) or sublethal irradiation (RagMLD). NSG mice received also unmanipulated mononuclear cells from NSG donors. The graph includes four sets of bars. The left most bar in each set is IV only (white), LIN IV LIN ICV (dark gray), KLS IV LIN ICV (medium gray), and BM IV LIN ICV (gray). FIG. 1F depicts representative dot plots from the analysis of brain mononuclear cells from NSG mice transplanted 20 weeks earlier with human CD34$^+$ cells transduced with a GFP LV. Frequency of human cells in the mouse brain is shown in two representative animals and with two methods of analysis (human CD45 on SSC, and human CD45 on murine CD45). The plots also show that the human CD45$^+$ cells identified in the NSG brains post-transplant express CDT Tb, CX3Cr1 and GFP. FIG. 1G is a graph depicting the frequency of human CD45$^+$CD11b$^+$ cells retrieved from the brain of NSG and RagMLD mice transplanted IV or ICV with umbilical cord blood-derived CD34$^+$ cells after BU-treatment or sub-lethal irradiation Rag$^{-/-}$γ-chain$^{-/-}$As2$_{-/-}$, 12-20 (NSG) and 5 (Rag$^{-/-}$γ-chain$^{-/-}$As2$^{-/-}$) weeks post-transplant. Values are expressed as fold to IV, with IV equal to 3+/−1.3 in NSG mice, and to 2.9+/−0.7 in RagMLD. N≥5 mice/group; average and SD are shown. P<0.001 at Student's t test in NSG mice; p<0.05 at one-way Anova with Bonferroni post-test in RagMLD mice. FIG. 1H depicts results from an immunofluorescence analysis for GFP, Iba-1 (co-staining), CD11b (co-staining), CD68 (no co-staining) and CD163 (no co-staining) on brain sections from NSG mice at 90 days after ICV transplantation of GFP-transduced CD34$^+$ cells. In blue, nuclei stained by TP III. Magnification 20× and 40× of the relative dotted box are shown. M=merge.

FIGS. 2A and B depict two graphs showing the frequency of GFP$^+$ cells identified within CD45$^+$ cells of the brain (FIG. 2A) and bone marrow (FIG. 2B) of BU-treated and transplanted (BU_TX) mice at the indicated time points after ICV injection of Lin⁻ HSPCs transduced with GFP-encoding LVs. N≥3 mice each time point; average and SD are shown. Analyzed by one Way Anova with Bonferroni post-test, 4 days at comparison with 1, 3, 6 and 24 hours shows P value<0.001. Engraftment of the ICV transplanted cells is mostly in the brain, with minor or null presence of GFP$^+$ cells detected in the bone marrow of the transplanted mice. FIGS. 2C and 2D show in two graphs the expression of the indicated hematopoietic stem cell (FIG. 2C) and myeloid/microglia (FIG. 2D) markers by GFP$^+$ (donor) and GFP (recipient) CD45$^+$ cells retrieved from the brain of BU_TX mice at different time points after ICV injection of transduced Lin⁻ HSPCs (input represents the HSPCs at time of infusion). N≥3 mice each time point; average and SD are shown. Two-way Anova showed a significant effect of the markers and time ($p<0.0001$). In FIG. 2C, for GFP$^+$ cells, arrows indicate % expression for c-Kit, Sca1, CD34, CXCR4, CD93, and Tie2. In FIG. 2C, for GFP cells, circles are from top to bottom, in each column: CXCR4, CD34, CD93, c-Kit, Sca1, and Tie2. In FIG. 2D, for GFP$^+$ cells, arrows indicate % expression for CD11b, CX3CR1, and CD115. In FIG. 2D, for GFP cells, circles are from top to bottom, in each column: CD11b, CX3CR1, and CD115. The transplanted cells/their progeny transiently increased the expression of hematopoietic stem cells and subsequently increased the level of expression of myeloid/microglia markers.

FIG. 3A is a graph showing the brain engraftment of donor (GFP$^+$) Lin$^-$ HSPCs transplanted at day 0 (24 hours after the last dose of busulfan) or 5 days later (at day 5) IV, within total myeloid CD45$^+$CD11b$^+$ cells, microglia ($\mu$), transiently amplifying $\mu$ (TA$\mu$) and CNS macrophages. The graph shows that transplantation of HSPCs at the 2 time points results in similar brain engraftment in the tested populations. FIG. 3B depicts the gating strategy for the identification of $\mu$, TA$\mu$ and CNS macrophages (CNSmac) as CD45$^{low}$CD11b$^{high}$, CD45$^{+low}$, CD11b$^{+low}$ and CD45$^{high}$CD11b$^{high}$ in 3 post-natal day (pnd) neonate mice, 21 and 60pnd adult mice and adult HSPC transplanted animals at 2 months post transplant. FIG. 3C depicts an experimental scheme showing the transplantation strategy of differentially labeled (with GFP or $\Delta$NGFR encoding LVs) hematopoietic cells IV and/or ICV into busulfan-conditioned recipients. The transplanted hematopoietic cells are Lin$^-$ HSPCs, or c-kit$^+$Sca1$^+$Lin$^-$ (KSL) cells or total bone marrow (BM). FIG. 3D is a graph depicting frequency of donor-derived cells (CD45.1=progeny of the IV transplanted cells, and GFP expressing cells=progeny of the ICV transplanted cells) within the BM of the transplanted mice at sacrifice 3 months after transplant. The GFP$^+$ ICV transplanted cells do not show a robust engraftment in the BM. FIG. 3E is a graph depicting the frequency of donor-derived cells (as a sum of $\Delta$NGFR and GFP expressing cells) within CD45$^+$CD11b$^+$ cells, $\mu$, TA$\mu$ and CNSmac of mice transplanted as indicated by the color-code at Day 0. ICV and IV co-delivery of hematopoietic cells results in an increased brain donor chimerism post-transplant in all the tested combinations as compared to IV only Lin-transplantation. The left most bar in each set is IV only (white), LIN IV LIN ICV (dark gray), KLS IV LIN ICV (medium gray), and BM IV LIN ICV (gray). FIG. 3F is a graph depicting the differential frequency of donor-derived $\Delta$NGFR (progeny of IV transplanted cells) and GFP (progeny of ICV transplanted cells) expressing cells within CD45$^+$CD11b$^+$ cells, $\mu$, TA$\mu$ and CNSmac of mice transplanted as indicated at Day 0. Lin$^-$ ICV delivery coupled to total BM IV transplantation results in the lowest engraftment of IV-transplanted cells/their progeny in the brain. The sets of bars (4 bars/set) are from left to right: IV only (NGFR), LIN IV LIN ICV (DNGFR), LIN IV LIN ICV (GFP), KLS IV LIN ICV (DNGFR), KLS IV LIN ICV (GFP), BM IV LIN ICV (DNGFR), and BM IV LIN ICV (GFP). FIG. 3G depicts an experimental scheme showing the transplantation strategy of differentially labeled (with GFP or $\Delta$NGFR encoding LVs) hematopoietic cells IV and/or ICV into busulfan-conditioned recipients, where the IV cells were transplanted at day 5 post-chemotherapy, while ICV cells on day 0. The transplanted hematopoietic cells are Lin$^-$ HSPCs, or KSL cells or total BM. FIG. 3H is a graph depicting frequency of donor-derived cells (CD45.1=progeny of the IV transplanted cells, and GFP expressing cells=progeny of the ICV transplanted cells) within total BM cells retrieved from transplanted mice at sacrifice 3 months after transplant. The GFP$^+$ ICV transplanted cells do not engraft in the BM. FIG. 3I is a graph depicting the frequency of donor-derived cells (as a sum of $\Delta$NGFR and GFP expressing cells) within CD45$^+$CD11b$^+$ cells, $\mu$, TA$\mu$ and CNSmac of mice transplanted as indicated by the color-code at Day 5. ICV and IV co-delivery of hematopoietic cells results in an increased brain donor chimerism post-transplant in all the tested combinations as compared to IV only Lin$^-$ transplantation. The left most bar in each set is IV only (white), LIN IV LIN ICV (dark gray), KLS IV LIN ICV (medium gray), and BM IV LIN ICV (gray). FIG. 3J is a graph depicting the differential frequency of donor-derived $\Delta$NGFR (progeny of IV transplanted cells) and GFP (progeny of ICV transplanted cells) expressing cells within CD45$^+$CD11b$^+$ cells, $\mu$, TA$\mu$ and CNSmac of mice transplanted as indicated at Day 5. Lin$^-$ ICV delivery coupled to total BM IV transplantation results in the lowest engraftment of IV-transplanted cells/their progeny in the brain. The sets of bars (4 bars/set) are from left to right: IV only (NGFR), LIN IV LIN ICV (DNGFR), LIN IV LIN ICV (GFP), KLS IV LIN ICV (DNGFR), KLS IV LIN ICV (GFP), BM IV LIN ICV (DNGFR), and BM IV LIN ICV (GFP). One way Anova with Bonferroni post-test, *=$p<0.05$, =$p<0.01$, *=$p<0.001$, ****=$p<0.0001$.

FIG. 4A is a graph depicting frequency of $\mu$ and TA$\mu$ cells in the brain of mice at 90 days after transplantation of GFP$^+$ HSPCs IV or ICV (n=5 per group). FIG. 4B depicts representative dot plots showing the cell populations sorted for gene expression analysis. In particular $\mu$ and TA$\mu$, identified by the CD45 and CD11b markers, in the brain of naïve P10 and adult control (ADULT_CT) animals, and busulfan-treated and transplanted mice (BU_TX) at 90 days after HCT are shown. The dot plots included in the dotted square show both GFP$^-$ endogenous cells and GFP$^+$ donor derived cell chimerism within $\mu$ and TA$\mu$ populations of a representative transplanted BU-treated mouse. FIG. 4C is a graph depicting fold change expression (calculated as $2^{-DDCT}$) of selected microglia genes, obtained by real time PCR in each indicated population retrieved from the brain of busulfan-treated, IV and ICV transplanted mice, or from P10 mice, calculated on expression of the same genes in ADULT_CT $\mu$ cells. Mean values are shown. FIG. 4D is a principal component analysis (PCA) and FIG. 4E is a heatmap, both showing expression analysis of the genes within the samples identified as microglia signature by Butovsky (Butovsky et al., Nature neuroscience 17, 131-143 (2014))($\mu$ and TA$\mu$ retrieved from naïve P10 and ADULT_CT, and HCT animals) and samples reported in Gosselin et al. (Gosselin et al. Cell 159, 1327-1340 (2014)), including microglia and macrophages (LPM=large peritoneal macrophages; SPM=small peritoneal macrophages; BMDM=bone marrow derived macrophages; TGEM=thioglycollate-elicited peritoneal macrophages). Overall, these data indicate that the cells isolated from the brain of the ICV and IV transplanted mice showed expression of these genes at levels similar to those of $\mu$ cells isolated from control mice, rather than of macrophages.

FIG. 5A shows functional enrichment of differentially upregulated genes in µCT cells vs µ transplanted cells. FIG. 5B shows functional enrichment of differentially downregulated genes in µCT cells vs µ transplanted cells. FIG. 5C shows functional enrichment of differentially upregulated genes in µCT cells vs TAµ transplanted cells. FIG. 5D shows functional enrichment of differentially downregulated genes in µCT cells vs TAµ transplanted cells. Gene set enrichment analysis (GSEA) pre-ranked analysis was performed using RNA-Seq differential gene expression data on Gene Ontology (GO) Biological processes (http://software.broadinstitute.org/gsea/msigdb/collection) with default parameters. Semantic Similarity of GOs (GOSemSim) was used to cluster significantly enriched GOs (GOs with FDR<0.05 for upregulation and FDR<0.001 for downregulation were chosen to enhance representation clarity). FIG. 5E is a graph showing fold change of RNA-Seq normalized expression values of genes whose expression is upregulated in adult mice (Matcovitch-Natan et al., Science. 353:6301 (2016)) in the indicated populations retrieved from the brain of busulfan-treated transplanted mice or P10 mice versus ADULT_CT µ cells.

FIG. 6A depicts an experimental scheme for HCT. CFUs were plated from bone marrow (BM) and brain of naïve (UT), BU-treated and irradiated (IRR) mice, as well as from mice previously transplanted with CD45.2 GFP-transduced HSPCs (BU-HCT). FIG. 6B is a graph depicting number of colonies (#CFC) obtained from the tissues of BU and IRR animals. FIG. 6C is a graph depicting number of colonies (#CFC) and of GFP$^+$ CFCs obtained from the tissues of BU-HCT animals. FIG. 6D is a graph depicting frequency of GFP$^+$ cells (and lineage differentiation for BM) retrieved by FACS analysis in BM and brain of secondary recipient mice receiving BM or brain cells or peripheral blood mononuclear cells from primary recipients; mice were sacrificed 4 months after transplant.

FIG. 7A depicts the experimental scheme of the transplant protocol for human CB CD34$^+$ HSPCs transplanted by either IV, IV+ICV or ICV only routes into sub-lethally irradiated (Sub-L-IRR) Rag2$^{-/-}$ γ-chain$^{-/-}$ As2$^{-/-}$ neonate mice, immunodeficient animals model of metachromatic leukodystrophy (MLD). Before transduction, HSPCs were transduced with an Arylsulfatase A (ARSA) encoding LV (Sessa et al., Lancet 2016). FIG. 7B are graphs showing ARSA activity (expressed as fold to the value measured in Rag$^{-/-}$ γ-chain$^{-/-}$ As2$^{+/+}$ wild type mice tissues) measured in the brain and bone marrow (BM) of Rag$^{-/-}$ γ-chain$^{-/-}$ As2$^{-/-}$ mice transplanted with ARSA-transduced cells ICV or IV or ICV+IV, as indicated. N=3 mice/group. Transplanted mice were sacrificed 5 weeks after transplantation. Overall, the co-delivery (IV+ICV) of the transduced HSPCs results in a greater ARSA delivery to the brain as compared to the IV-only or ICV-only approaches. FIG. 7C is a scheme of the transplantation experiment in mice deficient in iduronate sulfatase activity (IDS$^{-/-}$, animal model of Mucopolysaccharidosis type II-MPS II) of Lin$^-$ HSPCs from wild type (IDS$^{+/+}$) donors. Wild type cells were administered to 2 months old IDS$^{-/-}$ mice after busulfan myeloablation IV only or IV+ICV. Transplanted mice were followed up for 180 days by behavioral studies. FIGS. 7D-7E are graphs showing the performance of transplanted and control IDS- mice at rotarod testings. FIG. 7D show the latency on the rotarod of the animals. FIG. 7E shows the difference in the latency on rotarod between day 4 (last trial) and day 1 (first trial). ICV+IV transplanted mice show a better rotarod performance as compared to IV only and control mice. Average and SEM are shown, N=3-8 mice per cohort.

FIG. 8A depicts the experimental scheme for HLA-minor antigen mismatched HSPC IV+ICV transplantation in mice; mice received 10×10$^6$ total BM cells IV and 0.3 or 1×10$^6$ Lin$^-$ cells (murine equivalent of human CD34$^+$ cells) ICV. FIG. 8B is a Kaplan-Meyer survival curve of the transplanted animals. At the end of the experiment, IV+ICV Day 0 3e5 and IV only groups showed 100% survival, in contrast to the IV+ICV Day 0 1e6 group. FIG. 8C is a graph depicting donor CD45.2 cell chimerism in the peripheral blood (PB), BM, spleen (Spl) and thymus (Thy) of the transplanted mice at sacrifice. FIG. 8D shows the GFP$^+$ cell frequency within donor CD45.2 cells in the tissues from transplanted animals, indicating that the ICV transplanted GFP$^+$ cells did not engrafted in the hematopoietic tissues of the transplanted mice. N=5 per group. FIG. 8E is a graph depicting donor CD45.2 cell chimerism in the brain myeloid populations (total CD45$^+$CD11b$^+$ cells) of the transplanted mice at sacrifice. FIG. 8F shows the GFP$^+$ cell frequency within donor CD45.2 cells in the brain myeloid cells from the transplanted animals, indicating that the ICV transplanted GFP$^+$ cells contributed to an increased donor brain chimerism. N=5 per group.

FIG. 9A depicts the experimental scheme for HLA-minor antigen mismatched HSPC IV+ICV transplantation in mice; mice received 10×10$^6$ total BM cells IV and 0.3×10$^6$ Lin$^-$ cells (murine equivalent of human CD34$^+$ cells) ICV. FIG. 9B is a Kaplan-Meyer survival curve of the transplanted animals. At the end of the experiment, the IV+ICV Day 0 3e5 group showed 100% survival, in contrast to the IV only group. FIG. 9C is a graph depicting donor CD45.2 cell chimerism in the PB, BM, Spl and Thy of the transplanted mice at sacrifice. FIG. 9D shows the GFP$^+$ cell frequency within donor CD45.2 cells in the tissues from transplanted animals, indicating that the ICV transplanted GFP$^+$ cells did not engraft in the hematopoietic tissues of the transplanted mice. N=5 per group. FIG. 9E is a graph depicting donor CD45.2 cell chimerism in the brain myeloid population of the transplanted mice at sacrifice. FIG. 9F shows the GFP$^+$ cell frequency within donor CD45.2 cells in the brain myeloid cells from transplanted animals, indicating that the ICV transplanted GFP$^+$ cells contributed to an increased donor brain chimerism. N=5 per group.

FIG. 10A depicts the experimental scheme for differentially labeled HSPC transplantation IT+IV at comparison with ICV+IV and IV only (control IV) in mice. FIG. 10B shows graphs depicting donor cell chimerism, made by the sum of GFP$^+$ and Cherry$^+$ cell engraftment, in the BM, brain and spinal cord of the transplanted mice at sacrifice. In each column, GFP is on the bottom and Cherry is on top. N=3-5 per group. IT HSPC delivery can constitute a valuable route for the achievement of a robust hematopoietic and CNS chimerism.

FIG. 11A depicts an experimental scheme showing how Long term (LT)-HSCs and progenitors within the HSPC pool were prospectively isolated using c-kit$^+$, Sca-1 and lineage negative staining and SLAM receptors markers CD150 and CD48. The indicated sorted populations were then differentially transduced with lentiviral vectors (LVs) encoding GFP (KSL) and ΔNGFR (NOT-KSL), and GFP (LT-HSCs), ΔNGFR (MPP), Tag-BFP (HPC-1) and CHERRY (HPC-2), and subsequently transplanted IV or ICV in competitive fashion at their original ratio into busulfan-myeloablated mice. Animals transplanted ICV also received un-manipulated total BM cells for hematopoietic rescue at day 5 post-transplant. FIG. 11B shows histograms of the expression of the markers genes in the in vitro liquid progeny of the cells transduced with the indicated LVs and transplanted in the mice described in A. FIG. 11C is a graph depicting frequency of cells derived from each of the transplanted KSL sub-populations within total CD45$^+$ hematopoietic BM cells, myeloid (CD11b) and lymphoid (CD3 and B220) lineages of busulfan-treated transplanted (BU_TX) mice at sacrifice. N=10 mice/group. In each column, from bottom to top: LT-HSC (light gray), MPPs (dark gray), HPC2 (gray), and HPC1 (lighter gray). FIG. 11D is a graph depicting frequency of cells derived from IV transplanted KSL and NOT-KSL within total brain myeloid (CD45$^+$CD11b$^+$) cells, μ and TAμ of BU_TX mice at 90 days post-transplant. In each column, from bottom to top: KSL (gray) and not-KSL (white). FIG. 11E is a graph depicting frequency of cells derived from ICV transplanted KSL and NOT-KSL within total brain myeloid (CD45$^+$ CD11b$^+$) cells, μ and TAμ of BU_TX mice at 90 days post-transplant. In each column, from bottom to top: KSL (gray) and not-KSL (white). FIG. 11F is a graph depicting frequency of cells derived from each of the transplanted KSL sub-populations within total brain myeloid cells, μ and TAμ of busulfan-myeloablated mice transplanted IV, at different time points post-HCT. N=10 mice per group. In each column, from bottom to top: LT-HSC (light gray), MPPs (dark gray), HPC2 (gray), and HPC1 (lighter gray). FIG. 11G is a graph depicting frequency of cells derived from each of the transplanted KSL sub-populations within total brain myeloid cells, μ and TAμ of busulfan-myeloablated mice transplanted ICV, at different time points post-HCT. In each column, from bottom to top: LT-HSC (light gray), MPPs (dark gray), HPC2 (gray), and HPC1 (lighter gray). N=10 mice per group. FIG. 11H and FIG. 11I depict immunofluorescence analysis of brain slices of BU treated mice transplanted IV with KSL sub-populations at 90 days post-transplant. In FIG. 11H progeny cells of LT-HSCs are GFP$^+$ and of MPPs are ΔNGFR$^+$ (in light gray). Iba 1 staining is in the blue channel. Magnification 20×. M=merge. In the right panels other representative merged pictures at 20× (top) and their 40× magnifications (bottom) are shown. In FIG. 11I progeny cells of HPC2 are Cherry$^+$ and of MPPs are ΔNGFR$^+$ (in gray). No GFP$^+$ staining was detected in the absence of ΔNGFR immunofluorescence. TPIII (dark gray) for nuclei is shown. Magnification 20× in the upper panels. In the bottom panels other representative merged pictures at 20× (top) and its 40× magnification (bottom) are shown. Images were acquired by confocal microscope (Radiance 2100, Bio-Rad, and processed by the Soft Work 3.5.0.100). FIG. 11J depicts histogram plots showing the differential level of CXCR4 expression in KSL and NOT-KSL cells, and KSL sub-populations at the time of transplant.

FIG. 12A depicts an experimental scheme in which Fgd5$^+$ HSCs (Lin$^-$ ckit$^+$ Sca-1$^+$ Flk2$^-$ CD34$^-$) were isolated from CD45.2 Fdg5-green donor mice. Fgd5$^+$ HSCs (n=500) were transplanted IV or ICV into busulfan-myeloablated or lethally irradiated CD45.1 recipient mice. Transplanted animals also received un-manipulated CD45.1 total BM cells for hematopoietic rescue at day 5 post-transplant. FIG. 12B is a graph depicting frequency of donor cells (CD45.2$^+$) within brain myeloid CD11b$^+$ cells of mice transplanted IV with Fgd5 cells after Busulfan and irradiation conditioning. N≥4 per group. FIG. 12C is a graph depicting frequency of donor cells (CD45.2$^+$) within brain myeloid CD11b$^+$ cells of mice transplanted ICV with Fgd5 cells after Busulfan and irradiation conditioning. N≥4 per group. FIG. 12D is a graph depicting of μ, TAμ and CNSmac populations within donor derived cells in IV transplanted busulfan-conditioned mice. N≥4 per group. FIG. 12E is a graph depicting μ, TAμ and CNSmac populations within donor derived cells in ICV transplanted busulfan-conditioned mice. N≥4 per group.

FIG. 13A is a series of graphs showing the characterization of the bone marrow of CX3CR1-GFP mice, and in particular the expression of GFP in the different bone marrow sub-populations, as indicated. In each column, from bottom to top: GFP neg (light gray), GFP low (dark gray) and GFP high (light gray). FIG. 13B depicts the experimental set up that was employed for generating chimeric mice with cells isolated from CX3CR1-GFP mice reporter mice and the resulting chimerism in brain. Mice receiving GFP$^{+/high}$ Lin$^-$ HSPCs were not engrafted with CX3CR1 CD45.2 donor cells in brain (representative dot-plots are shown in the left box), while transplantation of total CX3CR1 unsorted bone marrow showed a sustained engraftment of the donor cells which upon mocroglia differentiation robustly expressed GFP (representative dot-plots are shown in the left box). This indicates that GFP$^-$ cells (not expressing CX3CR1) are to be transplanted for to the establishment of brain myeloid chimerism.

FIG. 14A is a representative dot plot showing the gating strategy for the identification of human CD34$^+$CD38$^+$ (progenitors) and CD34$^+$CD38$^-$ (stem enriched cells) from human mobilized peripheral blood. Cells were differentially transduced with GFP and Tag-BFP encoding LVs at the indicated frequency and mixed for transplantation into NSG myeloablated mice. FIG. 14B is a graph showing the frequency of cells marked with GFP (CD38$^-$) or Tag-BFP (CD38$^+$) within the human CD45$^+$ cell fraction retrieved in brain of NSG mice transplanted with the cells indicated in A. N≥5 mice/group. Mean values and SEM are shown. In each column, from bottom to top: CD38$^-$ (gray) and CD38$^+$ (white). FIG. 14C is a representative dot plot showing the gating strategy for the identification of human long and short term HSCs and progenitors according to the expression of the markers CD38 and CD90 on CD34$^+$ cells retrieved from human mobilized peripheral blood. Cells were differentially transduced with GFP, Cherry, Tag-BFP (Cyan) and m02 (Orange) encoding LVs at the indicated frequency and mixed for transplantation into NSG conditioned mice. FIG. 14D is a graph showing frequency of cells marked with the indicated markers within the human CD45+ cell fraction retrieved in brain of NSG mice transplanted with the cells indicated in 14A. From bottom to top: CD38− CD90+ (gray), CD38− CD90− low (light gray), CD38+ CD90− (medium gray) and CD38+ CD90+ high (lighter gray). N≥5 mice/group. Mean values and SEM are shown. Overall, CD34+ CD38− showed the greatest contribution to brain myeloid cell chimerism.

FIGS. 15A15-C depict identification of brain-resident putative μ progenitors by BU-susceptibility. FIG. 15A shows, five days after 1 or 4 doses of busulfan an increase in the fraction of apoptotic Annexin+ cells was detected within hematopoietic myeloid and most-importantly CD45+ c-kit+ cells. The left most bar in each set is CO (white), 1×BU (dark gray), and 4×BU (black). FIG. 15B shows representative FACS plots with γH2AX+ cells within vital CD45+ brain cells of control animals and mice treated with BU. FIG. 15C shows γH2AX marker distribution in the brain of mice analyzed one day after busulfan conditioning or control untreated mice (CTR). Inset is a representative laser-scanning confocal microscope photomicrographs of co-immunostaining for γH2AX, neurons (NeuN), microglia (Ibal) or astrocytes (GFAP). Scale bar=10 pm. Images were acquired at confocal microscope Radiance 2100 (Bio-Rad) 1×70 at magnification 20× and processed by the Soft Work 3.5.0; reconstruction was performed with Adobe Photoshop CS 8.0 software. Magnification 40× in the insets.

FIG. 16A depicts a representation and sequence of the murine TSPO (SEQ ID NO: 3) promoter. FIG. 16B shows the LV resulting from cloning the 2.7 Kbp upstream the Tspo gene into a SIN LV plasmid upstream of the GFP cDNA. We transduced with this vector BV-2 cells (mouse microglia cell line) to evaluate the expression driven by this promoter. TSPO expression is known to be stimulated in microglia cells in response to stress and can be mimic by LPS injection in vivo. FIG. 16C is a histogram showing the GFP positive transduced BV2 cells and the shift of GFP mean fluorescence intensity following LPS stimulation. FIG. 16D is a graph showing the mean fluorescence intensity (MFI) of GFP (normalized for vector content) of the transduced BV2 cells in basal conditions and upon LPS stimulation (n=4: Average±SEM), *=p<0.0001 Student T-test.

FIG. 17A shows the size of the employed first generation rhodaminate nanoparticles. FIGS. 17B-17D show distribution in the brain of first generation nanoparticles injected ICV as assessed by flow cytometry. Nanoparticle uptake by CD45+ cells increases in the presence of mannitol (FIG. 17B), is higher in CD45+c-kit+ cells as compared to CD45+CD11b+ cells (FIG. 17C) and within CD45+Edu+ cells as compared to CD45+Edu− cells (FIG. 17D). FIG. 17E is a representative epifluorescence microscope photomicrograph of rhodaminated NPs signal (red/light gray) and DAPI nuclear stain (blue/dark gray) in a sagittal brain slice from a mouse analyzed three days after NPs ICV injection. Images were acquired at Delta Vision Olympus at magnification 20× and processed by the Soft Work 3.5.0; reconstruction was performed with Adobe Photoshop CS 8.0 software. FIG. 17F is a graph showing the distribution of the nanoparticles in the indicated brain regions, expressed as % of total area being Rho+. FIG. 17G are an inset of FIG. 17E that highlights prominent distribution of NPs (red, with blue DAPI nuclei) close to the subventricular (SVZ) zone and rostral-migratory stream (RMS)(right panel) as well as representative confocal microscope images of rhodaminated NPs signal (red), Ibal (green), ki67 (proliferation marker, blue) and DAPI nuclear stain (light blue) in a sagittal brain slice from a mouse analyzed three days after NPs ICV injection. NPs are within Ki67+ microglia cells. FIG. 17H show that NPs are internalized by proliferating cells. is a representative laser-scanning confocal microscope photomicrograph of co-immunostaining for Iba1+, F4/80, Rhodamine and the proliferation marker Edu. Rh+ NPs can be detected in Iba1+ (arrows) as well as Iba1− (arrowhead) proliferating cells. FIG. 17I a reconstruction of Edu and Rhodamin signaling retrieve by fluorescence microscopy on sections from the brain of NP injected mice showing the co-localization of Edu and NP signal. Images were acquired at confocal microscope Radiance 2100 (Bio-Rad) I×70 and processed by the Soft Work 3.5.0.

FIG. 19A is a representative flow cytometric analysis and immunofluorescence staining for γH2AX in BV2 microglia-like cell lines exposed to busulfan. The graph shows the percentage of γH2AX+ cells (determined by flow cytometry) after exposure to different nanoparticles formulations loaded with busulfan or not (histograms represent the mean+/−SEM of n>=3 independent exp). FIG. 19B is a graph depicting the results of MTT cell viability assay on BV2 microglia-like cell line exposed to BU-NPs, which highlight the cytotoxicity exerted by exposure to busulfan encapsulated in NPs. FIG. 19C is a graph depicting frequency of γH2AX+ microglia cells in mouse brain assessed (by flow cytometry) 3 days after NPs administration ICV (histograms represent the mean+/−SEM of n=4 animals/group). FIGS. 19D and 19E are two graphs showing the viability of BV2 microglia cells exposed to NPs (self assembly formulations size 50 and 100 nm and PLC formulation) containing or not the chmetherapic etoposide and to etoposize as free formulation at the indicated concentration. MTT assay was employed to assess viability. Viability was measured after 48 and 72 hours of incubation. Etopodise delivery within NPs increasing its ability to kill the cells as compared to the free formulation. In FIGS. 19D and 19E, the left most bar in each set is Self assembly NPs (50 nm) (dark gray), Self assembly NPs (100 nm), PCL NPs (100 nm) (gray), and Etoposide (medium gray).

FIGS. 20A and 20C are experimental designs employed to induce microglia progenitor cell proliferation by a single busulfsn dose or 10 day of per mouth administration of the CSF 1R inhibitor ((Elmore et al., Neuron. 82(2): 380-397 (2014)) and administer then Etoposide containing NPs IV to adult wild type mice. FIGS. 20B and 20D are graphs showing the % of Annexin+ early apoptotic cells measured at flow cytometry on brain samples obtained 5 days after NP administration. % Annexin+ cells is calculated on the indicated cell subfractions. Empty NPs were used as control. FIG. 20E shows the % of CD45+c-kit+ cells in the same samples. Overall, an increase in apoptosis consistent to what observed ion control mice that received 4 busulfan doses were detected in animals receiving the Etoposide charged NPs within CD45+c-kit+ and CD45+CD11b+ cells.

DETAILED DESCRIPTION OF THE INVENTION

Figure 1:
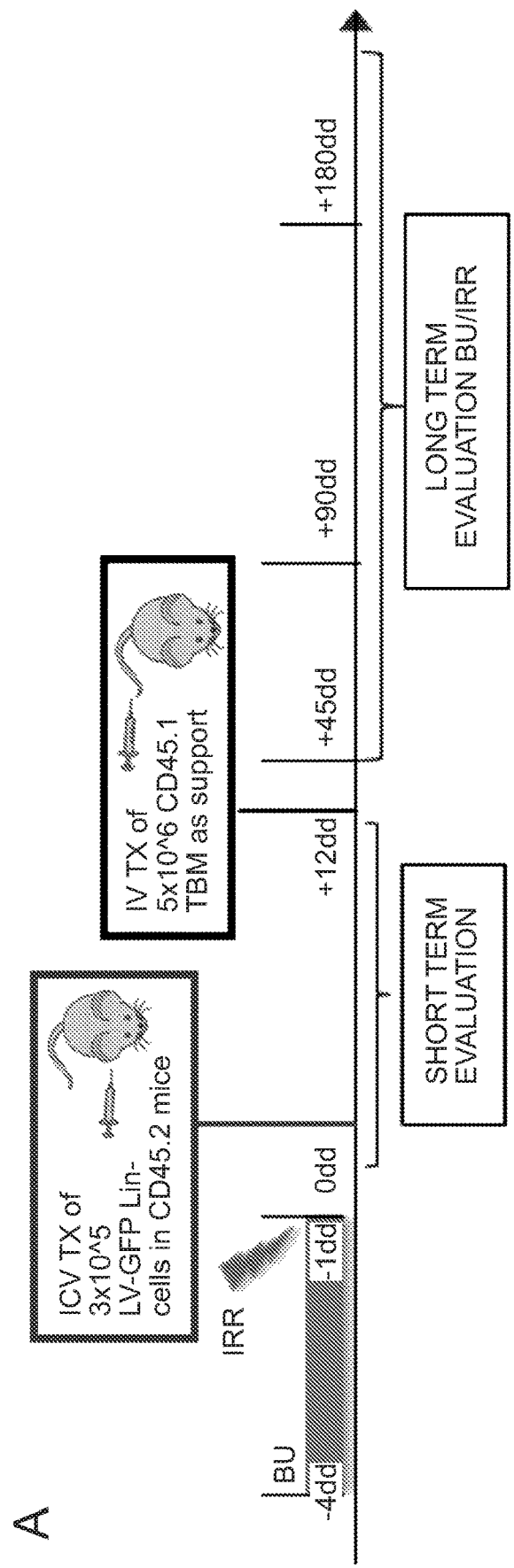
FIGS. 1A-1H depict myeloid cell reconstitution in brain following intra-cerebral ventricular injection of murine and human HSPCs.
Figure 1:
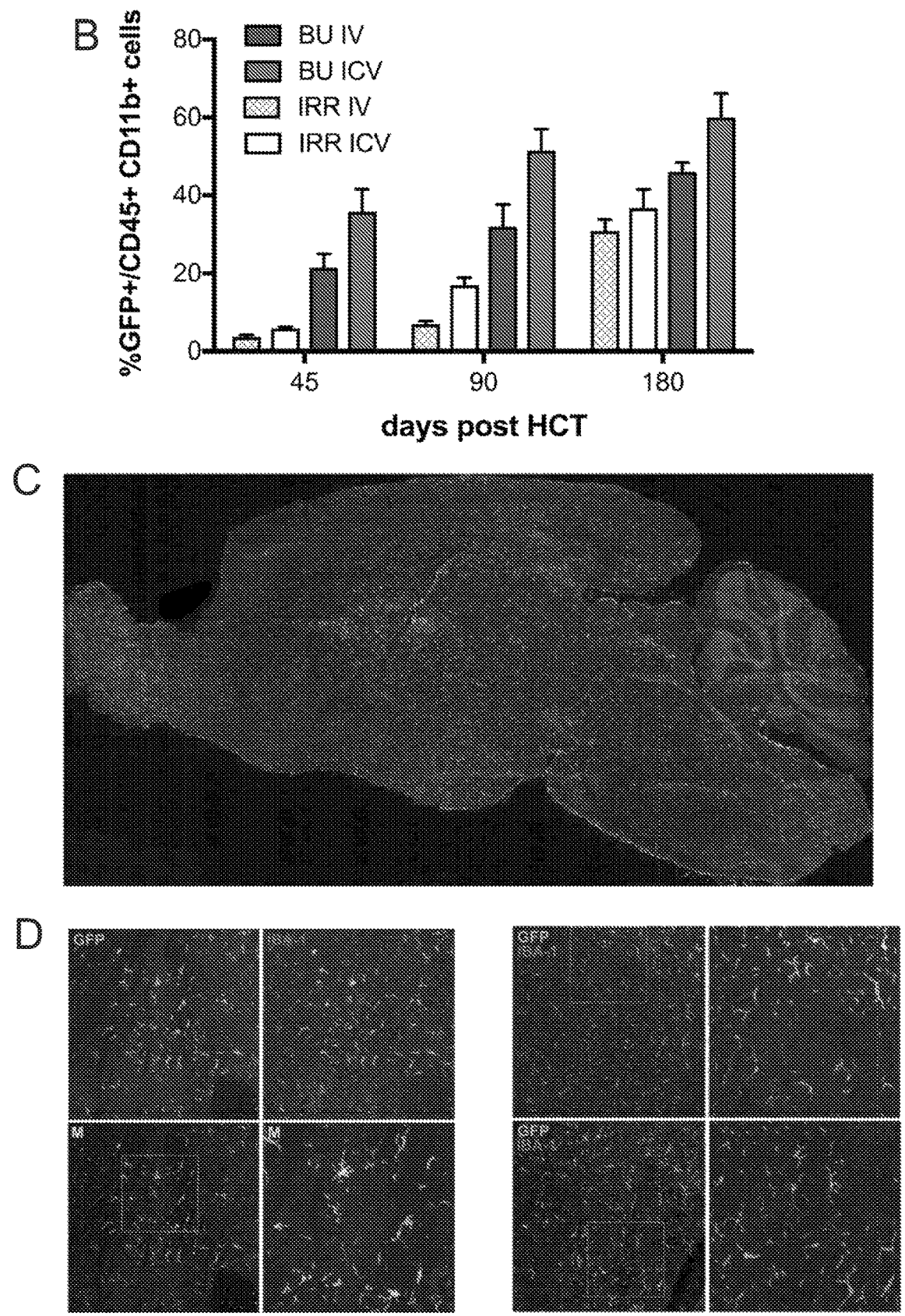
Figure 1:
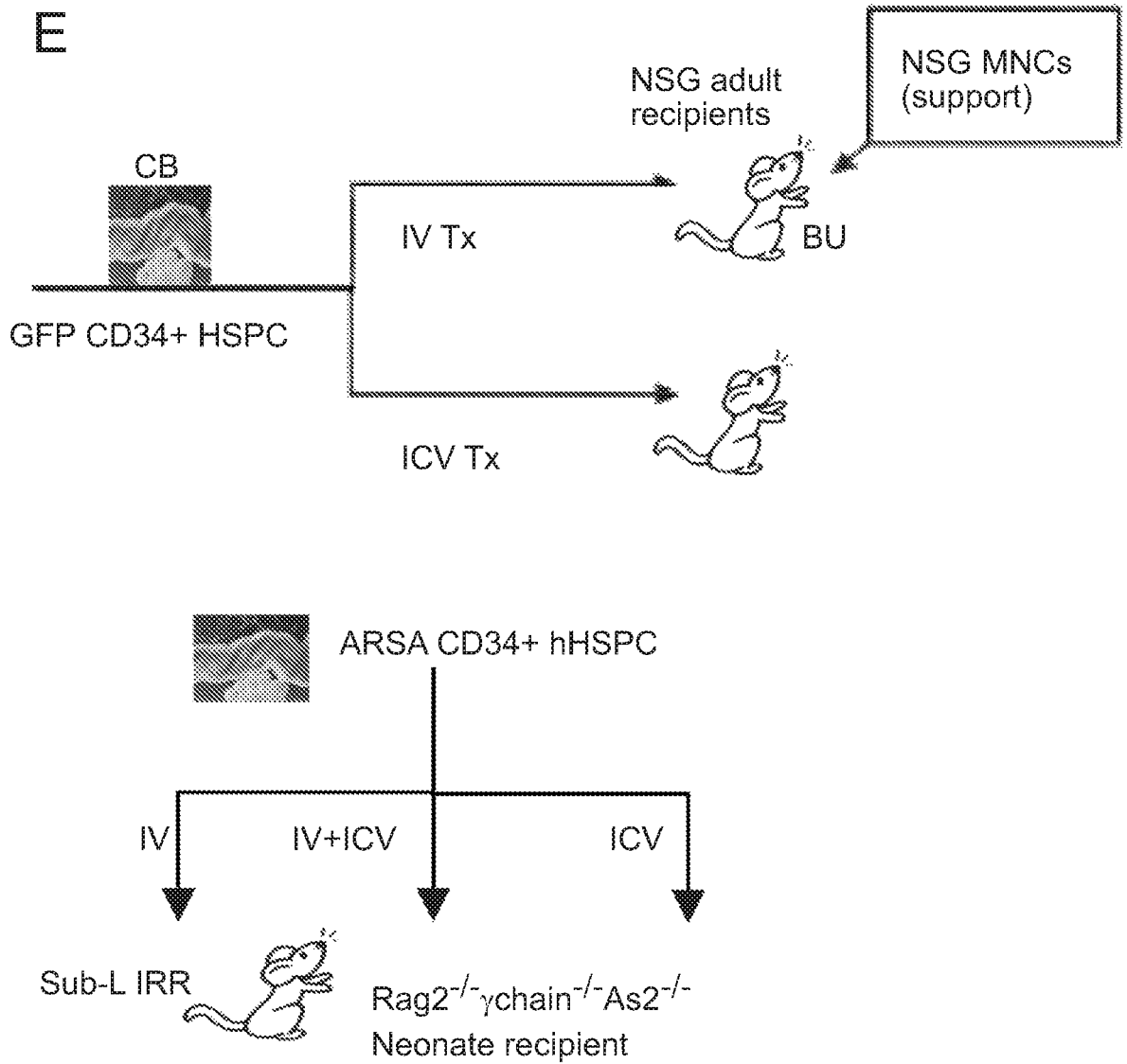
Figure 1:
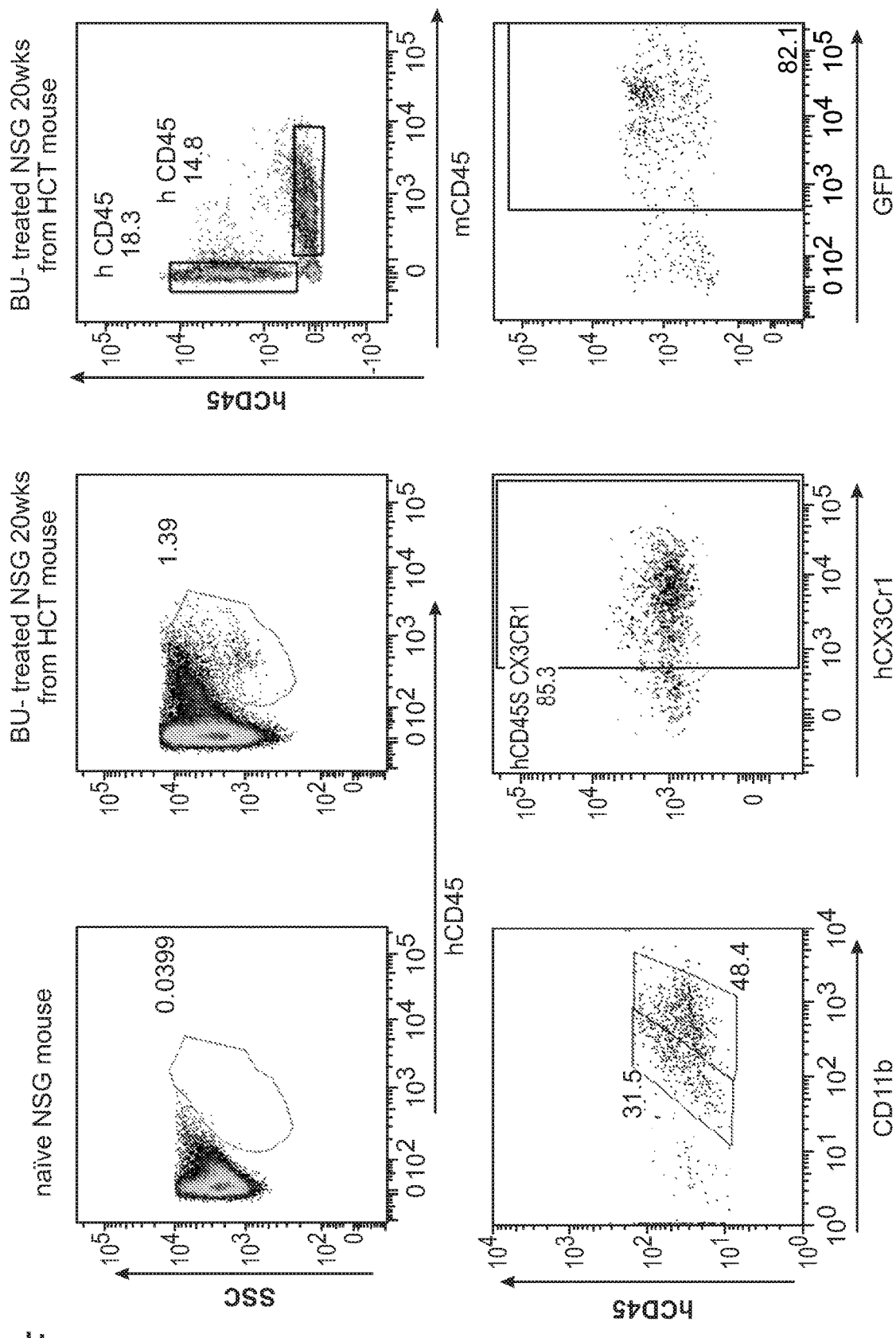
Figure 1:
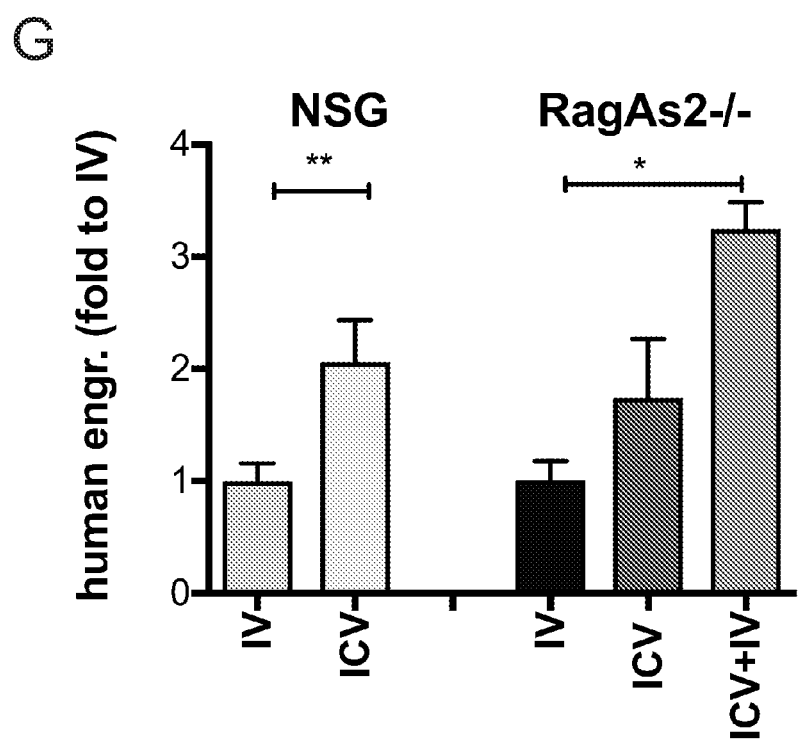
Figure 1:
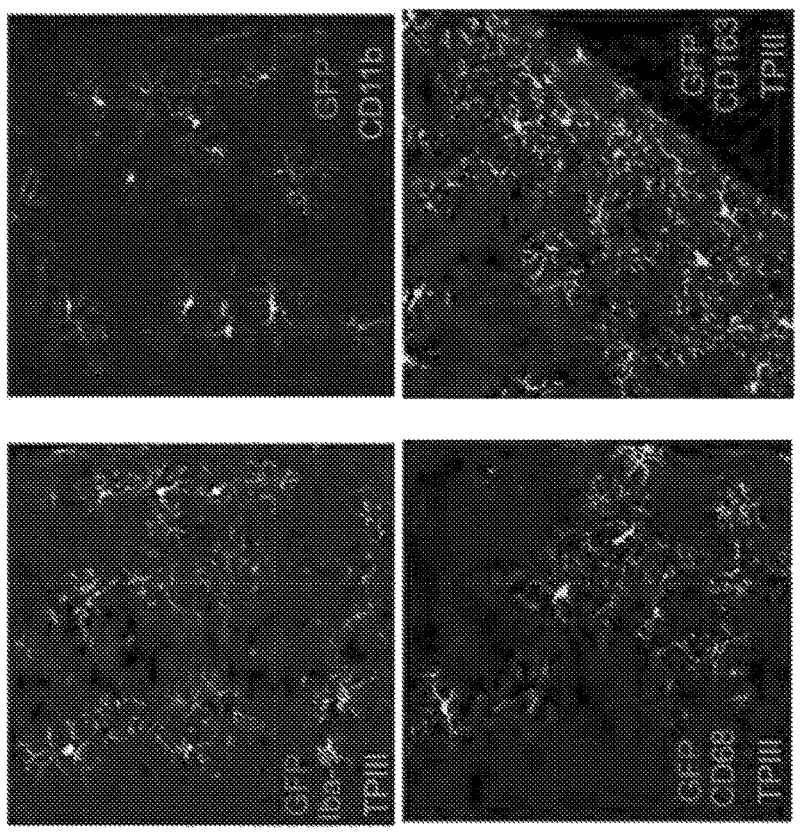
Figure 1:
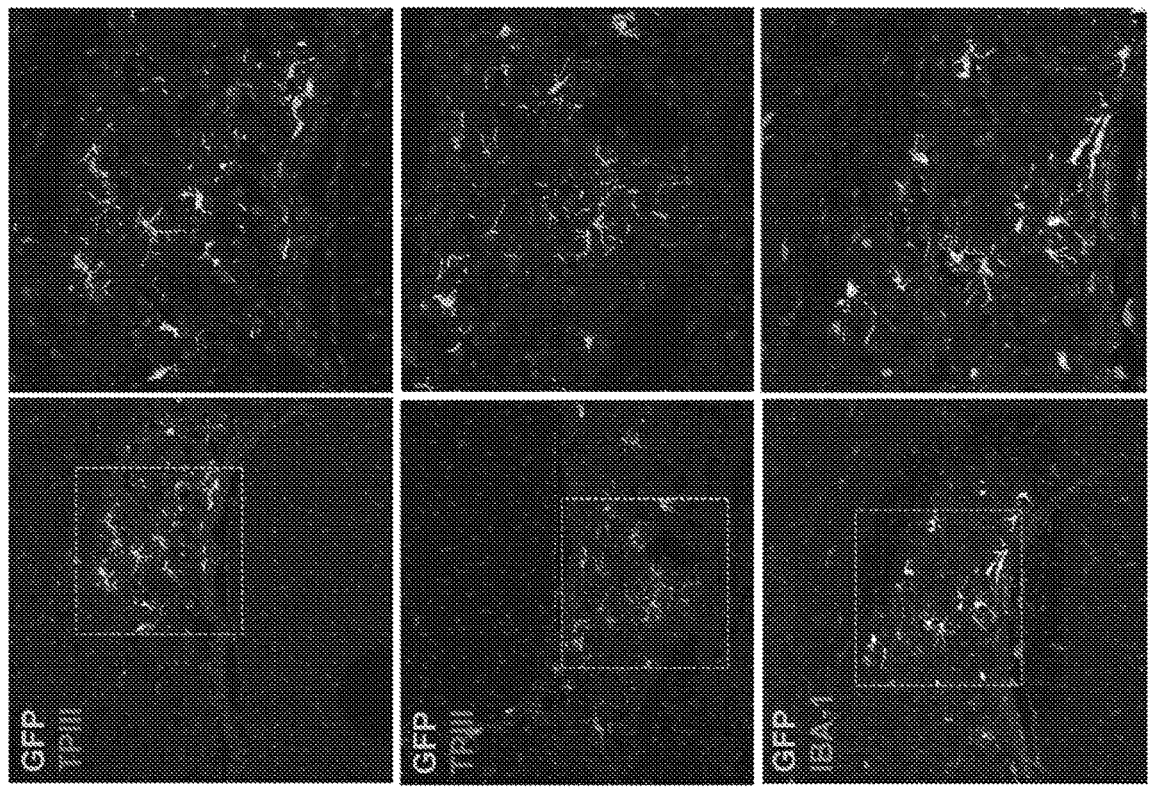

The invention features compositions and methods that are useful for reconstituting microglia upon transplantation of HSPCs, as well as for the treatment and prevention of neurological diseases or disorders of the central nervous system (e.g., a storage disorder, including lysosomal storage disorders, neurodegenerative disease, etc.).

The present invention is based at least in part on several discoveries described herein. Current methods for treating storage and neurodegenerative diseases using HSC transplantation are poorly effective on CNS disease manifestations because of the slow replacement of resident microglia by the progeny of the transplanted cells. Current methods for HSC transplantation into patients affected by SD and neurodegenerative disorders include the use of total bone marrow or apheretic products or cord blood, or of hematopoietic stem and progenitor cells (HSPCs, selective for CD34 expression) in the case of autologous gene therapy. Here, cell populations enriched in microglia-repopulating activity could be identified within these cell sources, whose use could eventually improve microglia reconstitution by the donor following transplantation. Moreover, it has been found that hematopoietic stem and progenitor cells (HSPC) or fractions of the HSPC pool delivered directly to the brain using Intra-cerebral Ventricular Injection (ICV) improved the speed and extent of microglia reconstitution by the transplanted donor cells and increase therapeutic protein delivery to the brain as compared to a single intra-venous (IV) transplantation approach. This approach is thus endowed with a great therapeutic potential and could be optimized in order to obtain a prevalent contribution of the ICV transplanted cells to microgliosis for advanced strategies aiming at exclusive microglia, and not hematopoietic tissue, replacement by the transplanted cells. This could be of great relevance in association with novel strategies being here developed for the molecular engineering of microglia for regulated therapeutic gene expression in response to neuroinflammatory or neurodegenerative stimuli.

As demonstrated herein, HSPC transplantation can generate transcriptionally-dependable new microglia through a stepwise process reminiscent of physiological post-natal microglia maturation. Hematopoietic cells able to generate new microglia upon transplantation into myeloablated recipients are retained within human and murine long-term hematopoietic stem cells (HSCs). Similar transcriptionally dependable new microglia cells can also be generated by intra-ventricular delivery of HSPCs. Importantly, this novel route is associated with a clinically relevant faster and more widespread microglia replacement compared to systemic HSPC injection. Thus, it was shown that:

Murine and human HSPC transplantation intra-venously (IV) and intracerebral ventricularly (ICV) give rise to a brain myeloid progeny The ICV delivery of murine and human HSPCs generates progeny myeloid cells in the brain with a faster kinetics and in greater amount as compared to IV ICV-injected HSPCs engraft and expand in the brain, while they do not engraft in the hematopoietic organs Contribution of the HSPCs injected ICV to brain myeloid chimerism can prevail over the contribution of IV co-injected HSPCs in specific conditions Contribution of HSPCs injected IV and ICV to brain myeloid chimerism can be equal in specific conditions Progeny cells of both IV- and ICV-transplanted HSPCs have a transcriptional profile consistent with microglia Progeny cells of ICV-injected HSPCs in brain are more similar to microglia than the progeny of IV-injected HSPCs Hematopoietic cells associated with the brain parenchyma of post-transplant mice have clonogenic and hematopoietic repopulation potential and microglia reconstitution potential Combined ICV+IV delivery of engineered HSPCs has therapeutic relevance in two representative LSDs Combined ICV+IV delivery of HSPCs is feasible in an allogeneic transplant setting Intra-thecal (IT) delivery of HSPCs can contribute to brain and hematopoietic chimerism in the context of combinatorial HSPC transplantation strategies Specific nanoparticles can be uploaded by c-kit$^l$ and nestin$^l$ myeloid proliferating cells in areas of interest in the brain Nanoparticles can encapsulate efficiently etoposide Etoposide is effective in cell killing when encapsulated in NPs rather than in the standard formulation Eto-NPs are uptaken by c-kit$^+$ CD45$^+$ cells in the mouse brain upon induction of microglia progenitor proliferation Eto-NPs can induce early apoptosis of c-kit$^l$ CD45$^l$ and CD45$^l$ cells in the mouse brain upon induction of microglia progenitor proliferation Previous work has hypothesized the existence of CNS resident microglia progenitors, whose ablation before HCT is essential for the establishment of microglia reconstitution. Here, the use of novel tools is proposed for the identification of these cells and novel methods for transplanting them in order to generate a systemic and CNS chimerism or a selective CNS chimerism with the transplanted cell progeny. Thus, the invention provides new tools for the identification of the cells, within the HSPC pool, to be employed for generating myeloid brain chimerism and transcriptionally-dependable new microglia upon transplantation (defined as "functional equivalent of microglia progenitors");

the optimal route and conditions to be employed for transplantation of functional equivalent of microglia progenitors in the case a sustained brain and hematopoietic organ chimerism is required for disease treatment;

the optimal route and conditions to be employed for transplantation of functional equivalent of microglia progenitors in the case a selective brain chimerism is sufficient and/or required for disease treatment;

the localization and targeting of microglia progenitors using nanocarriers the targeted delivery of ablating drugs to microglia progenitors for selective brain conditioning;

implementing novel therapeutic strategies in the context of advanced HSC transplantation protocols for myeloid CNS cells/microglia reconstitution for neurodegenerative diseases.

The results described herein indicate that optimized protocols of HSC transplantation could be used for the treatment of neurological diseases or disorders of the central nervous system, including, e.g., storage disorders and neurodegenerative diseases, by replacing diseased microglia with new cells endowed with novel/therapeutic functions. To this goal, molecular targets were identified to be employed for treating neurodegenerative diseases by the optimized microglia reconstitution approach. Thus, it was shown that:

Murine and human LT-HSCs are able to give rise to a brain myeloid progeny upon both IV and ICV delivery Less immature KSL fractions contribute to the generation of a brain myeloid progeny upon ICV delivery Functional equivalents of μ progenitors within the HSPC pool are comprised in LT_HSCs (both murine and human cells)

Functional equivalents of μ progenitors within the murine HSPC pool are Fdg5+

Functional equivalents of μ progenitors within the murine HSPC pool are CD11b negative Functional equivalents of μ progenitors within the murine HSPC pool are CX3Cr1 negative Functional equivalents of μ progenitors are comprised within CD34+ human HSPCs Functional equivalents of μ progenitors are enriched within the CD38− fraction of CD34+ human HSPCs.

Hematopoietic Cell Transplantation (HCT)

Recent pre-clinical and clinical evidences indicate that hematopoietic stem and progenitor cells (HSPCs) and/or their progeny can serve as vehicles for therapeutic molecule delivery across the blood brain barrier by contributing to the turnover of myeloid cell populations in the brain. However, the differentiation and functional characteristics of the cells reconstituted after transplantation are still to be determined, and in particular whether bonafide microglia could be reconstituted by the donor cell progeny post-transplant to be assessed. In the last three decades, Hematopoietic Cell Transplantation (HCT) and Hematopoietic Stem Cell (HSC)-based gene therapy have been applied with some benefit to patients affected by non-hematological and non-oncological diseases affecting the nervous system, such as peroxisomal disorders and lysosomal storage diseases (LSDs) (Cartier et al. *Science* 326, 818-823 (2009); Biffi et al. *Science* 341, 1233158 (2013); Sessa et al. *Lancet* 388, 476-487 (2016)) and neurodegenerative diseases (Simard et al. *Neuron* 49, 489-502 (2006)). These early clinical evidences, along with preclinical supporting data, suggest that hematopoietic stem and progenitor cells (HSPCs) and/or their progeny could serve as vehicles for therapeutic molecule delivery across the blood brain barrier (BBB). Indeed, HSPCs and/or their progeny could contribute to the turnover of myeloid cell populations in the brain (Ajami et al. *Nat Neurosci* 10, 1538-1543 (2007); Ajami et al. *Nat Neurosci* 14, 1142-1149 (2011); Biffi et al. *J. Clin. Invest.* 116, 3070-3082 (2006); Mildner et al. *Nat Neurosci* 10, 1544-1553 (2007); Capotondo et al. *Proc Natl Acad Sci USA.* 109, 15018-15023 (2012)), possibly including microglia, whose crucial role in the progression and outcomes of these disorders has been extensively described (Jeyakumar et al. *Brain* 126, 974-987 (2003); Wada et al. *Proc Nail Acad Sci USA* 97, 10954-10959 (2000); Ohmi et al. *Proc. Natl. Acad. Sci. USA* 100, 1902-1907 (2003); Eichler et al. *Ann Neurol* 63, 729-742 (2008)). Importantly, once integrated into the affected tissue, cells derived from the transplant were proven to favorably affect the local environment, i.e. by releasing therapeutic molecules in the brain of transplanted mice or patients. This concept was demonstrated in patients affected by the demyelinating LSD metachromatic leukodystrophy treated by HSC gene therapy (Biffi et al. *Science* 341, 1233158 (2013); Sessa et al. *Lancet* 388, 476-487 (2016)). Normal or above-normal activity of arylsulfatase A enzyme, defective in the patients and whose expression was induced by lentiviral vectors (LVs) integrated into the patients HSCs and their progeny, was measured in the treated children' cerebrospinal fluid (CSF) long after the treatment (Biffi et al. *Science* 341, 1233158 (2013); Sessa et al. *Lancet* 388, 476-487 (2016)). Notably, the enzyme is unable to efficiently cross per se the BBB (Biffi et al. *J. Clin. Invest.* 116, 3070-3082 (2006); Matzner et al. *Human Molecular Genetics* 14, 1139-1152 (2005)). These findings, which were associated with marked clinical benefit in the patients treated in pre-symptomatic stage, formally prove that the patients' brain were seeded by gene-corrected HSPC progeny cells. However, the differentiation and functional characteristics of the transplant-derived cells in the brain are still to be determined, and in particular whether bona fide microglia could be reconstituted by the donor cell progeny post-HCT to be demonstrated (Ajami et al. *Nat Neurosci* 10, 1538-1543 (2007); Capotondo et al. *Proc Natl Acad Sci USA.* 109, 15018-15023 (2012); Bennett et al. *Proc Natl Acad Sci USA* 113, E1738-1746 (2016)).

Despite microglia have a developmental origin distinct from that of bone marrow-derived myelomonocytes (Ginhoux et al. *Science* 330, 841-845 (2010)), others and us recently demonstrated that under specific experimental conditions, cells of donor origin showing a microglia-like phenotype and expressing some microglia surface markers could be successfully generated in the brain of mice transplanted with donor HSPCs. Essential for this to happen reproducibly and at high rates is the pre-transplant administration of a conditioning regimen based on the alkylating agent busulfan, capable of ablating functionally-defined brain-resident microglia precursors (Capotondo et al. *Proc Natl Acad Sci USA.* 109, 15018-15023 (2012); Wilkinson et al. *Mol Ther* 21, 868-876 (2013)). In this setting, the cells of donor origin found in the brain of transplanted animals were shown to derive from the local proliferation and differentiation of HSPCs migrated to the brain shortly after transplant.

In the present work, a substantial step forward has been made to better understand these events and increasing their translational potential for the treatment of neurological diseases. Indeed, here it is firstly demonstrated that donor derived myeloid cells appearing in the brain of mice receiving HSPCs after busulfan-based conditioning not only share the morphology and surface makers of microglia, but also a very similar transcriptional profile. Moreover, by using genome-wide expression analysis, it is shown that the transplanted HSPCs generate microglia-like progeny cells through a process that recapitulates some aspects of the physiologic post-natal microglia maturation. Importantly, it is also unambiguously proven that post transplant microgliosis derives from mouse and human early hematopoietic stem cells/progenitors that may be favored in their trafficking to the brain by CXCR4 expression. Finally, generation of microglia-like cells of donor origin is here firstly obtained also upon administration of HSPCs directly in the brain lateral ventricles of conditioned mice, instead of endovenously. Of note, this novel delivery route, which allows a clinically relevant faster and more widespread microglia replacement compared to systemic injection, confirms that microgliosis could derive from an independent seeding of the brain by the intra-venously transplanted HSPCs (Capotondo et al. *Proc Natl Acad Sci USA.* 109, 15018-15023 (2012)).

Overall, this work supports the relevance and feasibility of employing HSPCs for renewing brain myeloid and microglia cells with new populations endowed with the ability to exert therapeutic effects in the central nervous system (CNS), and identifies novel modalities, such as transplantation of enriched stem cell fractions and direct brain delivery of HSPCs, for increasing the actual contribution of the transplanted cells to microgliosis.

Storage Diseases (SDs)

Storage Disorders (SDs) comprise a class of inherited diseases characterized by disruption of normal lysosomal function resulting in the accumulation of incompletely degraded substrates that have been targeted for degradation after endocytosis or autophagy. The ensuing accumulation of the substrate itself or of the product(s) of an alternative metabolic route in lysosomes affects the architecture and function of the cells, leading to cell dysfunction or death. Further, the primary defect is frequently exacerbated by secondary responses. This is of particular relevance in the Central Nervous System (CNS) where neuroinflammation occurs representing a primary reaction to substrate accumulation within microglia and astrocytes and/or an inflammatory response to primary neuronal or oligodendroglial damage.

Examples of SDs include lysosomal storage diseases (LSDs), such as GM1 and GM2 Gangliosidosis, Alpha-mannosidosis, Globoid Cell Leukodystrophy (GLD), Neuronal Ceroid Lipofuscinosis (NCL), Metachromatic Leukodystrophy (MLD), Mucopolysaccharidoses disorders (MPSs), Multiple sulfatase deficiency (MSD), Niemann-Pick Disease, and peroxisomal storage disorders, such as Adrenoleukodystrophy. Approximately 50% of LSDs have movement of the CNS, as in the case of the examples listed above. A non-limiting list of exemplary SDs and their associated defective protein is provided at Table 1.

TABLE 1

Storage Disorders (SDs) and their associated defective protein

| Storage Disorder | Defective Protein |
| --- | --- |
| Pompe disease | Acid α-glucosidase |
| Gaucher disease | Acid β-glucosidase or glucocerebrosidase |
| $G_{M1}$-gangliosidosis | Acid β-galactosidase |
| Tay-Sachs disease | β-Hexosaminidase A |
| Sandhoff disease | β-Hexosaminidase B |
| Niemann-Pick disease | Acid sphingomyelinase |
| Krabbe disease | Galactocerebrosidase |
| Farber disease | Acid ceramidase |
| Metachromatic leukodystrophy | Arylsulfatase A |
| Hurler-Scheie disease | α-L-Iduronidase |
| Hunter disease | Iduronate-2-sulfatase |
| Sanfilippo disease A | Heparan N-sulfatase |
| Sanfilippo disease B | A-N-Acetylglucosaminidase |
| Sanfilippo disease C | Acetyl CoA; α-glucosaminide N-acetyltransferase |
| Sanfilippo disease D | N-acetylglucosamine-6-sulfate sulfatase |
| Morquio disease A | N-acetylgalactosamine-6-sulfate sulfatase |
| Morquio disease B | Acid B-galactosidase |
| Maroteaux-Lamy disease | Arylsulfatase B |
| Infantile neuronal ceroid lypofuscinosis | PPT1 |
| Sly disease | B-Glucoronidase |
| Alpha-mannosidosis | Acid α-mannosidase |
| Beta-mannosidosis | Acid β-mannosidase |
| Fucosidosis Acid | α-L-fucosidase |
| Sialidosis | Sialidase |
| Schindler-Kanzaki disease | α-N-acetylgalactosaminidase |

Information is provided of some LSDs of particular relevance for the use of HSC-transplant protocols as described in the present invention.

Metachromatic Leukodystrophy (MLD)

Metachromatic Leukodystrophy (MLD), a demyelinating LSD due to mutations in the Arylsulfatase A (ARSA) gene is a prototypical example of LSD with progressive accumulation of un-degraded substrates in the nervous system and secondary neuroinflammation and degeneration. The genetic transmission of MLD is autosomal recessive and its overall incidence is estimated to be 1:40.000-1:100.000.

Clinical manifestations, consisting of severe and unrelenting motor and cognitive impairment, and disease progression are more severe in the early onset clinical variants, leading to death usually within the first decade of life. A correlation between the phenotype of MLD patients and the type of ARSA mutation they bear has recently been demonstrated (Cesani et al. *Hum Mutat* 30, E936-945 (2009); Cesani et al. *Ann Neurol* 75, 127-137 (2014)). HSC gene therapy employing lentiviral vectors for autologous HSC transduction and exposure to systemic busulfan conditioning was shown to be effective in preventing or relenting disease manifestations in children affected by the most severe MLD variant and treated before symptom onset (Biffi et al. *Science* 341, 1233158 (2013); Sessa et al. *Lancet* 388, 476-487 (2016)).

Globoid Cell Leukodystrophy (GLD)

Globoid Cell Leukodystrophy (GLD), also known as Krabbe disease, is an autosomal recessive LSD caused by deficiency of the lysosomal enzyme Galactocerebrosidase (GALC) which catalyzes the catabolism of Galactosylceramide (GalCer), an important myelin constituent. GLD occurs in about 1 in 100,000 births. It typically occurs among infants and takes rapidly a fatal course, but rare late-onset forms also exist. The devastating neurodegenerative disorder is due to alterations in glycosphingolipid catabolism caused by GALC deficiency: the resulting accumulation of incompletely metabolized GalCer leads to progressive white matter disease which affects both the CNS and the Peripheral Nervous System (PNS). Galactosylsphingosine (or psycosine) is also a substrate of GALC and it is considered to play a critical role in the pathogenesis. GLD children can be treated when pre-symptomatic and below the age of 4-month-old by HCT from healthy compatible donors that delays disease onset and attenuates manifestations (Escolar et al. *N Engl J Med*. 352, 2069-2081 (2005)). HSC gene therapy was also proven to be potentially effective in GLD preclinical models (Gentner et al. *Sci Transl Med* 2 (2010)).

Mucopolysaccharidoses (MPSs)

Mucopolysaccharidoses (MPS) are a group of LSDs caused by the absence or malfunctioning of lysosomal enzymes needed to break down glycosaminoglycans.

MPS I is divided into three subtypes based on severity of symptoms. All three types result from an absence of, or insufficient levels of, the enzyme alpha-L-iduronidase. MPS I H (also called Hurler syndrome or α-L-iduronidase deficiency), is the most severe of the MPS I subtypes while MPS I S, Scheie syndrome, is the mildest form of MPS I. MPS I H-S, Hurler-Scheie syndrome, is less severe than Hurler syndrome alone. MPS II, Hunter syndrome or iduronate sulfatase deficiency, is caused by lack of the enzyme iduronate sulfatase. MPS III, Sanfilippo syndrome, is marked by severe neurological symptoms. There are four distinct types of Sanfilippo syndrome, each caused by alteration of a different enzyme needed to completely break down the heparan sulfate sugar chain. Sanfilippo A is the most severe of the MPS III disorders and is caused by the missing or altered enzyme heparan N-sulfatase. Children with Sanfilippo A have the shortest survival rate among those with the MPS III disorders. Sanfilippo B is caused by the missing or deficient enzyme alpha-N acetylglucosaminidase. Sanfilippo C results from the missing or altered enzyme acetyl-CoAlpha-glucosaminide acetyltransferase. Sanfilippo D is caused by the missing or deficient enzyme N-acetylglucosamine 6-sulfatase.

MPS IV, Morquio syndrome, results from the missing or deficient enzymes N-acetylgalactosamine 6-sulfatase (Type A) or beta-galactosidase (Type B) needed to break down the keratan sulfate sugar chain. MPS VI, Maroteaux-Lamy syndrome, shares many of the physical symptoms found in Hurler syndrome and is caused by the deficient enzyme N-acetylgalactosamine 4-sulfatase. MPS VII, Sly syndrome, one of the least common forms of the mucopolysaccharidoses, is caused by deficiency of the enzyme beta-glucuronidase.

Some MPS patients were shown to benefit from HCT from healthy compatible donors, whereas for some MPSs HSC GT strategies are being optimized (Visigalli et al. *Blood* 116, 5130-5139 (2010)).

Neuronal Ceroid Lipofuscinoses (NCLs)

Neuronal CeroidoLipofuscinoses are a class of inherited storage disorder that result in progressive neurological degeneration. Some variants, such as the infantile NCL (INCL), are caused by deficiency of a lysosomal enzyme. INCL is caused by mutations in the CLN2 gene that result in the deficiency of PPT1, a lysosomal enzyme that is responsible for degrading membrane proteins. Similarly, late infantile NCL (LINCL) is due to defiency of the lysosomal enzyme TPP1. Neurons are particularly sensitive to the lysosomal accumulation of this storage material, and individuals with INCL and LINCL have extensive, progressive neurodegeneration in all parts of the brain, resulting in a vegetative state and death by the age of 8-12 years.

X-Linked Adrenoleuukodystrophy (X-ALD)

X-linked adrenoleukodystrophy (X-ALD) is a metabolic genetic disease with a frequency of 1:17.000 males characterized by a progressive inflammatory demyelination in the brain. The mutation in the ABCD1 gene located in the chromosome Xq28 determined the loss of function of the related ALD protein which in turns results in the accumulation of unbranched saturated very long chain fatty acids (VLCFAs) within phospholipid fractions such as lysophatidylcholine (LPC), particularly in brain and adrenal cortex. Phenotypic variability in X-ALD appears to be linked to brain inflammation that causes progressive neurological decline mostly in children but also in adults with X-ALD. The initiation of cerebral demyelination could be directly linked to the amount of VLCFA in complex lipids and to their inefficient degradation by microglia cells. Thus, despite perivascular macrophages were shown to closely follow the leading edge of the demyelinating lesion and to play a crucial role in the removal of myelin debris, microglia cells behaved differently, being few in the same area and apoptotic in the surrounded ones (Eichler et al. *Ann Neurol* 63, 729-742 (2008)). Eichler et al. speculated that microglia in this region are unable to degrade VLCFA that in turns may cause microglial activation and apoptosis. The loss of microglia and/or microglia dysfunction may play an important role in the early phases of demyelination mainly due to the production of pro-inflammatory cytokines (CCL2, CCL4, IL-1a, CXCL8) and to the altered ability to provide neuroprotective factors to deficient oligodendrocytes. In this scenario microglia cells may be an appropriate target for intervention in X-ALD patients with evidence of cerebral demyelination. In this perspective, HSC transplantation (Aubourg et al. *N Engl J Med* 322, 1860-1866 (1990)) and, more recently, gene therapy (Cartier et al. *Science* 326, 818-823 (2009); Eichler et al. *N Engl J Med doi:* 10.1056/NEJMoa1700554 (2017)) have been explored as treatment options for X-ALD.

Neurodegenerative Diseases

Neurodegenerative diseases are a class of neurological diseases that are characterized by the progressive loss of the structure and/or function of neurons and/or neuronal cell death. Inflammation has been implicated for a role in several neurodegenerative diseases. Progressive loss of motor and sensory neurons and the ability of the mind to refer sensory information to an external object is affected in different kinds of neurodegenerative diseases. Non-limiting examples of neurodegenerative diseases include ALS, e.g., familial ALS or sporadic ALS, and Alzheimer's Disease.

Relationships between microglia and neurodegeneration have been observed. Activation of glial cells in ALS plays an important role in disease progression and spreading of the pathology to other CNS districts. Aberrant activation of microglia cells in ALS orchestrates a neurotoxic environment. Activated microglia cells are found in close proximity of $A\beta$ plaques in AD brain.

A health care professional may diagnose a subject as having a neurodegenerative disease by the assessment of one or more symptoms of a neurodegenerative disease in the subject. Non-limiting symptoms of a neurodegenerative disease in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disease. A health care professional may diagnose a subject as having a neurodegenerative disease upon presentation of a subject to a health care facility (e.g., a clinic or a hospital). In some instances, a health care professional may diagnose a subject as having a neurodegenerative disease while the subject is admitted in an assisted care facility. Typically, a physician diagnoses a neurodegenerative disease in a subject after the presentation of one or more symptoms.

Methods of Treatment

The present invention provides methods of treating disease and/or disorders or symptoms thereof which comprise administering a therapeutically effective amount of a pharmaceutical composition comprising a microglial progenitor described herein to a subject (e.g., a mammal such as a human). Thus, one embodiment is a method of treating a subject suffering from or susceptible to a disease or disorder or symptom thereof. The method includes the step of administering to the mammal a therapeutic amount of a cell herein sufficient to treat the disease or disorder or symptom thereof, under conditions such that the disease or disorder is treated.

The methods herein include administering to the subject (including a subject identified as in need of such treatment) an effective amount of a cell described herein, or a composition described herein to produce such effect. Identifying a subject in need of such treatment can be in the judgment of a subject or a health care professional and can be subjective (e.g. opinion) or objective (e.g. measurable by a test or diagnostic method).

Engraftment of transplanted cells provides the expression or activity of a polypeptide or other therapeutic agent. For example, a deficiency in or loss of function of a lysosomal enzyme results in a lysosomal storage disorder. Transplanted hematopoietic cells that express the therapeutic protein (e.g., an enzyme) either endogenously or via recombinant methods engraft and differentiate into microglia, thereby remedying the deficiency in the enzyme. Additionally, transplanted cells may serve as a vehicle for therapeutic polypeptides in neurodegenerative diseases.

In certain embodiments, engraftment is enhanced by ablating existing microglia (e.g., with alkylating agents). In particular, nanoparticle delivery of alkylating agents may be effective in creating an environment that allows the engraftment of microglia progenitors derived from the transplanted cells exclusively in the brain. Moreover, delivery of populations enriched in bone marrow-derived microglia progenitors by standard or innovative routes could allow sustained reconstitution of brain microglia with donor or engineered cells.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method). Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which myelination deficiency or loss may be implicated, including multiple sclerosis.

The present invention provides methods of delivering nanoparticles comprising a cytotoxic agent and/or ablating a microglial cell or progenitor thereof comprising administering a nanoparticle comprising a cytotoxic agent to a subject (e.g., a mammal such as a human).

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semi-conducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention. Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. In one embodiment, nanoparticles based on self assembling bioadhesive polymers are contemplated, which may be applied to oral delivery of agents, intravenous delivery of agents and nasal delivery of agents, all to the brain. Other embodiments, such as oral absorption and ocular deliver of hydrophobic drugs are also contemplated. The molecular envelope technology involves an engineered polymer envelope which is protected and delivered to the site of the disease (Mazza et al. ACS Nano 7, 1016-1026 (2013); Siew et al. Mol Pharm 9, 14-28 (2012); Lalatsa et al. J Control Release 161, 523-536 (2012); Lalatsa et al. Mol Pharm 9, 1665-1680 (2012); Garrett et al. J Biophotonics 5, 458-468 (2012); Uchegbu, Expert Opin Drug Deliv 3, 629-640 (2006); Uchegbu et al. Int J Pharm 224, 185-199 (2001); Qu et al. Biomacromolecules 7, 3452-3459 (2006)).

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation, which includes a particle in accordance with the present invention. A particle in accordance with the present invention is any entity having a greatest dimension (e.g. diameter) of less than 100 microns (.mu.m). In some embodiments, inventive particles have a greatest dimension of less than 10 p.m. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS).

Particle delivery systems within the scope of the present invention may be provided in any form, including but not limited to solid, semi-solid, emulsion, or colloidal particles. As such any of the delivery systems described herein may be provided as particle delivery systems within the scope of the present invention.

Antibodies

As reported herein, antibodies that specifically bind a marker (e.g., of a microglial cell or precursor thereof) are useful in the methods of the invention, including therapeutic methods. In particular embodiments, the invention provides methods of ablating microglia involving contacting microglia with a nanoparticle having a capture molecule that specifically binds a marker of a microglial cell and containing a cytotoxic agent (e.g., an alkylating agent).

Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. As used herein, the term "antibody" means not only intact antibody molecules, but also fragments of antibody molecules that retain immunogen-binding ability. Such fragments are also well known in the art and are regularly employed both in vitro and in vivo. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments.

The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). For example, F(ab')$_2$, and Fab fragments that lack the Fc fragment of an intact antibody, clear more rapidly from the circulation, and may have less non-specific tissue binding than an intact antibody (Wahl et al., *J. Nucl. Med.* 24:316-325 (1983). Thus, the antibodies of the invention comprise, without limitation, whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anticarcinoembryonic antigen (CEA) diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In various embodiments, an antibody is monoclonal. Alternatively, the antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Methods of preparing antibodies are well known to those of ordinary skill in the science of immunology. Antibodies can be made by any of the methods known in the art utilizing a soluble polypeptide, or immunogenic fragment thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding polypeptides or immunogenic fragments thereof, can be provided to the host in a delivery vehicle that is taken up by immune cells of the host. The cells will in turn express the polypeptide thereby generating an immunogenic response in the host. Alternatively, nucleic acid sequences encoding human polypeptides or immunogenic fragments thereof, can be expressed in cells in vitro, followed by isolation of the polypeptide and administration of the polypeptide to a suitable host in which antibodies are raised.

Alternatively, antibodies may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Recombinant Polypeptide Expression

In order to express the polypeptides of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a polypeptide, or fragment thereof, operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Methods for Evaluating Therapeutic Efficacy

In one approach, the efficacy of the treatment is evaluated by measuring, for example, the biological function of the treated organ (e.g., neuronal function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is neuronal tissue and, preferably, the organ is brain.

In another approach, the therapeutic efficacy of the methods of the invention is assayed by measuring an increase in cell number in the treated tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif). For example, assays for cell proliferation may involve the measurement of DNA synthesis during cell replication. In one embodiment, DNA synthesis is detected using labeled DNA precursors, such as [$^{3}H$]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302 (5650):1581-4, 2003; Gu et al., Science 302 (5644):445-9, 2003).

Kits

The invention provides kits for the treatment or prevention of a neurological disease or disorder of the central nervous system (e.g., a storage disorder, lysosomal storage disorder, neurodegenerative disease, etc.). In one embodiment, the kit includes a composition containing an isolated hematopoietic stem cell expressing a therapeutic polypeptide. In another embodiment, the kit includes a nanoparticle for ablative conditioning of endogenous microglial cells.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a neurological disease or disorder of the central nervous system. The instructions will generally include information about the use of the composition for the treatment or prevention of the disease or disorder. In other embodiments, the instructions include at least one of the following: description of the therapeutic agent; dosage schedule and administration for treatment or prevention of a neurological disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Intra-Cerebral Ventricular Injection of Murine HSPCs Results in Rapid and Robust Myeloid Cell Engraftment in Brain Recent results (Capotondo et al., *PNAS* 2012) propose that engraftment and persistent donor chimerism in the bone marrow hematopoietic niche might not be necessary for obtaining myeloid cell reconstitution in the brain following HCT. Based on these findings it was assessed whether myeloid and microglia-like cell reconstitution could occur upon direct transplantation of HSPCs into the cerebral ventricular space in conditioned mice. Murine lineage negative (Lin$^-$) HSPCs ($3\times10^5$ cells) were labeled with GFP-encoding Lentiviral Vectors (LVs) and transplanted by ICV injection in mice after exposure to a myeloablative busulfan dose or lethal irradiation (FIG. TA). Interestingly, transplantation resulted in a high and progressively increasing GFP chimerism in the CD45$^+$CD11b$^+$ brain myeloid compartment of the ICV-transplanted mice, conceivably derived from the local proliferation of the transplanted cells (FIG.

1B). For each time point and condition, control mice transplanted IV with GFP$^+$ HSPCs were used as terms of comparison. Notably, the kinetic of microglia reconstitution was faster and the extent of GFP chimerism was higher when the GFP$^+$ HSPCs were transplanted ICV as compared to IV (FIG. 1B) (significant effects of the route of cell administration and time were shown by two-way ANOVA analysis). This is remarkable considering the lower number of cells transplanted ICV as compared to IV. As in the case of IV injection, also upon ICV cell transplantation recipient mice pre-treated with busulfan showed a higher brain myeloid donor chimerism as compared to irradiated animals.

Immunofluorescence analysis of sagittal brain sections from the contralateral side of cell injection of ICV transplanted mice consistently demonstrated abundant GFP-expressing, donor-derived cells distributed throughout the recipient mice brain (FIG. 1C). GFP$^+$Iba1$^+$ ramified parenchymal cells were frequently grouped in small clusters, with the highest GFP$^+$ cell frequencies retrieved in the olfactory bulb, hypothalamic area, basal nuclei, sub ventricular zone and surrounding regions, striatum and in the pons (FIG. 1D). Importantly, GFP$^+$ cell morphology resembled that of intra-parenchymal microglia cells with ramification and thin processes departing from the cell body already at relatively short term (45-60 days) post-transplant.

Example 2. Intra-Cerebral Ventricular Injection of Human HSPCs Results in Rapid and Robust Myeloid Cell Engraftment in Brain In order to gain insight into the clinical relevance of this phenomenon, the ability of human HSPCs to generate microglia-like cells upon ICV delivery in conditioned immune deficient animal models was tested. ICV or IV human CD34$^+$ cells were isolated from cord blood, transduced with GFP-encoding LVs, and infused into NOD.Cg-Prkdc$^{scid}$Il2rg$^{tm1Wjl}$/SzJ (NSG) mice (FIG. 1E). Moreover, in order to determine the actual role of ICV cell transplantation in augmenting the potential of the transplant to deliver therapeutic molecules to the brain, a newly generated mouse model, the Rag$^{-/-}$ γ-chain$^{-/-}$ As2$^{-/-}$, was employed that reproduces the lysosomal disease Metachromatic leukodystrophy (MLD) due to Arylsulfatase A (ARSA) deficiency in an immune-deficient background. These mice received human cord blood CD34$^+$ cells transduced with an ARSA encoding LVs (Biffi et al., *Science* 341, 1233158 (2013); Sessa et al., *Lancet* 388, 476-487 (2016)) by IV only or ICV only injection, or by a combination of the IV and ICV routes (FIG. 1E).

Interestingly, a clearly defined human myeloid (CD45$^+$ CD11b$^+$) cell progeny was identified in brain of the transplanted mice long term after both IV and ICV transplant (FIG. 1F). ICV cell delivery resulted in a greater human cell engraftment in the brain as compared to IV delivery (FIG. 1G). ICV cell delivery in combination with IV resulted in even more human cell engraftment in the brain (FIG. 1G). In all the tested transplant settings, the human cells largely expressed the microglia markers CX3CR1 and CD11b (FIG. 1F) at cytofluorimetry. The engrafted cells were distributed within the brain parenchyma and displayed the morphological features of microglia cells. The engrafted cells also expressed Iba1 and CD11b (FIG. 1H) markers, but not CD68 and CD163 (FIG. 1H) that are mostly associated with macrophages. In the case of ICV delivery, the progeny cells were identified typically grouped in small clusters in the same regions where progeny cells of the ICV transplanted murine HSPC were identified, i.e. in the subventricular zone.

Figure 2:
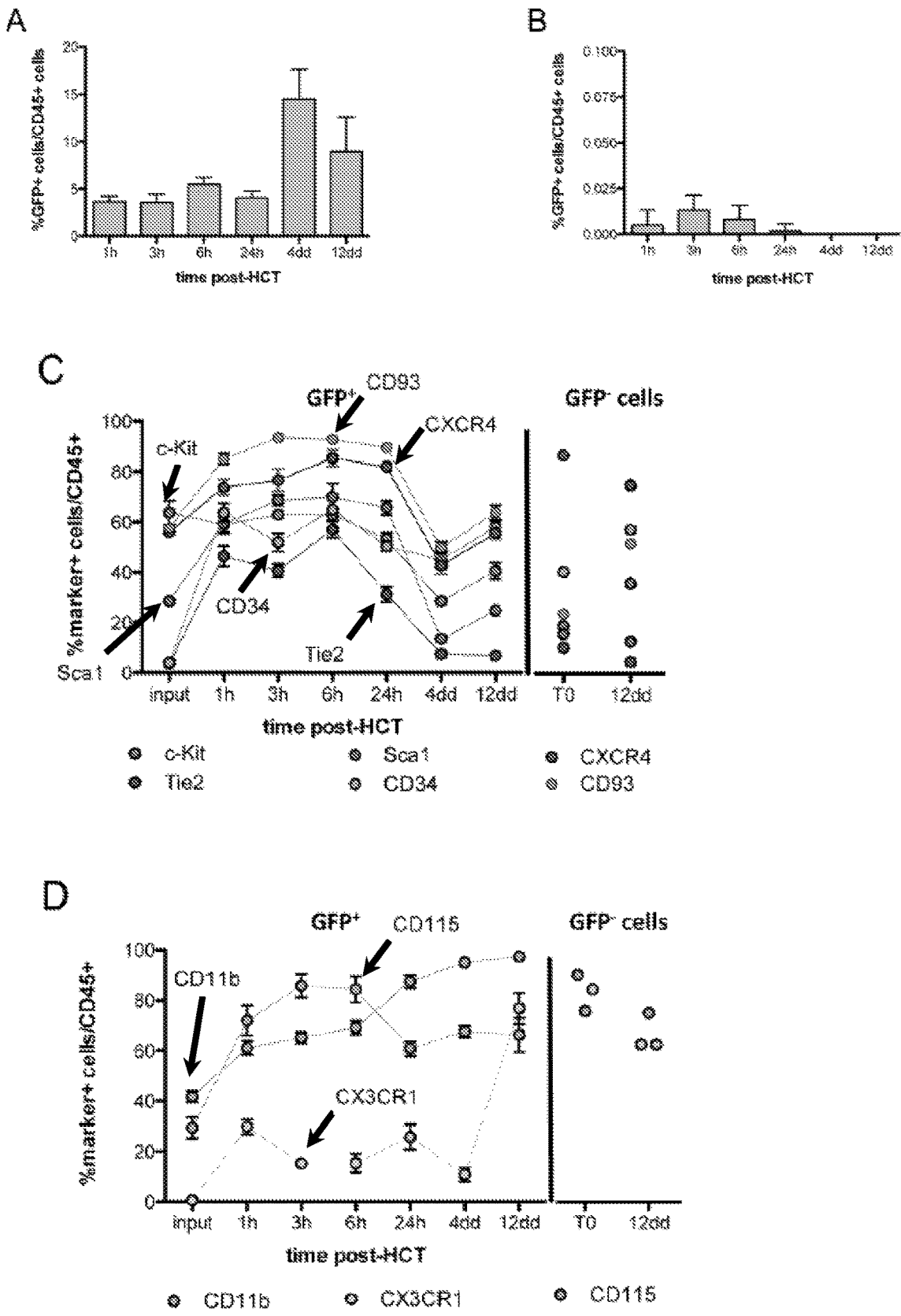
FIGS. 2A-2D show the short-term monitoring of mice transplanted ICV with GFP$^+$ Lin⁻ HSPCs.

Example 3. ICV-Injected HSPCs Engraft and Expand in the Brain, while they do not Engraft in the Hematopoietic Organs By short-term flow cytometry monitoring of the mice transplanted IV or ICV with GFP-labeled Lin$^-$ HSPCs the presence, persistence and moderate expansion of the ICV-delivered cells in the brain of the recipient animals was demonstrated (FIG. 2A). Conversely, only detected negligible amounts of GFP$^+$ cells were detected in the bone marrow of the ICV transplanted mice (<1%) (FIG. 2B). The GFP$^+$ cells transiently up-regulated early hematopoietic markers (FIG. 2C) and, afterwards, the CD11b, CX3CR1 and CD115 microglia markers up to levels similar to the endogenous microglia (FIG. 2D). The GFP CD45$^+$ endogenous cells transiently and slightly down-regulated CD 115, as a possible effect of the busulfan treatment (FIG. 2D).

Example 4. Optimized Combinatorial Transplant Protocols Allow Modulating the Contribution of IV Versus ICV Transplanted Cells for Proper Clinical Applications Development of ICV cell delivery for cell and gene therapy in conditioned recipients requires optimization of transplant conditions according to different foreseen target diseases—different options may be amenable that may be applied with different goals according to the disease of interest. In particular, two scenarios can be envisaged:
  A) Reconstitution of both the hematopoietic tissues (including extra-CNS myeloid populations) and microglia with i) autologous gene corrected or ii) healthy donor HSCs post-transplant for the treatment of SDs with systemic and neurologic involvement, with the goal of rendering microglia reconstitution efficient and rapid; examples of diseases amenable to this approach include MLD, GLD, MPSI, MPSII and MPSIII;
  B) Reconstitution of microglia with autologous gene corrected HSCs post-transplant for the treatment of SDs with exclusive neurologic involvement or neurodegenerative diseases; examples of diseases amenable to this approach include INCL, GM1 gangliosidoses, PD, ALS, AD.

Figure 3:
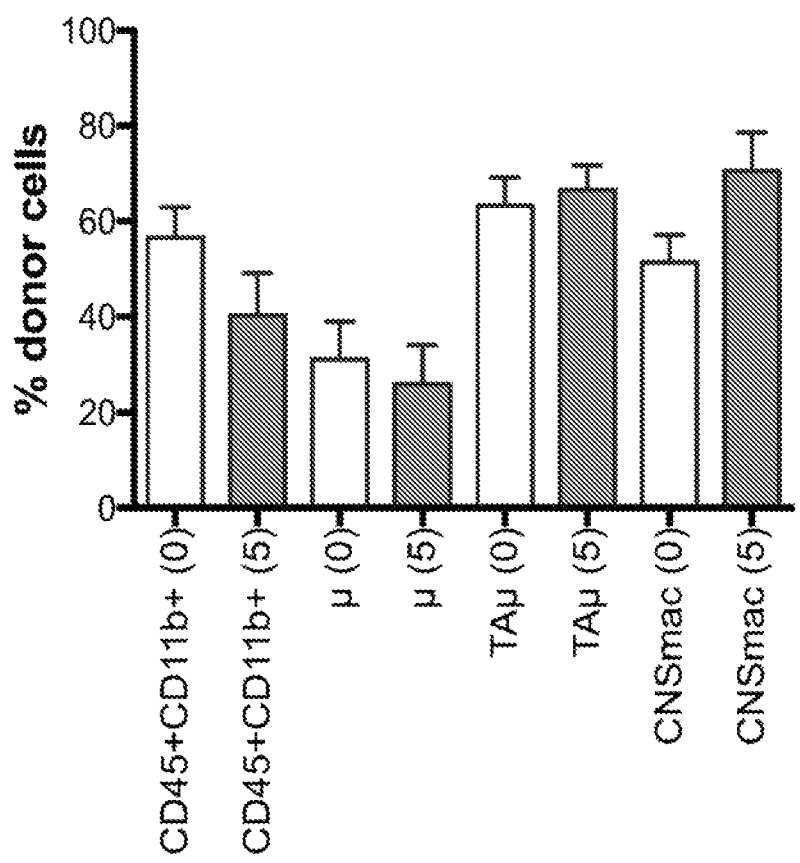
FIGS. 3A-3J show that optimized combinatorial transplant protocols allow modulating the contribution of IV versus ICV transplanted cells to donor myeloid brain chimerism post-transplant for proper clinical applications.
Figure 3:
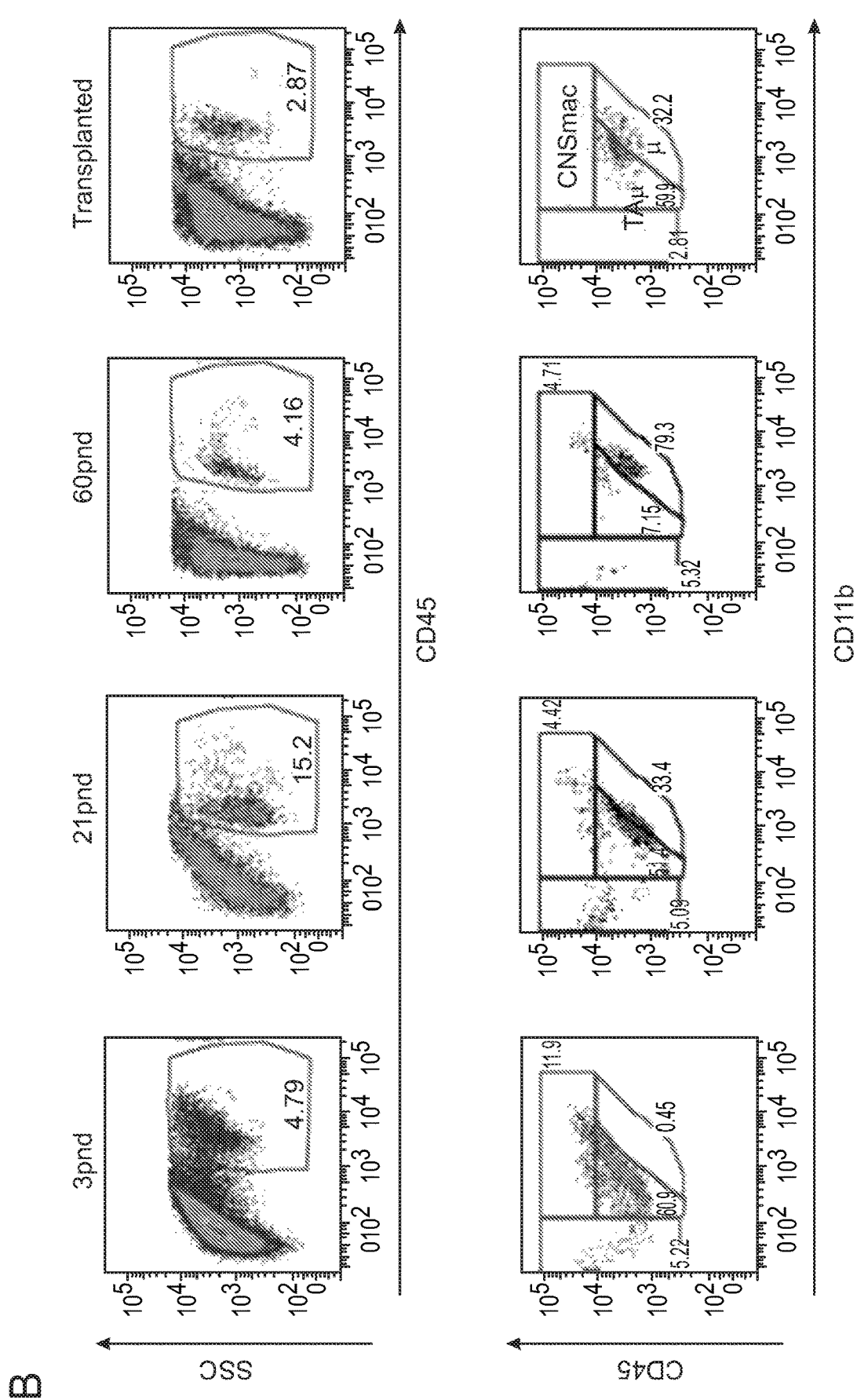
Figure 3:
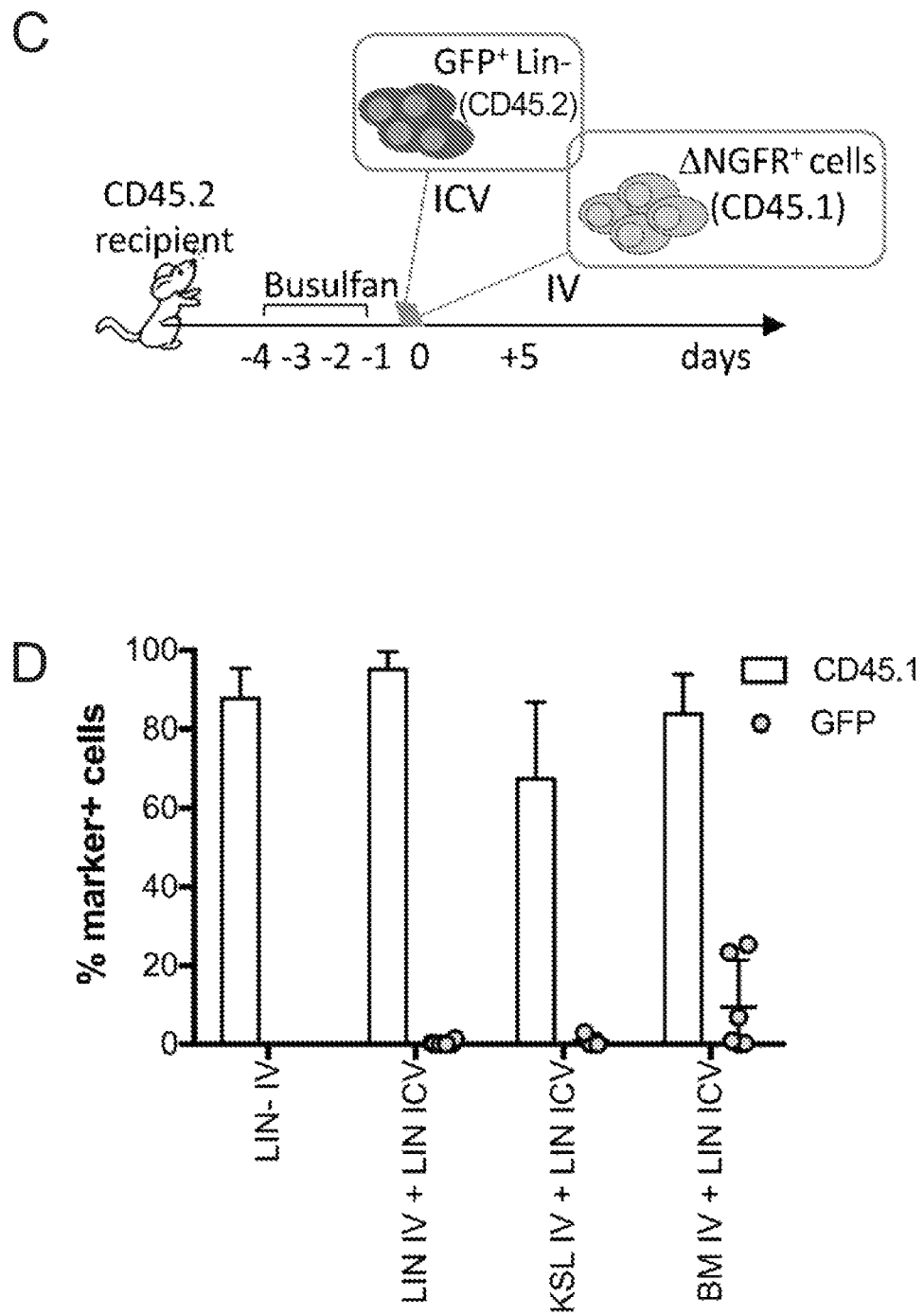
Figure 3:
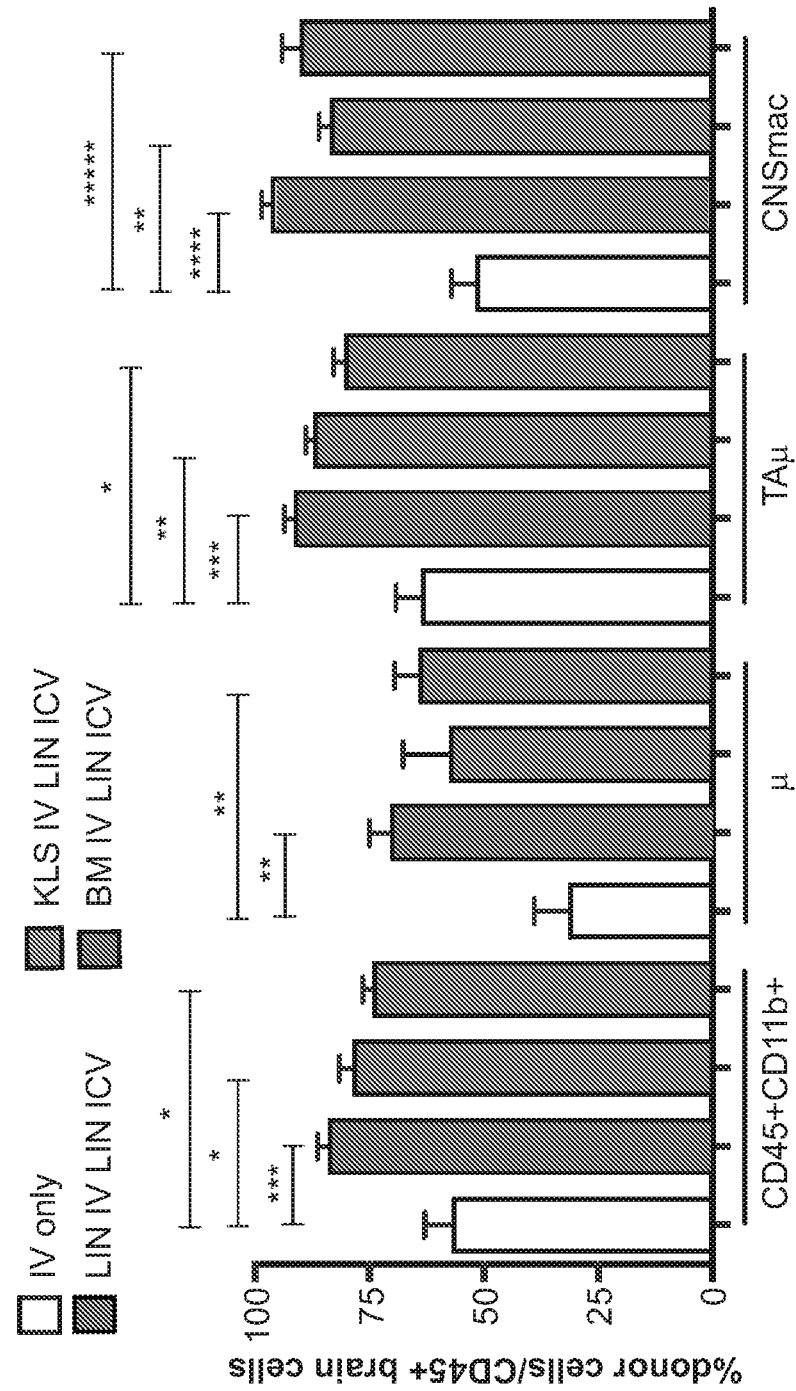
Figure 3:
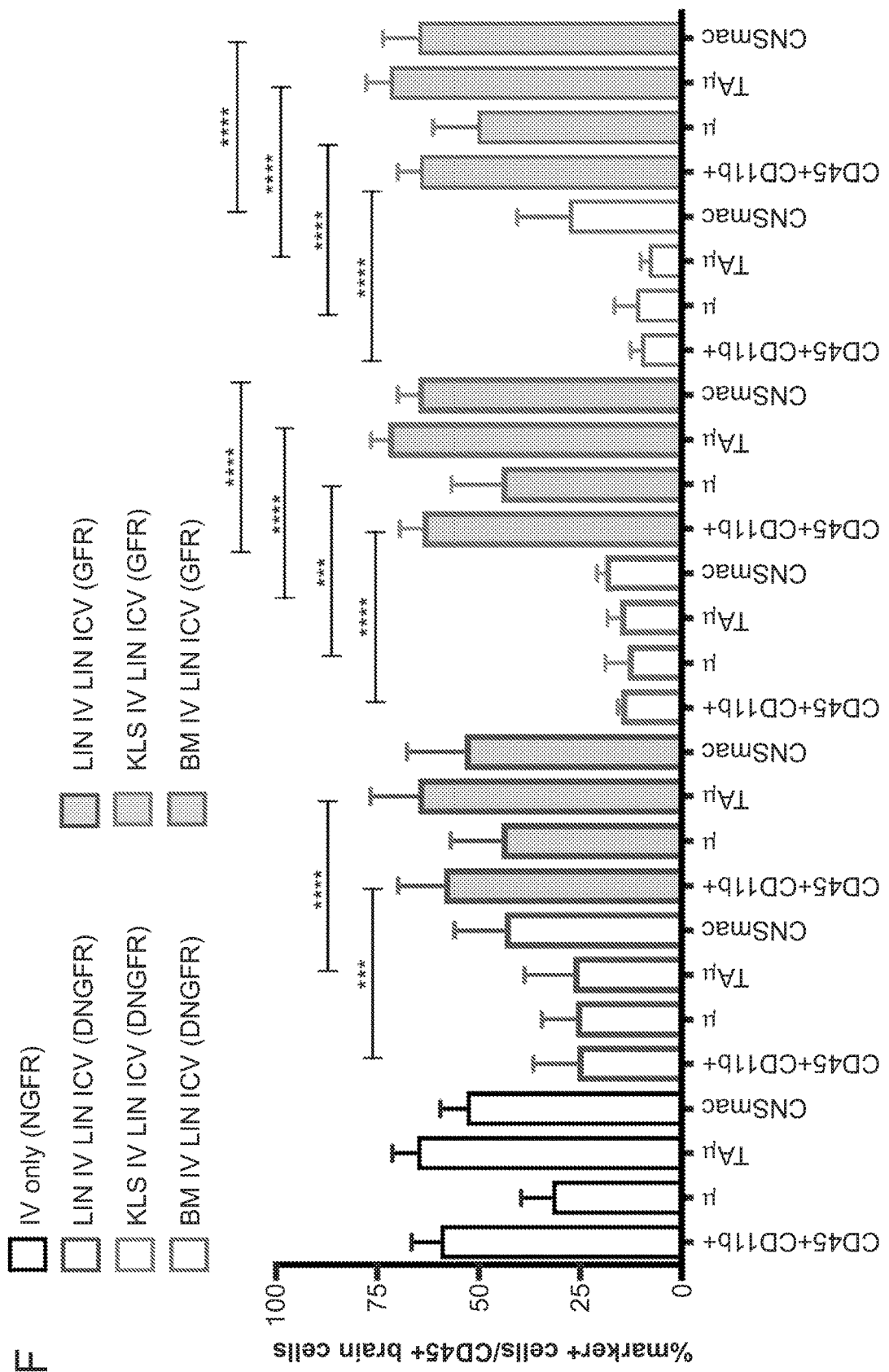
Figure 3:
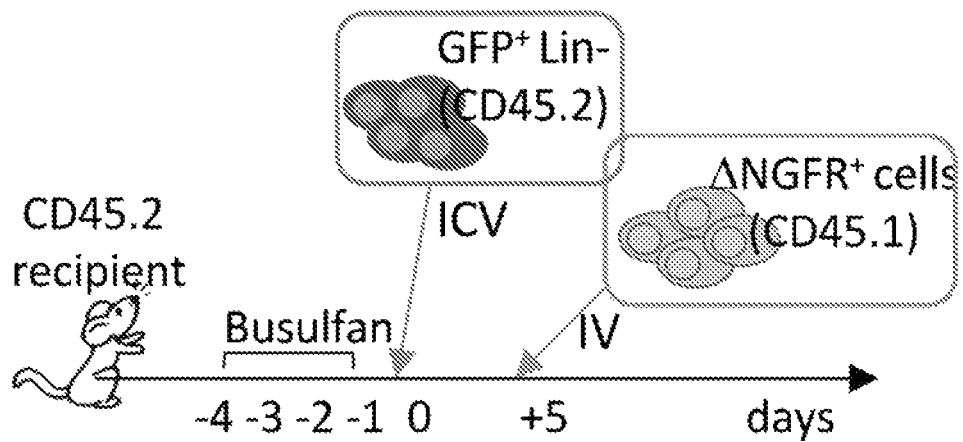
Figure 3:
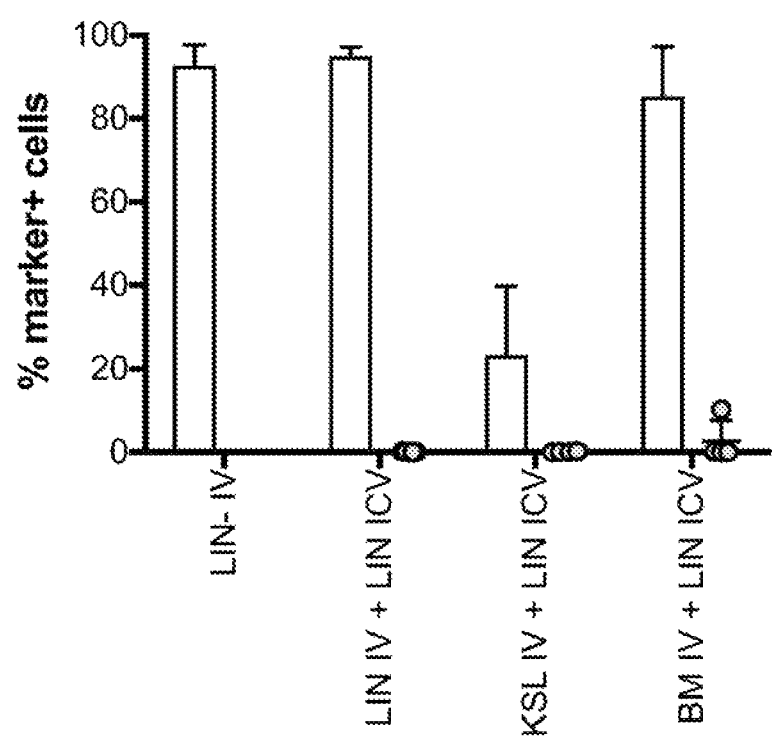
Figure 3:
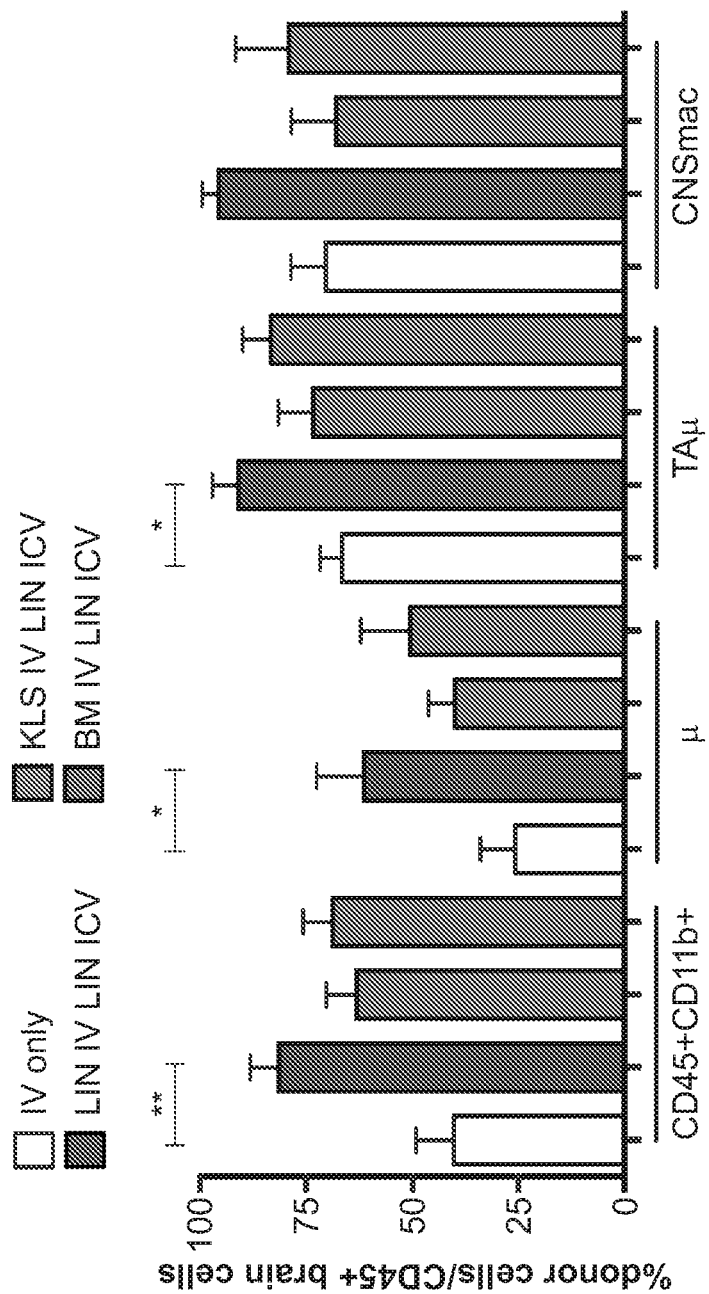
Figure 3:
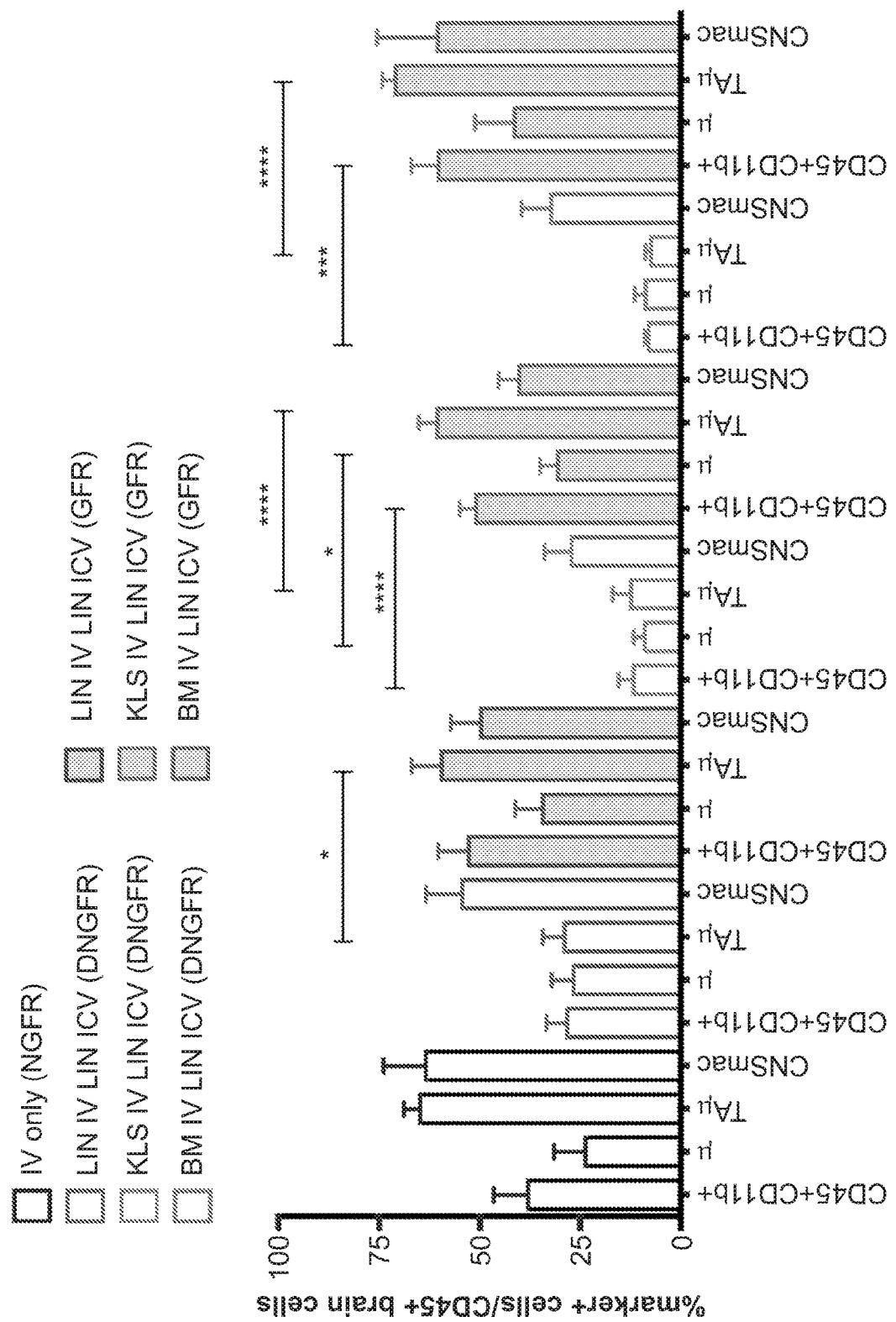
Figure 6:
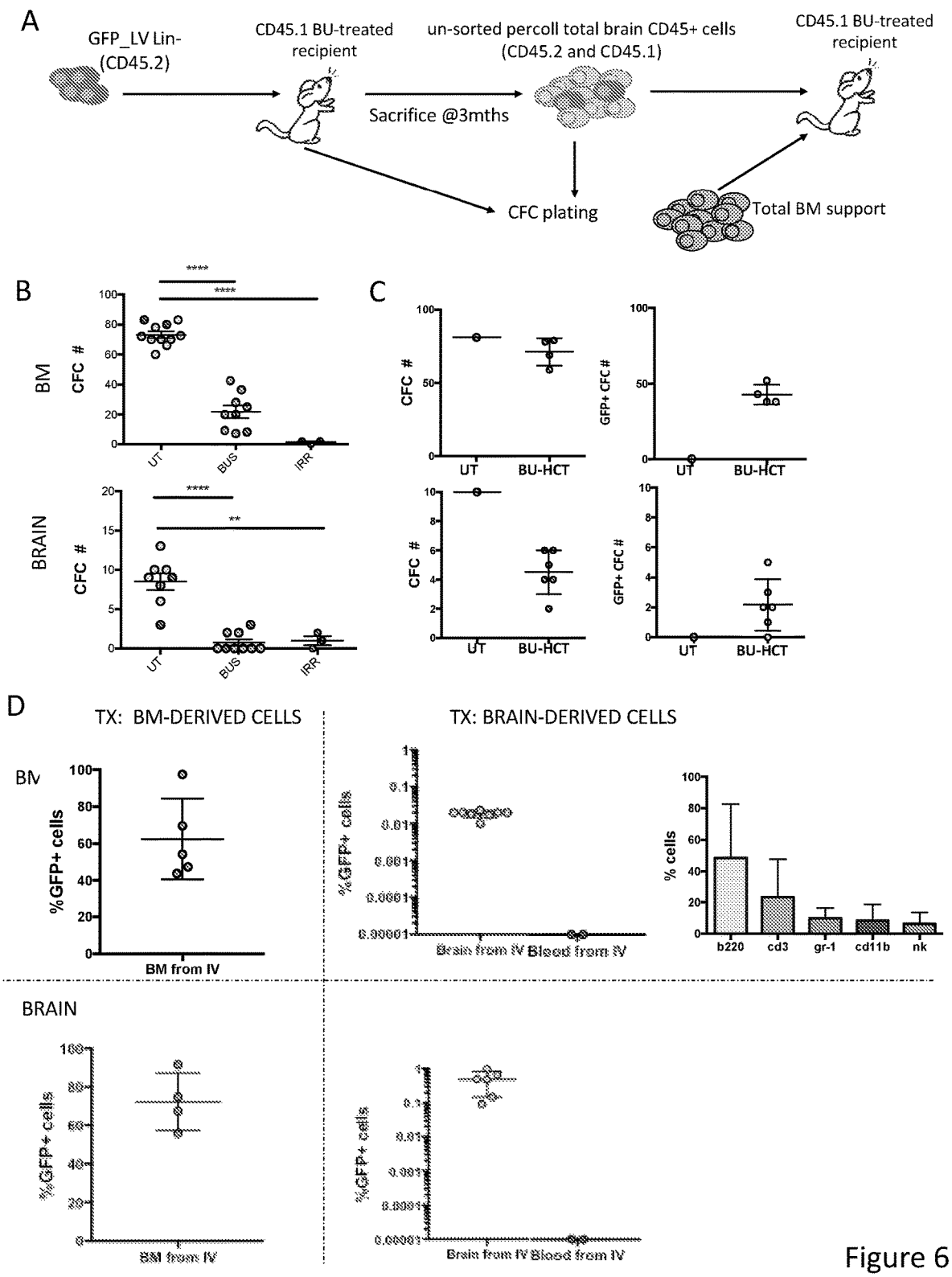
FIGS. 6A-6D show that hematopoietic cells associated with the brain parenchyma of naïve or post-transplant mice have clonogenic and hematopoietic repopulation potential and microglia reconstitution potential.
Figure 7:
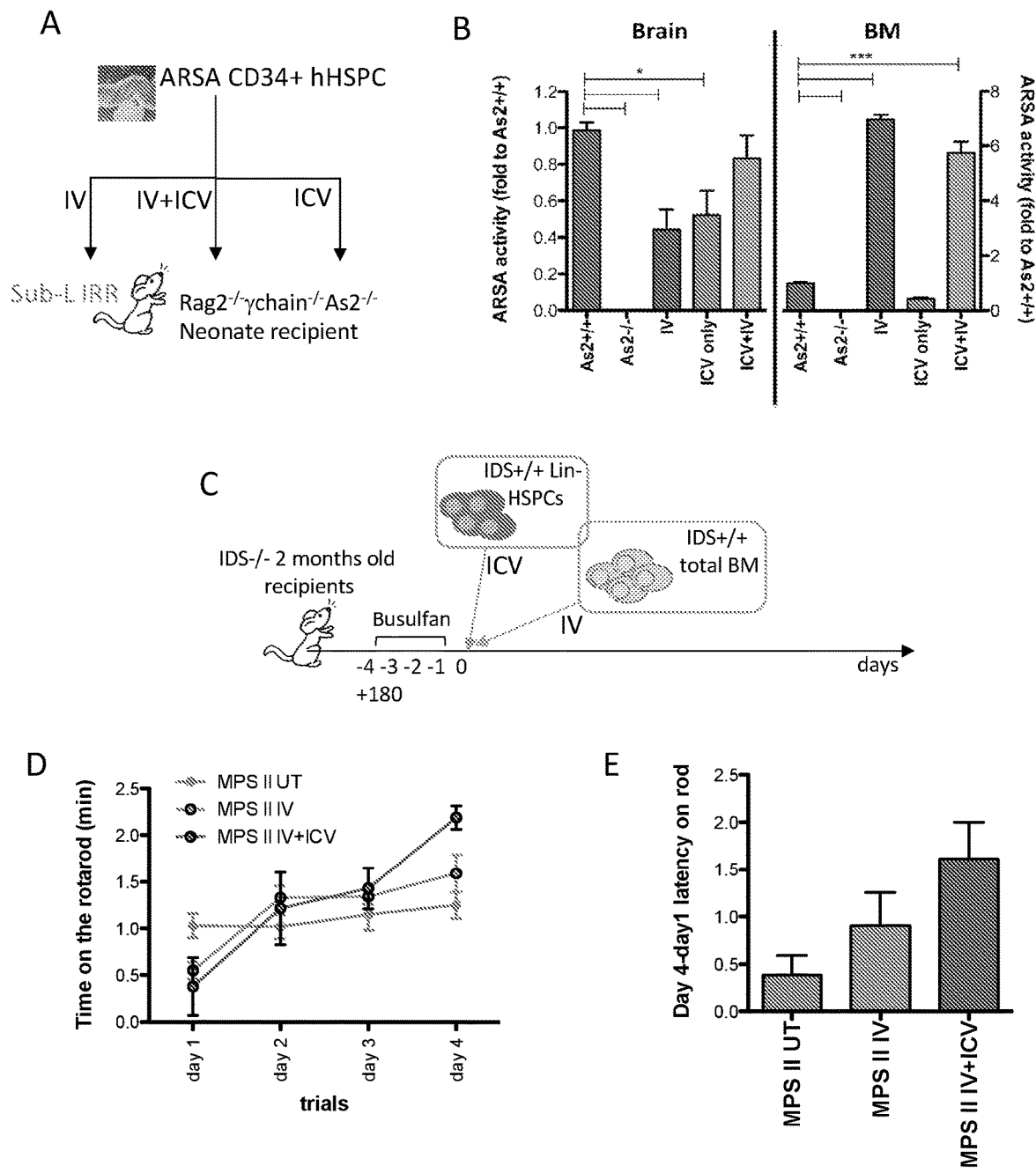
FIGS. 7A-7E show that ICV co-delivery of HSPCs has therapeutic relevance in two LSD animal models.

To develop efficacious protocols to be employed in these two settings for renewing brain myeloid populations with cells of donor origin, we differentially labeled cells to be transplanted IV (distinguished based on source and maturation stage in Lin$^-$, c kit$^+$ Sca1$^+$ Lin (KSL) cells and total BM) and ICV (Lin$^-$ HSPCs) at different timing (IV and ICV transplant delivered on the same day or IV 5 days after ICV) (FIGS. 3B and 3G). In these settings the progeny of the ICV transplanted cells remained restricted to the CNS and was not detected at significant levels in the hematopoietic tissues, i.e. in the BM (FIGS. 3D and 3H). Importantly, the combined delivery of HSPCs ICV and HSPCs, or KSLs or total BM resulted in an increased brain myeloid cell chimerism at comparison with the Lin$^-$ IV only control condition in every of the tested settings. Moreover:
  A) Contribution of HSPCs injected IV and ICV to brain myeloid chimerism was equal in specific conditions; in particular, the greater cell chimerism at the level of brain and BM, with a brain chimerism composed of both the ICV and IV cell progeny, was achieved by combining Lin$^-$ HSPCs both IV and ICV and transplanting the cells on the same day at both sites; similar results were obtained by combining Lin⁻ ICV with total BM IV, while slightly lower chimerism was associated to the use of KSL IV in all tested conditions; this protocol could thus be applied in conditions such as MLD or MPS II, as described in FIG. 6. For clinical translation of this protocol as a combined/co-transplant approach intended at fostering band fastening brain engrafment of the transplanted cells/their progeny, we might envisage the following options: in the case of gene therapy, autologous CD34⁺ cells, human equivalent of Lin⁻ cells, transduced with the vectors encoding the gene of interest for each disease would be transplanted both ICV and IV on the same day; in the case allogeneic healthy donor cells would be used, donor CD34⁺ cells would be administered ICV while either unmanipulated bone marrow or apheretic products would be transplanted IV on the same day of ICV transplant;

B) Contribution of the HSPCs injected ICV to brain myeloid chimerism prevails over the contribution of IV co-injected HSPCs in specific conditions; in particular, the lowest contribution to brain chimerism by the IV cell progeny was achieved in the context of high chimerism values in the combination of Lin⁻ cells ICV and total BM cells IV transplanted at day 5; this protocol allows obtaining a chimerism almost exclusively of the ICV cell progeny and thus would be applied in conditions associated to an exclusive CNS involvement, such as INCL described in FIGS. 7A-7E. For clinical translation of this protocol as a combined/co-transplant approach intended at generating a brain exclusive engrafment of the transplanted engineered cells/their progeny, we might envisage the following option: autologous CD34⁺ cells transduced with the vector encoding the gene of interest for each disease would be transplanted ICV, while an unmanipulated autologous bone marrow/apheretic product could be infused IV either on the same day or, ideally, 5 days after ICV infusion to further reduce competition with ICV transplanted cells; we do not anticipate use of this protocol in an allogeneic setting where hematopoietic engraftment of the transplanted cells would be required for establishment of tolerance to the donor.

Figure 4:
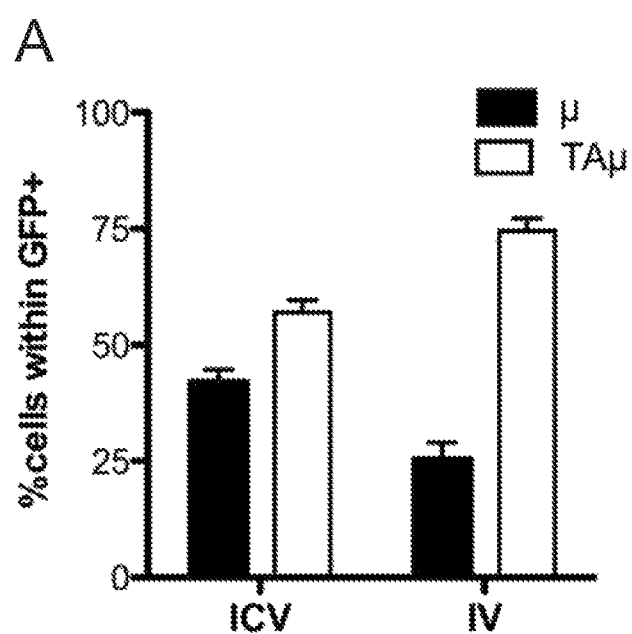
FIGS. 4A-4E show that microglia signature is present in myeloid cells retrieved from the brain of transplanted mice.
Figure 4:
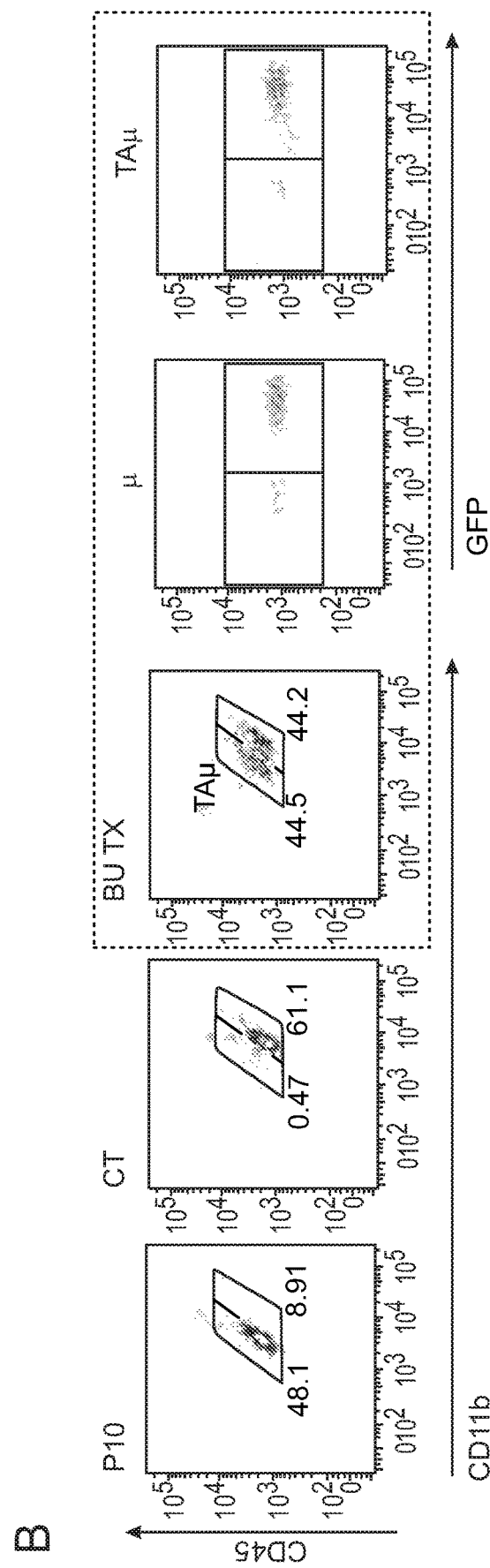
Figure 4:
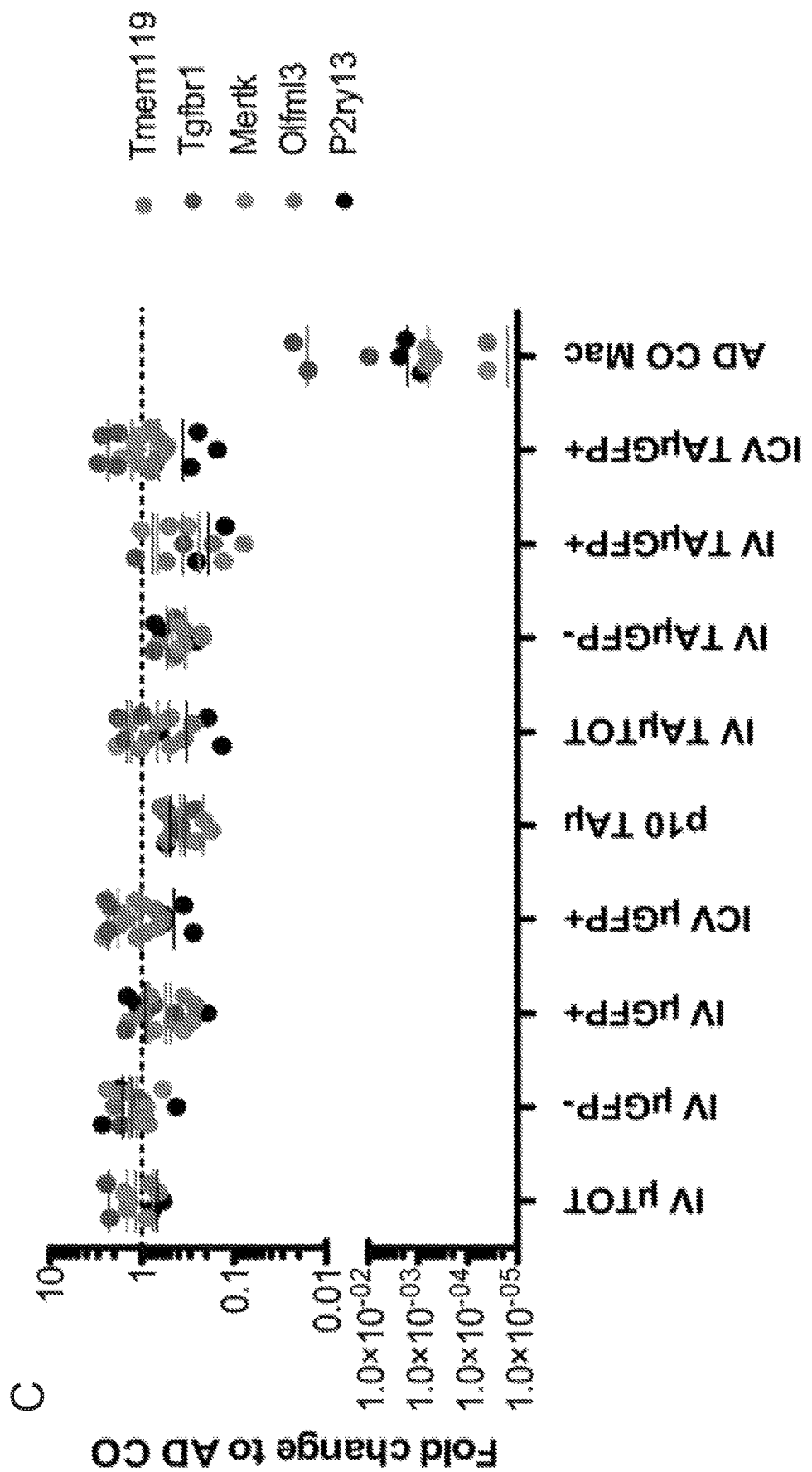
Figure 4:
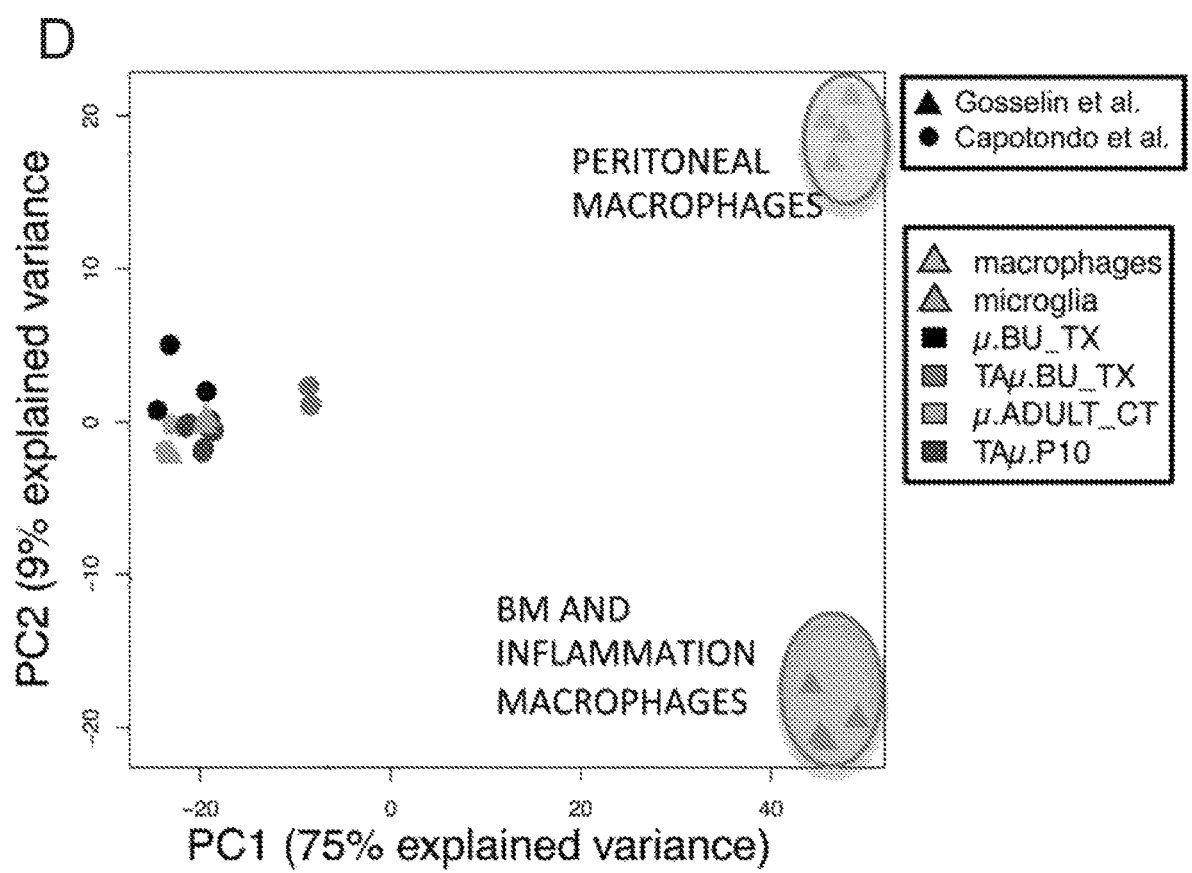
Figure 4:
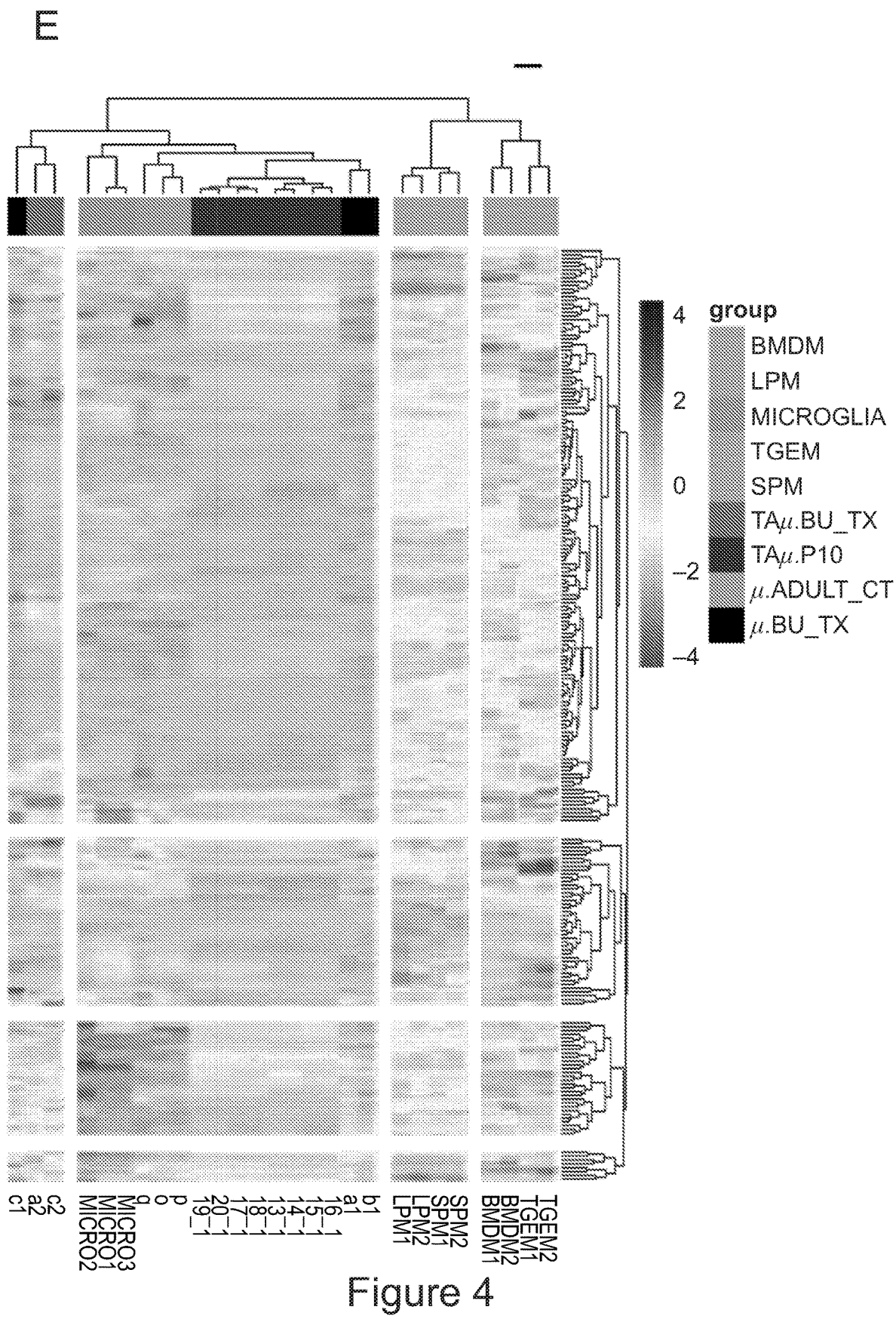
Figure 5:
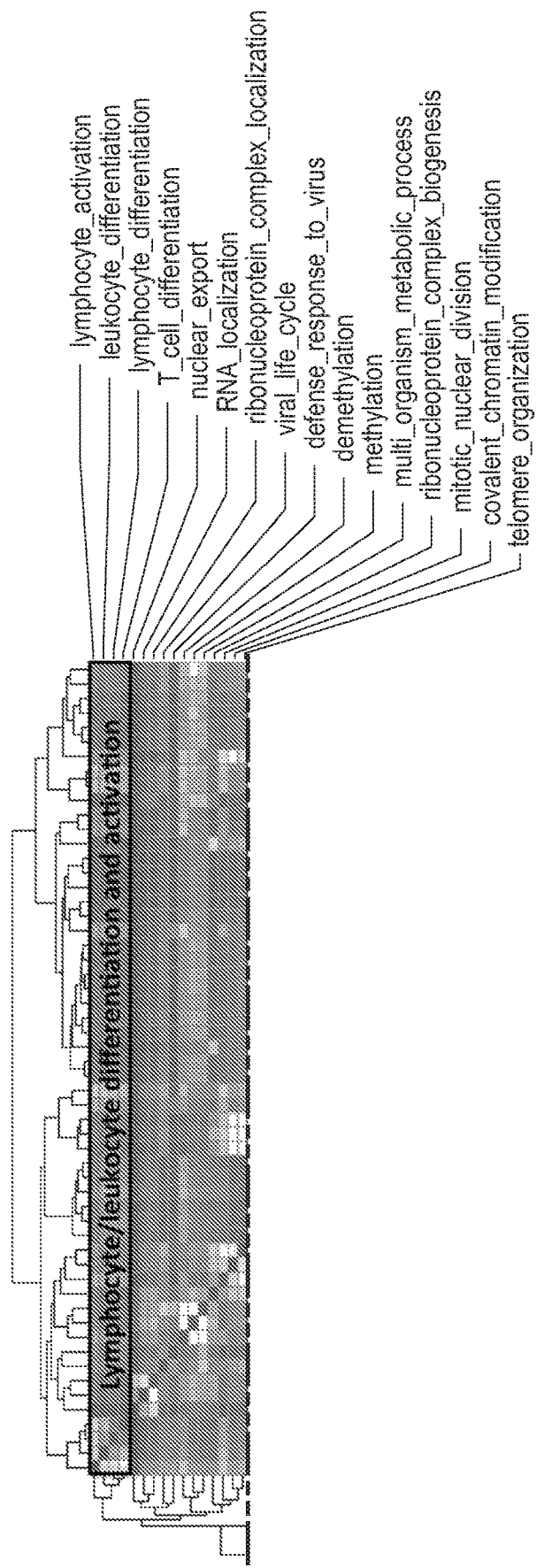
FIGS. 5A-5E show that myeloid cells from the brain of transplanted mice display functions of maturing microglia.
FIG. 5F is a graph showing fold change of RNA-Seq normalized expression values of genes whose expression is upregulated in p10 mice (Matcovitch-Natan et al., Science. 353:6301 (2016)) in the indicated populations retrieved from the brain of busulfan-treated transplanted mice or P10 mice versus ADULT_CT µ cells. For statistical tests, refer to Table 2.
Figure 5:
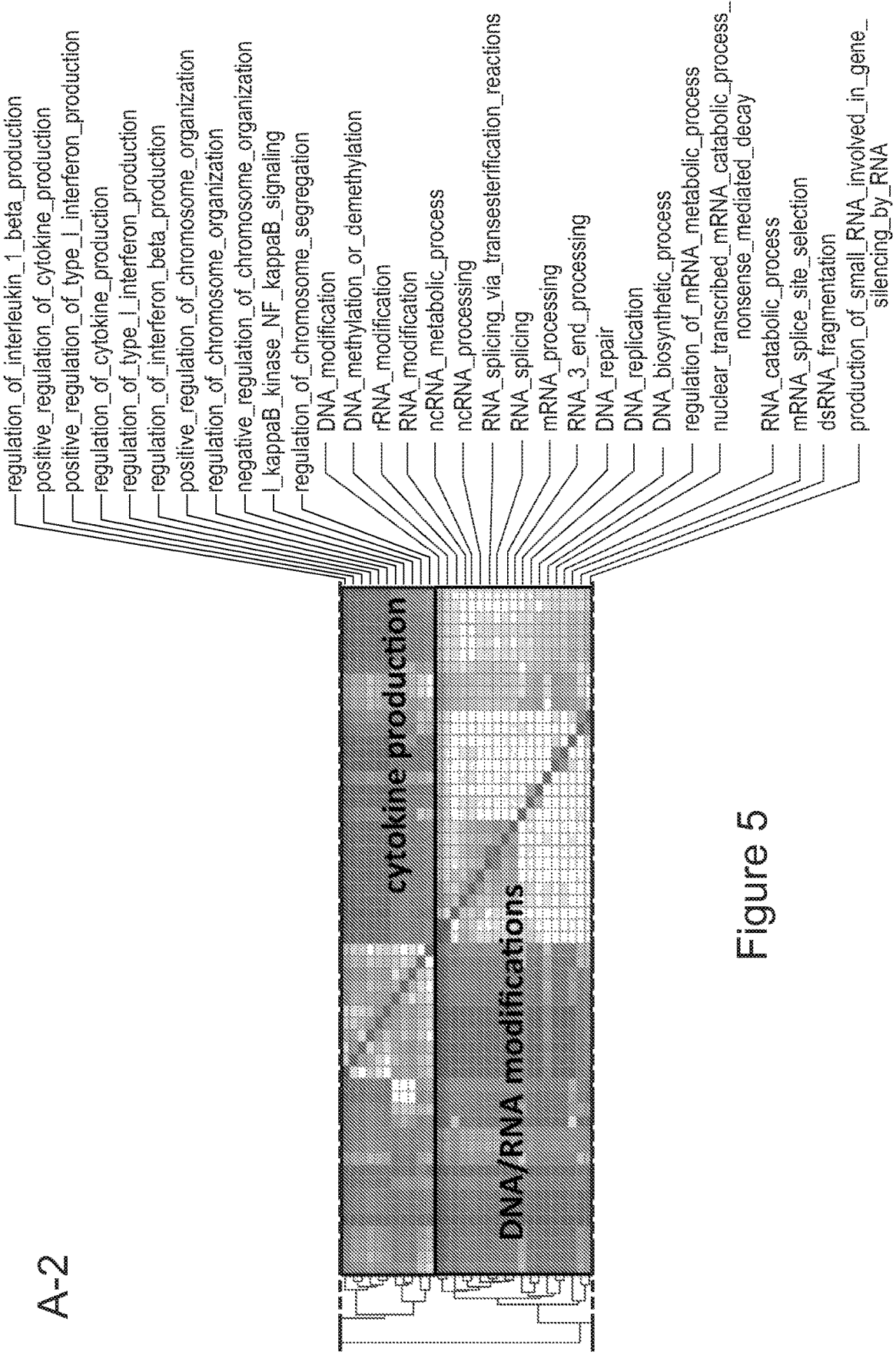
Figure 5:
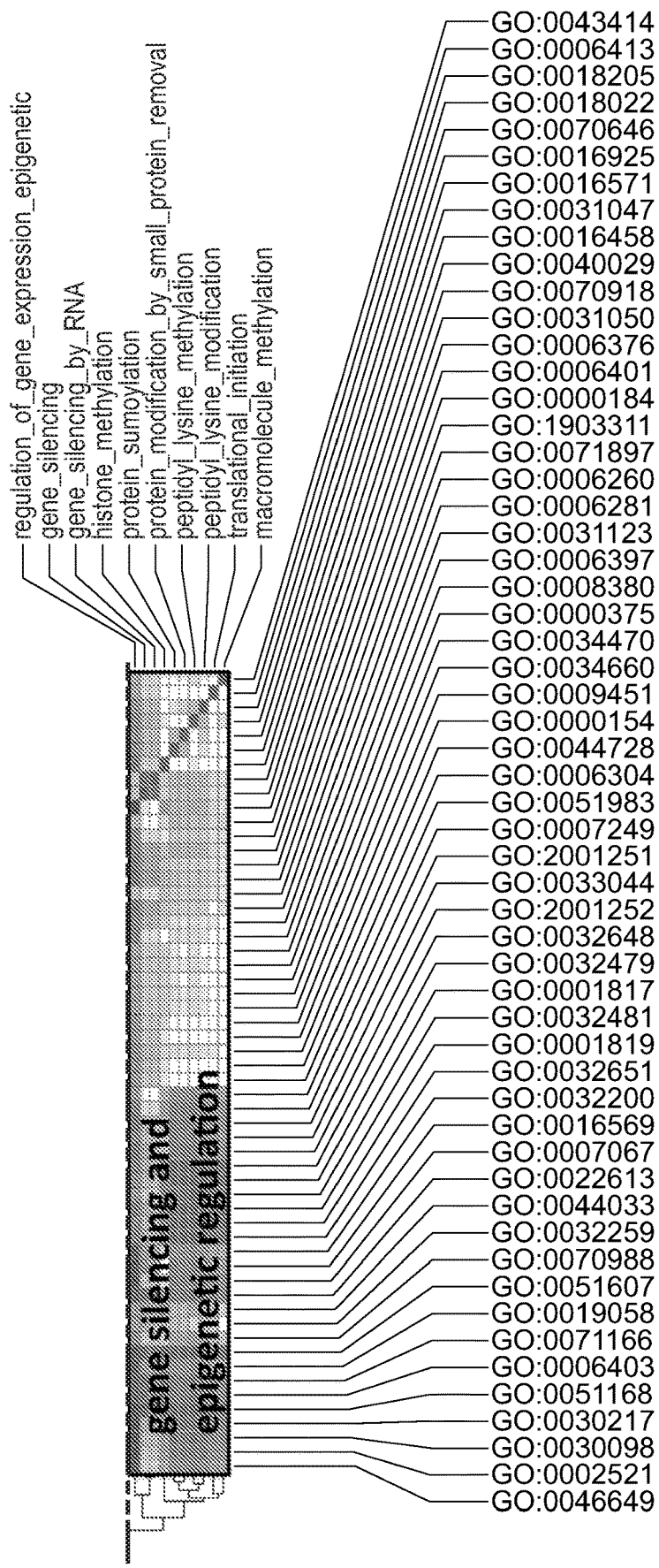
Figure 5:
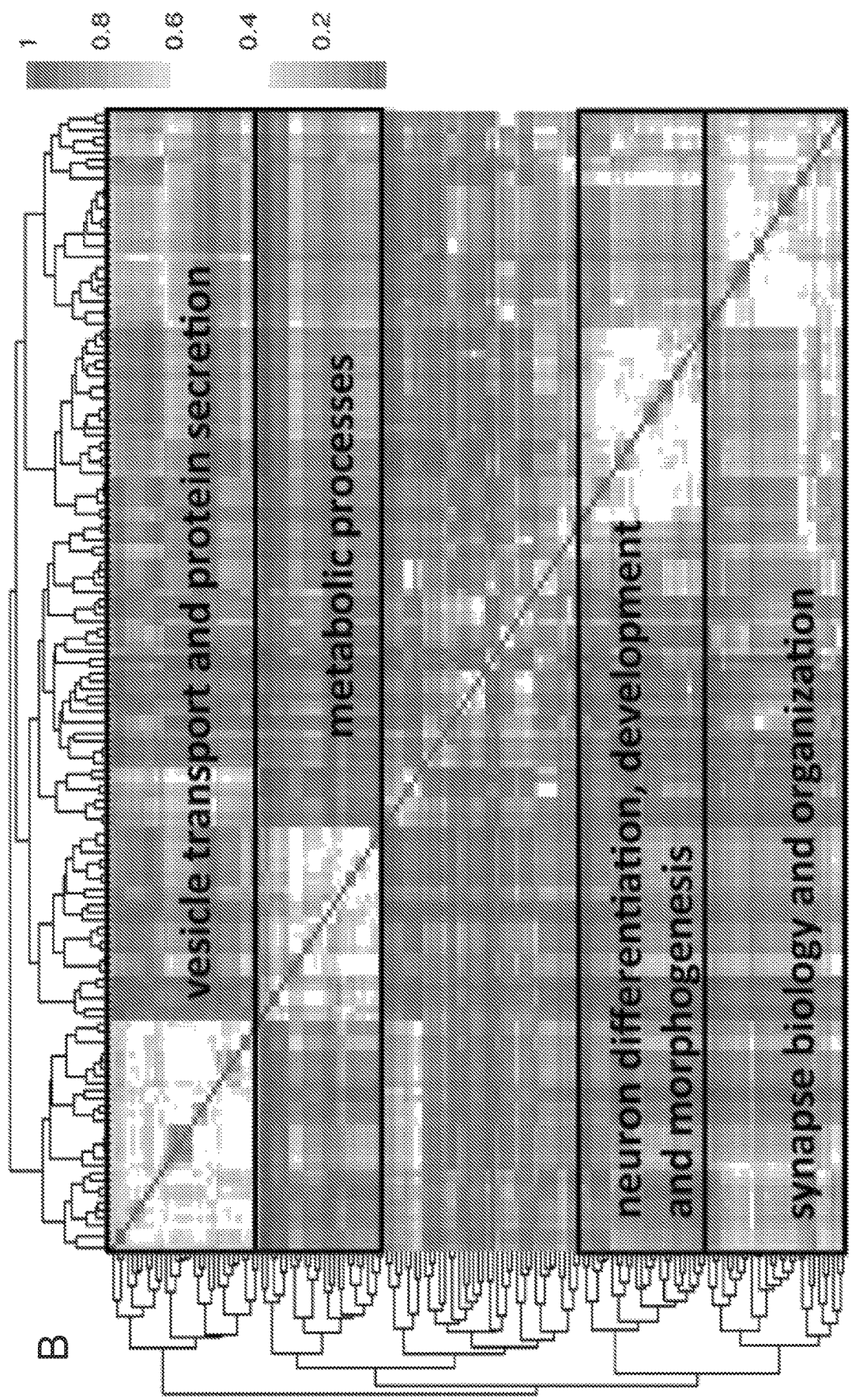
Figure 5:
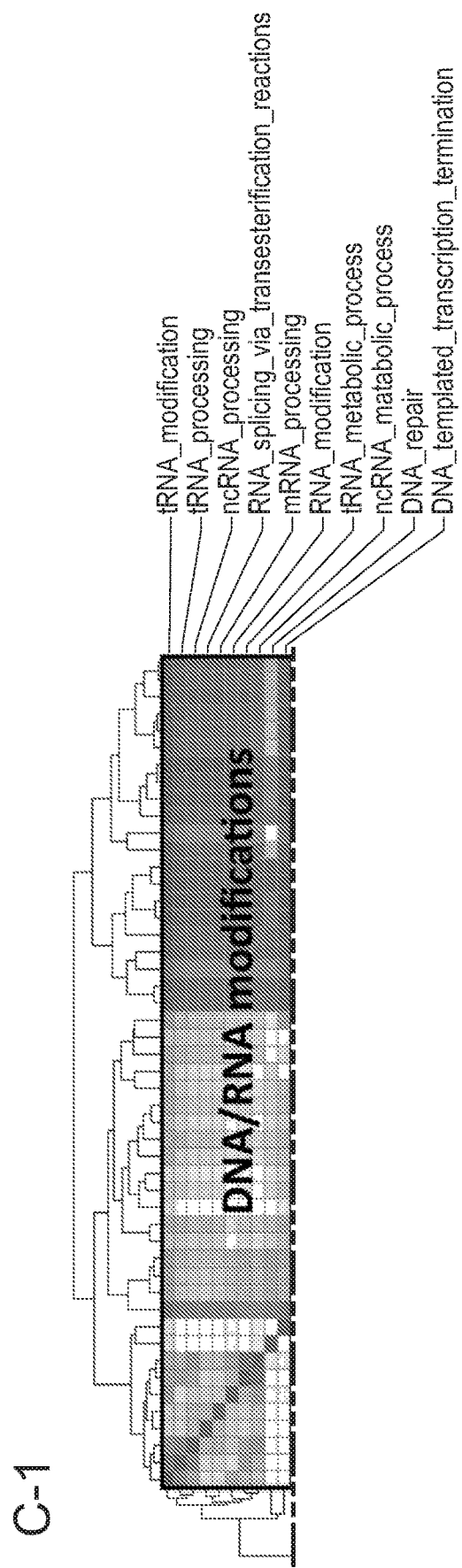
Figure 5:
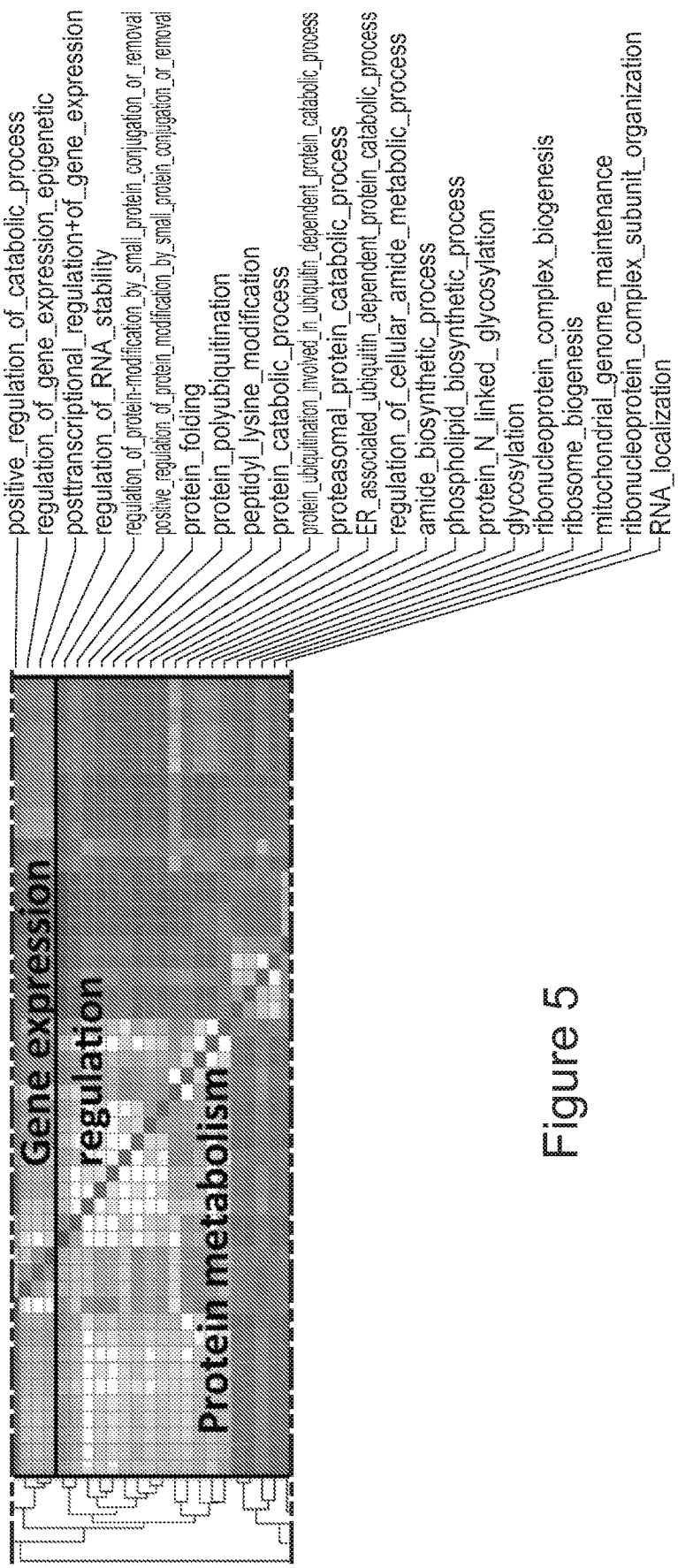
Figure 5:
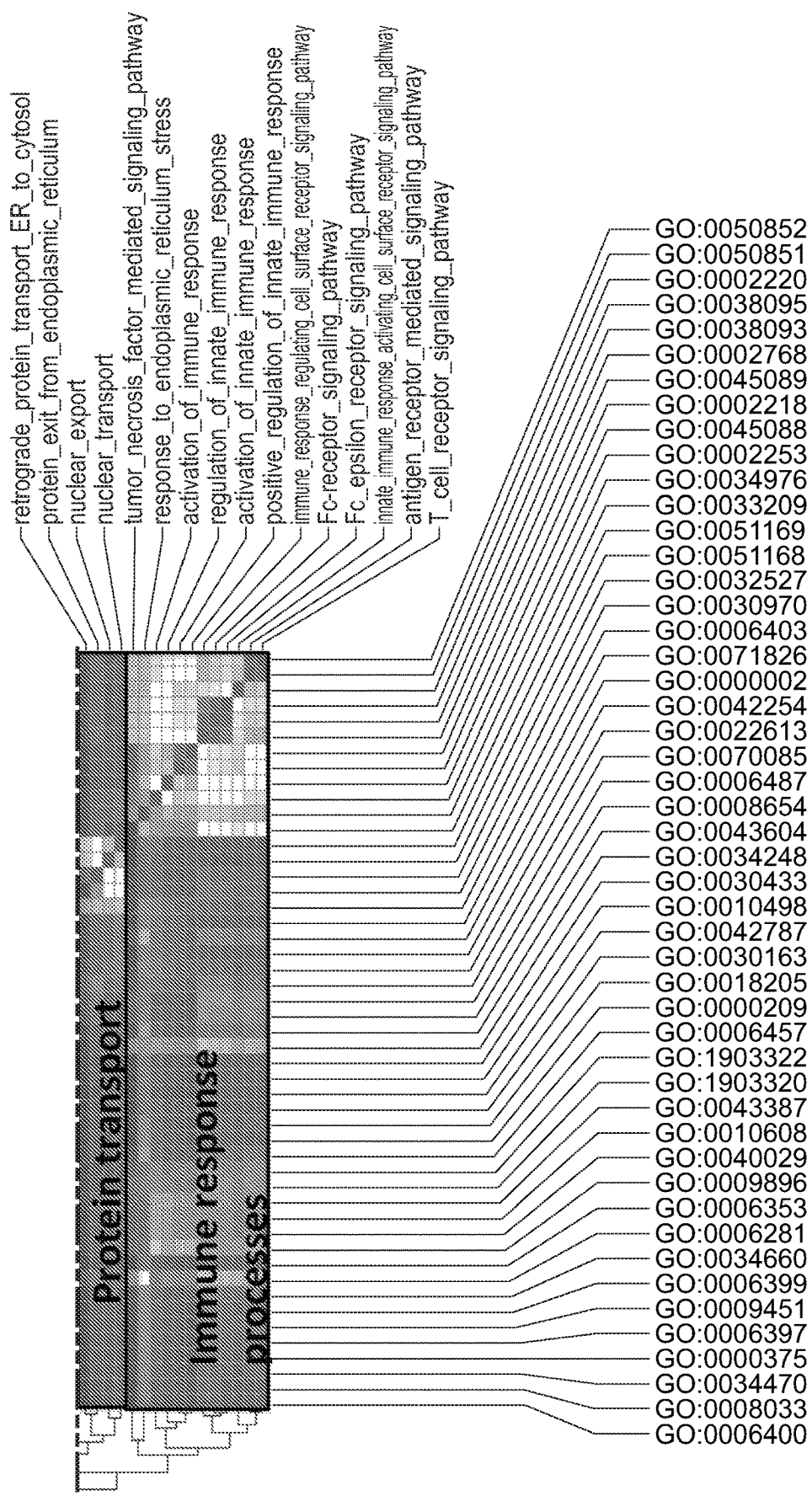
Figure 5:
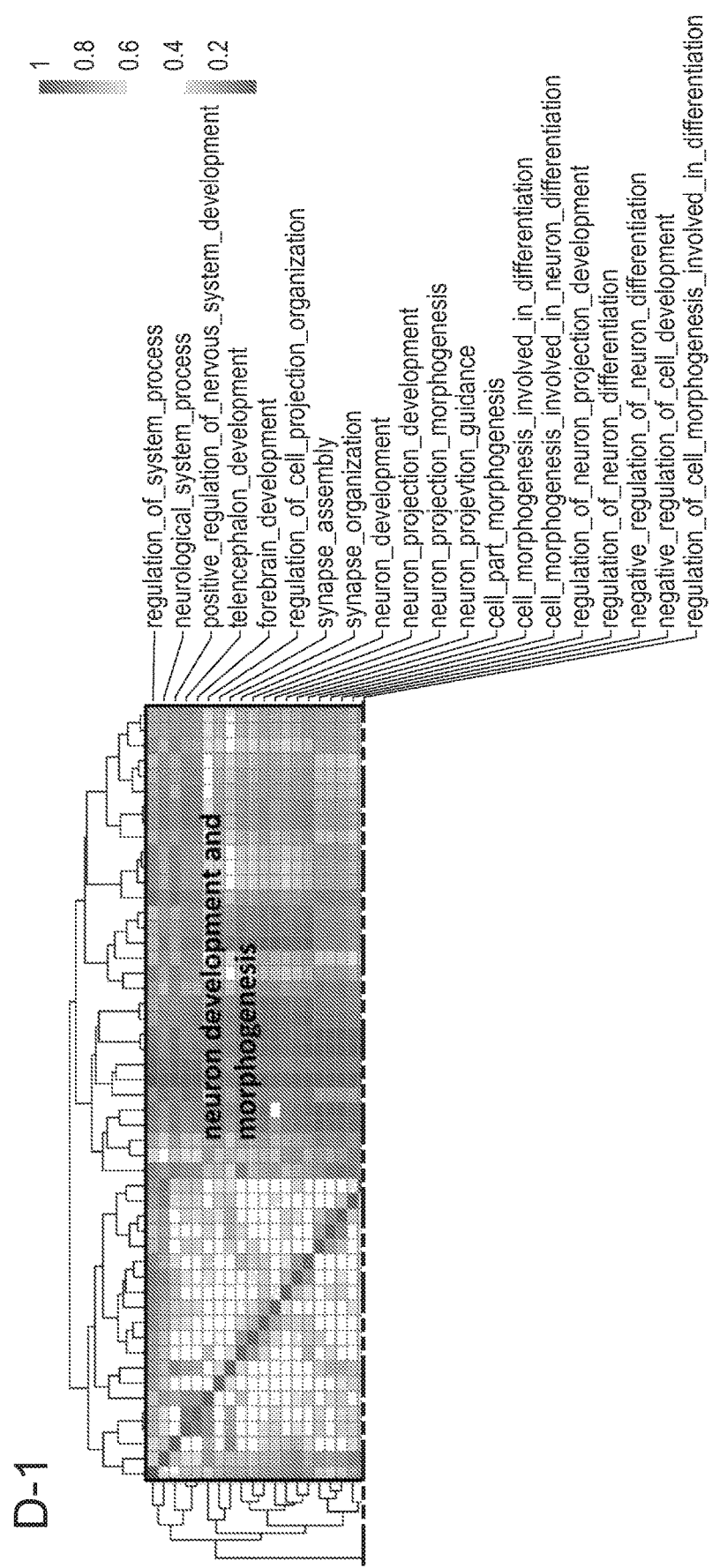
Figure 5:
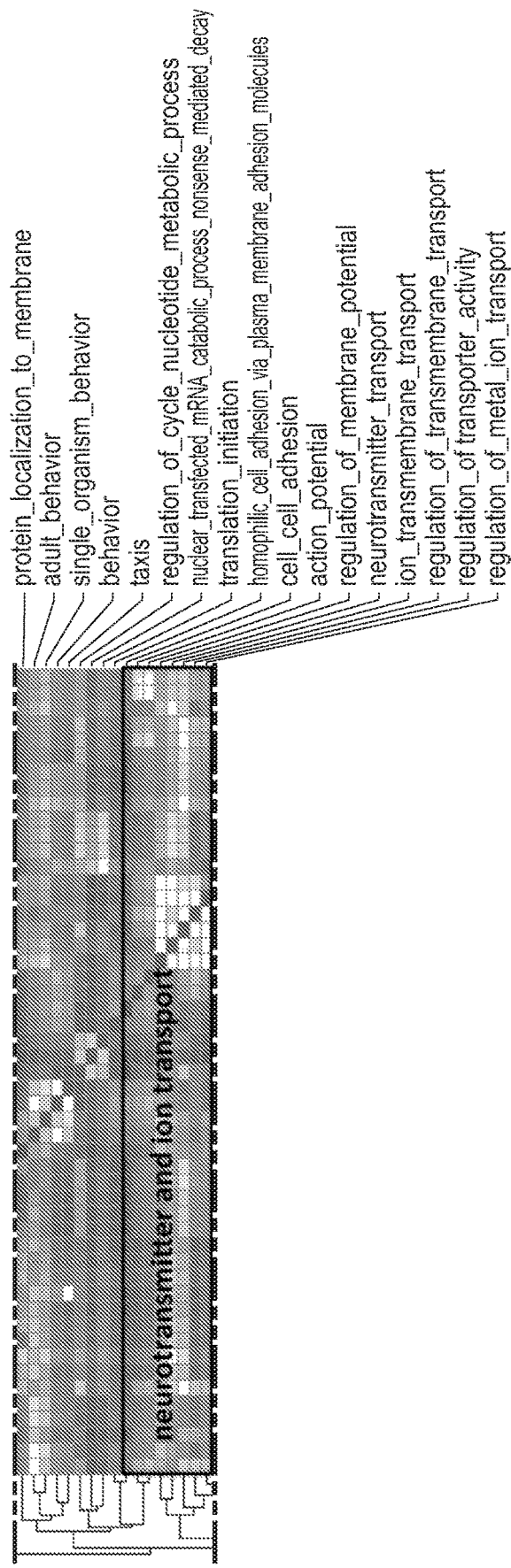
Figure 5:
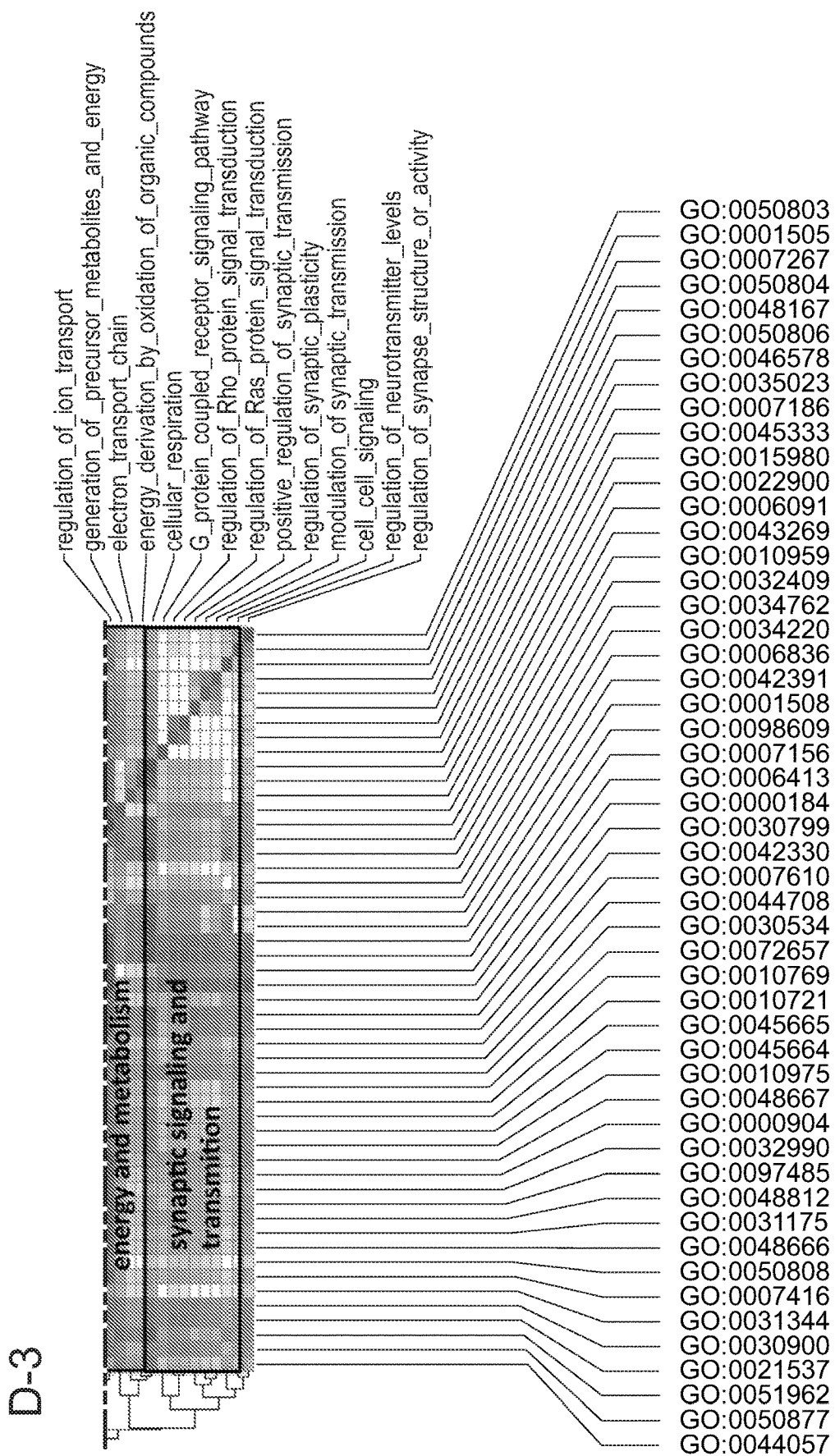
Figure 5:
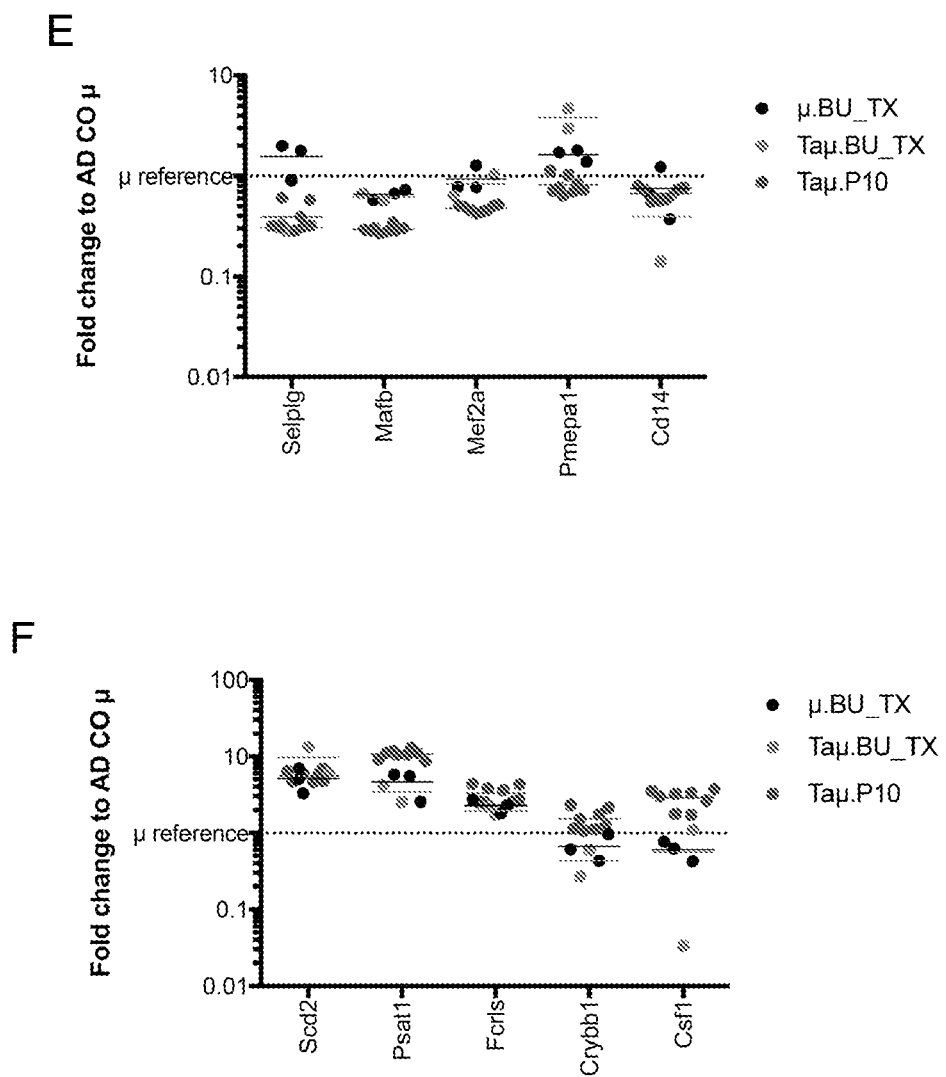

Example 5. Progeny Cells of Both IV- and ICV-Transplanted HSPCs have a Transcriptional Profile Consistent with Microglia Donor reconstitution of brain myeloid cells post-HCT was shown to be consequent to the local expansion and differentiation of a fraction of early brain HSPC immigrants finding favoring conditions in the brain of myeloablated recipients (Capotondo et al. *Proc Natl Acad Sci USA.* 109, 15018-15023 (2012)). Brain myeloid cells post-transplant share antigenic features with myeloid cells isolated from neonatal mice brains (FIGS. 3B and 4B). Indeed, in both settings CD45⁺CD11b$^{low}$ myeloid cells, previously described by us as transiently amplifying microglia (TAµ), are abundant. Interestingly, TAµ cells from transplanted mice brains are highly and preferentially enriched in donor elements in early post-transplant phases (FIG. 4B), while similar high levels of donor chimerism are observed within CD45⁺CD11b$^{+/high}$ cells, identified as microglia (p) based on antigenic and morphological features, only at later post-transplant stages (Capotondo et al. *Proc Natl Acad Sci USA.* 109, 15018-15023 (2012)). Interestingly, we observed that the CD45⁺CD11b$^{high}$GFP⁺ µ progeny of the HSPCs injected ICV was more abundant than the µ progeny of IV-injected cells, in the presence of a similar but overall higher contribution of the former to TAµ cells (FIG. 4A). To interpret these findings and further characterize the donor-derived cells, we FACS-sorted µ and TAµ cells (total populations and/or the GFP⁺ versus GFP fractions) (FIG. 4B) from mice that were ICV or IV transplanted 90 days earlier with GFP⁺ HSPCs after busulfan conditioning, and adult and p10 control animals. Previously identified microglia genes were amplified by real time PCR (Tmem119, Tgfbr1, P2ry13, Mertk, Olfml3) (Bennet et al, *Proceedings of the National Academy of Sciences of the United States of America* 113, E1738-1746 (2016); Butovsky et al., *Nature neuroscience* 17, 131-143 (2014); Chiu et al., *Cell Rep* 4, 385-401 (2013); Hickman et al., *Nature neuroscience* 16, 1896-1905 (2013); Grommes et al., *Journal of neuroimmune pharmacology* 3, 130-140 (2008)) on the sorted brain myeloid cells, as well as on bone marrow macrophages from adult control animals. The cells isolated from the brain of the ICV and IV transplanted mice were compared to the microglia gene expression profiles and ANOVA P-values with Tukey's Post-Hoc Test were obtained. Interestingly, the cells isolated from the brain of the ICV and IV transplanted mice showed expression of these genes at levels similar to those of µ cells isolated from control mice, rather than of macrophages (FIG. 4C). In addition, within both the µ and TAµ fractions, the GFP⁺ progeny of the ICV transplanted HSPCs showed expression levels very similar to those of adult control µ and of (GFP and GFP⁺) µ from IV-transplanted mice. The selected genes were expressed at slightly lower levels in the TAµ populations of IV-transplanted mice (particularly, GFP⁺) and in TAµ isolated from p10 mice. All this indicates that i) progeny cells of both IV- and ICV-transplanted HSPCs have a transcriptional profile consistent with microglia and ii) progeny cells of ICV-injected HSPCs in brain are more similar to microglia than the progeny of IV-injected HSPCs.

Example 6. Myeloid Cells from the Brain of Transplanted Mice Display Similar Functional Features of Maturing Microglia In order to analyze the transcriptomic differences between µ and TAµ cells from transplanted mice and mature µ retrieved from control naïve animals, a genome-wide expression analysis was performed by means of Illumina RNA-Seq platform on sorted µ and TAµ populations from mice transplanted 3 months earlier with GFP-expressing HSPCs and from adult and p10 control naïve mice (FIGS. 4D and 4E). To examine their differential gene expression, the obtained expression dataset was isolated together with that from Gosselin and colleagues (Gosselin et al., *Cell* 159, 1327-1340 (2014)), specifically focusing on the 239 genes identified by Butovsky (Butovsky et al., *Nature neuroscience* 17, 131-143 (2014)) (FIGS. 4D and 4E). Interestingly, all microglia samples included in this analysis clustered closely to each other (FIGS. 4D and 4E), confirming that µ and TAµ cells reconstituted after transplant share a pattern of gene expression consistent with that of microglia. differential gene expression coupled to GSEA pre-ranked analysis (Subramanian et al., *Proc Natl Acad Sci USA* 102, 15545-15550 (2005)) was performed on RNA-Seq data (FIGS. 5A-5F). The resulting Gene Ontology Biological Processes enriched in µ from adult controls versus p (FIG. 5A) and TAµ (FIG. 5C) from the transplanted mice were related to immune cell differentiation, immune responses, DNA/RNA processes, and DNA methylation, pointing to the mature immune function of control μ. On the other hand, the processes enriched in μ cells from the transplanted mice (FIG. 5B) covered neuronal related processes, such as neuron migration, differentiation and regulation of synaptic plasticity (Colonna and Butovsky, *Annu Rev Immunol*, (2017); Tay et al., *J Physiol* 595, 1929-1945 (2017))). Amongst the processes enriched we also found glial cell differentiation, gliosis, and metabolism and cellular respiration, supporting the idea that transplant-derived μ cells are more oriented to interact with/affect the neuronal environment, a process consuming a considerable amount of energy (Miyamoto et al., *Front Cell Neurosci* 7, 70 (2013).). Post-transplant TAμ enriched processes (FIG. 5D) presented a more intense neural function signature underlying a putative different stage of maturation with respect to μ cells, in agreement with the concept that microglia acquires different functions according to their maturation states (Matcovitch-Natan et al., *Science* 353, aad8670 (2016)). Interestingly, μ and TAμ cells from transplanted mice express the genes that were shown to be robustly modulated during microglia development (Matcovitch-Natan et al., *Science* 353, aad8670 (2016)). Notably, μ from transplanted animals matched control μ for the levels of expression of 4 out of the 5 selected genes associated to mature microglia function, while a different path was observed in TAμ from transplanted mice (FIG. 5E and Table 2) and in genes associated to neonatal stage (FIG. 5F and Table 2), possibly related to a different and dynamic maturation stage.

progenitors. Thus, it was attempted to better characterize cells with clonogenic potential in the brain and assess whether they could be transplantable, and amenable to ablation upon conditioning and replacement upon HSC transplantation in conditioned mice. Further work would also be intended at determining whether these cells have indeed microglia repopulation potential. Mononuclear cells were isolated from the bone marrow and brain (upon percoll enrichment of hematopoietic lineage cells) of naïve mice and animals receiving lethal myeloablation (by busulfan or irradiation conditioning) without or with the addition of GFP-LV transduced Lineage-HSPCs (FIG. 6A). These cells were plated in methylcellulose supplemented with citokynes for colony forming unit (CFU) generation. 14 days after plating, discrete hematopoietic colonies were retrieved from bone marrow and brain cultures from naïve mice, as expected (FIG. 6B). A drastic reduction in the CFU output was observed upon busulfan and irradiation conditioning from both bone marrow and brain tissues, with a greater effect of busulfan registered on brain CFU output. Importantly, the CFU output was restored in ice recovering from conditioning upon HSPC transplantation (FIG. 6C) both in bone marrow and brain. The CFU output was highly chimeric in $GFP^+$ colonies at both sites, indicating that HSPC transplantation can contribute to fixed brain hematopoietic clonogenic progenitors. Bone marrow and brain percol-enriched mononuclear cells from primary transplant recipients were also employed for secondary transplantation into busulfan-conditioned recipients (FIG. 6A). Surprisingly,

TABLE 2

Moderated tr test (limma) after FDR (Benjamini and Hochber) adjustement for the different

CONTRAST

| | μBUTX vs TAμBUTX | μCT vs μBUTX | p10.TAμ vs μBUTX | μCT vs TAμBUTX p10.TAμ |
|---|---|---|---|---|
| | | Up in p9 | | |
| Scd2 | 0.08811 | 0.00055 | 0.54206 | 0.00002 |
| Psat1 | 0.72021 | 0.00835 | 0.00103 | 0.02209 |
| Fcrls | 0.71736 | 0.00634 | 0.11386 | 0.02288 |
| Crybb1 | 0.42750 | 0.24540 | 0.11303 | 0.04204 |
| Csf1 | 0.33430 | 0.47249 | 0.00486 | 0.08511 |
| | | Up in adult | | |
| Selpig | 0.00073 | 0.13772 | 0.00001 | 0.00147 |
| Mafb | 0.87034 | 0.01088 | 0.00001 | 0.00771 |
| Mef2a | 0.69680 | 0.69008 | 0.00065 | 0.34090 |
| Pmega1 | 0.00519 | 0.04092 | 0.00119 | 0.00004 |
| Cd14 | 0.12897 | 0.41616 | 0.72535 | 0.01310 |

Example 7. Hematopoietic Cells Associated with the Brain Parenchyma of Naïve or Post-Transplant Mice have Clonogenic and Hematopoietic Repopulation Potential and Microglia Reconstitution Potential HSPCs have been identified within extramedullary tissues and thought to be transiently localized at those sites and able to proliferate locally giving rise to tissue-resident myeloid cells, preferentially dendritic cells. Clonogenic potential was referred to the presence of these cells also in the brain, however upon establishment of parabiotic pairs and differently from what observed in other extra-medullary tissues, chimerism between the two animals was not observed in the brain. This may suggest that brain clonogenic activity could be attributed to fixed tissue cells that are not amenable to chimerism in parabiotic pairs, as hypothesized for microglia $GFP^+$ cells derived from the primary recipients were identified in hematopoietic tissues and brain of secondary recipients long-term after transplantation (FIG. 6D). Hematopoietic tissue resident $GFP^+$ cells showed a multilineage marker expression, while brain-resident cells were mostly CD11b expressing.

Example 8. Combined ICV+IV Delivery of Engineered HSPCs has Therapeutic Relevance for Metachromatic Leukodystrophy, a Representative LSDs with Neurodegenerative and Extra-CNS Features To determine the actual role of ICV cell transplantation in augmenting the potential of the transplant to deliver therapeutic molecules to the brain, a newly generated mouse model, the $Rag^{-/-}$ γ-chain$^{-/-}$ As2$^{-/-}$, was employed that reproduces the lysosomal disease ML) due to ARSA deficiency in an immune-deficient background. These mice received human cord blood CD34+ cells transduced with an ARSA encoding lentivirus (LV) (Biffi et al., *Science* 341, 1233158 (2013); Sessa et al., *Lancet* 388, 476-487 (2016)) by IV only or ICV only injection, or by a combination of the IV and ICV routes (FIG. 1D and FIG. 6A). Interestingly, a clearly defined human myeloid (CD45$^l$CD11b$^l$) cell progeny was identified in brain of the transplanted mice long term after both IV and ICV transplant (FIGS. 1D-1G). ICV cell delivery resulted in a greater human cell engraftment in the brain as compared to IV delivery (FIG. 1G). ICV cell delivery in combination with IV resulted in even more human cell engraftment in the brain (FIG. 1G). It was then assessed whether greater human cell myeloid chimerism in the brain of Rag$^{-/-}$ γ-chain$^{-/-}$ As2$^{-/-}$ mice could determine greater delivery of the ARSA enzyme to the brain. Importantly, the increased contribution of the ICV-transplanted human HSPCs to brain myeloid chimerism resulted in greater ARSA enzyme delivery to the brain of the transplanted mice (FIG. 1G). This was particularly remarkable for the IV+ICV combined delivery, which reached levels that were indistinguishable from As2$^{+/+}$ controls. 16 weeks after transplantation comparable above normal ARSA activity levels were measured in the bone marrow of mice transplanted IV only or IV+ICV with the transduced cells (FIG. 6B). Interestingly, restoration of enzyme activity was also measured in the brain of the transplanted mice, with a favourable increasing trend towards wild type levels in the animals that had received the transduced cells in combination by IV and ICV (FIG. 6B). This data demonstrates that the combined transplant approach allows for a greater enzyme delivery to the brain as compared to the standard IV transplant approach, thus appearing as a promising strategy for increasing the overall therapeutic potential of HSC gene therapy for SD with CNS involvement. Moreover, it indicates that ICV only HSPC delivery is sufficient to deliver the same amount of therapeutic enzyme to the MLD brain as IV cell delivery.

Co-transplantation did not result in increased enzyme activity in the hematopoietic system. Without intending to be bound by theory, this indicates that the contribution of ICV delivered cells was mostly restricted to the brain, rather than extra-CNS, hematopoietic populations.

The short life span of this animal model and the limited severity of its phenotype in the short term prevented assessment of phenotypic effects of increased brain ARSA delivery. However, it has been demonstrated that when LV-transduced HSCs (HSC gene therapy) were administered to MLD mice (Biffi et al., *J Clin. Invest.* 116, 3070-3082 (2006); Biffi et al., *J. Clin. Invest.* 113, 1118-1129 (2004)) and patients (Biffi et al., *Science* 341, 1233158 (2013); Sessa et al., *Lancet* 388, 476-487 (2016)), as well as to other lysosomal storage disease models (Gentner et al., Sci Transl Med 2, 58ra84 (2010); Visigalli et al., *Blood* 116, 5130-5139 (2010)), a dose-effect relationship was present and the higher the enzyme activity reconstitution in hematopoietic cells and in brain, the greater the therapeutic efficacy in controlling CNS disease manifestations. Therefore, use of ICV cell delivery has the potential to enhance therapeutic efficacy of the transplantation of gene corrected HSPCs.

Example 9. Combined ICV+IV Delivery of Wild Type HSPCs has Therapeutic Relevance in Mucopolysaccharidosis Type 11, a Representative LSDs with Neurodegenerative and Extra-CNS Features To confirm these findings and in particular the actual role of ICV cell transplantation in augmenting the potential of HSPC transplant to deliver therapeutic molecules to the brain and exert benefit on LSDs with both brain and systemic involvement, Lin$^-$ HSPCs and total BM were transplanted from wild type donors into 2 months old myeloablated iduronate sulfatase (IDS)$^{-/-}$ recipients, mouse model of mucopolysaccharidosis type II (MPS II) (FIG. 6C). IV only mice received exclusively total BM from wild type IDS$^{+/+}$ donors IV. Controls were left untreated. 180 day later the behavior of the treated and control mice were tested by rotarod. Interestingly, both treatments improved the rotarod mice performance over 4 trials (FIG. 6D) and mice treated both IV and ICV+IV increased the time spent on the rod at fourth as compared to first trial (FIG. 6E). However, the performance of ICV+IV treated mice exceeded the one of IV only transplanted animals. Without intending to be bound by theory, this indicates that the use of ICV cell delivery has the potential to enhance therapeutic efficacy of the transplantation of wild type HSPCs in MPS II.

Figure 8:
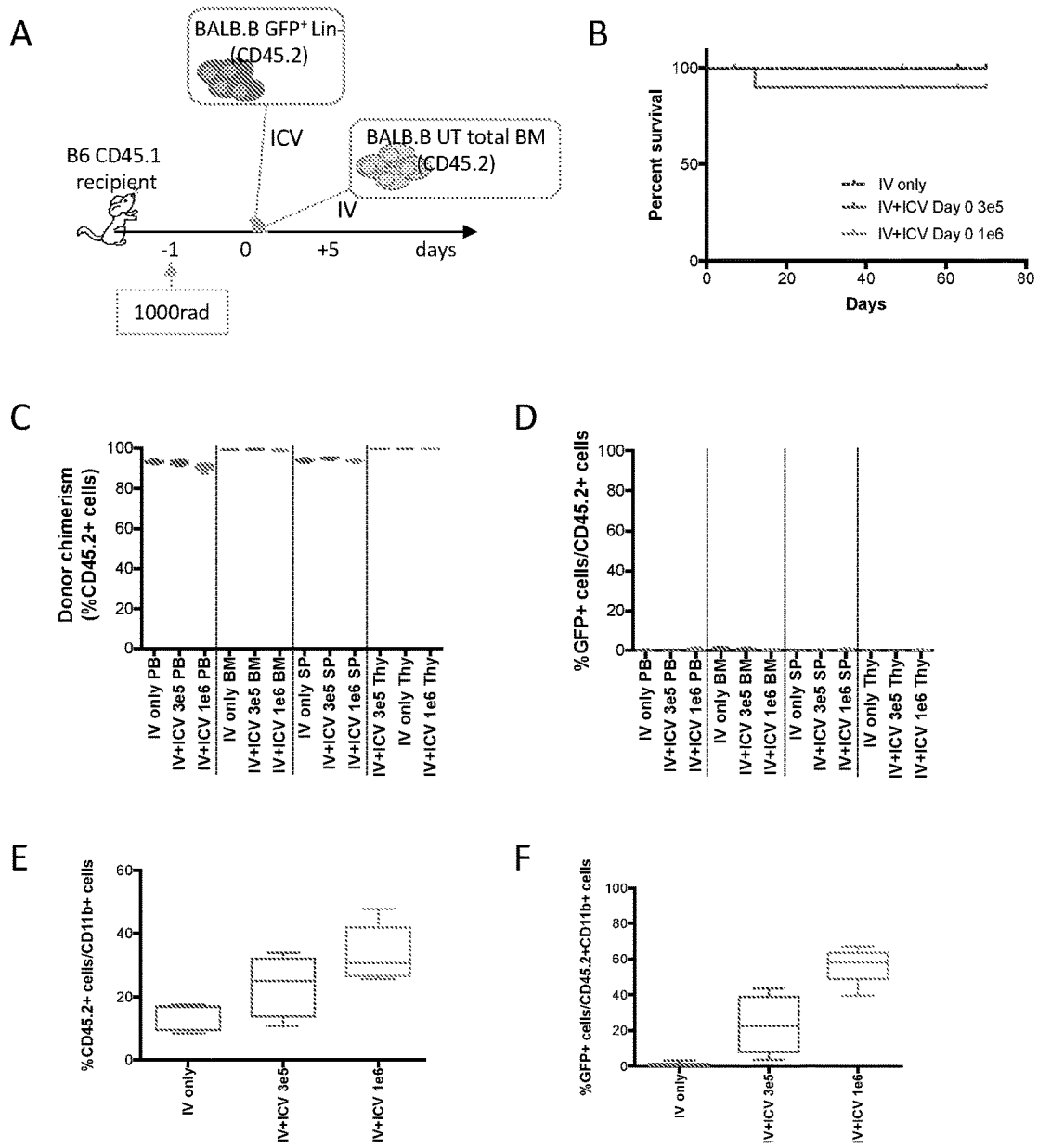
FIGS. 8A-8F show HLA-minor antigen mismatched HSPC IV+ICV transplantation in mice.
Figure 9:
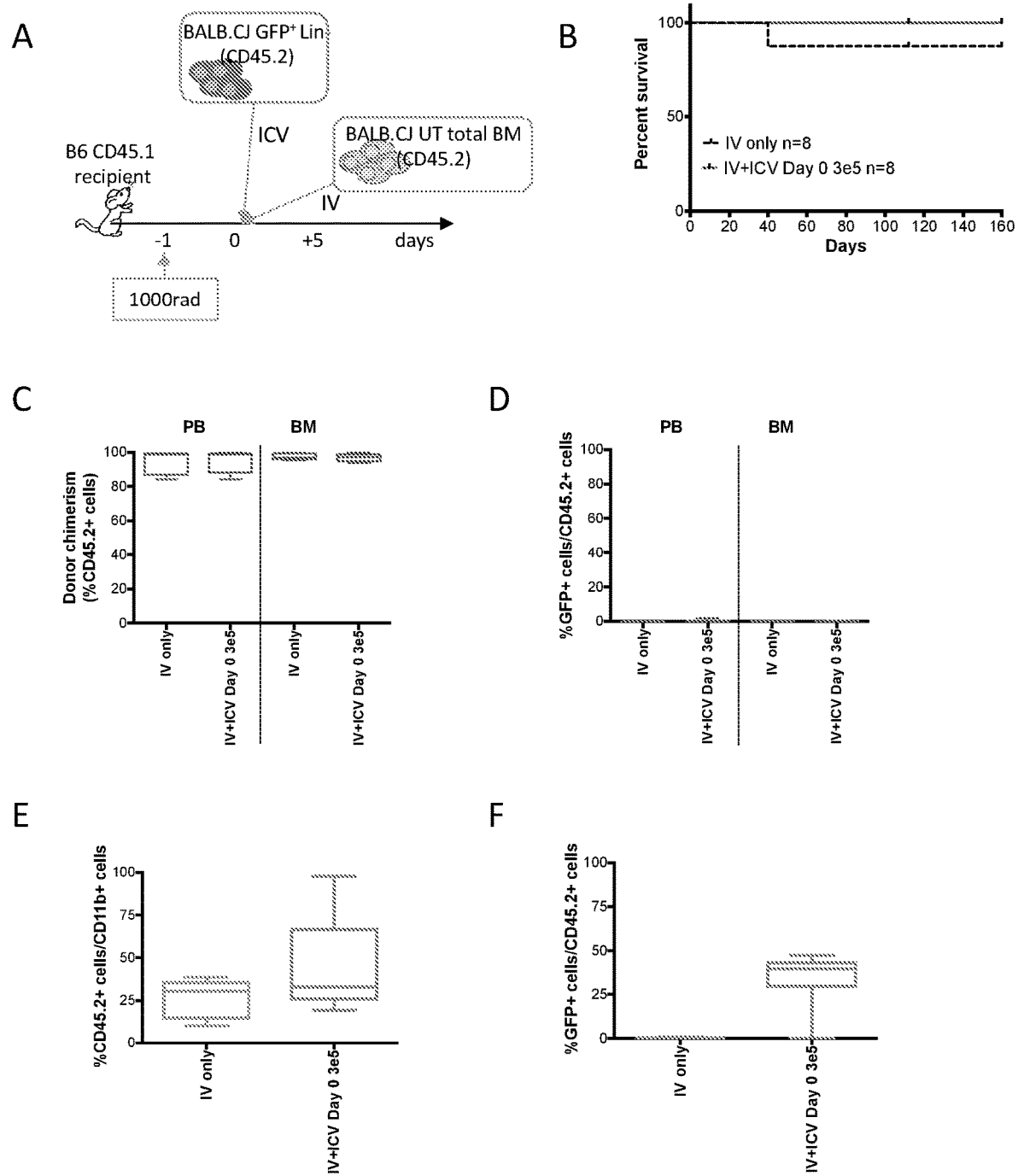
FIGS. 9A-9F show MHC mismatched HSPC IV+ICV transplantation in mice. In this setting the additive effect of ICV delivery to brain donor chimerism is maintained.

Example 10. HLA-Minor and MHC Antigen Miss-Matched HSPC IV+ICV Transplantation in Mice is Feasible and Associated to High Brain Donor Chimerism The potential applicability of the ICV HSPC transplantation approach in the context of allogeneic transplantation in patients was assessed, and in particular the combination of ICV and IV transplantation, in the context of both minor-antigen and MCH mis-matched transplantation settings. The impact of ICV delivery of allogeneic HSPCs on overall survival and CNS microglia engraftment in mice undergoing hematopoietic cell transplantation from mismatched donors was tested. ICV+IV HCT was applied in the context of MCH-mismatched (BALB/cJ CD45.2 donors into B6.SJL CD45.1 recipients; one cell ICV dose tested, 3×10$^5$ cells/mouse) as well as minor antigen-mismatched (MHC-matched; BALB_B CD45.2 donors into B6.SJL CD45.1 recipients; two ICV cell doses tested, 3×10$^5$ and 1×10$^6$/mouse) transplant settings. Total body irradiation (TBI) (1000 Rad) at day −1 was employed for conditioning of recipient mice. Mice received fresh total bone marrow (tBM) only or coupled with GFP transduced Lin$^-$ cells injected ICV (FIGS. 8A and 9A). They were followed up to 9 to 10 weeks (minor antigen-mismatched) and 16 weeks (MHC-mismatched) post transplantation. Rare inter-current death (TCD) were observed in recipients and were not associated to a specific treatment (FIGS. 8B and 9B). All surviving animals had stable increase in body weight and overall good health. Cytofluorimetric analysis performed on PB, BM, spleen and thymus (the latter organs for the minor-antigen mismatched transplantation) demonstrated successful engraftment of the donor cells (FIGS. 8C and 9C). Importantly, no GFP$^+$ cells, progeny of the ICV transplanted HSPCs, were detected in the tested hematopoietic tissues (FIGS. 8D and 9D). Compared with IV only recipients, IV+ICV minor-antigen mismatched animals demonstrated dose-dependent engraftment from donor-derived cells in the brain. In both minor-antigen and MHC-mismatched animals, ICV delivery of HSPCs conferred an advantage in donor-derived microglia chimerism in CNS at comparison to IV only transplantation. In conclusion, allogeneic hematopoietic stem/progenitor cell delivery to the lateral brain ventricles is feasible in a combined delivery approach and can enhance the donor-derived chimerism in the brain in both minor-mismatch and MHC-mismatched settings. This data supports the applicability of ICV transplantation in the context of an allogeneic hematopoietic cell transplant procedure for potentiating CNS-related benefit.

Figure 10:
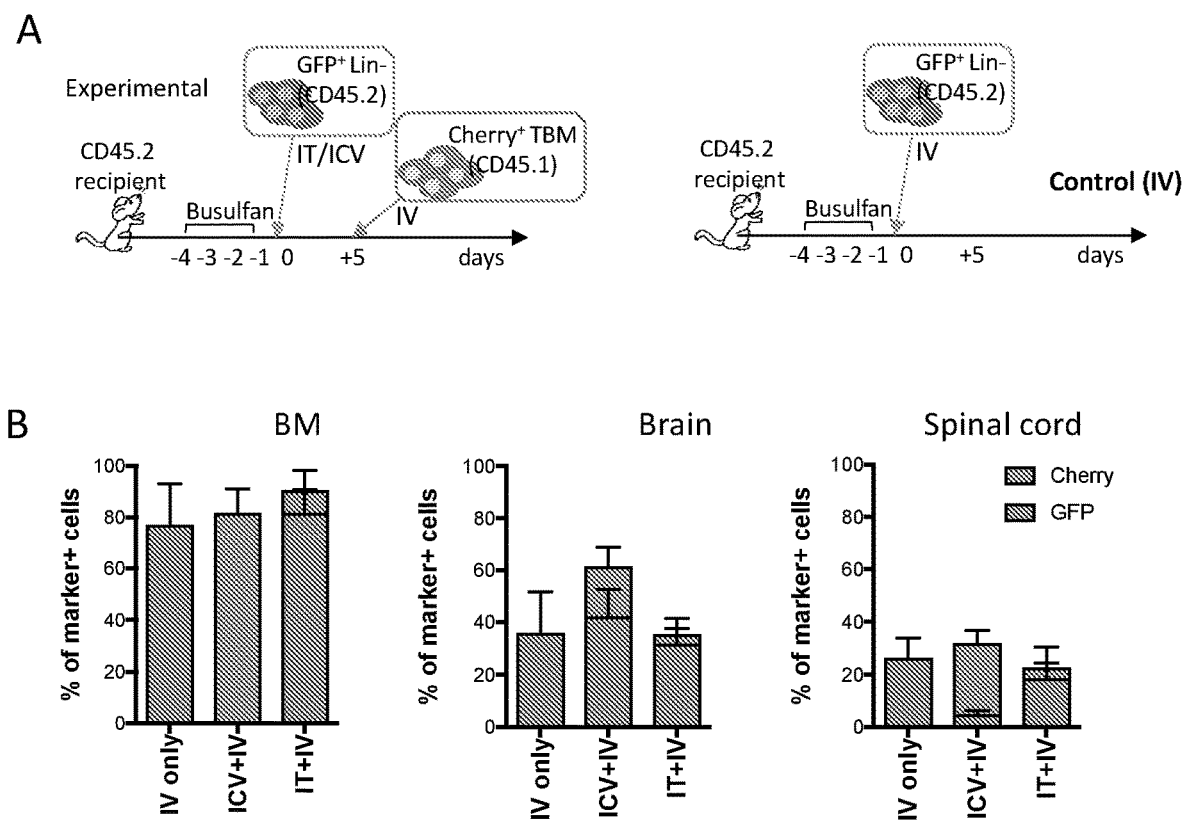
FIGS. 10A-10B show intra-thecal (IT) HSPC transplantation in mice.

Example 11. Intra-Thecal Delivery of HSPCs can Contribute to Brain and Hematopoietic Chimerism in the Context of Combinatorial HSPC Transplantation Strategies It was assessed whether the delivery of HSPCs intra-thecally could contribute to CNS donor chimerism similarly to the ICV cell delivery. Lin⁻ HSPCs were isolated from CD45.2 donor mice and transduced with a GFP encoding LVs. After transduction, cells were transplanted into CD45.1 myeloablated recipients IV ($1.0 \times 10^6$ cells/mouse), ICV ($0.3 \times 10^{\wedge 6}$ cells/mouse) or intra-thecally (IT)($0.3 \times 10^6$ cells/mouse. 5 days after transplantation, mice transplanted ICV and IT were provided with total BM cells from a CD45.1 donors transduced mCherry encoding LVs (FIG. 10A). Mice were sacrificed 45d post transplantation. A high and comparable engraftment of HSPCs (CD45.2 GFP$^+$) was observed in the BM of IV and IT transplanted mice, while no (or very low) CD45.2 GFP$^+$ cells were observed in the BM of ICV transplanted mice (FIG. 10B left graph). ICV transplanted mice showed a good BM engraftment of the mCherry$^+$ CD45.1 BM transplanted cells, while the same cells showed very little engraftment in IT transplanted mice, likely due to competition with the CD45.2 GFP$^+$ HSPCs transplanted at d0. CD45.2 GFP$^+$ HSPCs engrafted in the brain myeloid compartment of all the groups analyzed (FIG. 10B central graph), with ICV+IV injected mice showing the highest donor chimerism as compared to the other groups. The mCherry$^+$ CD45.1 cell progeny of the IV transplanted cells was observed in ICV transplanted mice. Donor (GFP$^+$ mCherry) cells engrafted in the spinal cord myeloid compartment of all the groups analyzed (FIG. 10B right graph), with ICV+IV injected mice showing the lowest GFP chimerism as compared to the other groups. An increased percentage of mCherry$^+$ CD45.1 BM transplanted cells was observed in ICV transplanted mice as compared to IT ones. Overall these data show that IT can be used as an additional route of administration for HSPCs in order to achieve myeloid cell reconstitution both in the brain and in the spinal cord of transplant recipients. ICV and IV only delivery are also associated to a remarkable spinal cord chimerism with the donor. Donor cells transplanted IT were also extensively observed in the peripheral blood and bone marrow, indicating that they are not retained in the CNS upon transplantation. Thus, this transplantation procedure can be considered particularly for those diseases with both CNS and systemic involvement.

Figure 11:
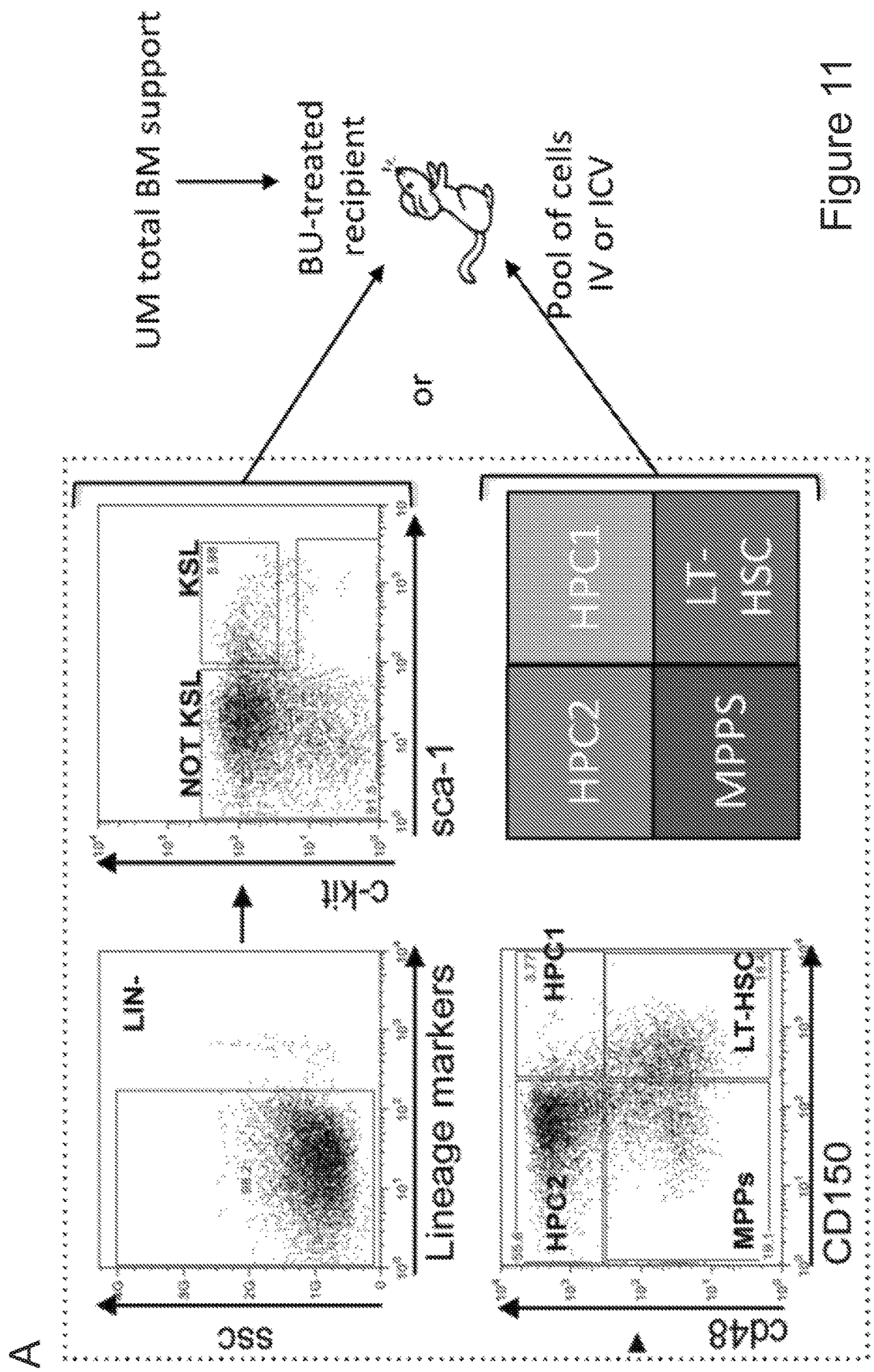
FIGS. 11A-11J show that post-transplant brain myeloid cells derive from early hematopoietic stem/progenitor cells.
Figure 11:
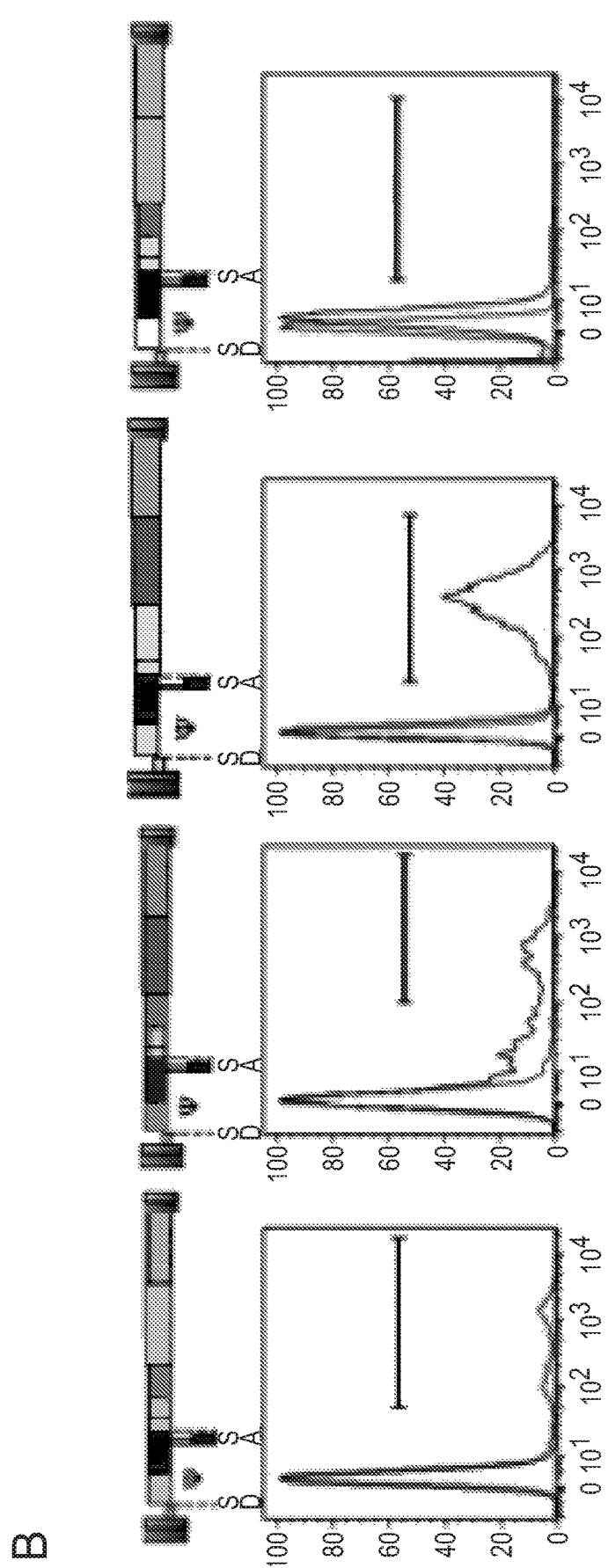
Figure 11:
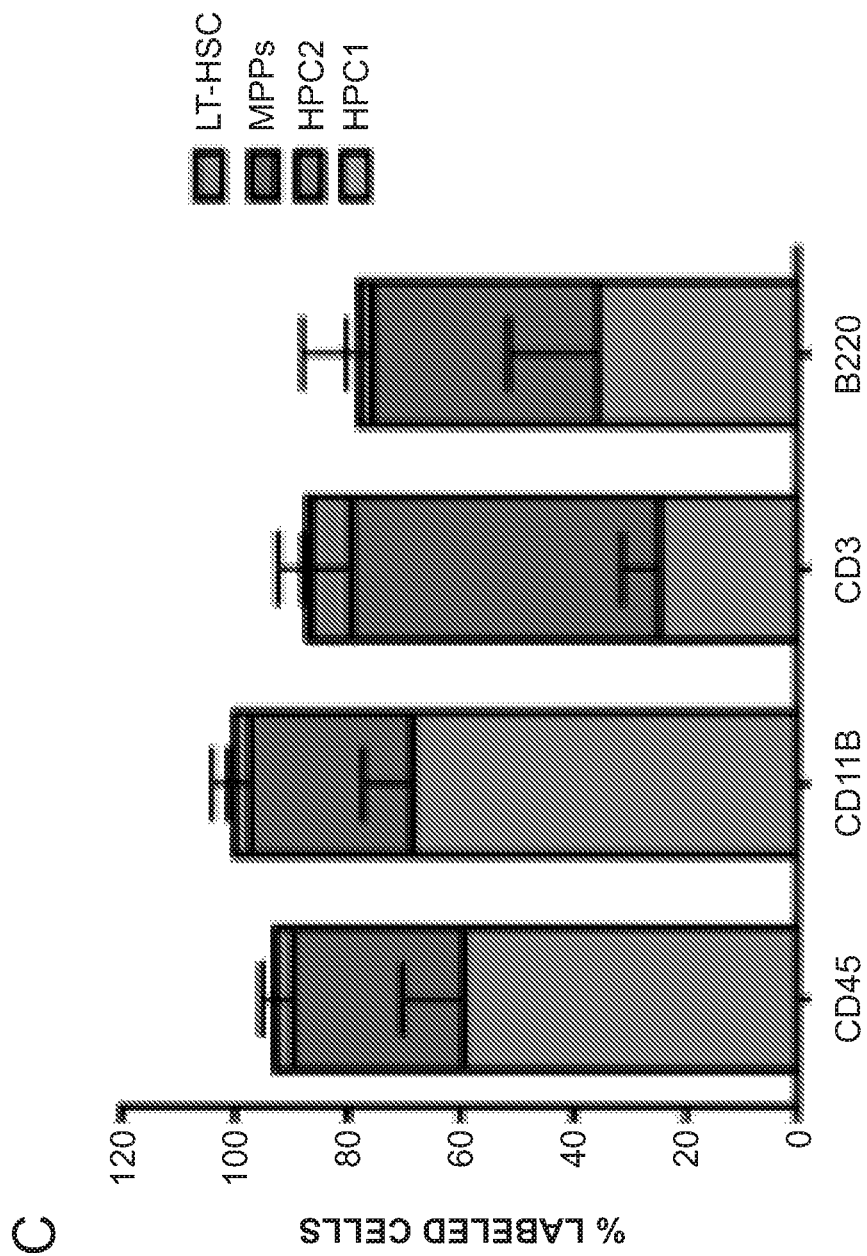
Figure 11:
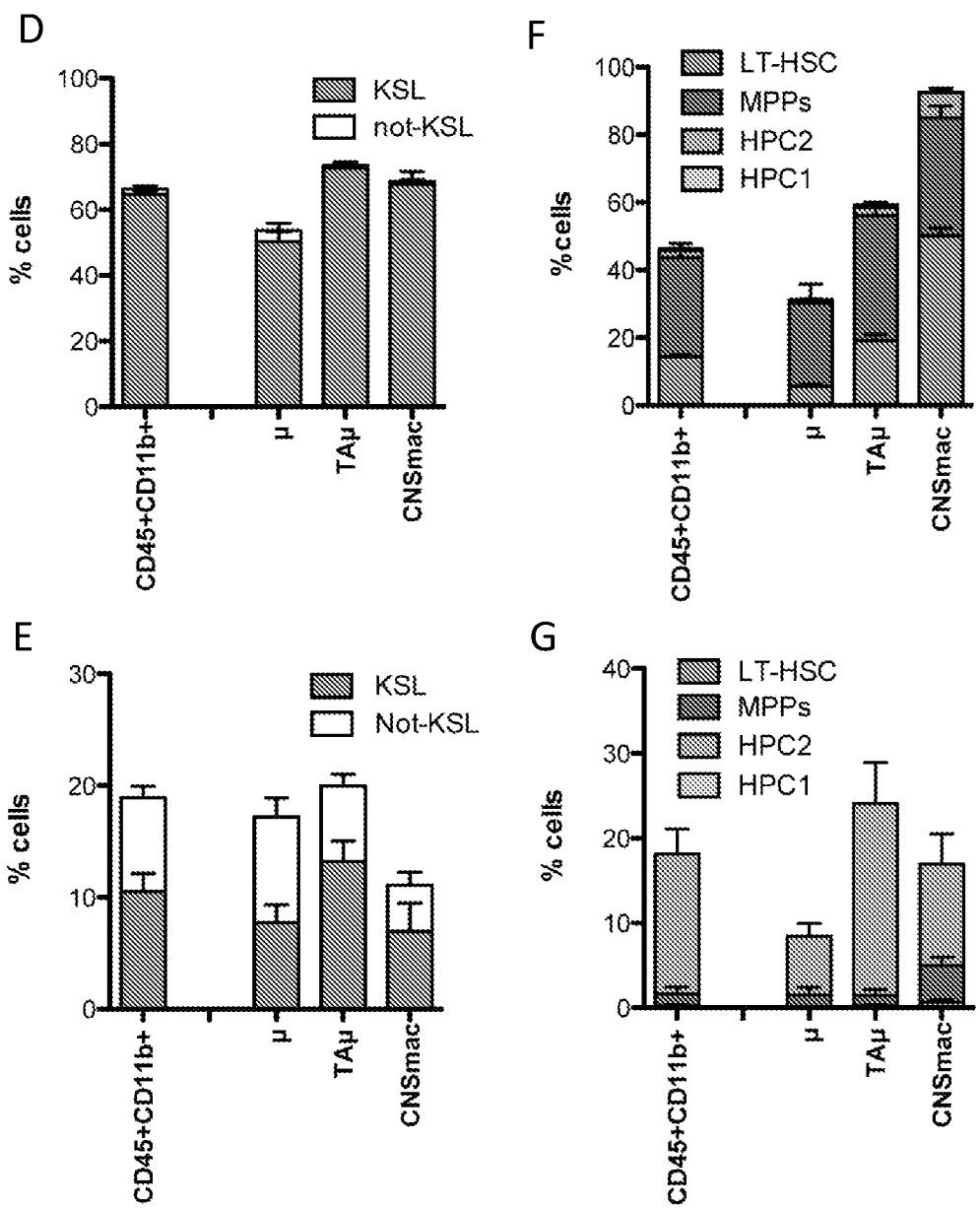
Figure 11:
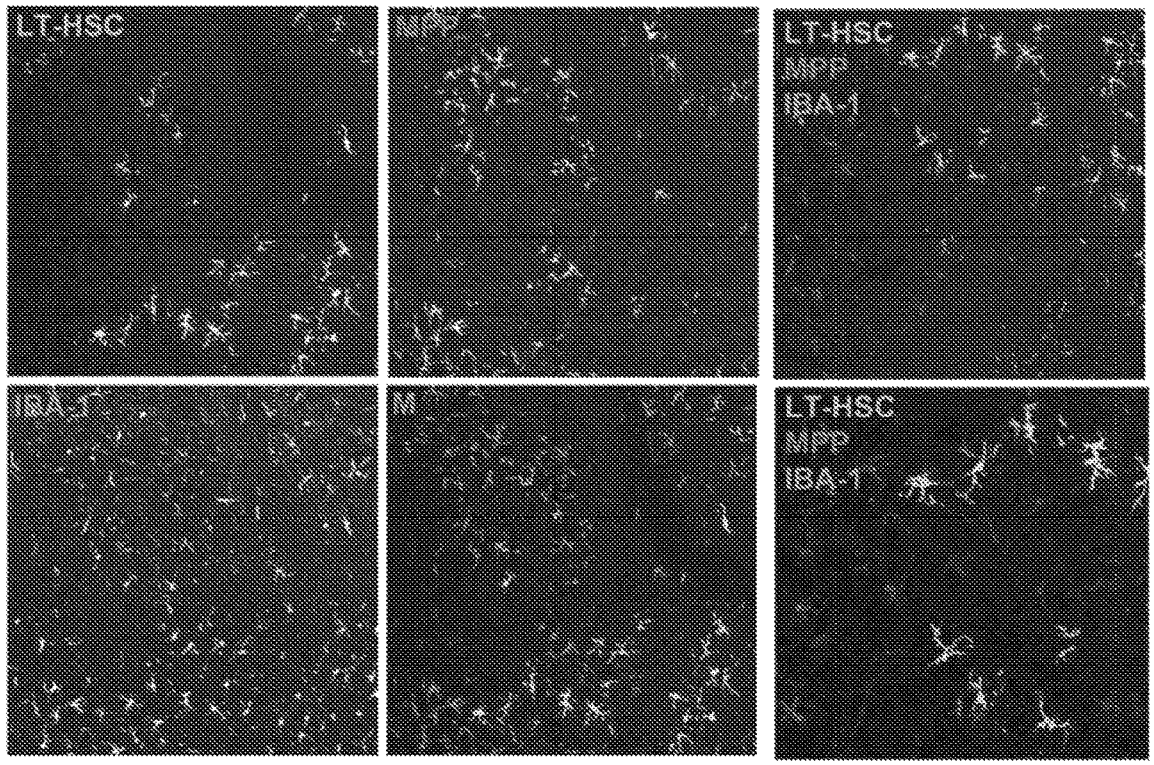
Figure 11:
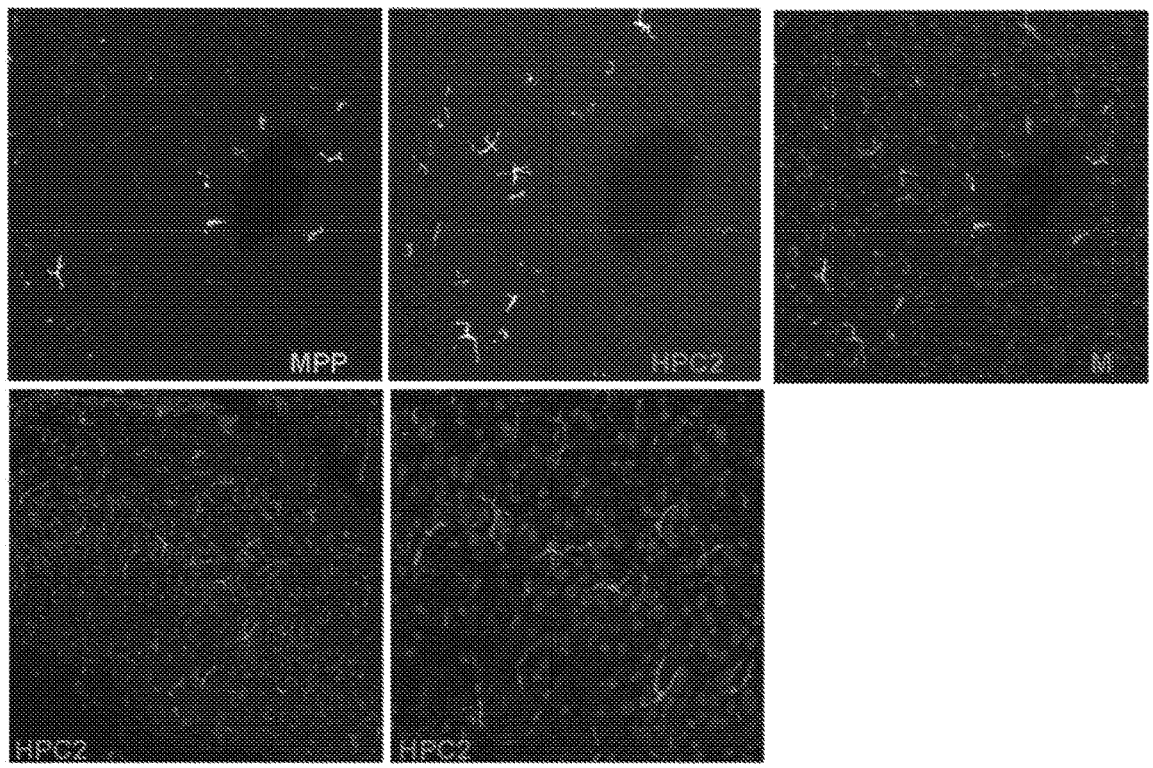
Figure 11:
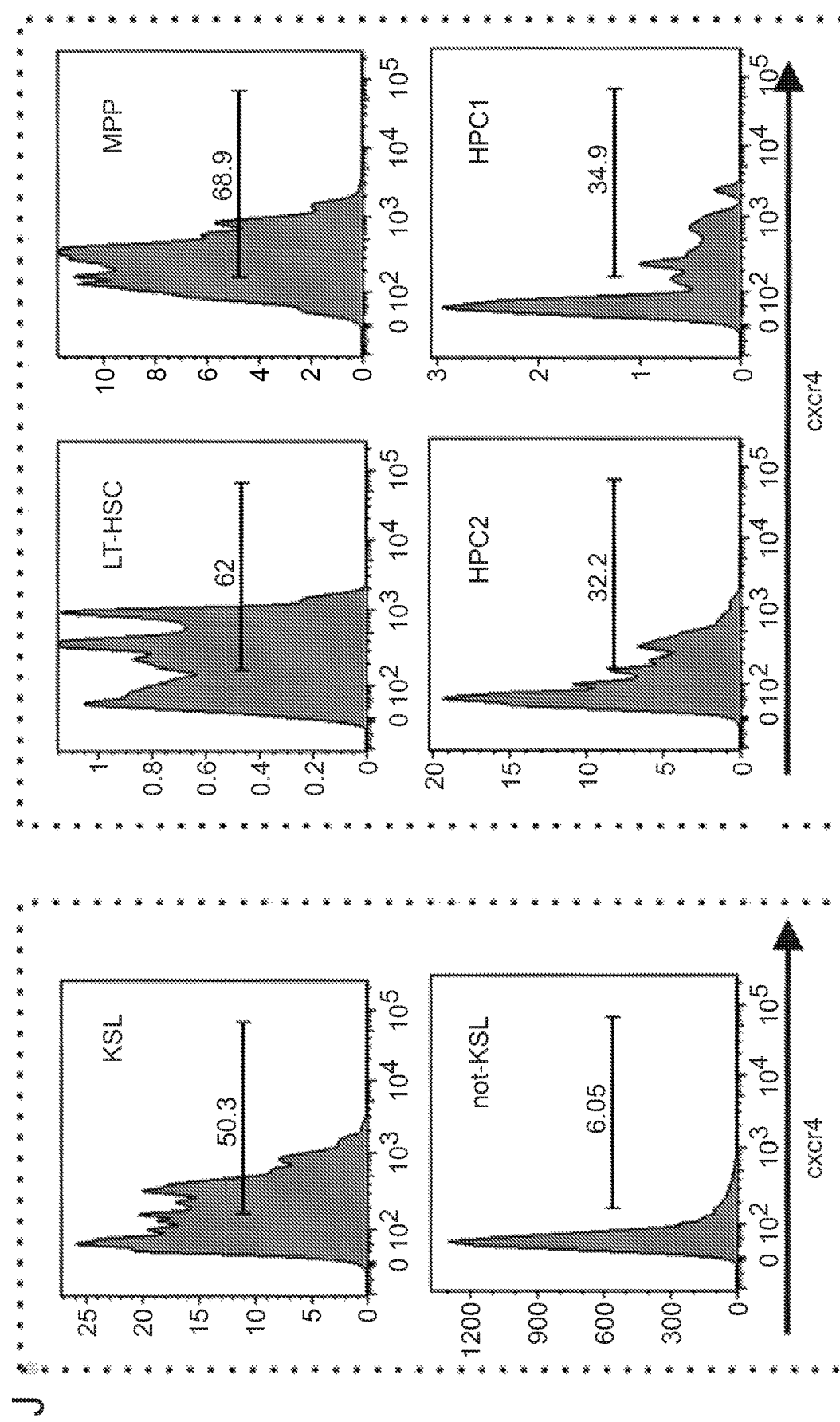

Example 12. Post-Transplant Brain Myeloid Cells Derive from Early Hematopoietic Stem/Progenitor Cells The c-kit$^+$, Sca-1$^+$, Lin⁻ (KSLs) fraction within HSPCs is able to give rise to TAμ and μ in brains of mice upon IV transplantation, whereas Lin⁻ progenitor cells that are not double positive for c-kit and Sca-1 (Not-KSL) do not (Capotondo et al., Proc Natl Acad Sci USA 109, 15018-15023 (2012)). This finding was further explored in a stringent competitive setting by co-transplanting differentially labeled KSLs and not-KSL cells in individual animals (FIGS. 11A, 11D and 11E) employing both the IV (FIG. 11D) and ICV (FIG. 11E) routes to assess a potential differential contribution of the transplanted cells to myeloid brain cell turnover. KSL cells, when injected IV with not-KSLs, contributed almost exclusively to the different brain myeloid cell populations (FIG. 11D), that are defined as CD45$^+$CD11b$^+$ myeloid brain cells; CD45$^+$CD11b$^{high}$ μ cells; CD45$^+$CD11b$^{+/low}$ Transiently Amplifying μ-TAμ cells; CD45$^{high}$CD11b$^{high}$ CNS associated macrophages, CNSmac (Capotondo et al., Proc Natl Acad Sci USA 109, 15018-15023 (2012)). KSL and not-KSL cells instead contributed to similar extent to brain myeloid cell reconstitution when injected ICV (FIG. 11E). The ability of differentially labeled sub-populations, identified within KSL compartment by differential expression of the SLAM markers CD150 and CD48, to contribute to brain myeloid cell engraftment upon transplantation was addressed (FIGS. 11A, 11B). Upon competitive IV transplantation, CD48/CD150$^+$ Long-term HSCs (LT-HSCs) and CD48⁻/CD150 Multipotent progenitors (MPPs) showed the greatest ability over the other injected populations to reconstitute the brain myeloid compartment (FIG. 11F). In contrast, more committed CD48$^+$ CD150 cells also contributed to the reconstitution of brain myeloid populations of mice transplanted ICV (FIG. 11G). Hematopoietic reconstitution of the transplanted mice is shown in FIG. 11C. Histology on cryostatic brain slices from IV and ICV transplanted mice confirmed these results (FIGS. 11H and 11I). Consistent with previous findings, also in these settings, donor-derived cells showed a ramified morphology with thin processes departing from the cell body, and expressed the myeloid markers Iba-1 and CD11b (FIGS. 11H and 11I).

In order to interpret these findings expression of the CXCR4 receptor, which is well known to be involved in HSC recruitment and homing to the BM (Dar et al., Experimental hematology 34, 967-975 (2006); Rettig et al., Leukemia 26, 34-53 (2012); Sugiyama et al., Immunity 25, 977-988 (2006)), was analyzed on KSLs, not-KSL cells and on the four KSL subpopulations described above (cells analyzed at the end of transduction, at time of transplantation). Interestingly, the cells enriched in microglia-like cell reconstitution potential in the IV infusion setting, namely KSL, LT-HSCs and MPPs, expressed CXCR4 at higher levels as compared to not-KSLs, and HPC-1 and HPC-2 (FIG. 11J). Without intending to be bound by theory, this finding indicates that cells expressing CXCR4 at high levels cells could be favored in early recruitment to the brain upon IV infusion and therefore in their ability to contribute to brain myeloid cell chimerism. This would not apply to ICV delivery where different signals could be important.

Figure 12:
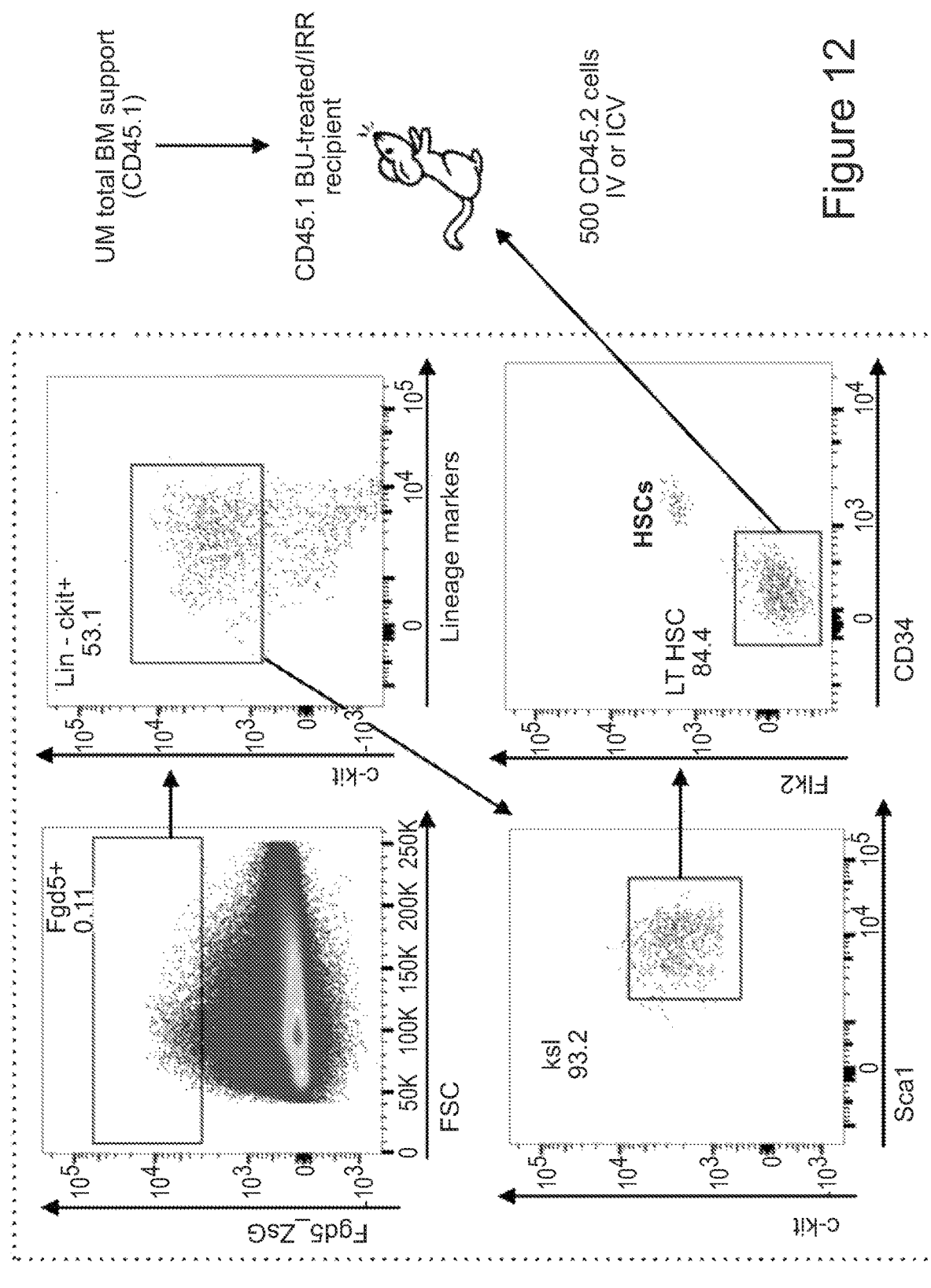
FIGS. 12A-12E show that Fgd5$^+$ HSCs generate a microglia-like progeny in the brain upon both ICV and IV transplantation.
Figure 12:
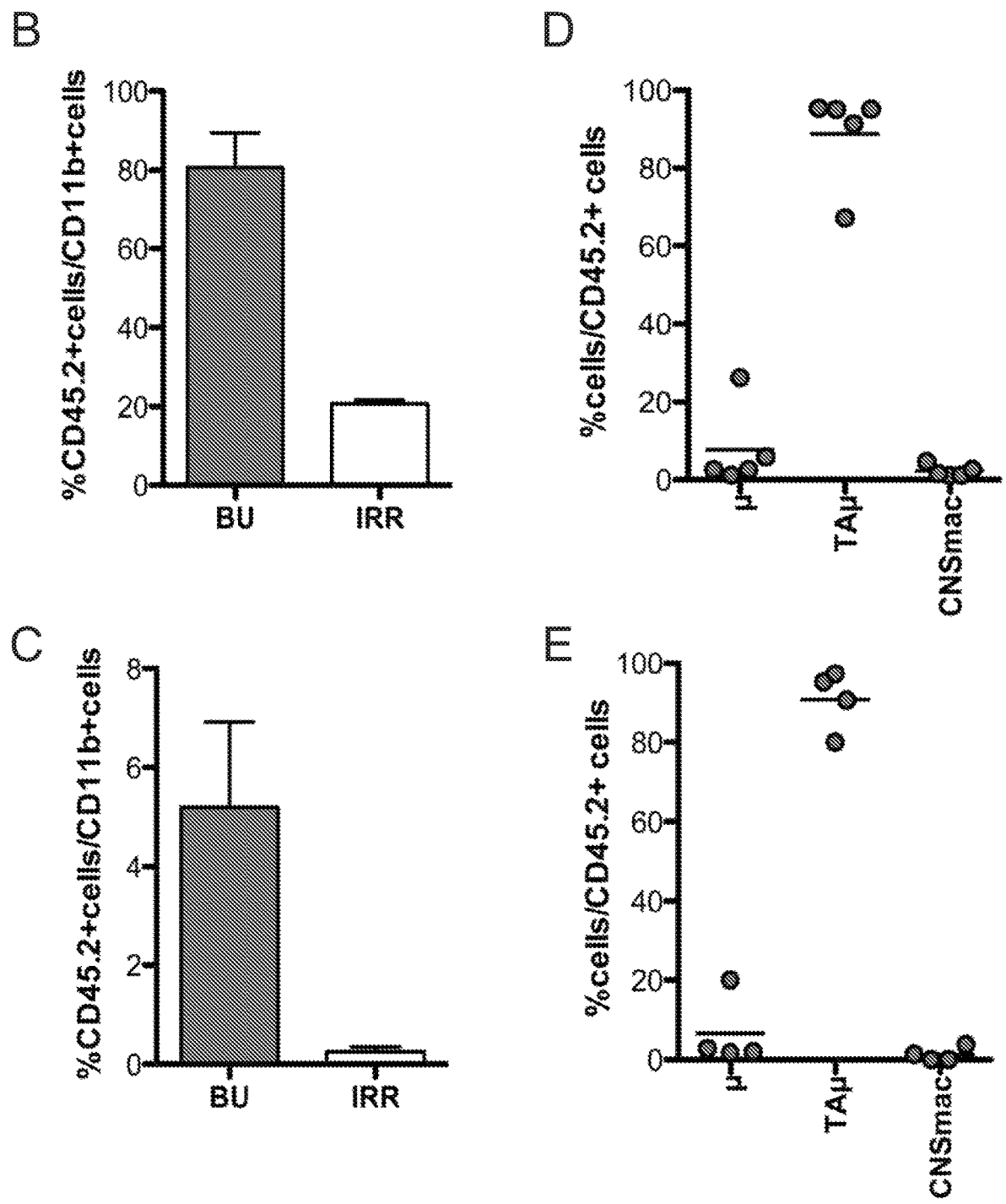

In order to more stringently assess whether bona fide HSCs could generate new microglia-like cells upon ICV transplantation, in the absence of competition, LT-HSCs were isolated with alternative markers and the functional signature of Fgd5 expression in Fgd5-Zsgreen animals (Gazit et al., J Exp Med 211, 1315-1331 (2014)). Indeed, the Fgd5-green reporter strain allows the ability to faithfully isolate cells that are highly enriched in HSC activity. Five hundred bona fide HSCs were isolated from CD45.2 Fgd5-Zsgreen donors as Zsgreen+, lineage⁻, c-kit$^+$, Sca1$^+$, Flkt-2⁻, CD34⁻ cells and transplanted IV or ICV into busulfan-conditioned or lethally irradiated CD45.1 recipient mice, along with un-manipulated total bone marrow CD45.1 support (FIG. 12A). IV cell delivery resulted in a robust hematopoietic donor chimerism, while ICV injected cells did not contribute to hematopoiesis in the peripheral blood. Interestingly, although the ICV transplanted animals did not show peripheral blood chimerism, donor-derived CD45.2$^+$ cells were identified in the brain in both transplant settings (FIGS. 12B and C). Reconstitution of brain myeloid cells was confirmed to be less efficient in irradiated rather than busulfan-ablated recipients, as described (Capotondo et al., *Proc Natl Acad Sci USA* 109, 15018-15023 (2012)). The donor-derived cells expressed CD45 and CD11b, and were mostly part of the TAµ cell compartment (FIGS. 12D and 12E).

These data demonstrate that bona fide HSCs generated a microglia-like progeny in the brain upon transplantation via ICV or IV. However, the process was much more efficient when early progenitors were also administered ICV.

Figure 13:
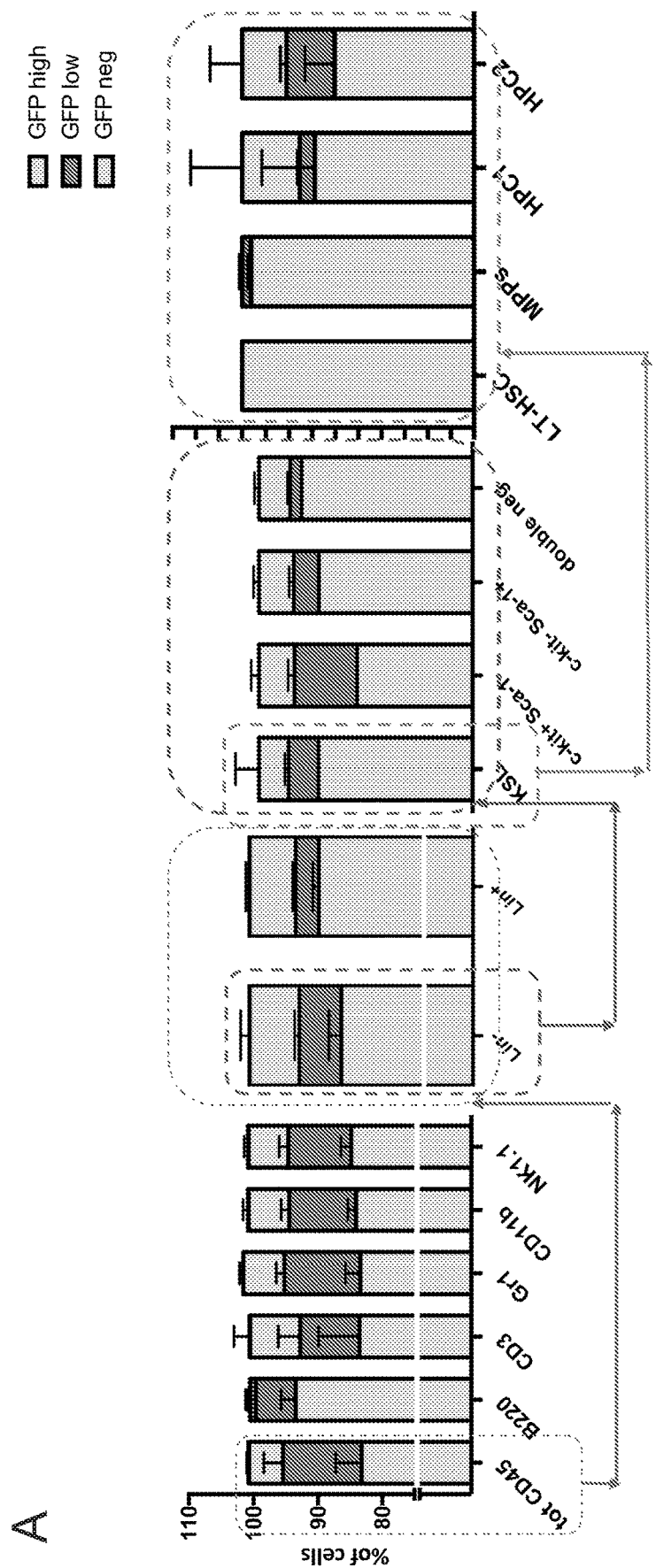
FIGS. 13A-13B describe the contribution of CX3CR1 expressing and negative cells to brain myeloid chimerism.
Figure 13:
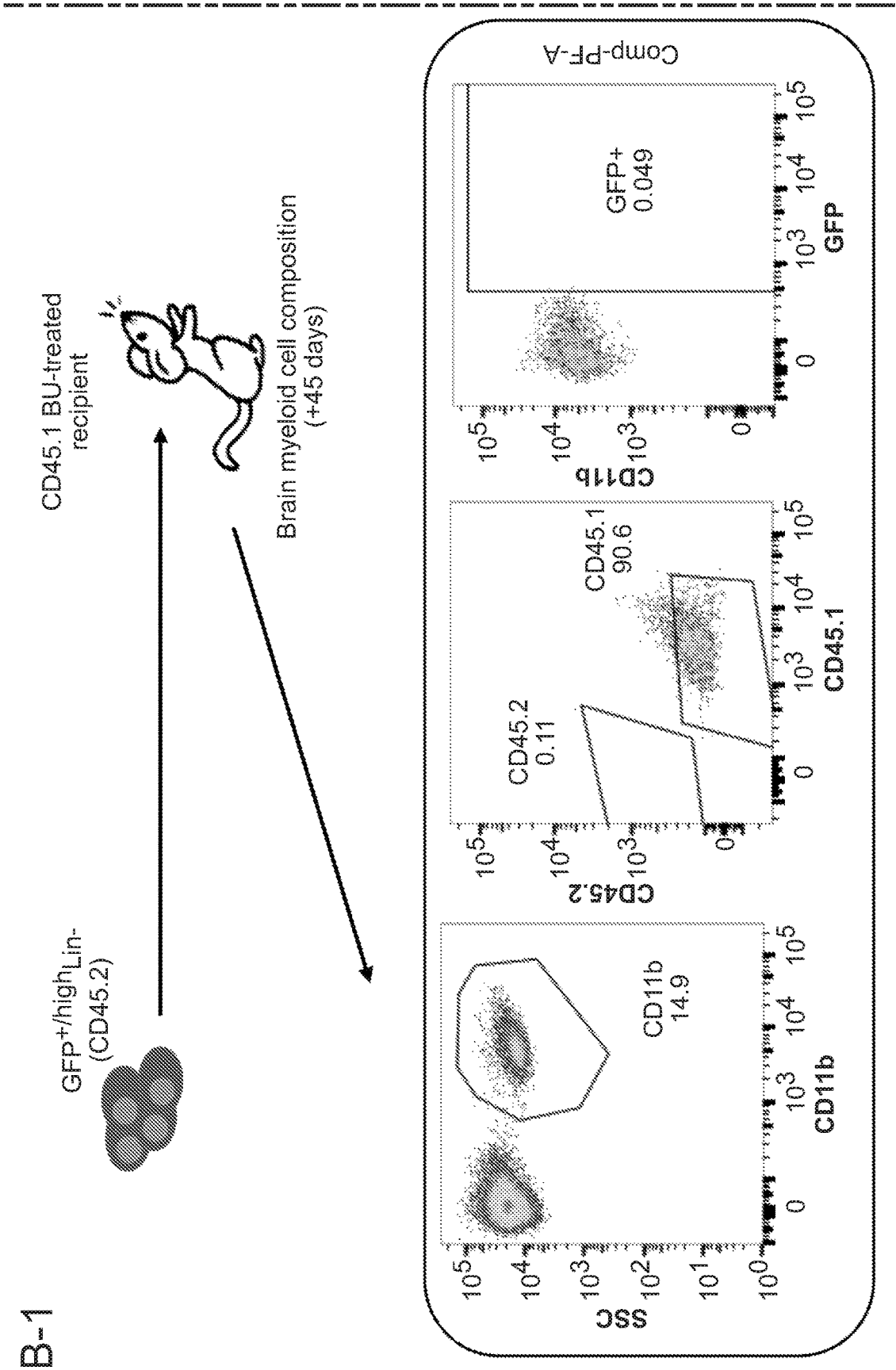
Figure 13:
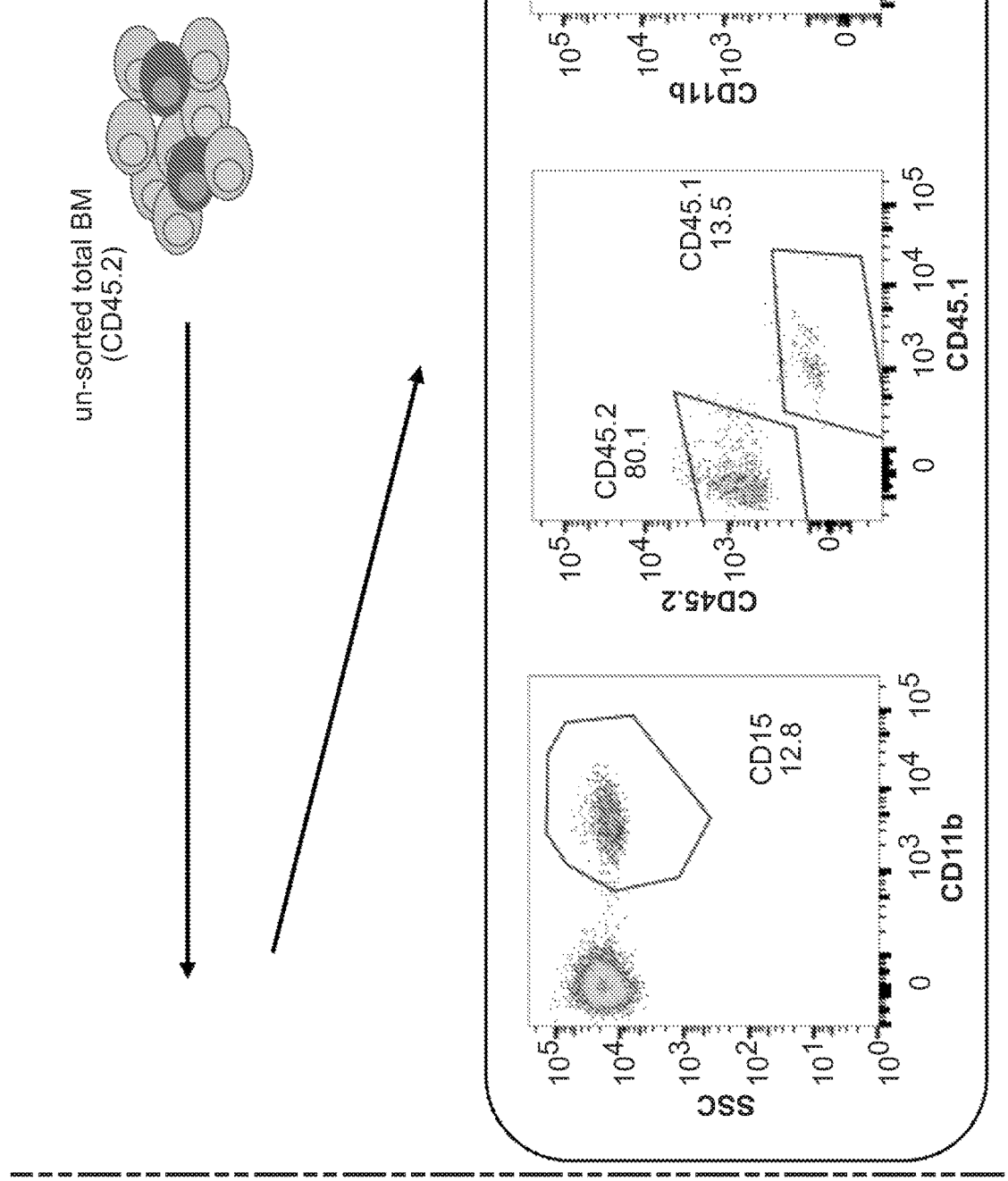

In order to further identify cells within HSCs capable of reconstitution potential by relevant markers the CX3CR1-GFP reporter mouse was used that expresses GFP reporter gene under the control of the seven-transmembrane receptor CX3CR1, a specific receptor for the novel $CX_3C$ chemokine fractalkine highly expressed on micorglia and myeloid lineage hematopoietic cells. In particular, it was assessed whether low but detectable levels of CX3CR1 expression could identify cells with microglia reconstitution potential within the HSC pool. To this goal, the bone marrow and HSPC pool a of CX3CR1-GFP heterozygous mice were characterized and it was confirmed that a fraction of the HSPC pool expressed CX3CR1, but no real expression could be detected within bona fide LT-HSCs (FIG. 13A). $GFP^+$ and high cells were sorted within the $Lin^-$ HSPC compartment and these cells were transplanted into busulfan-treated recipients along with un-manipulated total bone marrow from normal (nor CXCR1-GFP) donors as support. No $GFP^+$ progeny cells could be detected in the bone marrow and brain of the repopulated mice at 1.5 months post-transplant (FIG. 13B). Rather, GFP-expressing µ cells could be identified in the brain of control mice transplanted with un-sorted total bone marrow from CX3CR1-GFP mice (FIG. 13B). These data indicate that bone marrow equivalents of µ progenitors are retained into LT-HSCs and do not express CX3Cr1.

Figure 14:
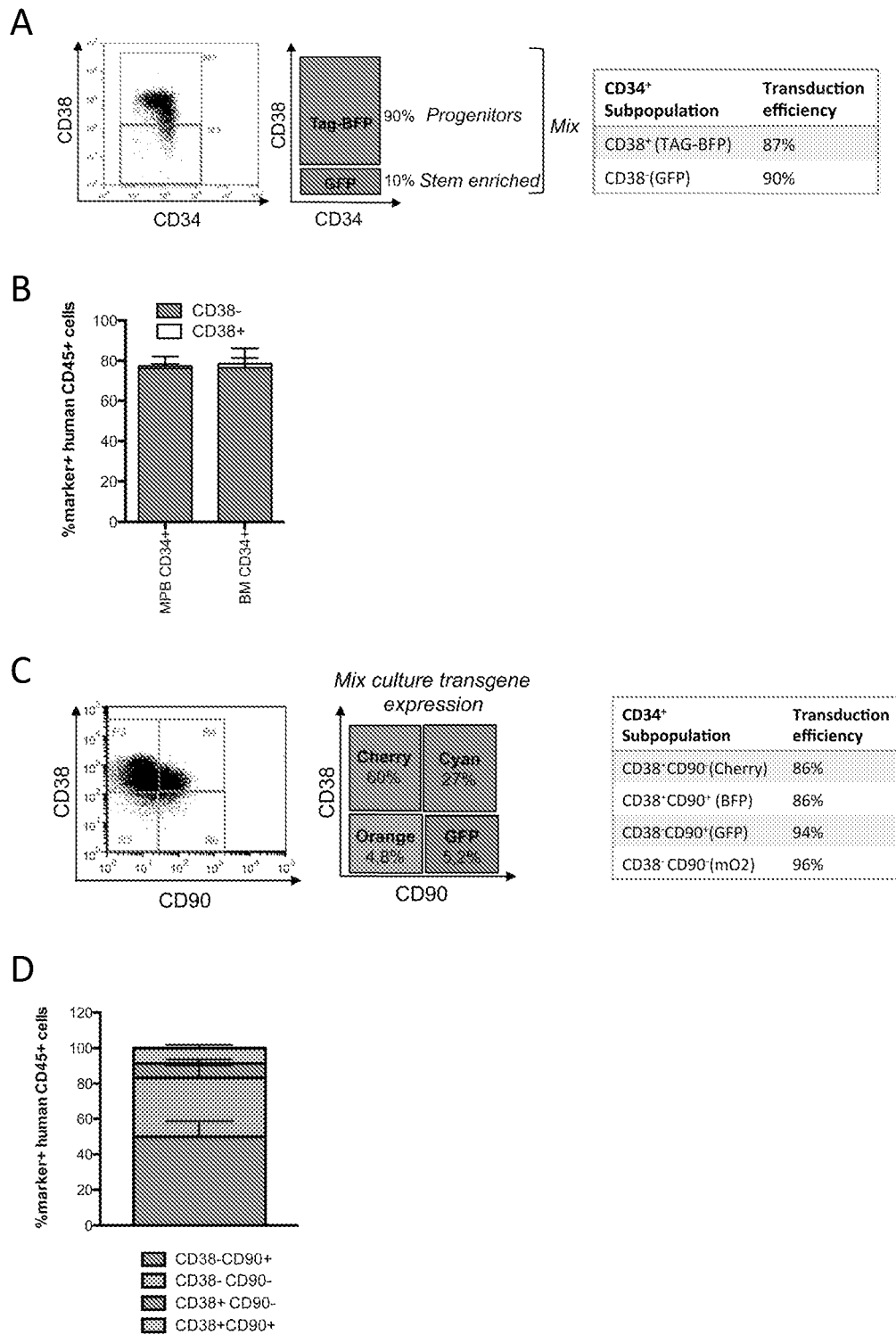
FIGS. 14A-14D show the contribution of human LT-HSCs defined as CD34$^+$ and CD38$^-$ to the generation of brain myeloid progeny cells.

An additional experiment was performed in the human setting by transplanting labeled $CD34^+$ cells and sub-fractions into immuno-deficient NOD/LtSz-scidIL2Rγ$^{null}$ (NSG) mice. In particular, co-transplantation of differentially labeled $CD34^+CD38^+$ (defined as progenitors based on literature) and $CD34^+CD38^-$ (enriched in long term stem cell activity) sorted cells was performed (FIG. 14A), Interestingly, only the $CD38^-$ cell fraction, highly enriched in stem cell activity in humans, was associated with the appearance of labeled myeloid human cells in the brain of the transplanted mice (FIG. 14B). Similarly to what was done in the murine setting, in this setting we proceeded at further dissecting HSPC fractions by CD38 and CD90 expression. $CD38^-CD90^+$ HSCs (labeled with GFP), $CD38^-CD90^-$ MPPs (transduced with mO2 encoding LVs), and $CD38^+ CD90^-$ and $CD38^+CD90^+$ committed progenitor cells (labeled with Cherry and Tag-BFP LVs, respectively) were isolated and labeled (by LVs carrying different reporter genes)(FIG. 14C). Interestingly, in line with what was observed in the mouse setting, the populations enriched in stem cell potential confirmed to possess the greater ability to contribute to brain human cell chimerism with microglia-reminiscent cells (FIG. 14D).

Example 13. Molecular Engineering of Microglia for Regulated Therapeutic Gene Expression The molecular engineering of the cells to be transplanted either IV or ICV in the context of the innovative protocols here described would need to address precise requirements of efficacy, safety and specificity/regulation of therapeutic gene expression. As far as this is concerned, two different strategies are being developed based on gene transfer by integrating vectors and targeted gene addition that could be applied to specific settings where sustained but regulated transgene expression may be required.

Neurodegenerative diseases of adulthood, such as Amyotrophic Lateral Sclerosis (ALS) or Alzheimer's disease (AD), as well as neurodegenerative SDs, are characterized by a prominent neuro-inflammatory response sustained by microglia activation and one of the molecules up-regulated by activated microglia in the course of pathological events is the 18 kDa translocator protein (TSPO), as shown by using selective TSPO radioligands for Positron Emission Tomography by others and us (Visigalli et al. *Neurobiol Dis* 34, 51-62 (2009); Turner et al. *Neurobiol Dis* 15, 601-609 (2004)). Microglia cells are the main cell type responsible for increased TSPO signal. Therefore, TSPO is a useful and sensitive marker to monitor microglia-related neuroinflammation in the brain and its promoter sequences could be used as an optimal regulatory sequence for marker or therapeutic protein production by newly engineered microglia in response to tissue damage and inflammation. Innovative tools allowing for a TSPO-targeted engineering of brain microglia via HSC-derivation for regulated delivery of therapeutic molecules to the brain, with potential application in neurodegenerative diseases and neuroLSDs are being developed. In particular, brain microglia are reconstituted in diseased brains with "sensor" cells engineered to express a gene of interest upon cell activation in response to local neuro-degeneration and neuro-inflammation employing advanced transplantation protocols detailed above (this setting would also be amenable to the use of conditioning regimens directed to µ progenitors).

Figure 16:
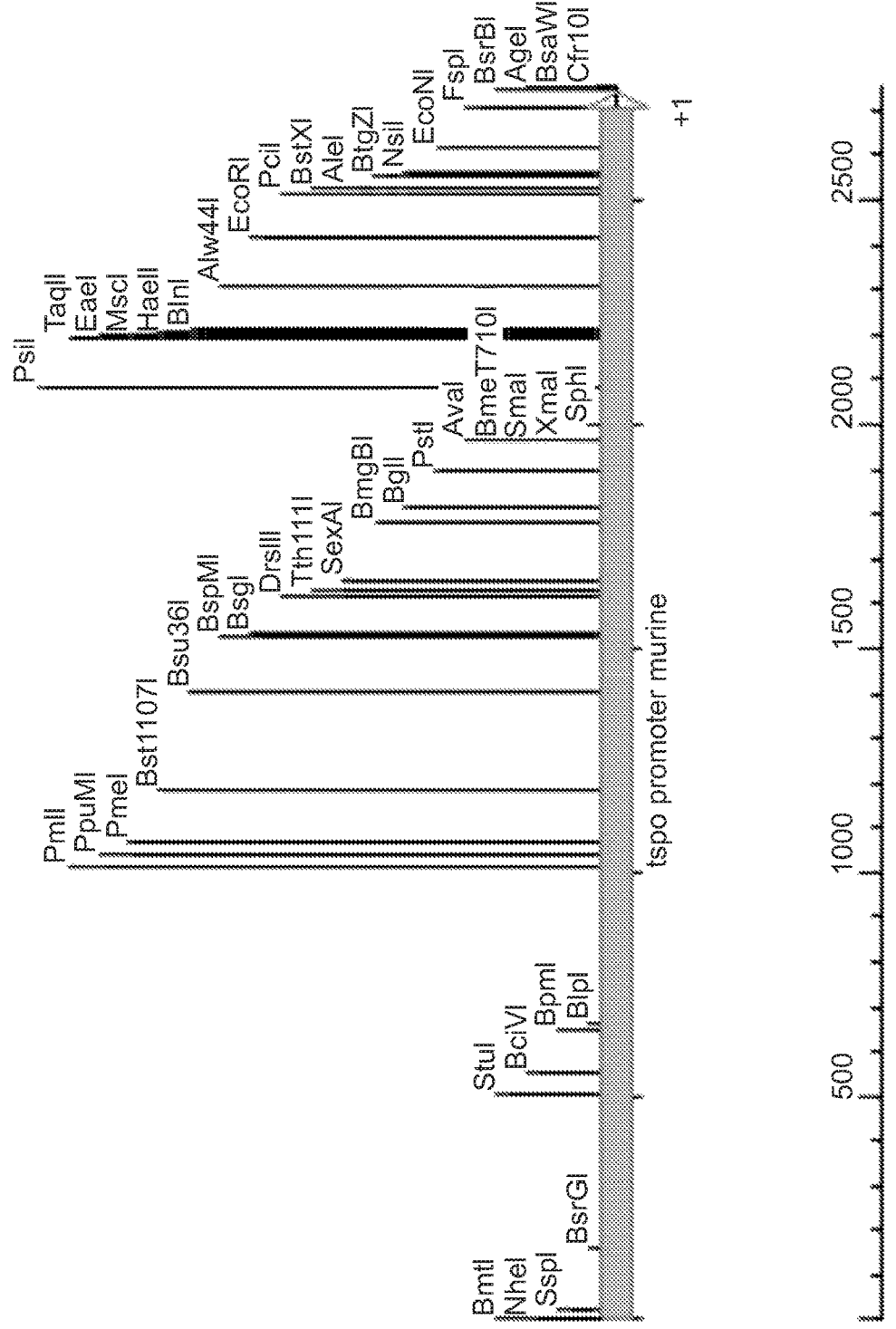
FIGS. 16A-16D depict molecular engineering of microglia for regulated therapeutic gene expression.
Figure 16:
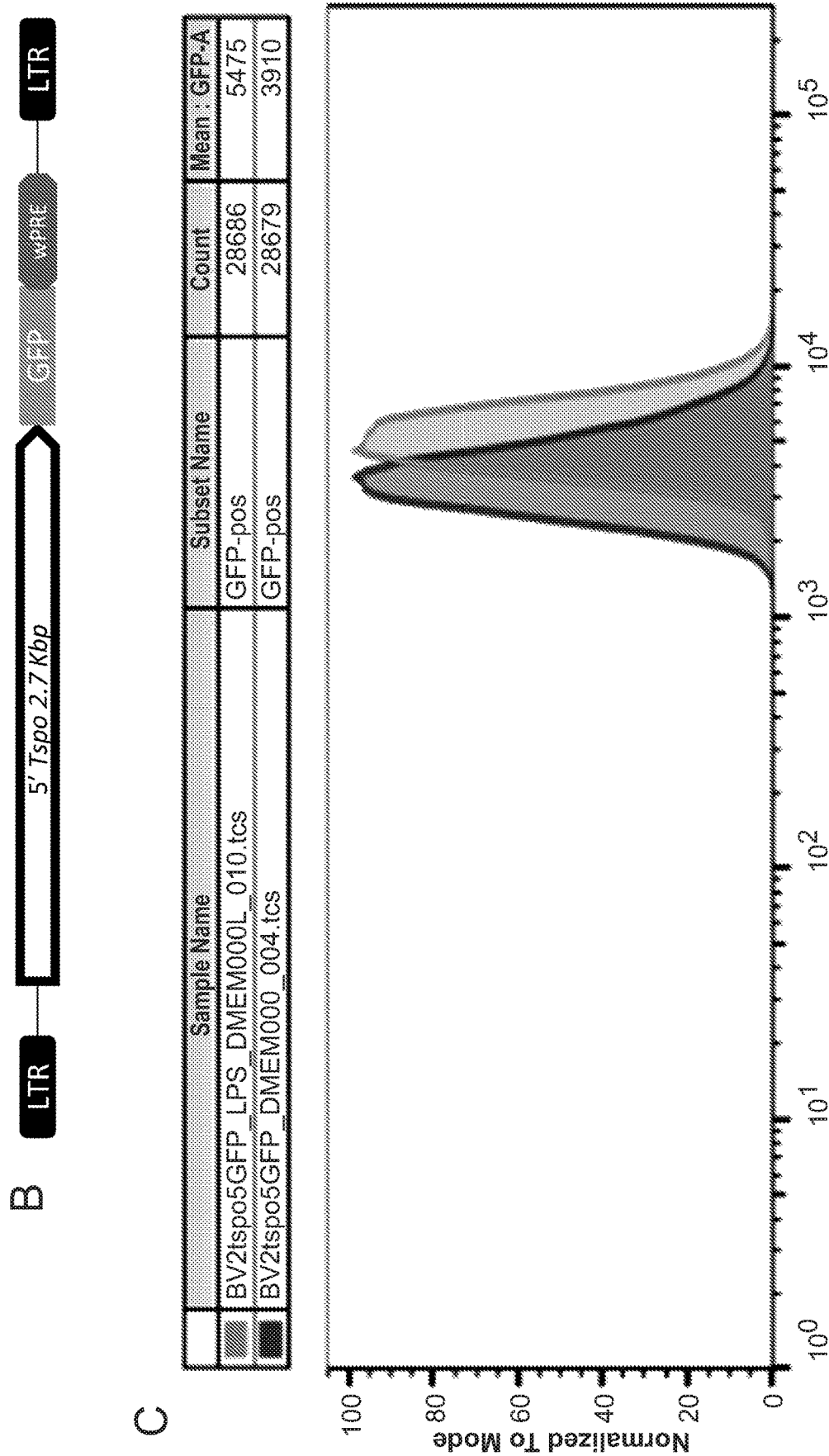
Figure 16:
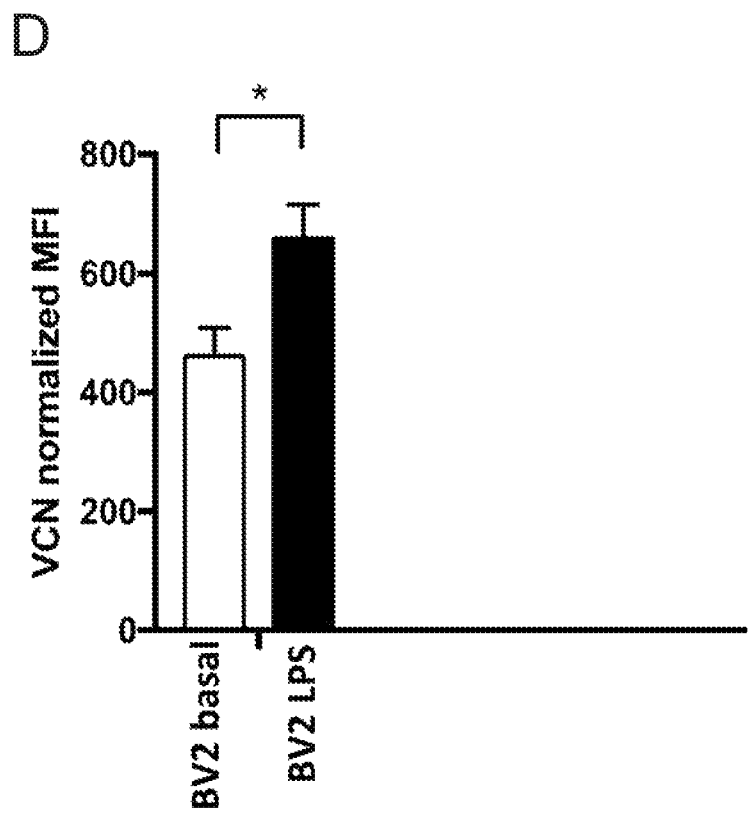

To this goal the TSPO promoter sequence for driving transgene expression is employed. This is being achieved by including evidence-based selected TSPO promoter sequence(s) (Wang et al. *Cell Tissue Res* 350, 261-275 (2012)) upfront of a marker or therapeutic gene in the context of advanced generation LVs to be used for HSC transduction and inserting a therapeutic gene upfront/within first introns/exons of the TSPO gene to exploit its promoter by targeted gene addition using the CRISPR-Cas technology, with different strategies being tested. TSPO knock-out mice testify about the feasibility of this latter strategy (Banati et al. *Nat Commun* 5, 5452 (2014)). Selected TSPO promoter sequence(s) (Wang el al. *Cell Tissue Res* 350, 261-275 (2012)) (FIG. 16A) inserted upfront of GFP as marker gene in the context of a 3rd generation LV (FIG. 16B) has been confirmed to drive a sustained transgene expression within microglia cells (in the microglia cell line BV2) and is responsive to simulation by bacterial LPS (FIGS. 16C and 16D), as expected by the naive sequence. Transduced and/or edited cells are then used for reconstituting exclusively brain myeloid cells in recipient mice with advanced protocols.

One working hypothesis is that upon transplantation of HSCs genetically modified/edited at the TSPO locus a population of brain myeloid cells and microglia are generated that upon cell activation in a neuro-inflamed and degenerated environment express a gene allowing for precise molecular monitoring of neuroinflammatory responses and/or endowed with therapeutic activity and contributing to disease phenotype amelioration. Reporter genes for characterization of the tools under development are validated in animal models characterized by microglia activation and TSPO up-regulation, such as the ALS mouse model (SOD1.G93A mice) (Peviani et al. *CNS Neurol Disord Drug Targets* 9, 491-503 (2010)) and the animal model of globoid cell leukodystrophy (GLD) (Visigalli et al. *Neurobiol Dis* 34, 51-62 (2009)). the tools are confirmed in their functionality, their potential for therapeutic effect are validated in the available animal models.

Figure 15:
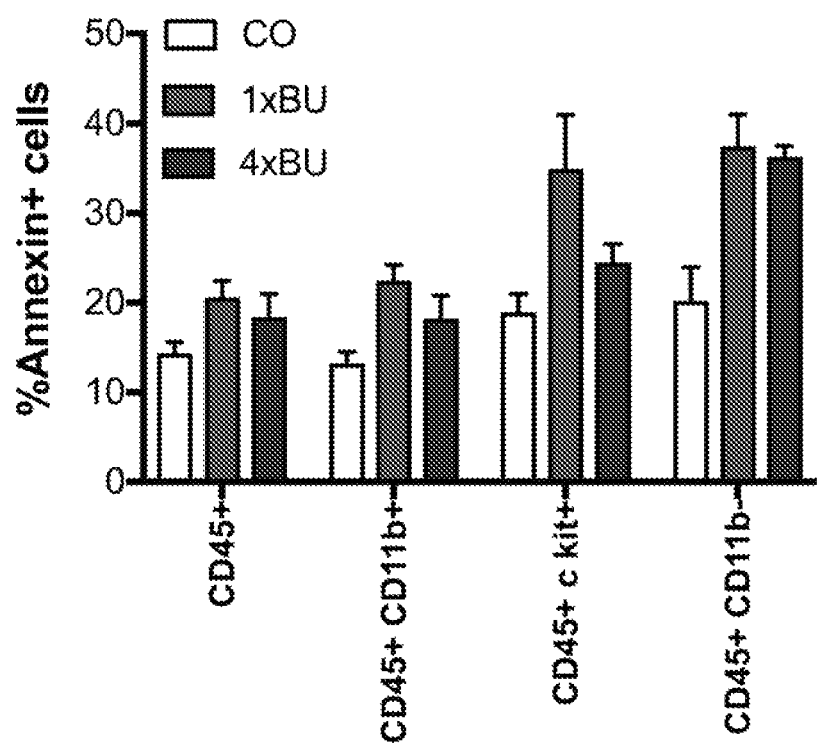
Figure 15:
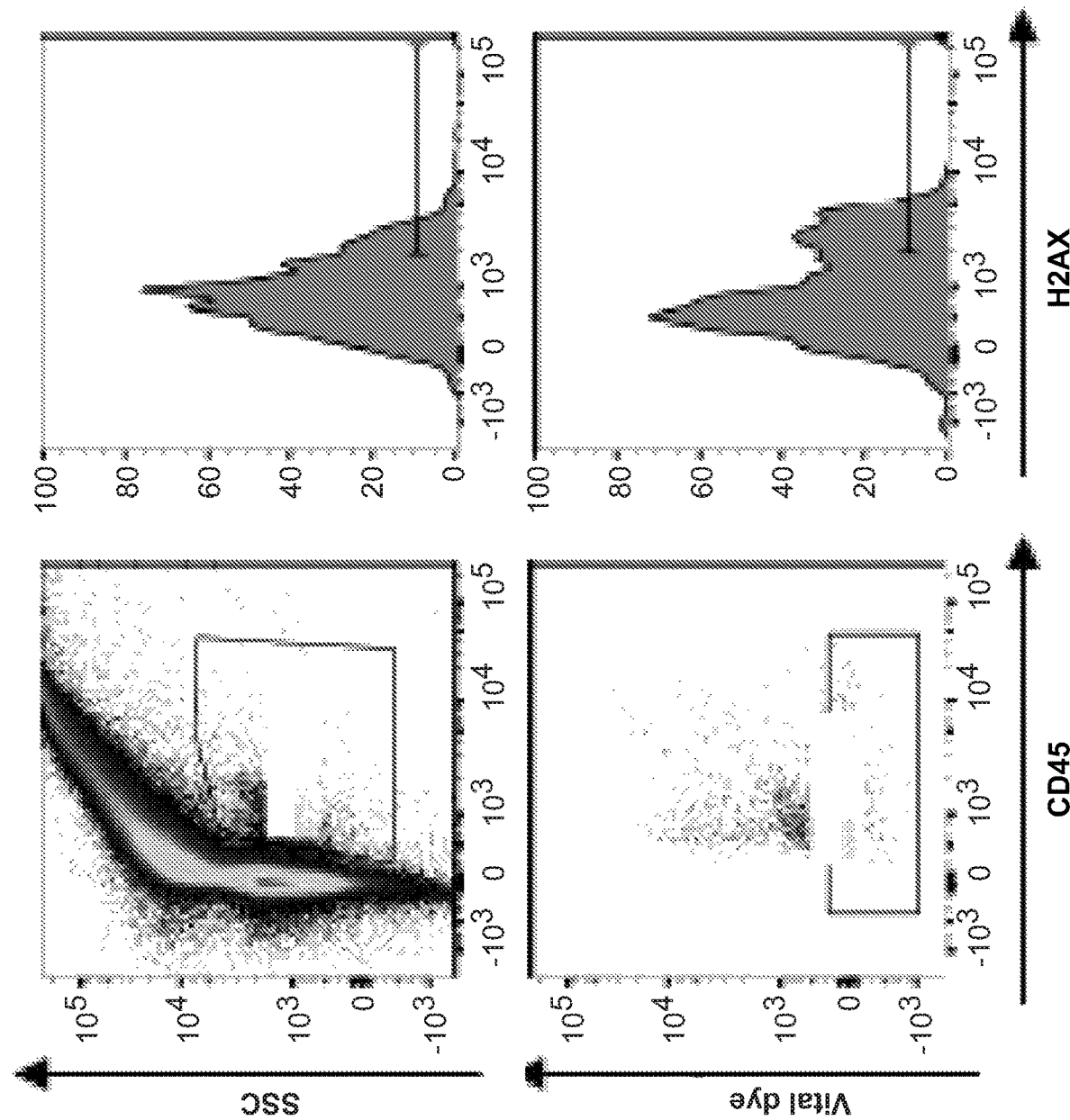
Figure 15:
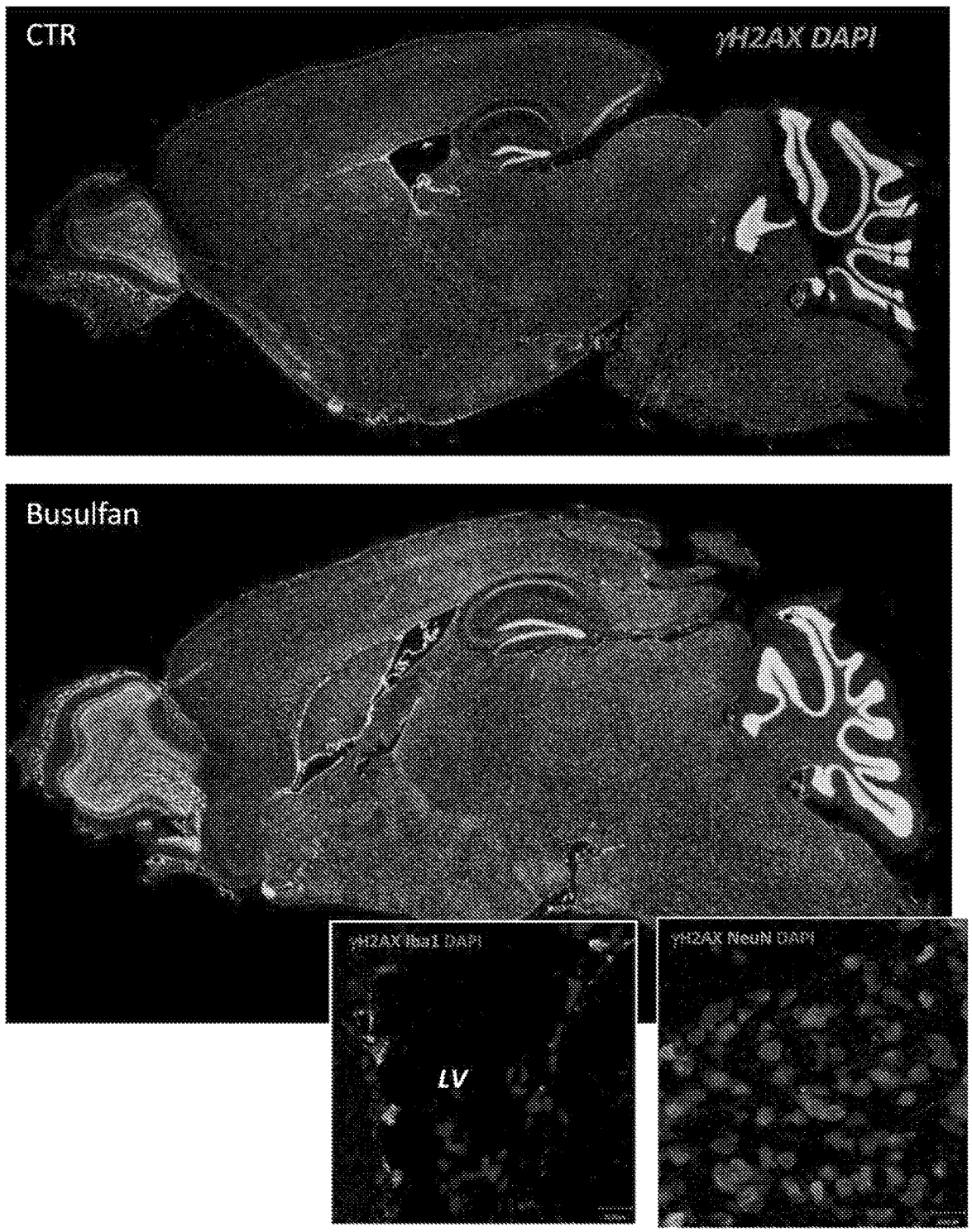

Example 14. Identification of Microglia Progenitors by the Use of the γH2AX Marker of Busulfan Toxicity and Fgd5-Reporter Mice Previous studies have provided evidence for the existence of i) a functionally defined microglia precursor population located in the brain and susceptible to ablation upon administration of a busulfan-based conditioning and that may coincide with endogenous CNS-resident microglial progenitors (μP). Phosphorylated histone 2AX (γH2AX) is a sensitive and specific biomarker to track the cells targeted by busulfan in the brain. Thus, functional brain resident μP could be identified by taking advantage of busulfan and γH2AX, which is a pharmacodynamic marker of its cytotoxicity within these cells. γH2AX was investigated as a biomarker of busulfan cytotoxicity. In particular, the presence, distribution and cellular localization of γH2AX were studied by flow cytometry (FC) and immunofluorescence (IF) on brain slices from mice treated with systemic busulfan conditioning. FC showed an increase of γH2AX signal in busulfan-treated versus control untreated animals, particularly within live CD45$^+$ cells, at 1 and 5 days from the last busulfan dose (FIG. 15B). At the same time post-busulfan treatment early apoptosis is also detected by annexin V staining within CD45$^+$ brain cells, particularly in CD1 b$^+$ and c-kit$^+$ cells (FIG. 15A). By IF, γH2AX was hardly detectable in control mice, except for some γH2AX$^+$ foci found in few neuronal cells, mainly localized in the hippocampus (FIG. 16C top picture), where a correlation between physiological neuronal activity and H2AX phosphorylation has previously been shown. In contrast, in busulfan-treated mice the γH2AX$^+$ signal was increased in nuclei of cells lining the lateral ventricles, sub-ventricular one (SVZ) and rostral-migratory stream (RMS) (FIG. 15C bottom picture). γH2AX$^+$ foci were localized both in neurons (FIG. 15C insert) and glial cells, i.e. microglia and astrocytes (FIG. 15C insert). Altogether these data indicated that both neuronal and non-neuronal cells, localized in well-defined areas of the brain including CNS stem-cell niche regions, became sensitive to busulfan. Thus, these results have the potential to identify microglia progenitor cells. Similar experiments are on going in mice expressing reporter genes expressed by the promoter of markers of hematopoietic stem cell- and microglia-specific genes, such as Fgd5 or Cx3Cr1 in order to better track busulfan-susceptible cells.

Example 15. Selective Brain Conditioning Targeting Microglia Progenitors Using Nanocarriers for Targeted Delivery Systemic administration of busulfan is instrumental to foster efficient turnover of brain microglia with donor-derived cells. A similar, but CNS-restricted regimen could preserve patients with CNS-restricted disease (e.g, INCL, PD, ALS etc.) from the side effects of a myeloablative systemic conditioning. In preliminary studies, the possibility of intra-brain administration of busulfan through a cannula implanted in the lateral ventricles in mice was explored. Different drug formulations of busulfan were tested, including a clinical grade busulfan formulation. However, ICV administration was not able to guarantee exposure of brain-resident μP to busulfan levels comparable to those reached by systemic drug administration nor able to favor transplanted HSPC engraftment (data not shown). It was rather associated with extensive neurotoxicity and local inflammation. Thus, a targeted drug delivery strategy using nanoparticles was implemented. Without intending to be bound by theory nanoparticles may have the potential to enable effective and selective delivery of ablating drugs to functionally defined μP.

Recently, polymeric nanoparticles (NPs) have attracted great interest as promising tools to improve the pharmacologic profile of drugs, including chemotherapeutics. NPs are tunable in material composition, surface functionalization and degradation rate, and allow: i) high selectivity for target cells, reducing the risk of side effects of drugs formulated with NPs as compared to same drugs free of NPs; ii) multiple-drugs delivery; iii) controlled drug release over time. NPs are made from artificial or natural polymers and have a size between 10 and 400 nm. Various biodegradable polymers such as chitosan, poly(ε-caprolactone) (PCL), poly(alkyl-cyanoacrylate) (PACA), poly-lactic acid (PLA) or poly(lactic-co-glycolic acid) (PLGA) can be used as the core matrix. Surface functionalization with a hydrophilic polymer such as poly(ethylene-glycol) (PEG) is used to improve biocompatibility, water-solubility and NP stability. The surface properties of NPs dictate the selectivity of uptake by target cells, thus influencing the biodistribution and half-life in biological fluids. On the other hand, the physicochemical properties of the NP core account for the drug loading capacity and drug release profile. Functionalization of NPs surface with targeting moieties, including antibodies, can determine preferential binding to receptors or transporters expressed at the blood-brain barrier (BBB) or on specific cell types to obtain enhanced CNS biodistribution or target-cell specificity. Adjusting the material biodegradation time through modification of lypophilicity, structure and composition of the nanoparticles core can allow optimizying drug loading and release profile.

Figure 17:
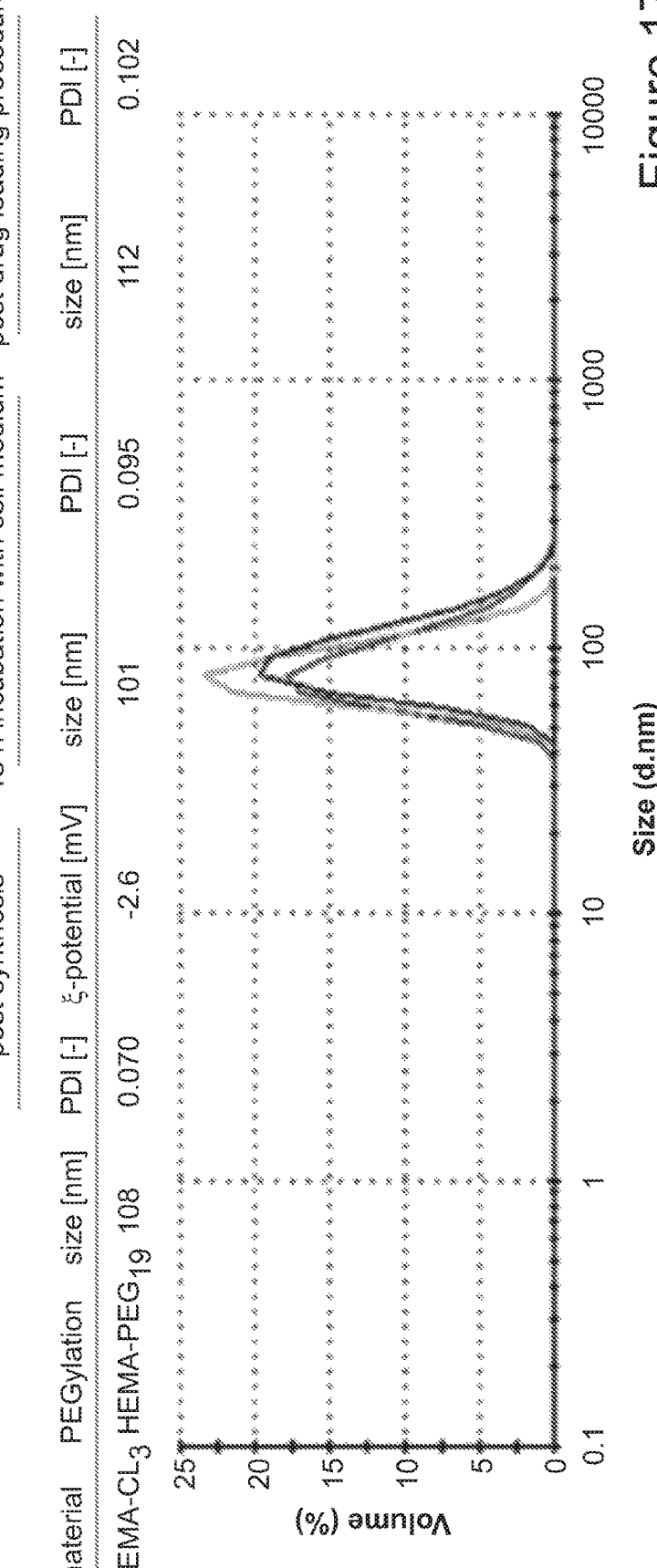
FIGS. 17A-17I depict nanoparticle (NP) characteristics and biodistribution upon ICV delivery.
Figure 17:
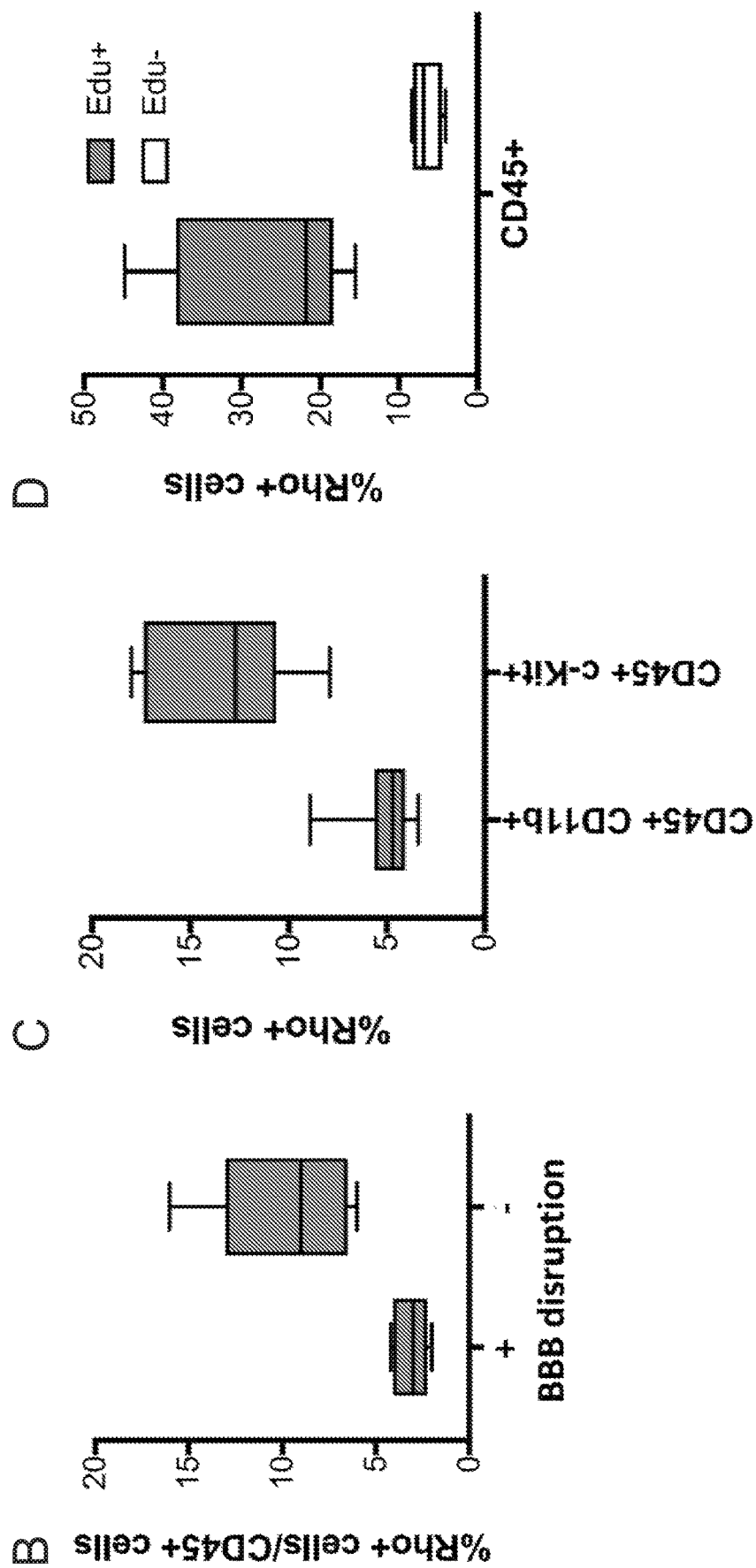
Figure 17:
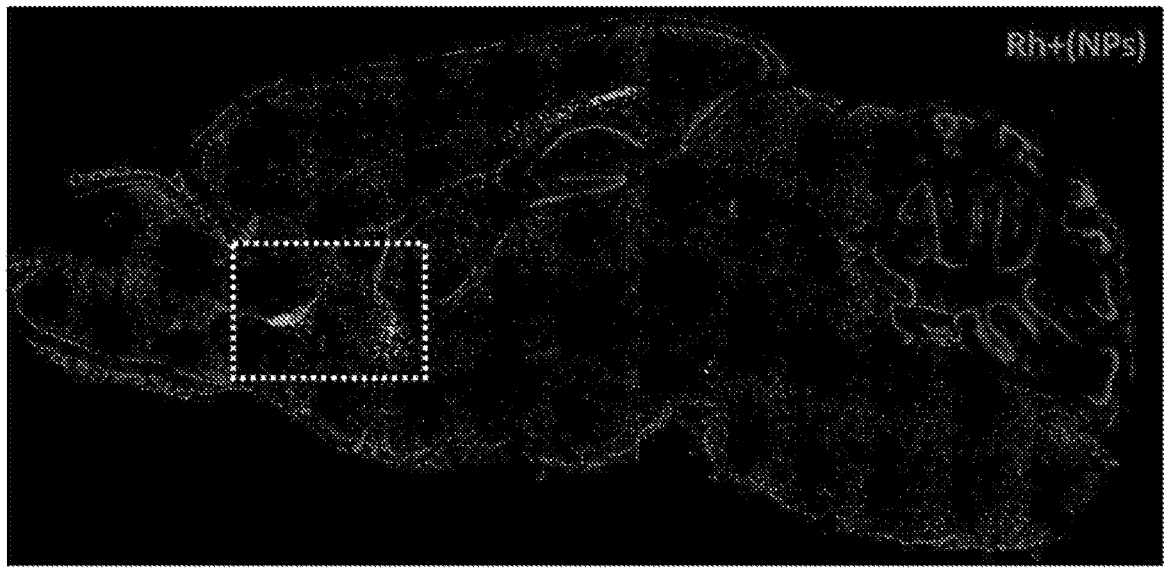
Figure 17:
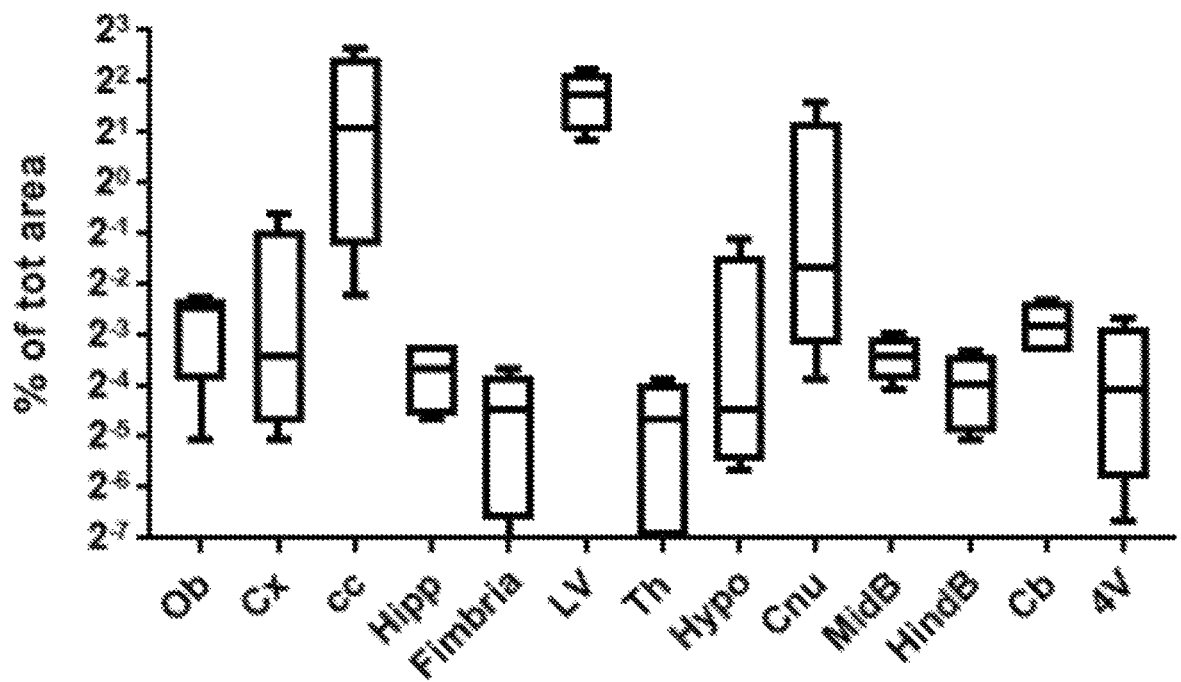
Figure 17:
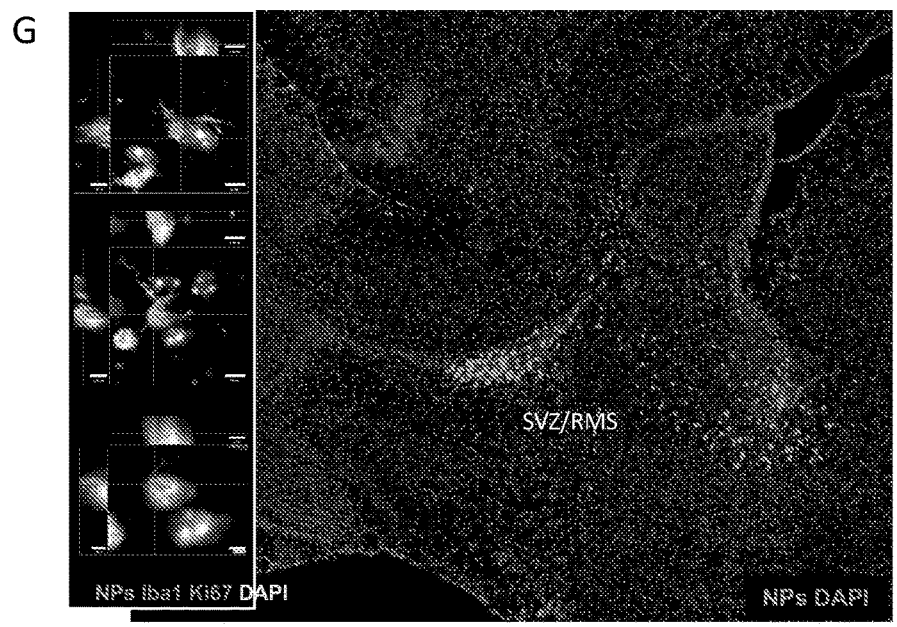
Figure 17:
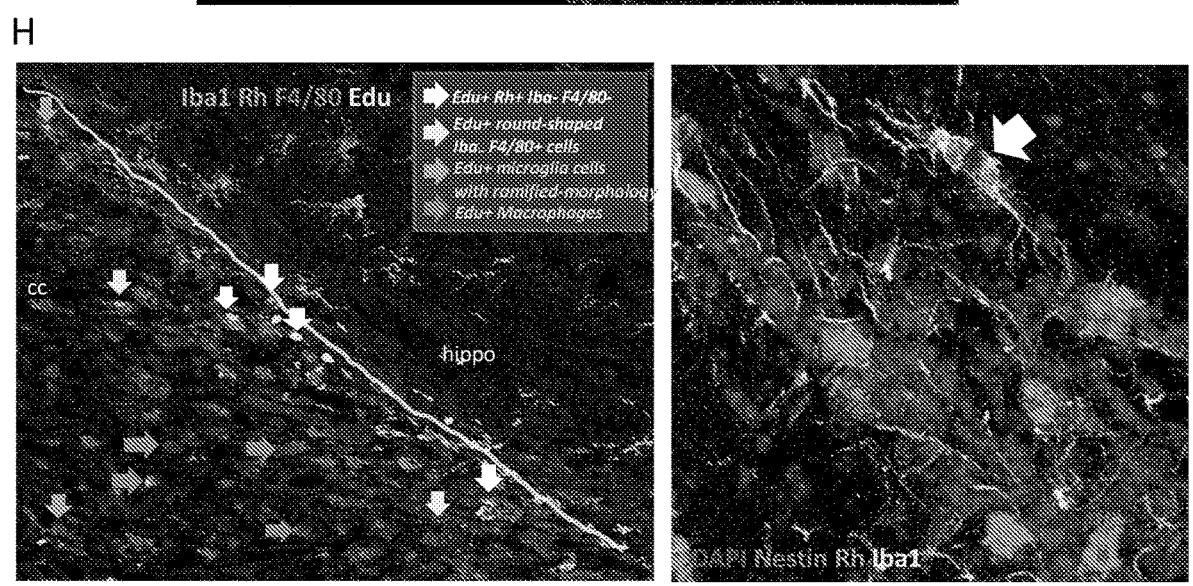
Figure 17:
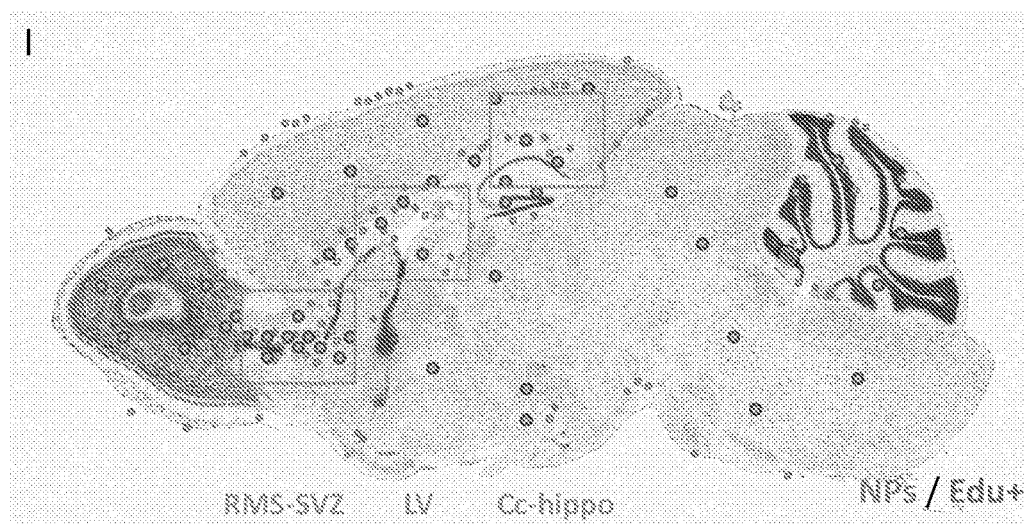

A new drug delivery biodegradable and biocompatible nanocarrier (based on PCL NPs) (FIG. 17A) was validated to selectively target microglia/macrophages after intra-parenchyma administration in a spinal cord injury mouse model. The biodistribution of these microglia-targeted NPs after ICV administration in mice was validated, and efficient uptake by microglia/macrophages and widespread distribution in different CNS areas was confirmed (FIGS. 17A-17I). Cytofluorimetry on injected mice brain showed that NPs were efficiently uptaken by CD45$^+$ brain cells, particularly if ICV injected in conjunction with mannitol for favouring BBB penetration (FIG. 17B), with a preference for uptake by CD45$^+$c-kit$^+$ cells (FIG. 17C) and proliferating Edu$^+$ cells (FIG. 17D). These microglia-targeted NPs were based on biodegradable, FDA-approved materials, including low molecular weight PEG chains that ensure NP stability, tune degradation rate and modulate drug release over time. Interestingly, immunofluorescence confocal analysis confirmed these findings and showed that NPs concentrate in brain areas, such as the SVZ and RMS, that are the first to be colonized by donor-derived HSPCs soon after transplant, during the process that lead to brain microglia reconstitution in the brain, as well as regions of intense γH2AX positive signal after busulfan administration—thus representative regions likely enriched in μP (FIG. 17G). Notably, Rhodamine$^+$ tba$^+$ myeloid cells containing the NPs were also proliferating, as suggested by both ki67 positive signal (FIG. 16G) and Edu administration prior to sacrifice and staining (FIG. 17H). The Edu$^+$ Rhodamine$^+$ cells were also positive for hematopoietic myeloid markers and showed the shape of both ramified and round microglia-like cells. Importantly, Rhodamine$^+$ Iba1$^+$ cells were also occasionally expressing the early/stem cell marker Nestin (FIG. 17H right picture). The presence and distribution in the NP-injected brain of Rhodamine signal was interestingly consistent with the the distribution of Edu signal, suggesting that NPs were preferentially occurring in proliferating cells (FIG. 17I), which may comprise cells with microglia progenitor features.

Figure 18:
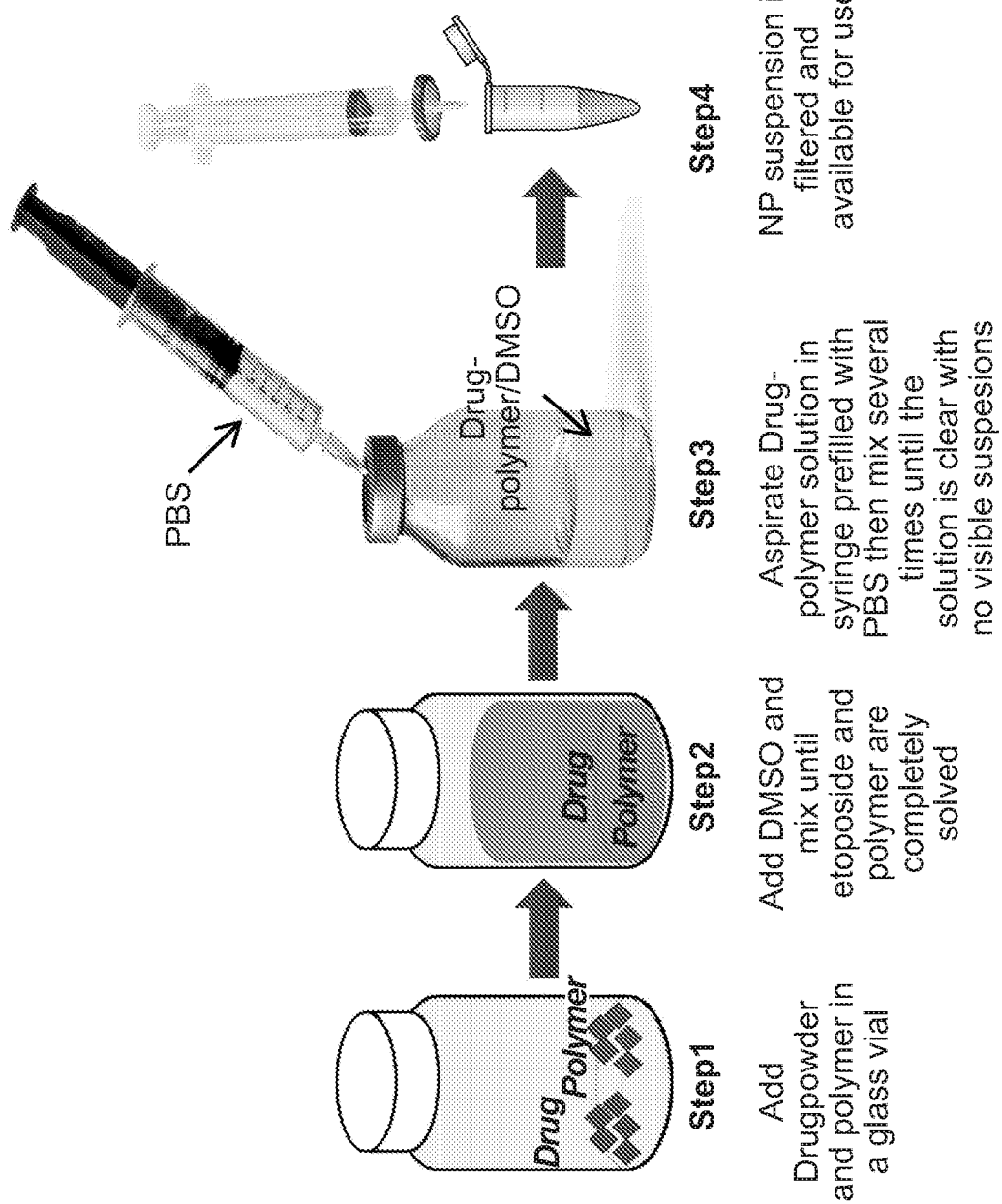
FIG. 18 shows the preparation of self assembly NP and chemotherapeutic drug complexes.

Optimization of new NPs by de novo chemical synthesis was then accomplished in order to allow loading with busulfan and etoposide, by exploiting two different chemical moieties, selected for their compatibility with the drugs (termed "SP" and "QMS"), covalently grafted on poly-(2-hydroxy-ethyl methacrylate) backbone (here called BK-510). This allowed the achievement of biologically relevant amounts of drugs encapsulated in NPs (i.e. for busulfan in the range of 210.7±5.3-257.6±7.2 µg/ml). The formulation of these nanoparticles loaded with chemotherapic drugs (such as busulfan or etoposide) was further ameliorated by introducing a so-called "self assembly" approach allowing the formation of NPs starting from lyophilized materials (FIG. 18). This makes the nanomaterials suitable for scale-up synthesis, long-term storage of the lyophilized medicinal product without loss of efficacy, and consistency among different batches.

Figure 19:
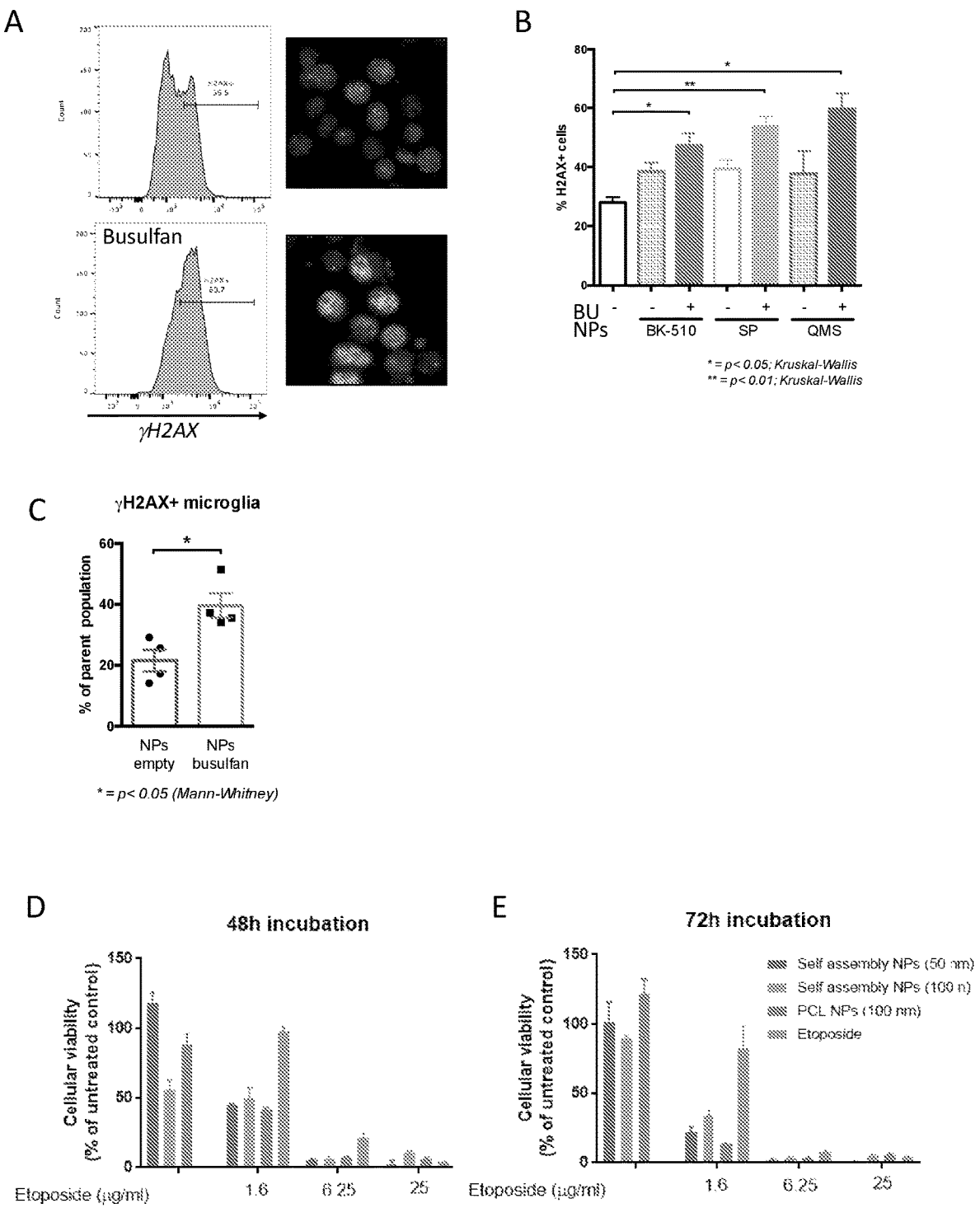
FIGS. 19A-19E depict the in vitro and in vivo effects of chemotherapic agents encapsulated in NPs.

By using γH2AX as a reliable pharmacodynamic marker of busulfan-related genotoxicity, an increased number of 7H2AX$^+$ cells was highlighted by immunofluorescence and flow cytometric analysis after in vitro exposure to busulfan loaded NPs (FIGS. 19A and 19B). This was further confirmed by cell viability assays, conducted on BV2 microglia-like cell lines, highlighting specific cytotoxicity of BU-loaded NPs after 72 hr incubation, indicating that encapsulation of BU in NPs did not impair drug efficacy. Busulfan loaded (NP-BUS) or empty NPs in mouse cerebral lateral ventricles induced a significant increase of 7H2AX signal in brain microglia (CD45$^+$/CD11b$^+$) cells upon exposure to NP-BUS (FIG. 19C).

Figure 20:
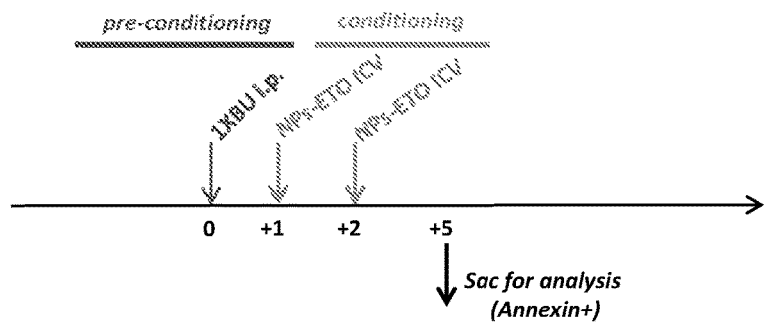
FIGS. 20A-20E shows that Etoposide containing NPs administered after induction of proliferation of microglia progenitors and expansion of the CD45+c-kit+ cell pool induced apoptosis of CD45+c-kit+ and CD45+CD11b+ cells.
Figure 20:
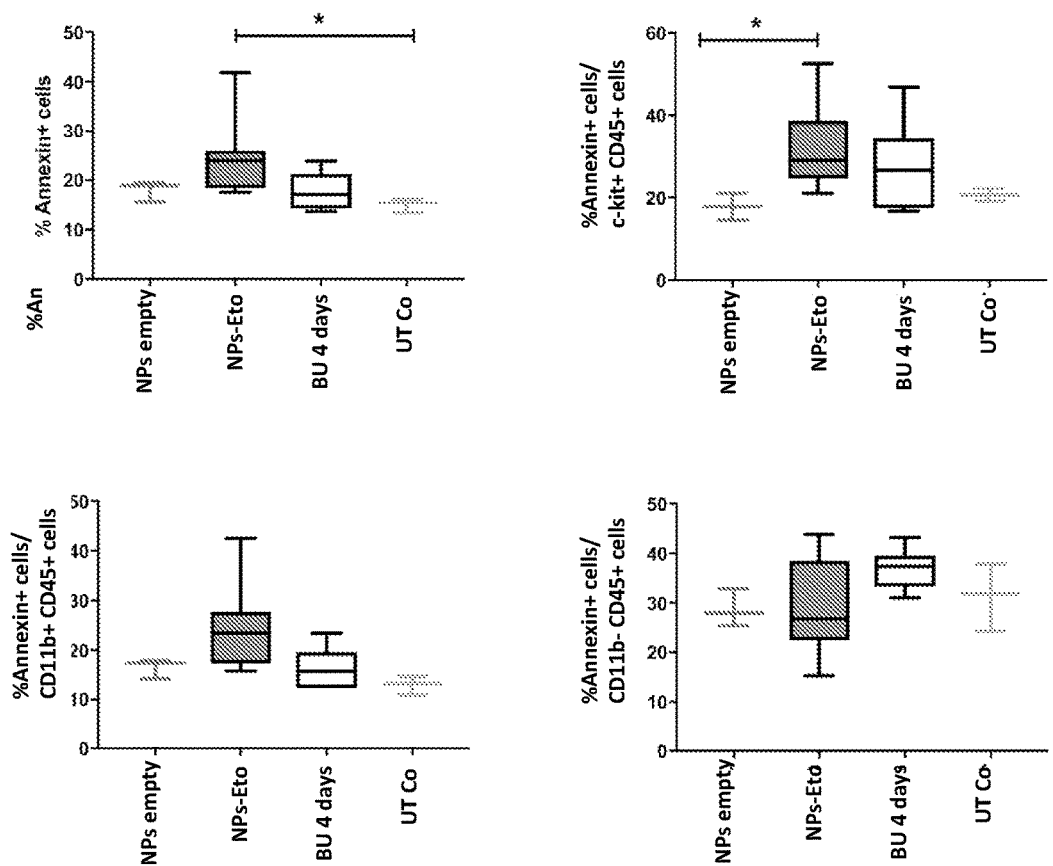
Figure 20:
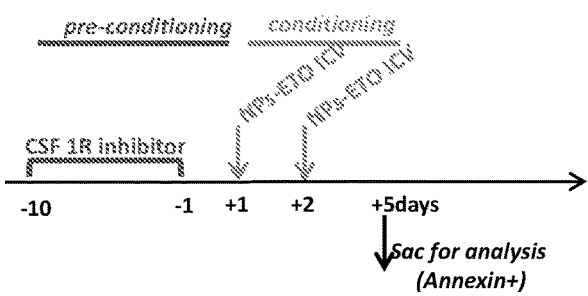
Figure 20:
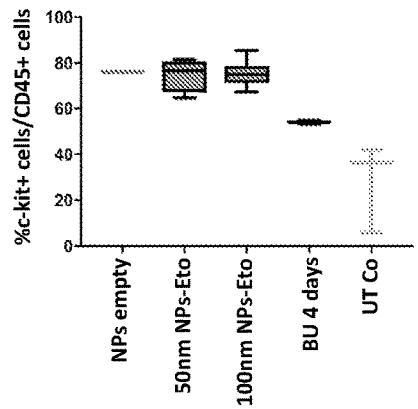
Figure 20:
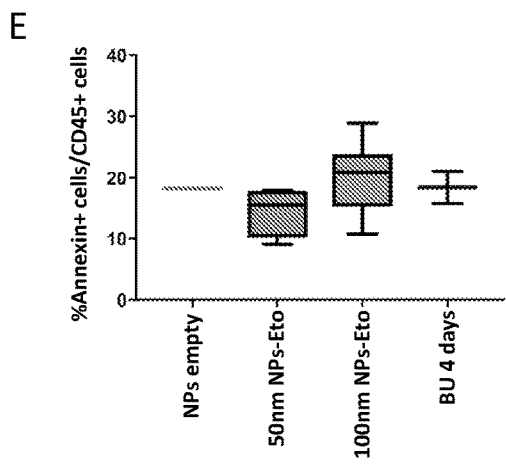
Figure 20:
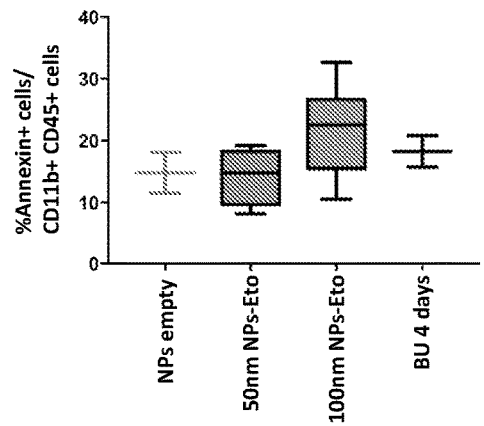
Figure 20:
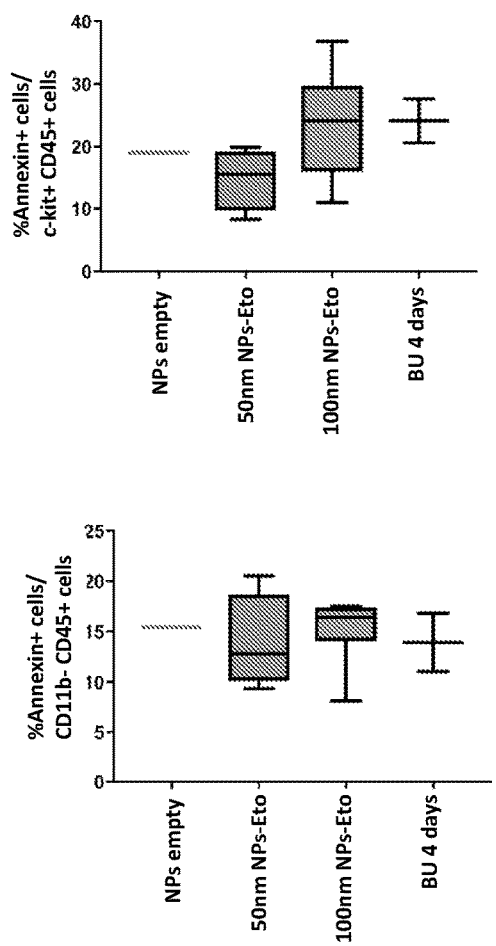

To facilitate the development of effective brain conditioning regimens NP loading was optimized with other drugs, such as etoposide and lomustine that showed preliminary supportive results (FIGS. 19D-19E). Cell proliferation assays were performed on the BV2 cell microglia-like cell line. Etoposide was loaded in different NPs formulations (preassembled 100 nm PCL NPs; self-assembly 100 nm NPs or self-assembly 50 nm NPs) at a nominal concentration of 275 ug/ml of drug. Etoposide-loaded NPs or the not encapsulated drug were added to the cell culture medium and then cellular viability was measured by the CellTiter cell proliferation MTS assay upon incubation at 37° C. for 48 and 72 hours post drug administration. Different drug concentrations were tested (1.6, 6.25 and 25 ug/ml). As control, the empty NPs (without drug) were tested; in this case the final NPs concentration in the medium was matched to the one used for administration of 25ug/ml of Etoposide encapsulated in NPs. As it can be observed in FIGS. 20D-20E, all three NPs formulations are equally effective in delivering etoposide, thus determining cell death. The empty NPs are either not toxic (preassembled 100 nm PCL NPs and self-assembly 50 nm NPs) or mildly toxic during the short-term incubations (self-assembly 100 nm NPs, 48 hr time-point). However, cellular viability for empty NPs always exceeds the one of the etoposide-loaded NPs, suggesting that the effect observed for etoposide-loaded NPs is due to the release of the drug rather than to the NPs per se. Interestingly, the effect observed with etoposide-loaded NPs tested at 1.6 ug/ml final drug concentration is more prominent than the one observed with the not encapsulated drug. This difference becomes even more pronounced at the 72 hr incubation time-point, suggesting that the encapsulation of etoposide in NPs enhances its efficacy, determining an improvement of the cytotoxicity of the drug already at very low concentrations.

These NP formulations were injected ICV in the brain of wild type adult animals that were pretreated with i) a single dose of busulfan 25 mg/kg or ii) ten days of oral administered CSF 1R inhibitor ((Elmore et al., Neuron. 82(2): 380-397 (2014)) that were shown to induce the proliferation of microglia progenitors and/or expand CD45$^+$c-kit$^+$ cells in the brain (FIGS. 19A, 19C, 19D). Five days after NP injection, animals were analyzed for the occurrence of Etoposide-mediated killing of microglia cells and/or their progenitors, using busulfan standard treatment (4 doses of 25 mg/kg) as reference for brain microglia progenitor ablation. Interestingly, Etoposide-loaded NPs induced apoptosis (as per Annexin V positive staining at flow cytometry) within CD45$^+$c-kit$^+$ and CD45$^+$CD11b$^+$ cells consistently to what observed upon standard ablative busulfan treatment (FIGS. 19B and 19E).

Overall, the NP formulations here tested achieved targeted delivery of ablating drugs to microglia progenitors for selective brain conditioning.

Example 13. Novel Transplantation Modalities for Generating Transcriptionally Dependable New Microglia from Hematopoietic Stem and Progenitor Cells Using a multifaceted approach, new strategies were identified to improve bonafide brain myeloid cell turnover with the donor following HCT and this phenomenon can result in robust and rapid engraftment of transcriptionally dependable new microglia through a process that may recapitulate the physiological maturation of post-natal brain myeloid cells.

Firstly, transcriptional profiling analysis was applied to newly formed myeloid cells (identified as and TAµ cells) retrieved form the brain of busulfan-treated chimeric mice. This analysis revealed that the gene expression pattern of donor-derived brain myeloid cells sorted for the expression of CD45, CD11b and a donor cell marker, is very close to that of endogenous microglia cells of naïve mice at different developmental ages. Of note, newly formed cells expressed typical microglia markers such as Tmem119, Tgfbr1, P2ry13, Olfml3, Mertk. Interestingly, these cells clustered in totally separated fashion as compared to macrophages, confirming that the brain cells reconstituted after the transplant are transcriptionally distinct from bone marrow resident or circulating myeloid cells, and are much more similar to endogenous brain myeloid populations (Gosselin et al. Cell 159, 1327-1340 (2014)). Bennett and colleagues (Bennett et al. Proc Natl Acad Sci USA 113, E1738-1746 (2016)) showed that cells in the adult CNS derived from total bone marrow transplantation do not express Tmem 119, considered by the authors as a marker able to distinguish microglia from other myeloid cells. These findings, apparently conflicting with data that show robust Tmem 119 expression in donor-derived brain myeloid cells, could be interpreted based on the use of different experimental conditions. Indeed, the use of total bone marrow cells instead of purified HSPCs may affect the outcome of the transplant procedure as far as brain progeny is concerned. Indeed, the data indicates that the latter are enriched in the ability to give rise to new microglia. Moreover, the use of intense irradiation on top of busulfan for mice conditioning could have induced the recruitment of circulating myeloid cells by affecting BBB permeability, which is not instead affected by a regimen based on busulfan alone (Capotondo et al. *Proc Natl Acad Sci USA*. 109, 15018-15023 (2012)).

Gene expression profiling coupled to flow cytometry also confirmed previous data showing that μ and TAμ isolated from HCT mice display similarities with microglia cells from adult untreated animals and immature microglia from P10 mice, respectively. In particular, biological process and functional pathway analysis showed that the gene patterns of TAμ populations from transplanted mice and P10 animals are more related to neural developmental processes, cellular component organization and cell cycle/differentiation, suggesting that they could represent an immature microglia population, possibly playing a role during brain remodeling, as recently described (Matcovitch-Natan et al. *Science* 353, aad8670 (2016)). Differently, μ populations from both transplanted animals and adult control mice are enriched in genes related to immuno-response, cell communication and phagocytosis, indicating that these cells are mostly composed by mature microglia. Thus, these data may support the hypothesis that microglia reconstitution after HCT occurs through a transition from an intermediate TAμ population, which is typically enriched in donor derived elements short term after transplant, to a μ stage, that becomes progressively more enriched in donor elements in the long term after transplant. This phenomenon may remind post-natal microglia development along transition from the immature cells identified at p10 to microglia cells isolated from adult control animals. In support of this hypothesis, the expression of selected genes associated with microglia differentiation (Matcovitch-Natan et al. *Science* 353, aad8670 (2016)) was investigated in the data set, confirming that HSPC derived cells follow a stepwise maturation program upon HCT. However, by analyzing transcription factors involved in the adult microglia developmental phase, as MAFB (Matcovitch-Natan et al. *Science* 353, aad8670 (2016)), a higher expression of this gene in TAμ cells retrieved from HCT mice compared to P10 mice was observed. Without intending to be bound by theory, the newly formed TAμ microglia cells generated upon HSCP transplantation in adult conditioned mice are more committed towards a mature stage as compared to P10 cells. A deep investigation of the gene expression dataset and related changes during this transition could help in identifying crucial factors involved in microglia development and maintenance, which could be used to further improve microglia reconstitution.

The process of reconstitution of microglia cells by the donor was studied. Interestingly, the cell fraction that mostly retains the ability to reconstitute microglia upon transplantation was identified in the very early stem compartment within HSPCs. In particular, upon competitive transplantation of differently labeled HSPC sub-populations, KSL cells and, within them, LT-HSCs and MPPs showed the highest potential not only to reconstitute the hematopoietic system, but also to give rise to extensive microgliosis in the brain. These data suggest that cells with the ability to behave as source of novel microglia in the brain following transplantation are retained within the fractions mostly enriched in hematopoietic stem cell activity in mice. Interestingly, this ability correlates with the levels of CXCr4 expression on the cell surface. Without intending to be bound by theory, this indicates a role of SDF1-CXCr4 signaling in homing of HSPCs not only to the bone marrow niche, but also to the brain. The contribution of human HSPCs to microgliosis in humanized NSG mice was also explored, by adapting the busulfan-based conditioning regimen applied in the murine setting to this model, in order to favor human engraftment into the brain. By this strategy, human $CD34^+$ cells, purified from different sources (cord blood, bone marrow and peripheral blood), were demonstrated to give rise to microglia reminiscent cells in the recipient mice brains. Interestingly, as observed for the murine cells, the most immature hematopoietic compartment ($CD38^-$ and $CD38^-$ $CD90^{+/-}$ cells) contributed to greater extent to brain human microgliosis. These evidences may lead to further studies investigating the modality of generation of microglia from early HSPCs/HSCs, but could also have important translational implications for transplant clinical practice in LSDs and related diseases by supporting the use of cell preparations enriched in stem cell activity rather than un-manipulated products. Moreover, these observations could contribute explaining the great efficacy observed in HSC gene therapy trials in patients with neurodegenerative storage diseases, who received grafts enriched in early hematopoietic cells as compared to what present in standard cord blood/apheretic/bone marrow explant preparations.

Based on previous observations on the clonal independence of microglia and peripheral hematopoietic cells in repopulated transplant recipients (Capotondo et al. *Proc Natl Acad Sci USA*. 109, 15018-15023 (2012)), the transplantation protocol was challenged and HSPCs were directly infused into the brain ventricular space after proper recipient mice conditioning. Interestingly, upon ICV HSPC transplantation microglia reconstitution could be observed both in busulfan treated and, to a less extent, in irradiated mice, confirming that donor cell engraftment in the hematopoietic tissue is not necessary for microglia replacement.

Rather, HSPCs seeding in the brain could generate new bona fide microglia by local engraftment, proliferation and differentiation. Importantly, this transplantation route was associated with a more rapid reconstitution of the myeloid brain compartment, and in particular of the mature μ cell pool, as compared to the replacement achieved upon IV transplantation. Differently from the findings obtained by IV transplantation, also committed HSPC fractions participated to long-term microgliosis when locally injected. These findings could be interpreted in different ways. Firstly, the brain microenvironment could create conditions that may in turn favor the engraftment of more committed cells. In support of this hypothesis, the brain environment influenced the fate of the transplanted cells by inducing the expression of typical microglia markers (CD115 and CX3CR1) early after transplant, possibly favoring their engraftment. Moreover, it is speculated that upon ICV injection, cells that were quantitatively more represented among the others (HPC-2), independently from the CXCR4-SDF-1 signaling pathway, could be advantaged and favored in engrafting locally and expanding. Finally, the more committed cells if transplanted intravenously could be disfavored due to intrinsically lower ability to migrate to the brain as compared to LT-HSC and MPPs, as per the CXCR4 analysis discussed above. Nevertheless, it could not be excluded that upon ICV cell injection the transplanted cells could respond to a different signaling pathway. To this regard, further studies, as gene expression analysis, would provide precious indications to better assess the mechanisms underlying microglia reconstitution achieved upon ICV transplantation compared to IV injection. Importantly, contribution of HSPCs to brain myeloid cell reconstitution by ICV delivery was also confirmed in a humanized setting transplanting human HSPCs in NSG mice. To translate these clinically relevant findings to current gene and cell based transplantation protocols, it is proposed to couple the potential of ICV HSPCs transplantation, providing a faster and higher microglia reconstitution compared to the standard transplant setting, with the benefit achieved upon IV transplantation. This strategy could address the need to anticipate the clinical benefit of the therapy in those diseases characterized by a severe CNS involvement and a rapid progression of the pathology. Obviously, this approach requires a deep evaluation of the timing of the transplant and of the cell subsets to be transplanted according to the different route of cell administration.

In summary, the present data provide strong evidence that reconstitution of cells with microglia features occurs upon HSPC transplantation. Generation of these cells occurs by maturation from intermediate stages into more mature cells, a process that closely resembles post-natal microglia development. This process is dependent from the presence of early HSPCs in the brain and independent from mature cell infiltration from the circulation into the brain. Indeed, microglia replacement could be obtained and even enhanced upon direct brain injection of HSPCs, generating evidences supporting the development of an innovative transplantation approach for the treatment of CNS disorders with a severe and rapid progression.

The results described herein were obtained using the following materials and methods.

Mice Studies

C57BL6/J and C57BL/6-Ly5.1 mice were provided by Charles River. NOD.Cg-NOD.Cg-Prkdc$^{scid}$Il2rg$^{tm1Wjl}$/SzJ (NSG) mice were purchased by Jackson Laboratory. Rag$^{-/-}$ γ-chain$^{-/-}$ As2$^{-/-}$ and Rag$^{-/-}$ γ-chain$^{-/-}$ As2$^{I/I}$ mice were generated in the animal facility at San Raffaele Scientific Institute (Meneghini et al., *Stem Cells Transl Med*, (2016)). Fgd5ZsGr·ZsGr/+ (Fgd5– ZsGreen) (The Jackson Laboratory Stock #027788) were kindly provided by Derrick J. Rossi's laboratory, Harvard University/Boston Children's Hospital (Gazit et al., *J Exp Med* 211, 1315-1331 (2014)).

All procedures were approved by the Animal Care and Use Committee of the Fondazione San Raffaele del Monte Tabor (IACUC 573) and communicated to the Ministry of Health and local authorities according to Italian law.

Isolation, Transduction and Transplantation of Murine Hematopoietic Cells

Young adult mice (5 to 8 weeks) were killed with $CO_2$, and BM was harvested by flushing the femurs and tibias. Murine HSPCs were purified and transduced with LV and transplanted by tail vein injection as described (Capotondo et al., *Proc Natl Acad Sci USA* 109, 15018-15023 (2012)).

HSPCs were purified by Lineage (Lin) selection using the Miltenyi Biotec Lineage Cell Depletion Kit with Magnetic separation with the autoMACS™ Separator, following manufacturer's instruction. When KSL (c-kit$^+$ sca-1$^+$) and, among this fraction, CD150$^{+/-}$ CD48$^{+/-}$ cell isolation was performed, Lin– cells were stained with Biotin-Antibody Cocktail (Miltenyi Biotec Lineage Cell Depletion Kit)/Streptavidin Pe-Cy5 (BD Pharmingen) in order to exclude the few Lin+ cells (5-10%) remained after lineage negative selection. For the isolation of the KSL fraction, cells were then stained with rat APC-eFluor 780 anti-mouse CD117(c-kit) (eBioscience) and with rat Pe-cy7 anti-mouse Ly-6A/E Sca-1 (Sca-1) (BD Bioscence). For CD150$^{+/-}$CD48$^{+/-}$ cell selection hamster PE anti-mouse CD48 (Biolegend) and rat APC anti-mouse CD150 (BioLegend) were added. At the end of the staining the cells were isolated by the cell sorter MOFLO XDP (Becton Dickinson), according to the expression of the selected markers. The gating strategy with reporter is shown at FIG. 2F. Isolated Lin–, KSL or CD150+/–CD48+/– KSL cells were transduced using different Lentiviral Vectors (LVs), for 16 hours at Multiplicity of Infection (MOI) 100, as described (Biffi et al., *J. Clin. Invest.* 116, 3070-3082 (2006)). In particular the following LVs were used:

pCCLsin.cPPT.humanPGK.GreenFluorescentProtein.Wpre (GFP-LV) (Dull et al., *J. Virol* 72, 8463-8471 (1998)) for Lin$^-$, KSL and CD150$^+$ CD48$^-$ KSL cells; pCCLsin-.cPPT.humanPGK.DeletedNerveGrowthFactorReceptor.Wpre (ΔNGFR-LV) (Dull et al., *J. Virol* 72, 8463-8471 (1998)) for not-KSL cells and CD150$^-$CD48$^-$ KSL cells; pCCLsin.cPPT.humanPGK.mCherryProtein.Wpre (mCherry-LV) (Biffi et al., *Science* 341, 1233158 (2013)) for CD150$^-$CD48$^+$ KSL cells; pCCLsin.cPPT.humanPGK.TagBlueFluorescentProtein.Wpre (Tag-BFP-LV) for CD150$^+$ CD48$^+$ KSL cells. A fraction of the transduced cells were cultured for 10 days as described (Biffi et al., *J. Clin. Invest.* 116, 3070-3082 (2006)) in order to assess transgene expression by cytofluorimetric analysis.

Transduced cells were injected via the tail vein into seven/eight-week-old conditioned C57BL6/J female mice 24 hours after irradiation (2×400cGy) or the fourth Busulfan dose (25 mg/kg×four days), at different concentration according to the different experimental settings:

Intravenous (IV) Transplantation

Lin-cells: $10^6$ cells/mouse; KSL: $0.3×10^5$ cells/mouse; Not KSL: $5×10^5$ cells/mouse; HPC1≅$0.12×10^4$ cells/mouse; LT-HSC≅$0.55×10^4$ cells/mouse; HPC2≅$1.8×10^4$ cells/mouse; MPPs≅$0.55×10^4$ cells/mouse. Five days after transplantation of KSL cells, mice received $5×10^5$ of total bone marrow (TBM) cells from CD45.1 C57 mice as support. Mice were maintained in sterile conditions.

Intra-Cerebral Ventricular (ICV) Transplantation

Lin-cells: $0.3×10^6$ cells/mouse; KSL: $0.3×10^5$ cells/mouse; Not KSL: $3×10^5$ cells/mouse; HPC1≅$0.12×10^4$ cells/mouse; LT-HSC≅$0.55×10^4$ cells/mouse; HPC2≅$1.8×10^4$ cells/mouse; MPPs≅$0.55×10^4$ cells/mouse. Five days after transplantation, mice received $5×10^5$ of total bone marrow (TBM) cells from CD45.1 C57 mice as support.

For isolation of Fgd5 HSCs, 8 weeks Fgd5zsGr ZsGr/+ CD45.2 mice (The Jackson Laboratory Stock #027788) were used as donors. Enrichment of c-kit$^+$ cells was performed using CD117 (c-kit) MicroBeads (CD117 MicroBeads, mouse-Miltenyi Biotec) following manufacturer's instruction. c-kit enriched cells were then stained in PBS 2 mM EDTA, 2% FBS at 4° C. with combinations of the following antibodies: the lineage markers Ter 19, Mac-1 (ml/70), Gr-1 (8C5), CD3 (17A2), CD4 (RM4-5), CD8 (53-6.7), B220 (RA3-6B2), and IL7Ra (A7R34); CD34 (RAM34), Flk2(A2F10), c-kit (2B8), Sca1 (D7), CD45.2 (104) (all from BioLegend or eBioscience). After staining, cells were washed and resuspended in PBS 2 mM EDTA, 2% FBS with P1 (0.05 μg/μL), and kept on ice. FACSAria 11 (BD) was used for cell sorting.

Sorted cells were transplanted IV (500) or ICV (500). Five days after transplantation, mice received $1.0×10^6$ TBM from CD45.1 C57 mice as support. Recipients of cell transplantation were 2-month old female CD45.2 C57BL6/J mice conditioned with 25-27 mg/kg of busulfan (Sigma) administered i.p. or with a lethal irradiation dose (2×500cGy). For IV transplantation cells were injected in the tail vein. ICV transplantation was performed by surgery, upon anesthesia (ketamine (100 mg/kg) and xylazine (10 mg/kg). The head of the mouse, shaved and disinfected, was fixed with ear bars in a stereotactic frame and the skin was disclosed longitudinally. Bregma was visualized and coordinates were recorded. From bregma, injection coordinates (1 mm lateral, 0.5 mm anterior) were adjusted before the cranial bone was enclosed under visual control with a drill head of 0.7 mm diameter. Five µl of the cell suspension were injected through a 10 µl Hamilton syringe upon insertion into the brain 2 mm distal from the cranial bone. Following wound closure, animals received a single dose of atipamezole (1 µl/g) and were maintained in sterile conditions.

Prophylactic Antibiotic (Gentamycin Sulfate, 80 mg/250 mL) was administered via the drinking water for 2 weeks following conditioning and transplantation. Depending on the strain and experimental setting, mice were sacrificed 1.5, 3, 4 and 6 months spo-transplant, and peripheral blood/BM and brain were analyzed for donor cell engraftment.

Isolation, Transduction and Transplantation of human $CD34^+$ Cells

Human cord blood (CB)-derived $CD34^+$ cells were purchased from Lonza (2C-101). Upon thawing, cells were pre-stimulated for 24 hours in CellGro medium (CellGenix, Freiburg, Germany) supplemented with hIL-3 [60 ng/µL], hTPO [100 ng/µL], hSCF [300 ng/µL], hFlt3-L [300 ng/µL] (all of them from Peprotech, Hamburg, Germany) and transduced by one round of LV exposure at MOI 100, as described (Biffi et al., *Science* 341, 1233158 (2013)) with GFP (Dull et al., *J Virol* 72, 8463-8471 (1998)) or ARSA (Sessa et al., *Lancet* 388, 476-487 (2016)) encoding laboratory grade LVs. The gating strategy is shown on FIGS. 3M, 3N, and 3O. After isolation the cells were pre-stimulated as described before and transduced with different LVs. In particular the following LVs were used: pCCLsin.cPPT.humanPGK.mOrangeFluorescentProtein.Wpre (Orange-LV) for MPB $CD38^-$ and $CD38^-CD90^-$ cells; pCCLsin.cPPT.humanPGK.mCherryProtein.Wpre (mCherry-LV) for MPB CD38mid and $CD38^+Cd90^-$ cells; pCCLsin.cPPT.humanPGK.CyanFluorescentProtein.Wpre (Cyan-LV) for MPB CD38int cells; pCCLsin.cPPT.humanPGK.GreenFluorescentProtein.Wpre (GFP-LV) for MPB CD38high, $CD38^-CD90^+$ cells and for BM $CD38^-$ cells; pCCLsin.cPPT.humanPGK.Tag-BlueFluorescentProtein.Wpre (Tag-BFP-LV) for MPB $CD38^+CD90^+$ cells and BM $CD38^+$ cells. A fraction of the transduced cells were cultured for 10 days as described (Biffi, 2013) in order to assess transgene expression by cytofluorimetric analysis. After transduction, the cells were washed and infused into the tail vein of sublethally irradiated (200cGy) or myeloablated busulfan-treated (16.25 mg/kg/day for four days) 7-9-week-old female NSG mice. $5 \times 10^5$ $hCD34^+$ cells or $5 \times 10^5$ $hCD34^+$ cells were transplanted, composed of a mix of the different sorted cells, according to their physiological proportion. When NSG mice were pre-treated with busulfan, $4 \times 10^6$ TBM from male NSG mice were transplanted as support. ICV transplantation of $hCD34^+$ cells in NSG mice was performed as described for murine HSPC ICV transplantation in C57 mice. After 12 weeks mice were sacrificed and BM and brain were analyzed for human hematopoietic cell engraftment.

Post-natal day 2 $Rag^{-/-}$ γ-chain$^{-/-}$ $As2^{-/-}$ were conditioned with a sub-lethal dose of 300+250 RAD total body irradiation. Mice received transduced cells IV via temporal vein injection ($2.5 \times 10^5$ cells/mouse) or ICV (in the lateral ventricle through a glass capillary) (Neri et al., *Stem Cells* 29, 1559-1571 (2011)) ($0.75 \times 10^5$ cells/mouse). Five weeks post-transplant mice were sacrificed and BM and brain were analyzed for human hematopoietic cell engraftment by cytofluorimetry and ARSA activity by using 4-methylumbelliferyl-sulfate substrate (Martino et al., *J Biotechnol* 117, 243-251 (2005)).

Mouse Tissue Collection and Processing for Cytofluorimetry and Histology

Mice were euthanized under deep anesthesia by extensive intra-cardiac perfusion with cold PBS for 15 minutes after clumping the femur. Organs were then collected and differentially processed. Bone marrow (BM) cells were collected from the clumped femur as described (Biffi et al., *J. Clin. Invest.* 116, 3070-3082 (2006)). Brain was removed and the two hemispheres were differently processed. For immunofluorescence analysis, one hemisphere was fixed for 24 hours in 4% PFA, embedded in OCT compound and stored at −80° C., after equilibration in sucrose gradients (from 10 to 30%). For cytofluorimetry analysis, cells from the other hemisphere were mechanically disaggregated to obtain a single cell suspension in 20 ml of GKN/BSA buffer (8 g/L NaCl, 0.4 g/L KCl, 1.42 g/L NaH2PO4, 0.93 g/L Na2HPO4, 2 g/L D+ Glucose, pH 7.4+0.002% BSA).

For the analysis of $Fgd5^+$ cell engraftment, hCD34+ derived cell engraftment in the brain of NSG and $Rag^{-/-}$γ-chain$^{-/-}As2^{-/-}$ transplanted mice, an enrichment for myeloid cells was performed using a 30% Percoll gradient (Nikodemova et al., *J Neuroinflammation* 9, 147 (2012)) after enzymatic (19 mg papain, 10 mg cystein, 2.5 mg DNAse) digestion of the brain tissue.

Flow-Cytometric Analysis

Cells from BM and brain were analyzed by flow cytometry upon re-suspension in blocking solution (PBS 5% FBS, 1% BSA) and labeling at 4° C. for 15 minutes with the following specific antibodies: rat PE anti-mouse CD45 (BD Pharmingen) 1:100; rat APC anti-mouse CD45 (BD Biosciences) 1:150; rat Brilliant Violet 510 anti-mouse CD45, (BioLegend) 1:150; rat Pacific Blue anti-mouse CD45.2 (Bio Legend) 1:100; mouse PE anti-Mouse CD45.1 (BD bioscience) 1:100; rat APC anti-mouse $CD11b^-$ (eBioscience) 1:100; mouse Alexa Fluor 647 anti-Human CD271 (NGF receptor) (BD Pharmingen) 1:30; rat APC 780 anti-mouse $CD11b^-$ (eBioscience) 1:100; rat APC 780 anti-mouse CD117(c-kit) (eBioscience) 1:100; rat PE-Cy7 anti-mouse Ly-6A/E Sca-1 (Sca-1) (BD Bioscience) 1:150; Hamster PE anti-mouse CD48 (Biolegend) 1:100; rat APC anti-mouse CD150 (Biolegend) 1:75; rat PE anti-mouse CD202b (Tie2) (eBioscence) 1:150; rat PE anti-mouse CD184 (CXCR4) (BD Bioscence) 1:150; rat PE anti-mouse CD34 (eBioscience) 1:150; rat PE-Cy7 anti-mouse CD93 (AA4.1) (eBioscience) 1:150; rat Biotin anti-mouse CD115 (eBioscience) 1:150; goat APC anti-mouse CX3CR1 (R&D systems) 1:75; APC streptavidin (BD Pharmingen) 1:500; rat APC-Cy7 anti-mouse B220 (BD Bioscience) 1:100; hamster APC-Cy7 anti-mouse CD3e (eBiosciences) 1:100; mouse APC-Cy7 anti-human CD45 (BD Pharmingen); rat PE-cy7 anti-human CX3CR1 (eBioscience) 5:100. For the exclusion of death cells we either used 7-AAD (1 mg/ml) (Sigma-Aldrich), a membrane-impermeable dye, added to the cells prior to analysis for dead cell exclusion. BM and brain cells were analyzed by LSR Fortessa (Beckton Dickinson).

Immunofluorescence Analysis

Brains were serially cut in the sagittal planes on a cryostat in 15 µm sections. Tissue slides were washed twice with PBS, air dried and blocked with 0.3% Triton, 2% BSA, 10% NGS (Vector Laboratories) for 2 hours. Then sections were incubated over night with primary antibodies diluted in PBS, 0.1% Triton, 2% BSA, 10% NGS at 4° C. as follows: rat APC anti $CD11b^-$ (eBioscience) 1:50; rabbit anti Iba1 (Wako) 1:100; chicken anti-GFP (Abcam) 1:250; rabbit anti GFP (Invitrogen) 1:100; mouse PE anti-human CD271 (NGF Receptor) (BD Pharmingen) 1:50; rabbit anti-cherry (Abcam) 1:100. The secondary antibodies goat IgG anti-Chicken Alexa Fluor 488, goat IgG anti-Rabbit Alexa Fluor 488, 546 or 633, goat IgG anti-Rat Alexa Fluor 546 or 633, goat IgG anti-Mouse Alexa Fluor 546 (Molecular Probes, Invitrogen) were diluted 1:500 in the same blocking solution used for primary antibodies staining and incubated with sections for 2 hours at room temperature. Nuclei were stained with—TO-PRO III (Molecular Probes, Invitrogen) 1:1000 in PBS or by DAPI (Roche) 1:30 in PBS. Slices were washed in PBS, air dried and mounted with Fluorsafe Reagent (Calbiochem). Samples were analyzed with a confocal microscope (Zeiss and Leica TCS SP2; Leica Microsystems Radiance 2100; Bio-Rad) (λexcitation=488, 586, 660). Fluorescent signal was processed by Lasersharp 2000 software. Images were imported into Adobe Photoshop CS 8.0 software and processed by using automated level correction.

For the reconstruction of brain sections we used a fluorescence microscope Delta Vision Olympus Ix70 for the acquisition of the images, which were then processed by Soft Work 3.5.0 software. Images were then imported into the Adobe Photoshop CS 8.0 software and reconstructed.

RNA Extraction and Gene Expression Analysis by Real Time PCR

Total RNA was isolated for gene expression analysis from the following populations previously sorted from adult or P10 naïve control and transplanted mice: total CD45+ CD11b+, μ and TAμ, sorted according to the expression of CD45, CD11b and GFP (only HCT-mice); macrophages, sorted according to the expression of CD45, CD11b, F4/80, Ly6C and GFP (only HCT-mice). RNA quantity was determined using QuantiFluor® RNA system and Quantus™ Fluorometer (Promega). cDNA was generated starting from 1 ng up to 100 ng of purified mRNA by using SuperScript VILO Master mix (Thermo Fisher Scientific). cDNA was then pre-amplified using Custom Taqman® PreAmp Pools (Thermo Fisher Scientific). Thermal cycling for cDNA generation and preamplification was performed on T100 Thermal cycler (BIO-RAD) following manufacturer's instructions. Gene expression analysis was performed using a custom design TaqMan-based microfluidic card gene expression assay (Applied Biosystems) to measure the expression of 16 selected genes (13 targets, 2 endogenous housekeeping and 1 internal control). Real time PCR was run in standard mode on Applied Biosystems® ViiA™ 7 Real-Time PCR System, using the following thermal cycling conditions: one cycle at 50° C. for 2 min, one cycle at 95° C. for 10 min, 40 cycles at 95° C. for 15 seconds and 60° C. for 1 min. (Applied Biosystems). The ViiA™ 7 Software vi 0.2.2 was used to extract raw data. The difference (dCT) between the threshold cycle (CT) of each gene and that of the reference gene (mean of HPRT and 18S CTs) was used to determine gene expression. Fold change expression of selected microglia genes in ICV versus IV transplanted mice was calculated by $2^{-ddCT}$ method, (Livak et at., Methods 25, 402-408 (2001)) where ddCT represents the difference between the dCT of each samples retrieved from ICV transplanted mice and the dCT mean of the samples retrieved from IV transplanted mice, matched for μ and TAμ cells.

RNA Sequencing and Analysis

RNeasy Plus Micro kit (Qiagen) was used to extract RNA from the sorted myeloid brain populations. In particular, we retrieved by sorting different myeloid brain sub-populations from: P10 (n=4 in duplicate) (TAμ cells), 5 month old C57bl6/j (n=3) mice (p cells), and BU-treated mice (n=3; we excluded from the analysis one sample of TAμ due to its diversity from the other samples analyzed by FACS)(μ and TAμ cells) at 3 months from GFP HSPC transplantation. Before the sorting, mice were euthanized under deep anesthesia by intra-cardiac perfusion with cold PBS after clumping the femur. The brain was collected and processed as described before. RNA was collected and stored at −80° C. Small aliquot were used to check the quality of the RNA extracted with Agilent RNA 6000 Pico kit.

RNA sequencing was performed by IGA Technology Services at Udine. Briefly, amplification of cDNA from total RNA (starting amount=100 ng per sample) was performed using the Ovation RNA-Seq System V2 (Nugen), cDNA was then fragmented and ligated into a sequencing library using NuGEN's Ovation Ultralow Library Systems. After barcoding, the RNA libraries were pooled, denatured and diluted to an 8 pM final concentration. Cluster formation was performed on cBot (Illumina) (single-end) using flow cells v.3. The SBS (sequencing by synthesis) was performed according to TruSeq SR protocol (Illumina) for the HiSeq 2500 (Illumina) set to 50 cycles, yielding an average of $30 \times 10^6$ clusters for each sample. Raw sequences (fastq) were filtered for good quality scores using FastQC software. Sequences obtained were aligned to the Mouse genome (mm10 release) using STAR aligner (STAR_2.3.0e_r291) (Dobin et al., Bioinformatics 29, 15-21 (2013)). Only uniquely mapped reads were used to estimate gene counts using the reported Ensembl gene annotations (v72) through the Python script 'HTSeq-count' (model type—union, http://www-huber.embl.de/users/anders/HTSeq/) (Anders et al., Bioinformatics 31, 166-169 (2015)). Subsequent to mapping the gene count, data was normalized using the "weighted trimmed mean of M-values" described elsewhere (Robinson et al., Genome Biol 11, R25 (2010)). After normalization, differential gene expression was performed using the "limma" package in R (Ritchie et al., Nucleic Acids Res 43, e47 (2015)).

Statistical Analysis on RNA Sequencing

Principal Component Analysis (PCA). PCA was made using mixOmics library in R (Kim-Anh Le Cao, Florian Rohart, Ignacio Gonzalez, Sebastien Dejean with key contributors Benoit Gautier, Francois Bartolo, contributions rom Pierre Monget, Jeff Coquery, FangZou Yao and Benoit Liquet. (2016). mixOmics: Omics Data Integration Project. R package version 6.0.0. https://CRAN.R-project.org/package=mixOmics) (Le Cao et al., Bioinformatics 25, 2855-2856 (2009)) on $\log_2$ normalized expression values generated by the voom function in limma.

Hierarchical Clustering. Hierarchical clustering was made using the pheatmap function of the R library with the same name ('Euclidean distance' and 'complete' method.) on log 2 normalized expression values generated by the voom function in limma.

Boxplots. Boxplots for qPCR data were produced with R on the −dCT (Gapdh as reference) to keep the log 2 scale of data. Asterisks (* p.value <0.05,  p.value <0.01, * p.value <0.001) represent an ANOVA-Tukey's post-hoc test.

Analysis of RNA-Seq data in Gosselin et al. (Gosselin, D. et al. Cell 159, 1327-1340 (2014)). Raw expression data from control microglia and macrophages of diverse origin were downloaded from the GEO dataset GSE62826 from SRA archive (SRR1634675, SRR1634676, SRR1634677, SRR1634678, SRR1634708, SRR1634709, SRR1634710, SRR1634711, SRR1634712, SRR1634721) and fastq files with raw sequences were obtained. Reads from Gosselin macrophages and microglia were processed together with reads from and TAμ cells, as described herein, and PCA and heatmaps were produced in order to compare μ and TAμ populations' expression with both adult microglia and macrophages in the study of Gosselin et al. (Gosselin et al., *Cell* 159, 1327-1340 (2014)).

Venn Diagrams. Venn Diagrams were made using the Venny online tool (Oliveros, J. C. (2007-2015) Venny. An interactive tool for comparing lists with Venn's diagrams. http://bioinfogp.cnb.csic.es/tools/venny/index.html)

Functional Enrichment. To evaluate pathways related to differences between cell populations, GSEA pre-ranked analysis was performed. Lists of $\log_2$ FoldChanges estimated with limma were used as pre-ranked lists with gsea pre-ranked command line tool with default parameters (gsea2-2.2.3.jar). Gene Ontology Biological Processes (c5.go.bp) was used as gmt file after translating human entrez id to mouse gene symbols using ensembl-mart homology maps. Due to the higher number of significant categories found correlated to μ.BUTX and TAμ.BUTX cells, the standard FDR cut off for the enrichment was increased from 0.05 to 0.001. GOSemSim semantic similarities matrix was calculated using GOSemSim R package (1.24.1)(Yu et al., *Bioinformatics* 26, 976-978 (2010)). The matrix of similarities was shown as heatmap of clustered GOs using pheatmap in R (with "euclidean" distance and "complete" method for clustering).

Accession codes. Gene Expression Omnibus: RNA-Seq data are available under accession code GSE87799 and data re-analyzed in Gosselin et al. are available under the accession code GSE62826 (Gosselin, D. et al. Cell 159, 1327-1340 (2014)).

Nanoparticle (NP) Biosynthesis and Administration

Materials. Hydroxyethyl methacrylate (HEMA, 97%, Sigma Aldrich), ε-caprolactone (CL, 97%, Sigma Aldrich), 2-ethylhexanoic acid tin(II) salt (Sn(Oct)2, ☐95%, Sigma-Aldrich), poly(ethylene glycol)methyl ether methacrylate (PEGMA950, Mn 950 Da, Sigma Aldrich), 3-sulfopropyl methacrylate potassium salt (SPMAK, 98%, Sigma Aldrich), 4-cyano-4-(phenylcarbonothioylthio)-pentanoic acid (CPA, >97%, Sigma Aldrich), 4-4' azobis(cyanovaleric acid) (ACVA, 98%, Sigma Aldrich), potassium persulfate (KPS; >99% purity, ACS reagent), Rhodamine B (RhB, Sb sensitivity <0.1 μg mL-1, Carlo Erba reagents), dicyclohexylcarbodiimide (DCC; 99% purity, Sigma Aldrich), 4-(dimethylamino)-pyridine (DMAP; >99% purity, Sigma Aldrich) were used as received except when specifically noted. Poly (ethylene glycol)methyl ether methacrylate (PEGMA2000, Mn 2000 Da, 50 wt. % in H2O, Sigma Aldrich) was extracted with DCM and dried under reduced pressure. All the solvents used were of analytical-grade purity and were purchased from Sigma Aldrich.

PCL-based macromonomers (HEMA-CLn) and HEMA-RhB synthesis and characterization. Poly ε-caprolactone-based macromonomers were produced via ring opening polymerization (ROP) of CL in bulk with HEMA as initiator and St(Oct)2 as catalyst according to a previous protocol. The initiator to catalyst ratio was kept constant to 200 while the monomer to initiator molar ratio was set to 3 and 5 in order to obtain a macromonomer with 3 (HEMA-CL3) and 5 (HEMA-CL5) caprolactone units, respectively. For HEMA-CL5, 4.5 g of HEMA and 71 mg of St(Oct)2 were mixed in a 10 ml vial at room temperature until complete dissolution. 20 g of caprolactone and 82.6 mg of $Na_2SO_4$ were mixed in a septum sealed flask and placed at 130° C. under stirring in a controlled temperature oil bath. The HEMA and St(Oct)2 mixture was then added into the flask and the reaction was left to react for 3 h. After cooling, the macromonomers were characterized via 1H-NMR (400 MHz, Bruker, Swizterland). A Fluorescent monomer based on Rhodamine B was synthesized via steglich esterification of RhB with HEMA in the presence of DCC and DMAP and characterized according to a protocol reported in literature.

Block copolymer synthesis and characterization—self assembly NPs. Two PCL-based block copolymers were synthesized via two subsequent RAFT solution polymerizations. In the first step, a PEGylated macro RAFT agent (5PEGMA2000) was synthesized via the RAFT polymerization of PEGMA2000 with a monomer to CPA and ACVA to CPA molar ratio equal to 5. Briefly, 14.8 g of PEGMA2000, 425 mg of CPA and 85 mg of ACVA were dissolved in 75 ml of ethanol and poured in a septum sealed flask. After purging with nitrogen for 30 min, the mixture was heated to 65° C. in a controlled temperature oil bath under stirring. After 24 h, other 85 mg of ACVA were dissolved in 2.5 ml of ethanol and injected into the reactor with a syringe. The reaction was stopped after other 24 hr and the mixture was dried under nitrogen. The final macro RAFT agent was washed 3 times with diethyl ether to remove the unreacted PEGMA2000. In the second step, two different block copolymers were synthesized with and without the addition of SPMAK in order to produce a neutral and negatively charged polymeric surfactant, respectively. For the neutral one, named 510 (5 for the number of PEGMA2000 units and 10 for the number of HEMA-CL5 repeating units), the RAFT solution polymerization of HEMA-CL5 was carried out at a monomer to RAFT agent and initiator to RAFT agent molar ratio equal to 10 and 3, respectively. 5.8 g of 5PEGMA2000, 4 g of HEMA-CL5, 54 mg of ACVA and 13.8 mg of HEMA-Rh were dissolved in 50 ml of ethanol and poured in a round bottom flask. After purging with nitrogen for 30 min, the mixture was heated to 65° C. and left to react for 24 h under stirring. The final polymer was dried under nitrogen and washed three times with diethyl ether. For the production of the negatively charged block copolymer (510-SP), the same amount of initiator, macro-RAFT agent, HEMA-Rh and 5PEGMA2000 were dissolved with 0.28 g of SPMAK into 39 g of an acetic buffer/ethanol (20/80 wt. %) mixture. The same reaction conditions and purification protocol of the 510 were applied. Conversion, MW and dispersity (Đ) of each step were determined via GPC with a Jasco (Series) apparatus. The samples were dissolved in THF at a concentration of 4 mg mL−1 and filtered through a 0.45 μm pore-size filter syringe before injection. The separation was performed at 35° C. with a flow rate of 0.5 mL min-1 through three Superchrom PLgel 5 m columns (600×7.5 mm, measuring range 0.5-1000 kDa). Mn, GPC and dispersity (D) were determined via direct calibration from differential refractive index (RI) data and were relative to poly(styrene) standards (from 580 to 3,250,000 g/mol, Polymer Laboratories). Conversion was estimated via the area under the RI signal curve of the polymer (Apol) and monomer (Amon) according to:

$$X_{GPC}=A_{pol}/A_{pol}+A_{mon}$$

In the case of the block copolymer 510SP, the characterization was performed via 1H-NMR because of its insolubility in the eluent of the GPC. 10 mg of the 510SP was dissolved in 0.7 mg of DMSO-d6 in order to perform the 1H-NMR analysis.

NPs production via nanoprecipitation of 510 and 510SP—self assembly NPs. The two fluorescent block copolymers were used to produce NPs directly into PBS via self-assembly. 60 mg of the polymeric surfactant (e.g. 510) was dissolved in 0.3 g of DMSO and then aspirated with a 5 ml syringe pre-loaded with 3 ml of PBS. After three cycles of aspiration and ejection, the mixture was filtered through a 0.2 m PES pore-size filter syringe (Millex). The NP Dn and PDI were determined by dynamic laser light scattering analysis (DLLS, Zetasizer Nano Series, Malvern Instruments).

NPs produced via emulsion polymerization—1$^{st}$ generation NPs. PEGylated PCL-based NPs were synthesized via monomer starved semi-batch emulsion polymerization (MSSEP) of HEMA-CL3 as previously described3. Briefly, 0.4 g of PEGMA950 were dissolved in 45 ml of deionised water in a three-neck round-bottom flask and heated to 80° C. After three nitrogen/vacuum cycles, 2.1 g of HEMA-CL3 were mixed with 2.1 mg of HEMA-Rh and added into the reactor at a feeding rate of 2 mL h−1. 0.02 g of KPS were dissolved in 2.5 mL of deionized water and injected with a syringe at the beginning of the lipophilic monomer feeding. After 3 hr, the reaction was stopped and the final latex was characterized via DLLS.

Statistical Analysis

All statistical tests were two-sided. For comparisons other than RNA-Seq results, Students's t test was used for 2-group comparisons. For comparisons with more than two groups, one-way ANOVA with Tukey's post-hoc test was used. Differences were considered statistically significant at a value of P<1.5 (*0). P<0.01, *P<0.001. In all Figures with error bars, the graphs depict means±SD.

Other Embodiments

From the foregoing description, it will be apparent that variations and modifications may be made to the invention described herein to adopt it to various usages and conditions.

Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. A method of delivering a Hematopoietic Stem Progenitor Cell (HSPC) to a human subject that has or is at increased risk of developing a lysosomal storage disorder or neurodegenerative disease, the method comprising administering to the subject a human CD34$^+$ Hematopoietic Stem Progenitor Cell by Intra-cerebral Ventricular Injection (ICV), wherein the subject was previously treated with a cytotoxic agent or radiation in connection with the ablation of microglia and/or their progenitors wherein the cytotoxic agent is an alkylating agent, and the administration reconstitutes microglia by HSPC engraftment in the subject.

2. The method of claim 1, wherein the human CD34+ Hematopoietic Stem Progenitor Cell (HSPC) is CD38–.

3. The method of claim 2, wherein the Hematopoietic Stem Progenitor Cell (HSPC) is Fgd5$^+$, CX3CR1$^-$, and/or CD11b$^-$.

4. The method of claim 1, wherein the subject has or is at increased risk of developing a lysosomal storage disorder or neurodegenerative disease.

5. The method of claim 4, wherein the lysosomal storage disorder is selected from Adrenoleukodystrophy, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, globoid leukodystrophy, GM1 gangliosidosis, I-Cell disease/Mucolipidosis II, Infantile Free Sialic Acid Storage Disease/ISSD, Juvenile Hexosaminidase A Deficiency, Infantile neuronal ceroid lipofuscinosis, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease/Glycogen storage disease type II, Pycnodysostosis, Sandhoff disease, Schindler disease, Salla disease/Sialic Acid Storage Disease, Tay-Sachs/GM2 gangliosidosis and Wolman disease or wherein the neurodegenerative disease is selected from amyotrophic lateral sclerosis (ALS), Parkinsons disease and Alzheimer's disease.

6. A method of delivering a Hematopoietic Stem Progenitor Cell (HSPC) to a human subject that has or is at increased risk of developing a lysosomal storage disorder or neurodegenerative disease, the method comprising administering to the subject a human CD150$^+$ CD48$^-$, Hematopoietic Stem Progenitor Cell by Intra-cerebral Ventricular Injection (ICV), wherein the subject was previously treated with a cytotoxic agent or radiation in connection with the ablation of microglia and/or their progenitors wherein the cytotoxic agent is an alkylating agent, and the administration reconstitutes microglia by HSPC engraftment in the subject.

7. A method of delivering a Hematopoietic Stem Progenitor Cell (HSPC) to a subject that has or is at increased risk of developing a lysosomal storage disorder or neurodegenerative disease, the method comprising administering to the subject a Lin-Hematopoietic Stem Progenitor Cell by Intra-cerebral Ventricular Injection (ICV), wherein the subject was previously treated with a cytotoxic agent or radiation in connection with the ablation of microglia and/or their progenitors wherein the cytotoxic agent is an alkylating agent, and the administration reconstitutes microglia by HSPC engraftment in the subject.

8. The method of claim 7, wherein the HSPC is c-kit$^-$, Sca-1$^+$.

\* \* \* \* \*